US009816084B2

(12) United States Patent
Buechler et al.

(10) Patent No.: US 9,816,084 B2
(45) Date of Patent: Nov. 14, 2017

(54) ASPARTYL-TRNA SYNTHETASES

(71) Applicant: aTyr Pharma, Inc., San Diego, CA (US)

(72) Inventors: Ying Ji Buechler, Carlsbad, CA (US); Chi-Fang Wu, San Diego, CA (US); Ryan Andrew Adams, San Diego, CA (US); Kristi Helen Piehl, San Diego, CA (US); Jeffrey Greve, Berkeley, CA (US); John D. Mendlein, Encinitas, CA (US)

(73) Assignee: aTyr Pharma, Inc., San Diego, CA (US)

( * ) Notice: Subject to any disclaimer, the term of this patent is extended or adjusted under 35 U.S.C. 154(b) by 296 days.

(21) Appl. No.: 14/360,576

(22) PCT Filed: Dec. 6, 2012

(86) PCT No.: PCT/US2012/068282
§ 371 (c)(1),
(2) Date: May 23, 2014

(87) PCT Pub. No.: WO2013/086216
PCT Pub. Date: Jun. 13, 2013

(65) Prior Publication Data
US 2014/0302075 A1 Oct. 9, 2014

Related U.S. Application Data

(60) Provisional application No. 61/567,559, filed on Dec. 6, 2011.

(51) Int. Cl.
C12N 9/96 (2006.01)
A61K 38/43 (2006.01)
C12N 9/00 (2006.01)
A61K 38/00 (2006.01)

(52) U.S. Cl.
CPC .............. C12N 9/93 (2013.01); A61K 38/00 (2013.01); C07K 2319/40 (2013.01)

(58) Field of Classification Search
CPC ...... C12N 9/96; A61K 38/43; C07K 2319/30; C12Y 601/01012; C12Y 601/01023
See application file for complete search history.

(56) References Cited

U.S. PATENT DOCUMENTS

| 5,370,995 | A | 12/1994 | Hennecke et al. |
| 5,484,703 | A | 1/1996 | Raben et al. |
| 5,663,066 | A | 9/1997 | Raben et al. |
| 5,747,315 | A | 5/1998 | Lowlor |
| 5,750,387 | A | 5/1998 | Hodgson et al. |
| 5,753,480 | A | 5/1998 | Lawlor |
| 5,756,327 | A | 5/1998 | Sassanfar et al. |
| 5,759,833 | A | 6/1998 | Shiba et al. |
| 5,776,749 | A | 7/1998 | Hodgson et al. |
| 5,795,757 | A | 8/1998 | Hodgson et al. |
| 5,798,240 | A | 8/1998 | Martinis et al. |
| 5,801,013 | A | 9/1998 | Tao et al. |
| 5,866,390 | A | 2/1999 | Lawlor |
| 5,885,815 | A | 3/1999 | Sassanfar et al. |
| 5,928,920 | A | 7/1999 | Hodgson et al. |
| 5,939,298 | A | 8/1999 | Brown et al. |
| 6,225,060 | B1 | 5/2001 | Clark et al. |
| 6,255,090 | B1 | 7/2001 | Famodu et al. |
| 6,265,188 | B1 | 7/2001 | Brown et al. |
| 6,428,960 | B1 | 8/2002 | Clark et al. |
| 6,548,060 | B1 | 4/2003 | Kim |
| 6,696,619 | B1 | 2/2004 | Famodu et al. |
| 6,852,512 | B2 | 2/2005 | Choi et al. |
| 6,903,189 | B2 | 6/2005 | Schimmel et al. |
| 7,037,505 | B2 | 5/2006 | Kim et al. |
| 7,067,126 | B2 | 6/2006 | Schimmel et al. |
| 7,144,984 | B2 | 12/2006 | Schimmel et al. |
| 7,196,068 | B2 | 3/2007 | Kim et al. |
| 7,273,844 | B2 | 9/2007 | Schimmel et al. |
| 7,282,208 | B2 | 10/2007 | Kim |
| 7,413,885 | B2 | 8/2008 | Schimmel et al. |
| 7,459,529 | B2 | 12/2008 | Kim |
| 7,476,651 | B2 | 1/2009 | Schimmel et al. |
| 7,521,215 | B2 | 4/2009 | Schimmel et al. |
| 7,528,106 | B2 | 5/2009 | Friedlander et al. |
| 7,572,452 | B2 | 8/2009 | Kim |
| 7,745,391 | B2 | 6/2010 | Mintz et al. |
| 7,842,467 | B1 | 11/2010 | Heidbrink et al. |

(Continued)

FOREIGN PATENT DOCUMENTS

| CA | 2531146 | 3/2005 |
| CN | 1341725 | 3/2002 |

(Continued)

OTHER PUBLICATIONS

International Preliminary Report on Patentability for International Application No. PCT/US2009/048915, dated Jan. 5, 2011.
International Search Report and Written Opinion for International Application No. PCT/US2009/048915, dated Nov. 2, 2009.
Office Action for U.S. Appl. No. 12/482,151, dated Oct. 11, 2011, 43 pages.
Office Action for U.S. Appl. No. 12/482,151, dated Mar. 18, 2011, 11 pages.
International Preliminary Report on Patentability for International Application No. PCT/US2009/046910, dated Dec. 13, 2010.
International Search Report and Written Opinion for International Application No. PCT/US2009/046910, dated Mar. 4, 2010.
Supplementary European Search Report for European Application No. 06838844.6, dated Apr. 9, 2009, 10 pages.
Office Action for European Patent Application No. 06838844.6, dated Apr. 9, 2009.

(Continued)

Primary Examiner — Kagnew H Gebreyesus
(74) Attorney, Agent, or Firm — Cooley LLP

(57) ABSTRACT

The present invention provides aspartyl-tRNA synthetase derived proteins (DRS polypeptides) with altered cysteine content, compositions comprising the same, and methods of using such polypeptides and compositions for treating or diagnosing a variety of conditions. The DRS polypeptides of the invention have immunomodulatory properties, and exhibit improved activity and stability.

24 Claims, 5 Drawing Sheets

(56) References Cited

U.S. PATENT DOCUMENTS

| | | |
|---|---|---|
| 7,901,917 B2 | 3/2011 | Schimmel et al. |
| 7,902,165 B2 | 3/2011 | Kim |
| 7,981,426 B2 | 7/2011 | Kim |
| 8,003,780 B2 | 8/2011 | Kim et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 8,404,471 B2 | 3/2013 | Greene et al. |
| 8,481,296 B2 | 7/2013 | Yang |
| 8,747,840 B2 | 6/2014 | Greene et al. |
| 8,753,638 B2 | 6/2014 | Zhou et al. |
| 8,828,395 B2 | 9/2014 | Watkins et al. |
| 8,835,387 B2 | 9/2014 | Chiang et al. |
| 8,945,541 B2 | 2/2015 | Greene et al. |
| 8,946,157 B2 | 2/2015 | Greene et al. |
| 8,961,960 B2 | 2/2015 | Chiang et al. |
| 8,961,961 B2 | 2/2015 | Greene et al. |
| 8,962,560 B2 | 2/2015 | Greene et al. |
| 8,969,301 B2 | 3/2015 | Greene et al. |
| 8,980,253 B2 | 3/2015 | Greene et al. |
| 8,981,045 B2 | 3/2015 | Greene et al. |
| 8,986,680 B2 | 3/2015 | Greene et al. |
| 8,986,681 B2 | 3/2015 | Greene et al. |
| 8,993,723 B2 | 3/2015 | Greene et al. |
| 8,999,321 B2 | 4/2015 | Greene et al. |
| 9,029,506 B2 | 5/2015 | Greene et al. |
| 9,034,320 B2 | 5/2015 | Greene et al. |
| 9,034,321 B2 | 5/2015 | Greene et al. |
| 9,034,598 B2 | 5/2015 | Greene et al. |
| 9,062,301 B2 | 6/2015 | Greene et al. |
| 9,062,302 B2 | 6/2015 | Greene et al. |
| 9,068,177 B2 | 6/2015 | Greene et al. |
| 9,127,268 B2 | 9/2015 | Watkins et al. |
| 9,273,302 B2 | 3/2016 | Chiang et al. |
| 9,315,794 B2 | 4/2016 | Greene et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0018985 A1 | 1/2003 | Falco et al. |
| 2003/0082575 A1 | 5/2003 | Schultz et al. |
| 2003/0158400 A1 | 8/2003 | Tang et al. |
| 2003/0165921 A1 | 9/2003 | Tang et al. |
| 2003/0166241 A1 | 9/2003 | Famodu et al. |
| 2003/0215827 A1 | 11/2003 | Yue et al. |
| 2004/0009163 A1 | 1/2004 | Schimmel et al. |
| 2004/0018505 A1 | 1/2004 | Lee et al. |
| 2004/0048290 A1 | 3/2004 | Lee et al. |
| 2004/0101879 A1 | 5/2004 | Seidel-Dugan et al. |
| 2004/0152079 A1 | 8/2004 | Schimmel et al. |
| 2004/0203094 A1 | 10/2004 | Martinis et al. |
| 2004/0214216 A1 | 10/2004 | Famodu et al. |
| 2004/0224981 A1 | 11/2004 | Janjic et al. |
| 2005/0136513 A1 | 6/2005 | Zhang |
| 2005/0196754 A1 | 9/2005 | Drmanac et al. |
| 2005/0208536 A1 | 9/2005 | Schultz et al. |
| 2006/0024288 A1 | 2/2006 | Glidden |
| 2006/0035232 A1 | 2/2006 | McGregor et al. |
| 2006/0046250 A1 | 3/2006 | Kim |
| 2006/0078553 A1 | 4/2006 | Glidden |
| 2006/0160175 A1 | 7/2006 | Anderson et al. |
| 2006/0248617 A1 | 11/2006 | Imanaka et al. |
| 2007/0048322 A1 | 3/2007 | Schimmel et al. |
| 2007/0061916 A1 | 3/2007 | Kovalic et al. |
| 2007/0111238 A1 | 5/2007 | Jamieson et al. |
| 2007/0224201 A1 | 9/2007 | Wu et al. |
| 2008/0044854 A1 | 2/2008 | Wang et al. |
| 2008/0113914 A1 | 5/2008 | Hays et al. |
| 2008/0153745 A1 | 6/2008 | Tian |
| 2009/0123971 A1 | 5/2009 | Paulsel et al. |
| 2009/0221794 A1 | 9/2009 | Kim et al. |
| 2009/0226966 A1 | 9/2009 | Yokoyama et al. |
| 2009/0227002 A1 | 9/2009 | Schultz et al. |
| 2009/0227662 A1 | 9/2009 | Schimmel et al. |
| 2009/0285792 A1 | 11/2009 | Friedlander et al. |
| 2009/0305973 A1 | 12/2009 | Kim et al. |
| 2010/0003230 A1 | 1/2010 | Glidden |
| 2010/0028352 A1 | 2/2010 | Greene et al. |
| 2010/0048413 A1 | 2/2010 | Arcus et al. |
| 2010/0092434 A1 | 4/2010 | Belani et al. |
| 2010/0093082 A1 | 4/2010 | Tian et al. |
| 2010/0138941 A1 | 6/2010 | Kim et al. |
| 2010/0167997 A1 | 7/2010 | Kim |
| 2010/0297149 A1 | 11/2010 | Zhou et al. |
| 2010/0310576 A1 | 12/2010 | Adams et al. |
| 2011/0104139 A1 | 5/2011 | Faber |
| 2011/0110917 A1 | 5/2011 | Schimmel et al. |
| 2011/0117572 A1 | 5/2011 | Kim et al. |
| 2011/0124582 A1 | 5/2011 | Kim et al. |
| 2011/0136119 A1 | 6/2011 | Kim et al. |
| 2011/0150885 A1 | 6/2011 | Watkins et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0010141 A1 | 1/2012 | Kim |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0052177 A1 | 2/2013 | Schimmel et al. |
| 2013/0108630 A1 | 5/2013 | Watkins et al. |
| 2013/0129703 A1 | 5/2013 | Chiang et al. |
| 2013/0129704 A1 | 5/2013 | Greene et al. |
| 2013/0129705 A1 | 5/2013 | Greene et al. |
| 2013/0142774 A1 | 6/2013 | Greene et al. |
| 2013/0195832 A1 | 8/2013 | Greene et al. |
| 2013/0202574 A1 | 8/2013 | Greene et al. |
| 2013/0202575 A1 | 8/2013 | Greene et al. |
| 2013/0202576 A1 | 8/2013 | Greene et al. |
| 2013/0209434 A1 | 8/2013 | Greene et al. |
| 2013/0209472 A1 | 8/2013 | Greene et al. |
| 2013/0224173 A1 | 8/2013 | Greene et al. |
| 2013/0224174 A1 | 8/2013 | Greene et al. |
| 2013/0230505 A1 | 9/2013 | Greene et al. |
| 2013/0230507 A1 | 9/2013 | Greene et al. |
| 2013/0230508 A1 | 9/2013 | Greene et al. |
| 2013/0236440 A1 | 9/2013 | Greene et al. |
| 2013/0236455 A1 | 9/2013 | Greene et al. |
| 2013/0243745 A1 | 9/2013 | Greene et al. |
| 2013/0243766 A1 | 9/2013 | Zhou et al. |
| 2013/0273045 A1 | 10/2013 | Watkins et al. |
| 2013/0280230 A1 | 10/2013 | Greene et al. |
| 2013/0287755 A1 | 10/2013 | Greene et al. |
| 2013/0315887 A1 | 11/2013 | Greene et al. |
| 2013/0330312 A1 | 12/2013 | Greene et al. |
| 2013/0344096 A1 | 12/2013 | Chiang et al. |
| 2014/0066321 A1 | 3/2014 | Xu et al. |
| 2014/0255375 A1 | 9/2014 | Belani et al. |
| 2014/0255378 A1 | 9/2014 | Watkins et al. |
| 2014/0335087 A1 | 11/2014 | Buechler et al. |
| 2014/0349369 A1 | 11/2014 | Buechler et al. |
| 2014/0363415 A1 | 12/2014 | Greene et al. |
| 2014/0371294 A1 | 12/2014 | Zhou et al. |
| 2015/0064188 A1 | 3/2015 | Greene |
| 2015/0093799 A1 | 4/2015 | Chiang et al. |
| 2015/0140072 A1 | 5/2015 | Watkins et al. |
| 2015/0159148 A1 | 6/2015 | Buechler et al. |
| 2015/0231214 A1 | 8/2015 | Greene et al. |
| 2015/0240227 A1 | 8/2015 | Greene et al. |
| 2015/0240228 A1 | 8/2015 | Greene et al. |
| 2015/0252347 A1 | 9/2015 | Greene et al. |
| 2015/0252348 A1 | 9/2015 | Greene et al. |
| 2015/0252349 A1 | 9/2015 | Greene et al. |
| 2015/0284704 A1 | 10/2015 | Greene et al. |
| 2015/0284705 A1 | 10/2015 | Greene et al. |
| 2015/0284706 A1 | 10/2015 | Greene et al. |
| 2015/0290304 A1 | 10/2015 | Greene et al. |
| 2015/0290305 A1 | 10/2015 | Greene et al. |
| 2015/0344866 A1 | 12/2015 | Greene et al. |
| 2015/0353914 A1 | 12/2015 | Greene et al. |
| 2015/0361411 A1 | 12/2015 | Greene et al. |
| 2015/0361412 A1 | 12/2015 | Greene et al. |

(56) References Cited

U.S. PATENT DOCUMENTS

| | | | |
|---|---|---|---|
| 2015/0361413 | A1 | 12/2015 | Greene et al. |
| 2016/0010075 | A1 | 1/2016 | Greene et al. |
| 2016/0017311 | A1 | 1/2016 | Greene |

FOREIGN PATENT DOCUMENTS

| | | |
|---|---|---|
| CN | 1341727 | 3/2002 |
| CN | 1352242 | 6/2002 |
| CN | 1352252 | 6/2002 |
| EP | 0785265 | 7/1997 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 2177610 | 4/2010 |
| EP | 1274834 | 7/2010 |
| EP | 2084190 | 3/2011 |
| JP | 2008-508349 | 3/2008 |
| WO | WO 97/25426 | 7/1997 |
| WO | WO 97/26351 | 7/1997 |
| WO | WO 97/39017 | 10/1997 |
| WO | WO 98/14591 | 4/1998 |
| WO | WO 98/50554 | 11/1998 |
| WO | WO 99/45130 | 9/1999 |
| WO | WO 01/07628 | 2/2001 |
| WO | WO 01/19999 | 3/2001 |
| WO | WO 01/64892 | 9/2001 |
| WO | WO 01/74841 | 10/2001 |
| WO | WO 01/75067 | 10/2001 |
| WO | WO 01/75078 | 10/2001 |
| WO | WO 01/88188 | 11/2001 |
| WO | WO 01/90330 | 11/2001 |
| WO | WO 01/94568 | 12/2001 |
| WO | WO 02/44349 | 6/2002 |
| WO | WO 02/055663 | 7/2002 |
| WO | WO 02/059323 | 8/2002 |
| WO | WO 02/067970 | 9/2002 |
| WO | WO 03/009813 | 2/2003 |
| WO | WO 03/080648 | 10/2003 |
| WO | WO 03/094862 | 11/2003 |
| WO | WO 2004/030615 | 4/2004 |
| WO | WO 2004/087875 | 10/2004 |
| WO | WO 2005/019258 | 3/2005 |
| WO | WO 2005/019415 | 3/2005 |
| WO | WO 2005/102395 | 11/2005 |
| WO | WO 2005/117954 | 12/2005 |
| WO | WO 2006/016217 | 2/2006 |
| WO | WO 2006/057500 | 6/2006 |
| WO | WO 2007/064941 | 6/2007 |
| WO | WO 2007/139397 | 12/2007 |
| WO | WO 2008/007818 | 1/2008 |
| WO | WO 2008/016356 | 2/2008 |
| WO | WO 2008/021290 | 2/2008 |
| WO | WO 2008/133359 | 11/2008 |
| WO | WO 2009/059056 | 5/2009 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2011/139714 | 11/2011 |
| WO | WO 2011/139799 | 11/2011 |
| WO | WO 2011/139801 | 11/2011 |
| WO | WO 2011/139853 | 11/2011 |
| WO | WO 2011/139854 | 11/2011 |
| WO | WO 2011/139907 | 11/2011 |
| WO | WO 2011/139986 | 11/2011 |
| WO | WO 2011/139988 | 11/2011 |
| WO | WO 2011/140132 | 11/2011 |
| WO | WO 2011/140135 | 11/2011 |
| WO | WO 2011/140266 | 11/2011 |
| WO | WO 2011/140267 | 11/2011 |
| WO | WO 2011/143482 | 11/2011 |
| WO | WO 2011/146410 | 11/2011 |
| WO | WO 2011/150279 | 12/2011 |
| WO | WO 2011/153277 | 12/2011 |
| WO | WO 2012/009289 | 1/2012 |
| WO | WO 2012/021247 | 2/2012 |
| WO | WO 2012/021249 | 2/2012 |
| WO | WO 2012/027611 | 3/2012 |
| WO | WO 2012/048125 | 4/2012 |
| WO | WO 2012/158945 | 11/2012 |
| WO | WO 2013/022982 | 2/2013 |
| WO | WO 2013/086216 | 6/2013 |
| WO | WO 2013/086228 | 6/2013 |
| WO | WO 2013/115926 | 8/2013 |
| WO | WO 2013/123432 | 8/2013 |

OTHER PUBLICATIONS

Office Action for U.S. Appl. No. 12/085,884, dated Jan. 20, 2011.
International Preliminary Report on Patentability for International Application No. PCT/US2006/046106, dated Jun. 4, 2008.
International Search Report and Written Opinion for International Application No. PCT/US2006/046106, dated Aug. 9, 2007.
Supplementary European Search Report for European Application No. 10746935.5, dated Oct. 26, 2012.
Office Action for U.S. Appl. No. 13/203,831, dated Oct. 7, 2013, 20 pages.
International Preliminary Report on Patentability for International Application No. PCT/US2010/025642, dated Aug. 30, 2011.
International Search Report and Written Opinion for International Application No. PCT/US2010/025642, dated Oct. 29, 2010.
Supplementary European Search Report for European Application No. 10764856.0, dated Sep. 5, 2012.
Office Action for U.S. Appl. No. 12/751,358, dated Dec. 2, 2014.
Office Action for U.S. Appl. No. 12/751,358, dated Jun. 11, 2014.
Office Action for U.S. Appl. No. 12/751,358, dated Oct. 3, 2011.
Office Action for U.S. Appl. No. 12/751,358, dated Mar. 3, 2011.
International Preliminary Report on Patentability for International Application No. PCT/US2010/029377, dated Oct. 4, 2011.
International Search Report and Written Opinion for International Application No. PCT/US2010/029377, dated Jan. 26, 2011.
Office Action for U.S. Appl. No. 12/725,272, dated Jul. 13, 2012, 9 pages.
Restriction Requirement for U.S. Appl. No. 12/725,272, dated Apr. 27, 2012.
International Preliminary Report on Patentability for International Application No. PCT/US2010/027525, dated Sep. 20, 2011.
International Search Report and Written Opinion for International Application No. PCT/US2010/027525, dated Jan. 10, 2011.
International Search Report and Written Opinion for International Application No. PCT/US2010/059964, dated Aug. 25, 2011.
International Preliminary Report on Patentability for International Application No. PCT/US2010/059964, dated Jun. 12, 2012.
International Preliminary Report on Patentability for International Application No. PCT/US2010/059963, dated Jun. 12, 2012, 18 pages.
International Search Report and Written Opinion for International Application No. PCT/US2010/059963, dated May 12, 2011.
International Search Report and Written Opinion for International Application No. PCT/US2011/000210, dated Aug. 12, 2011.
International Preliminary Report on Patentabiltity for International Application No. PCT/US2011/000210, dated Aug. 7, 2012.
Supplementary European Search Report for European Application No. 11778025.4, dated Nov. 6, 2013.

(56) References Cited

OTHER PUBLICATIONS

International Search Report and Written Opinion for International Application No. PCT/US2011/034387, dated Mar. 23, 2012.
International Preliminary Report on Patentability for International Application No. PCT/US2011/034387, dated Oct. 30, 2012.
Supplementary European Search Report for European Application No. 11778026.2, dated Oct. 22, 2013.
International Search Report and Written Opinion for International Application No. PCT/US2011/034388, dated Mar. 23, 2012.
International Preliminary Report on Patentability for International Application No. PCT/US2011/034388, dated Oct. 30, 2012.
Supplementary European Search Report for European Application No. 11807357.6, dated Dec. 22, 2014.
Notice of Allowance for U.S. Appl. No. 13/809,750, dated Oct. 17, 2014, 10 pages.
International Search Report and Written Opinion for International Application No. PCT/US2011/043596, dated Feb. 29, 2012.
International Preliminary Report on Patentability for International Application No. PCT/US2011/043596, dated Jan. 15, 2013.
Supplementary European Search Report for European Application No. 11778118.7, dated Aug. 19, 2013.
International Search Report and Written Opinion for International Application No. PCT/US2011/034838, dated Jan. 9, 2012.
International Preliminary Report on Patentability for International Application No. PCT/US2011/034838, dated Nov. 6, 2012.
International Search Report and Written Opinion for International Application No. PCT/US2011/033988, dated Feb. 9, 2012.
International Preliminary Report on Patentability for International Application No. PCT/US2011/033988, dated Oct. 30, 2012.
International Search Report and Written Opinion for International Application No. PCT/US2011/038240, dated Feb. 9, 2012.
International Preliminary Report on Patentability for International Application No. PCT/US2011/038240, dated Nov. 27, 2012.
Supplementary European Search Report for European Application No. 11778296.1, dated Nov. 12, 2013.
International Search Report and Written Opinion for International Application No. PCT/US2011/035250, dated Jan. 19, 2012.
International Preliminary Report on Patentability for International Application No. PCT/2011/035250, dated Nov. 6, 2012.
International Search Report and Written Opinion for International Application No. PCT/US2011/043756, dated Mar. 2, 2012.
International Preliminary Report on Patentability for International Application No. PCT/US2011/043756, dated Jan. 15, 2013.
International Search Report and Written Opinion for International Application No. PCT/US2011/043758, dated Mar. 2, 2012.
International Preliminary Report on Patentability for International Application No. PCT/US2011/043758, dated Jan. 15, 2013.
International Search Report and Written Opinion for International Application No. PCT/US2011/034205, dated Feb. 8, 2012.
International Preliminary Report on Patentability for International Application No. PCT/US2011/034205, dated Oct. 30, 2012.
International Search Report and Written Opinion for International Application No. PCT/US2011/036684, dated Feb. 9, 2012.
International Preliminary Report on Patentability for International Application No. PCT/US2011/036684, dated Nov. 20, 2012.
International Search Report and Written Opinion for International Application No. PCT/US2011/038813, dated Mar. 28, 2012.
International Preliminary Report on Patentability for International Application No. PCT/US2011/038813, dated Dec. 4, 2012.
International Search Report and Written Opinion for International Application No. PCT/US2011/035056, dated Mar. 23, 2012.
International Preliminary Report on Patentability for International Application No. PCT/US2011/035056, dated Nov. 6, 2012.
International Search Report and Written Opinion for International Application No. PCT/US2011/035053, dated Mar. 23, 2012.
International Preliminary Report on Patentability for International Application No. PCT/US2011/035053, dated Nov. 6, 2012.
Supplementary European Search Report for European Application No. 11778120.3, dated Nov. 15, 2013.
International Search Report and Written Opinion for International Application No. PCT/US2011/034840, dated Feb. 10, 2012.
International Preliminary Report on Patentability for International Application No. PCT/US2011/034840, dated Nov. 6, 2012.
Supplementary European Search Report for European Application No. 11777984.3, dated Oct. 18, 2013.
International Search Report and Written Opinion for International Application No. PCT/US2011/034207, dated Feb. 8, 2012.
International Preliminary Report on Patentability for International Application No. PCT/US2011/034207, dated Oct. 30, 2012.
International Search Report and Written Opinion for International Application No. PCT/US2011/055130, dated May 14, 2012.
International Preliminary Report on Patentability for International Application No. PCT/US2011/055130, dated Apr. 9, 2013.
International Search Report and Written Opinion for International Application No. PCT/US2011/049223, dated Mar. 27, 2012.
International Preliminary Report on Patentability for International Application No. PCT/US2011/049223, dated Feb. 26, 2013.
International Search Report and Written Opinion for International Application No. PCT/US2011/034626, dated Jan. 19, 2012.
International Preliminary Report on Patentability for International Application No. PCT/US2011/034626, dated Oct. 30, 2012.
Supplementary European Search Report for European Application No. 11781304.8, dated Oct. 23, 2013.
International Search Report and Written Opinion for International Application No. PCT/US2011/036326, dated Feb. 9, 2012.
International Preliminary Report on Patentability for International Application No. PCT/US2011/036326, dated Nov. 20, 2012.
International Search Report and Written Opinion for International Application No. PCT/US2011/035251, dated Feb. 8, 2012.
International Preliminary Report on Patentability for International Application No. PCT/US2011/035251, dated Nov. 6, 2012.
International Search Report and Written Opinion for International Application No. PCT/US2012/068282, dated Apr. 1, 2013.
International Search Report and Written Opinion for International Application No. PCT/US2012/068296, dated Apr. 19, 2013.
Supplementary Partial European Search Report for European Application No. 12867497.5, dated Apr. 29, 2015.
International Preliminary Report on Patentability for International Application No. PCT/US2012/071762, dated Jul. 1, 2014.
Adams, M. D. et al., "The genome sequence of *Drosophila melanogaster*," Science, 287(5961):2185-2195 (2000).
Aderem, A. et al., "Toll-like receptors in the induction of the innate immune response," Nature, 406:782-787 (2000).
Amaar, Y. G. et al., "Cloning and characterization of the C.elegans histidyl-tRNA synthetase gene," Nucleic Acids Research, 21(18):4344-4347 (1993).
Antonellis, A. et al., "The Role of Aminoacyl-tRNA Synthetases in Genetic Diseases," Annual Review of Genomics and Human Genetics, 9(1):87-107 (2008).
Ascherman, D. P. et al., "Critical Requirement for Professional APCs in Eliciting T Cell Responses to Novel Fragments of Histidyl-tRNA Synthetase (Jo-1) in Jo-1 Antibody-Positive Polymyositis," J. Immunol., 169:7127-7134 (2002).
Ascherman, D. P., "The Role of Jo-1 in the Immunopathogenesis of Polymyositis: Current Hypotheses," Current Rheumatology Reports, 5:425-430 (2003).
Barbasso, S. et al., "Sera From Anti-Jo-1-Positive Patients with Polymyositis and Interstitial Lung Disease Induce Expression of Intercellular Adhesion Molecule 1 in Human Lung Endothelial Cells," Arthritis & Rheumatism, 60(8):2524-2530 (2009).
Bernstein, R. M. et al., "Anti-Jo-1 antibody: a marker for myositis with interstitial lung disease," British Medical Journal, 289:151-152 (1984).
Blechynden, L.M. et al., "Sequence and polymorphism analysis of the murine gene encoding histidyl-tRNA synthetase," Gene, 178:151-156 (1996).
Blechynden, L.M. et al., "Myositis Induced by Naked DNA Immunization with the Gene for Histidyl-tRNA Synthetase," Human Gene Therapy, 8:1469-1480 (Aug. 10, 1997).
Blum, D. et al., "Extracellular toxicity of 6-hydroxydopamine on PC12 cells," Neuroscience Letters, 283(3):193-196 (2000).

(56) References Cited

OTHER PUBLICATIONS

Branden et al., "Introduction to Protein Structure," Garland Publishing Inc., New York, p. 247 (1991).
Brightbill, H. D. et al., "Toll-like receptors: molecular mechanisms of the mammalian immune response," Immunology, 101:1-10 (2000).
Broun, P. et al., "Catalytic plasticity of fatty acid modification enzymes underlying chemical diversity of plant lipids," Science, 282:1315-1317 (1998).
Brown, M. V. et al., "Mammalian aminoacyl-tRNA synthetases: Cell signaling functions of the protein translation machinery," Vascular Pharmacology, 52(1-2):21-26 (2010).
Car, B. D. et al., "Interferon y Receptor Deficient Mice Are Resistant to Endotoxic Shock," J. Exp. Med., 179:1437-1444, 1994.
Casciola-Rosen, L. et al., "Cleavage by Granzyme B Is Strongly Predictive of Autoantigen Status: Implications for Initiation of Autoimmunity," J. Exp. Med., 190(6):815-825 (1999).
Casciola-Rosen, L., "Histidyl-Transfer RNA Synthetase: A Key Participant in Idiopathic Inflammatory Myopathies," Arthritis and Rheumatism, 63(2):331-333 (2011).
Cheong et al., "Structure of the N-terminal extension of human aspartyl-tRNA synthetase: implications for its biological function," The International Journal of Biochemistry & Cell Biology, 35:1548-1557, 2003.
Chica, R. A. et al., "Semi-rational approaches to engineering enzyme activity: combining the benefits of directed evolution and rational design," Curr. Opin. Biotechnol., 16:378-384 (2005).
Choi, W. S. et al., "Two Distinct Mechanisms Are Involved in 6-Hydroxydopamine-and MPP+-Induced Dopaminergic Neuronal Cell Death: Role of Caspases, ROS, and JNK," Journal of Neuroscience Research, 57(1):86-94 (1999).
Datson, N. A. et al., "Development of the first marmoset-specific DNA microarray (EUMAMA): a new genetic tool for large-scale expression profiling in a non-human primate," BMC Genomics, 8(190):1-9 (2007).
Deiters, A. et al., "Site-specific PEGylation of proteins containing unnatural amino acids," Bioorg Med Chem Lett, 14(23):5743-5745 (2004).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Dumont, J. A. et al., "Monomeric Fc Fusions: Impact on pharmacokinetic and biological activity of protein therapeutics," Biodrugs: Clinical Immunotherapeutics, Biopharmaceuticals and Gene Therapy, 20(3):151-160 (2006).
Eriani, G. et al., "Cytoplasmic aspartyl-tRNA synthetase from *Saccharomyces cerevisiae*. Study of its functional organisation by deletion analysis," European Journal of Biochemistry, 200(2):337-343 (1991).
Escalante, C., et al., "Expression of human aspartyl-tRNA synthetase in COS cells," Molecular and Cellular Biochemistry, 140(1):55-63 (1994).
Escalante, C. et al., "Expression of Human Aspartyl-tRNA Synthetase in *Escherichia coli*: Functional Analysis of the N-Terminal Putative Amphiphilic Helix," The Journal of Biological Chemistry, 268(8):6014-6023 (1993).
Ewalt, K. L. et al., "Activation of Angiogenic Signaling Pathways by Two Human tRNA Synthetases," Biochemistry, 41(45):13344-13349 (2002).
Fontanesi, L. et al., "Identification and association analysis of several hundred single nucleotide polymorphisms within candidate genes for back fat thickness in Italian large white pigs using a selective genotyping approach," J Anim Sci, 90(8):2450-2464 (2012).
Frommhold, D. et al., "Sialyltransferase ST3Gal-IV controls CXCR2-mediated firm leukocyte arrest during inflammation," Journal of Experimental Medicine, 205(6):1435-1446 (2008).
GenBank Accession No. AA131122, Nov. 27, 1996.
GenBank Accession No. AA281081, Apr. 2, 1997.
GenBank Accession No. AA355758, Apr. 21, 1997.
GenBank Accession No. AA984229, published May 27, 1998.
GenBank Accession No. AAP36306.1, published May 13, 2003.
GenBank Accession No. BT007638.1, published May 13, 2003.
GenBank Accession No. AI985978, Aug. 31, 1999.
GenBank Accession No. AK055917, published Jan. 19, 2008.
GenBank Accession No. AK124831, published Jul. 3, 2008.
GenBank Accession No. AK225776, published Jul. 22, 2006.
GenBank Accession No. AK293154, published Jul. 24, 2008.
GenBank Accession No. AK295219, published Jul. 24, 2008.
GenBank Accession No. AK302295, published Jul. 24, 2008.
GenBank Accession No. AK303778, published Jul. 24, 2008.
GenBank Accession No. AU129836, published Feb. 18, 2011.
GenBank Accession No. AV685924, Sep. 25, 2000.
GenBank Accession No. AW070887, Oct. 13, 1999.
GenBank Accession No. BE561651, Aug. 10, 2000.
GenBank Accession No. BE695954, Sep. 11, 2000.
GenBank Accession No. BE872272, published Jan. 13, 2011.
GenBank Accession No. BF437672, Nov. 29, 2000.
GenBank Accession No. BF526055, Dec. 4, 2000.
GenBank Accession No. BF791754, published Jan. 13, 2011.
GenBank Accession No. BG108830, published Jun. 1, 2001.
GenBank Accession No. BG700836, May 7, 2001.
GenBank Accession No. BI559642, Sep. 4, 2001.
GenBank Accession No. BI599431, Sep. 5, 2001.
GenBank Accession No. BM827507, Mar. 6, 2002.
GenBank Accession No. BP268250, published Feb. 10, 2011.
GenBank Accession No. BQ002750, Mar. 26, 2002.
GenBank Accession No. BU599828, Sep. 19, 2002.
GenBank Accession No. CA865450, Dec. 20, 2002.
GenBank Accession No. CA865692, Dec. 20, 2002.
GenBank Accession No. CD694017, Jun. 25, 2003.
GenBank Accession No. CR749809, Oct. 7, 2008.
GenBank Accession No. DA083923, published Feb. 17, 2011.
GenBank Accession No. DB146646, published Feb. 16, 2011.
GenBank Accession No. J05032, published Apr. 27, 1993.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9W60, published May 1, 2000.
GenBank Accession No. Z11518, published Oct. 7, 2008.
Goldgur, Y. et al., "The crystal structure of phenylalanyl-tRNA synthetase from Thermus thermophilus complexed with cognate tRNA," Structure, 5(1):59-68 (1997).
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of Bacillus stearothermophilus Tyrosyl-tRNA Synthetase," Structure, 10(3):311-317 (2002).
Guo, R-T. et al., "Crystal structures and biochemical analyses suggest a unique mechanism and role for human glycyl-tRNA synthetase in Ap4A homeostasis," Journal of Biological Chemistry, 284(42):28968-28976 (2009).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).
Hanrott, K. et al., "6-Hydroxydopamine-induced Apoptosis Is Mediated via Extracellular Auto-oxidation and Caspase 3-dependent Activation of Protein Kinase C8," The Journal of Biological Chemistry, 281(9):5373-5382 (2006).
Hausmann, C. D. et al., "Aminoacyl-tRNA synthetase complexes: molecular multitasking revealed," FEMS Microbiol. Rev., 32(4):705-721 (2008).

(56) References Cited

OTHER PUBLICATIONS

Hengstman, G. J. D. et al., "Anti-Jo-1 positive inclusion body myositis with a marked and sustained clinical improvement after oral prednisone," J. Neurol. Neurosurg. Psychiatry, 70(5):706 (2001).
Hou, Y-M. et al., "Sequence determination and modeling of structural motifs for the smallest monomeric aminoacyl-tRNA synthetase," Proc. Nat. Acad. Sci., 88(3):976-980 (1991).
Howard, O. M. Z. et al., "Histidyl-tRNA Synthetase and Asparaginyl-tRNA Synthetase, Autoantigens in Myositis, Activate Chemokine Receptors on T Lymphocytes and Immature Dendritic Cells," The Journal of Experimental Medicine, 196(6):781-791 (2002).
Howard, O. M. Z. et al., "Autoantigens signal through cheokine receptors: uveitis antigens induce CXCR3- and CRCR5-expressing lymphocytes and immature dendritic cells to migrate", Blood, 105(11) 4207-4214 (2005).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Ivanov, K. A. et al., "Non-canonical Functions of Aminoacyl-tRNA Synthetases," Biochemistry (Moscow), 65(8):888-897 (2000).
Izumi, Y. et al., "p-Quinone Mediates 6-Hydroxydopamine-Induced Dopaminergic Neuronal Death and Ferrous Iron Accelerates the conversion of p-Quinone Into Melanin Extracellularly," Journal of Neuroscience Research, 79(6):849-860 (2005).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jura, M. et al., "Comprehensive Insight into human aminoacyl-tRNA synthetases as autoantigens in idiopathic inflammatory myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Katsumata, Y. et al., "Species-specific immune responses generated by histidyl-tRNA synthetase immunization are associated with muscle and lung inflammation," Journal of Autoimmunity, 29(2-3):174-186 (2007).
Katsumata, Y. et al., "Animal models in myositis," Current Opinion in Rheumatology, 20:681-685 (2008).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kochendoerfer, G. G., "Site-specific polymer modification of therapeutic proteins," Current Opinion in Chemical Biology, 9:555-560 (2005).
Kovaleski, B. J. et al.,"In vitro characterization of the interaction between HIV-1 Gag and human lysyl-tRNA synthetase," J. Bio. Chem., 281(28):19449-19456 (2006).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Levine, S. M., et al., "Novel Conformation of Histidyl-Transfer RNA Synthetase in the Lung", Arthritis & Rheumatism, 56(8): 2729-2739 (2007).
Link, A. J. et al., "Discovery of aminoacyl-tRNA synthetase activity through cell-surface display of noncanonical amino acids, " Proc. Nat. Acad. Sci., 103(27):10180-10185 (2006).
Lorber, B. et al., "Properties of N-terminal truncated yeast aspartyl-tRNA synthetase and structural characteristics of the cleaved domain," Eur. J. Biochem. 174, pp. 155-161 (1988).

Ma, P. T. S. et al., "Mevinolin, an inhibitor of cholesterol synthesis, induces mRNA for low density lipoprotein receptor in livers of hamsters and rabbits," Proc. Natl. Acad. Sci. USA, 83:8370-8374 (1986).
Martin, A. et al., "Epitope studies indicate that histidyl-tRNA synthetase is a stimulating antigen in idiopathic myositis," The FASEB Journal, 9:1226-1233 (1995).
Merritt, E. A. et al., "Crystal structure of the aspartyl-tRNA synthetase from Engamoeba histolytica," Mol. Biochem. Parasitol, 169(2):95-100 (2009).
Miller, F. W., et al., "Origin and Regulation of a Disease-specific Autoantibody Response, Antigenic Epitopes, Spectrotype Stability, and Isotype Restriction of Anti-Jo-1 Autoantibodies," J. Clin. Invest., 85:468-475 (1990).
Mirande, M. et al., "Engineering mammalian aspartyl-tRNA synthetase to probe structural features mediating its association with the multisynthetase complex," Eur. J. Biochem., 203(3):459-466 (1992).
Molecular Modeling Database (MMDB), "Solution Structures of the Whep-trs domain of human histidyl-trna synthetase," MMDB ID No. 35920, available for www.ncbi.nlm.nih.gov/Structure/mmdb, accessed Aug. 24, 2012.
Mukhopadhyay, R. et al., "The GAIT System: a gatekeeper of inflammatory gene expression," Trends in Biochemical Sciences, 34(7):324-331 (2009).
Nackley, A. G. et al., "Human Caechol-O-Methyltransferase haplotypes modulate protein expression by altering mRNA secondary structure," Science, 314:1930-1933 (2006).
NCBI Accession No. NP001340, Feb. 27, 2011.
Ngo, J. T. et al., "Computational complexity, protein structure prediction, and the Levinthal paradox," In the Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Nishikai, M. et al., "Heterogeneity of Precipitating Antibodies in Polymyositis and Dermatomyositis," Arthritis and Rheumatism, 23(8):881-888 (1980).
O'Hanlon, T. P. et al., "Genomic organization, transcriptional mapping, and evolutionary implications of the human bi-directional histidyl-tRNA synthetase locus (HARS/HARSL)," Biochemical and Biophysical Research Communications, 294:609-614 (2002).
Oppenheim, J. J. et al., "Autoantigens act as tissue-specific chemoattractants," Journal of Leukocyte Biology, 77:854-861 (2005).
Park, S. G., et al., "Aminoacyl tRNA synthetases and their connections to disease," PNAS, 105(32):11043-11049 (2008).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Human lysyl-tRNA syntetase is secreted to trigger proinflammatory response," PNAS, 102(18):6356-6361 (2005).
Park, S. G. et al., "Is there an answer? Do aminoacyl-tRNA synthetases have biological functions other than in protein biosynthesis?" IUBMB Life, 58(9):556-558 (2006).
Parker, L. C. et al., "Toll-Like Receptor (TLR)2 and TLR4 Agonists Regulate CCR Expression in Human Monocytic Cells," The Journal of Immunology, 172:4977-4986 (2004).
Pierce, S. B. et al., "Mutations in mitochondrial histidyl tRNA synthetase HARS2 cause ovarian dysgenesis and sensorineural hearing loss of Perrault syndrome," PNAS, 108(16):6543-6548 (2011).
Quesniaux, V. F.J. et al., "Hematopoiesis, including lymphocyte developmet and maturation," Principles of Immunopharmacology, pp. 3-17 (2005).
Raben, N. et al., "A Motif in Human Histidyl-tRNA Synthetase Which Is Shared among Several Aminoacyl-tRNA Synthetases is a Coiled-coil That is Essential for Enzymatic Activity and Contains the Major Autoantigenic Epitope," The Journal of Biological Chemistry, 269(39):24277-24283 (1994).

(56) References Cited

OTHER PUBLICATIONS

Reed, V. S. et al., "Characterization of a Novel N-terminal Peptide in Human Aspartyl-tRNA Synthetase," Journal of Biological Chemistry, 269(52):32937-32941 (1994).
Rho, S. B. et al., "Genetic dissection of protein-protein interactions in multi-tRNA synthetase complex," Proc. Natl. Acad. Sci. USA, 96:4488-4493 (1999).
Richardson, R. M. et al., "Role of the cytoplasmic tails of CXCR1 and CXCR2 in mediating leukocyte migration, activation, and regulation," Journal of Immunology, 170(6):2904-2911 (2003).
Rudinger-Thirion et al., "Misfolded human tRNA isodecoder binds and neutralizes a 3' UTR-embedded Alu element," Proc. Natl. Acad. Sci. USA, 108(40):E794-E802 (2011).
Sato et al., "Synergy and Cross-Tolerance Between Toll-Like Receptor (TLR) 2- and TLR4-Mediated Signaling Pathways," The Journal of Immunology, 165:7096-7101 (2000).
Sauna, Z. E. et al., "Silent polymorhisms speak: How they affect pharmacogenomics and the treatment of cancer," Cancer Res., 67(20):9609-9612 (2007).
Seburn, K. L. et al., "An active dominant mutation of glycyl-tRNA synthetase causes neuropathy in a Charcot-Marie-Tooth 2D mouse model," Neuron, 51(6):715-726 (2006).
Sen, S. et al., "Developments in directed evolution for improving enzyme functions," Appl. Biochem. Biotechnol., 143:212-223 (2007).
Smith, D. F. et al., "Leukocyte phosphoinositide-3 kinase γ is required for chemokine-induced, sustained adhesion under flow in vivo," Journal of Leukocyte Biology, 80(6):1491-1499 (2006).
Soejima, M. et al., "Role of Innate Immunity in a Murine Model of Histidyl-Transfer RNA Snythetase (Jo-1)-Mediated Myositis," Arthritis and Rheumatism, 63(2):479-487 (2011).
Sultan, S. M. et al., "Re-classifiyng myositis," Rheumatology, 49:831-833 (2010).
Tarabishy, A. B. et al., "Retinal Vasculitis Associated with the Anti-Synthetase Syndrome," Ocular Immunology & Inflamation, 18(1):16-18 (2010).
Targoff, I. N., "Update on myositis-specific and myositis-associated autoantibodies," Current Opinion in Rheumatology, 12:475-481 (2000).
Traves, S. L. et al., "Specific CXC but not CC chemokines cause elevated monocyte migration in COPD: a role for $CXCR_2$," Journal of Leukocyte Biology, 76(2):441-450 (2004).
Tsui, H. W. et al., "Transcriptional analyses of the gene region that encodes human histidyl-tRNA sysnthetase: identification of a novel bidirectional regulatory element," Gene, 131:201-208 (1993).
Tzioufas, A. G. et al., "Antisynthetase syndrome," Orphanet Encyclopedia, http://www.orpha.net/data/patho/GB/uk-antisynthetase.pdf, pp. 1-5 Nov. 2001.
Veronese, F. M. et al., "Preface: Introduction and overview of peptide and protein pegylation," Advanced Drug Delivery Reviews, 54:453-456 (2002).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," PNAS USA, 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wallace, E. A. et al., "Diagnosis and management of inflammatory muscle disease," The Journal of Musculoskeletal Medicine, 27(12):1-7 (2010).
Wan et al., "Epitope Map for a Growth Hormone Receptor Agonist Monoclonal Antibody, MAb 263," Molecular Endocrinology, 17(11):2240-2250 (2003).
Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
WPI Database Accession No. 2002-090149 (2013).
WPI Database Accession No. 2002-501208 (2013).
WPI Database Accession No. 2002-501210 (2013).
WPI Database Accession No. 2002-692409 (2013).
WPI Database Accession No. 2002-714440 (2013).
Xie, W. et al., "Long-range structural effects of a Charcot-Marie-Tooth disease-causing mutation in human glycyl-tRNA synthetase," PNAS, 104(24):9976-9981 (2007).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Gain-of-Function Mutational Activation of Human tRNA Synthetase Procytokine," Chemistry & Biology, 14(12):1323-1333 (2007).
Yokoyama, M. et al., "Effects of lipoprotein lipase and statins on cholesterol uptake into heart and skeletal muscle," J. Lipid Res., 48:646-655 (2007).
Yousem, S. A. et al., "The pulmonary histopathologic manifestations of the anti-Jo-1 tRNA synthetase syndrome," Modern Pathology, 23:874-880 (2010).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Chapter 21 In: Poly(Ethylene Glycol) Chemistry: Biotechnical and Biomedical Applications, Harris, J. M. (ed.), pp. 347-370, Plenum Press, New York (1992).
Zhou, Q. et al., "Orthogonal use of a human tRNA synthetase active site to achieve multifunctionality," Nature Structural & Molecular Biology, 17(1):57-62 (2010).
Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.
International Search Report and Written Opinion for International Application No. PCT/US2012/071762, dated Aug. 20, 2013, 12 pages.
Chappel, M. S. et al., "Identification of the Fcγ Receptor Class I Binding Site in Human IgG Through the Use of Recombinant IgG1/IgG2 Hybrid and Point-Mutated Antibodies," PNAS USA, 88(20):9036-9040 (1991).
Guo, H. H., "Protein tolerance to random amino acid change," PNAS, 101(25):9205-9210 (Jun. 22, 2004).
Kern, D. et al., "The three cysteine residues of cytoplasmic aspartyl-tRNA synthetase from *Saccharomyces cerecisiae* are not essential for its activity," Eur. J. Biochem., 193(1):97-103 (1990).
Matthews, B. W., "Structural and genetic analysis of protein stability," Annu. Rev. Biochem., 62:139-160 (1993).

ASPARTYL-TRNA SYNTHETASES

CROSS-REFERENCE TO RELATED APPLICATIONS

This application claims benefit under 35 U.S.C.§119(e) of U.S. Provisional Application No. 61/567,559, filed Dec. 6, 2011, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR107_01WO_ST25.txt. The text file is about 198 KB, was created on Dec. 6, 2012, and is being submitted electronically via EFS-Web.

BACKGROUND

Technical Field

The present invention relates generally to aspartyl-tRNA synthetase derived proteins (DRS polypeptides) with an altered cysteine content, compositions comprising the same, and methods of using such DRS polypeptides and compositions thereof for treating diseases and disorders.

Description of the Related Art

Toll-like receptors (TLRs) are a family of pattern recognition receptors that play a key role in initiating the rapid innate immune response in an organism. TLRs recognize certain pathogen or host derived cellular components which can be generally characterized as being either pathogen associated molecular patterns, (PAMPs), or damage-associated molecular pattern molecules, (DAMPS) respectively. PAMPS are typically unique to a given class of pathogen, and include for example bacterial components such as the lipopolysaccharide of Gram negative bacteria, and viral specific nucleic acid motifs or viral specific modifications of RNA or DNA. By contrast DAMPS are typically endogenous molecules released from dying host cells upon cellular stress or tissue damage.

There are at least 10 human TLRs identified to date and each TLR has a unique ligand specificity, and varied subcellular distribution. For example, TLR4 which recognizes lipopolysaccharides (LPS) of Gram negative bacteria, and TLR2, which recognizes peptidoglycan from Gram positive bacteria are located on the cell surface. By contrast TLR3 which recognizes double stranded RNA (dsRNA) produced during virus replication and TLR9 which recognizes the CpG motif found in the DNA of bacteria are located in intracellular membranes such as endosomes or phagosomes of cells. In addition to the recognition of exogenous, microbe derived PAMPs, there is increasing support for the proposition that there are several endogenous ligands for TLRs, which may play potential roles in immune-modulation.

Structurally, TLRs are type I transmembrane proteins with leucine rich repeats in the extracellular domain for ligand recognition, and Toll/IL-1 receptor (TIR) domain in the cytoplasmic portion for intracellular signaling. TLRs are typically expressed on immune cells that are most likely to first encounter microbes, such as neutrophils, monocytes, macrophages, and dendritic cells (DCs). Ligand recognition by TLRs facilitates the dimerization of TLRs that triggers the activation of signaling pathways, which originates from the cytoplasmic TIR domain, and culminates in the activation of the transcription factor, nuclear factor κB (NF-κB), leading to the expression of pro-inflammatory genes such as TNF-α, IL-1, and IL-12.4

Innate recognition of PAMPs through TLR activation induces the expression of various pro-inflammatory cytokines, chemokines, adhesion molecules, and activates the effector functions of innate immune cells such as phagocytosis, and thus initiates a rapid inflammatory response characterized by the recruitment of leucocytes to the site of infection to eliminate the invading pathogen.

TLRs expressed on professional antigen presenting cells (APCs), such as DCs and macrophages, are a critical link between the innate and adaptive immunity TLR mediated activation of DCs induces DC maturation, with the production of pro-inflammatory cytokines, up-regulation of co-stimulatory and major histocompatibility complex (MHC) molecules, and thereby enhances the antigen presenting capacity of DCs. Thus, TLR stimulation of APCs leads to the activation and priming of antigen specific, naive T cells, triggering the adaptive arm of the immune response. Various factors influence the differentiation of T helper type 1 (Th1) versus Th2 responses, but DC derived cytokines present during the initial phase of T cell activation play the most important part in this process It has been shown that specific PAMPs that stimulate different TLRs, induce distinct patterns of cytokines resulting in a Th1/Th2 polarization that is most appropriate for the pathogen. For example, activation of TLR4 or TLR9 in DCs induces production of IL-12, thereby skewing Th differentiation towards the Th1 type. Although indirect activation of DCs by inflammatory mediators alone was shown to be able to support T cell clonal expansion, it could not promote Th cell differentiation, for which the direct recognition of PAMPs by DCs appears to be of critical importance. Thus TLRs are important in both triggering and modulating the activation of the adaptive immune response. In addition to innate immune cells, an array of TLRs is expressed by epithelial cells at host/environment interfaces including that of the skin, gastrointestinal tract, respiratory tract, and the urogenital tract. Strategic expression of TLRs at such host/environment interfaces appears to have an important role in the first line of defense against microbial invasions at these sites.

TLRs are implicated in several chronic inflammatory and immune mediated disorders by various potential mechanisms, including those in which infectious agents have been proposed to initiate disease progression. For example in scenarios in which endogenous damage signals or self-antigens cause chronic inflammation in a TLR dependent manner, or where TLRs may be involved in the breakdown of immune tolerance. TLRs have been implicated in the pathogenesis of chronic inflammatory diseases such as inflammatory bowel disease, rheumatoid arthritis, psoriasis, and multiple sclerosis.

It is now increasingly recognized that the successful treatment of some autoimmune and inflammatory conditions of tissues requires effective control of the inflammatory reaction in order to preserve tissue integrity and function, without immune-compromising the patient. Recent experimental evidence has shown that specific modulation of TLR pathways induces an improvement in several inflammatory conditions, without comprising tissue function, or enhancing bacterial or viral infections, suggesting the potential for new therapeutic anti-inflammatory strategies with significantly improved side effect profiles. Moreover TLR agonists have already proved useful in clinical trials in allergic, infectious and autoimmune diseases and are under development for a broad range of other diseases including cancer, arthritis, multiple sclerosis, inflammatory bowel disease, see generally Zhu and Mohan (2010) Mediators of Inflammation doi:10.1155/2010/781235; Hennessy et al., Nat. Rev. (2010) 9 293-307). Therefore TLRs are becoming novel potential therapeutic targets for the modulation of a broad variety of diseases and disorders.

Recently it has been established that certain aspartyl-tRNA synthetase fragments (DRS polypeptides) are highly potent, endogenously produced, TLR receptor modulators. Without being bound to any one specific theory of operation, it is believed that such DRS polypeptides can be released from macrophage cells upon proteolytic cleavage, or through alternative splicing of the full length aspartyl-tRNA synthetase and are capable of binding to and modulating the activity of immune, immunomodulatory, and other cell types. Such DRS polypeptides when administered to a subject, provide for a novel mechanism of selectively modulating inflammatory responses, without the side effect profiles typically associated with traditional anti-inflammatory agents such as steroids.

The present invention relates inter alia to the development of improved aspartyl-tRNA synthetase fragments (DRS polypeptides) that have one or more mutations in the cysteine residues within the DRS polypeptides. Such modified proteins exhibit improved manufacturing stability and enhanced activity compared the corresponding wild-type proteins.

BRIEF SUMMARY OF THE INVENTION

Figure 1:
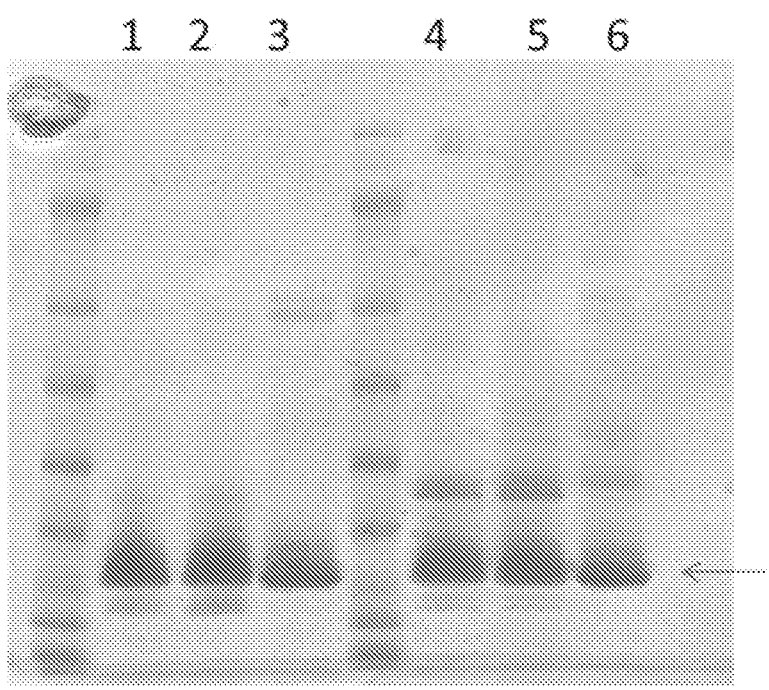
FIG. 1 shows an SDS-PAGE analysis of the purified proteins AspRS1$^{N1}$ (C76S) and the corresponding non mutated protein AspRS1$^{N1}$. Lanes 1-3 were run under reduced conditions, and lanes 4-6 were run under non-reduced conditions. Lanes 1 and 4: AspRS1$^{N1}$ lot # D-N1-V5H-046, lanes 2 and 5 AspRS1$^{N1}$ lot # D-N1-V5H-047, lanes 3 and 6: AspRS1$^{N1}$ (C76S) lot # D-N1:1-V5H-048.

In one embodiment, the current invention includes an aspartyl-tRNA synthetase (DRS) polypeptide, comprising an amino acid sequence at least 80% identical as any of the amino acid sequences set forth in SEQ ID NOS:1, 3-24, 29, 31, or 48-91, comprising at least one mutation at either Cys76 or Cys130. In some embodiments, the DRS polypeptide is about 50-200 amino acids in length and comprises amino acid residues 1-154, 11-146, 13-146, 23-154, 1-171, or 1-174 of SEQ ID NO:1, one aspect the DRS polypeptide comprises amino acid residues 1-154.

In some embodiments, the Cys76 residue has been selectively mutated to another amino acid. In some embodiments, the Cys130 residue has been selectively mutated to another amino acid. In some embodiments both the Cys76 residue and the Cys130 residue have been mutated to another amino acid.

In some embodiments of any of these DRS polypeptide, the Cys76 residue or the Cys130 residue is mutated to an amino acid group independently selected from group consisting of Ser, Ala, Gly, Met, Leu, Val, Ile and Thr. In some embodiments of any of these DRS polypeptides, the Cys76 residue or the Cys130 residue is mutated to an amino acid group independently selected from group consisting of Ser, Ala, and Gly. In some embodiments of any of these DRS polypeptides, the Cys76 residue or the Cys130 residue is mutated to an amino acid group independently selected from group consisting of Asp, Glu, Arg, Lys, Gln, and Asn. In some embodiments of any of these DRS polypeptides, the Cys76 residue or the Cys130 residue is mutated to an amino acid group independently selected from group consisting of His, Pro, Tyr, Trp and Phe. In some embodiments of any of these DRS polypeptides, the Cys76 residue or the Cys130 residue is mutated to an amino acid group independently selected from group consisting of Ser, Ala, Gly, Met, Leu, Val, Ile and Thr, and a non-naturally occurring amino acid.

In some embodiments of any of these DRS polypeptides the DRS polypeptide is characterized by an increased production yield after expression in *E. coli* compared to a non-cysteine mutated DRS polypeptide. In some embodiments of any of these DRS polypeptides, the DRS polypeptide is characterized by a production yield in *E. coli* of greater than about 1.5 mg/g cell pellet.

In some embodiments of any of these DRS polypeptides the DRS polypeptide is characterized by a decreased endotoxin content after expression in *E. coli* compared to a non-cysteine mutated DRS polypeptide. In some embodiments of any of these DRS polypeptides, the DRS polypeptide is characterized by an endotoxin content of less than about 10 EU/mg.

In some embodiments of any of these DRS polypeptides, the DRS polypeptide is characterized by an increased activity and/or affinity to a TLR 2 receptor. In some embodiments of any of these DRS polypeptides, the DRS polypeptide is characterized by an increased activity and/or affinity to a TLR 4 receptor. In some embodiments of any of these DRS polypeptides, the DRS polypeptide is characterized by an apparent affinity ($EC_{50}$) to a TLR 2 receptor of at least 2 fold higher than the unmodified protein. In some embodiments of any of these DRS polypeptides, the DRS polypeptide is characterized by an apparent affinity ($EC_{50}$) to a TLR 4 receptor of at least 2 fold higher than the unmodified protein.

In some embodiments of any of these DRS polypeptides, the DRS polypeptide is characterized by an apparent ability to activate a TLR 2 receptor of at least 2 fold higher than the unmodified protein. In some embodiments of any of these DRS polypeptides, the DRS polypeptide is characterized by an apparent ability to activate a TLR 4 receptor of at least 2 fold higher than the unmodified protein.

In some embodiments of any of these DRS polypeptides, the DRS polypeptide comprises a heterologous fusion protein. In some aspects, of any of these embodiments, the heterologous fusion protein is a host cell antigen. In some aspects, of any of these embodiments, the heterologous fusion protein is a host cell self-antigen. In some aspects, of any of these embodiments, the heterologous fusion protein is a viral antigen. In some aspects, of any of these embodiments, the heterologous fusion protein is a bacterial antigen. In some aspects, of any of these embodiments, the heterologous fusion protein is a cancer cell antigen. In some aspects, of any of these embodiments, the heterologous fusion protein is attached to the DRS polypeptide through Cys130. In some aspects, of any of these embodiments, the heterologous fusion protein is attached to the DRS polypeptide through Cys76.

Certain embodiments include a full-length aspartyl-tRNA synthetase (DRS) polypeptide, comprising an amino acid sequence at least 80% identical to the amino acid sequence set forth in SEQ ID NO:1, and comprising at least one mutation at a position selected from Cys203, Cys259, Cys334, and Cys349. In some embodiments, the mutation is at position Cys203. In some embodiments, the Cys residue is mutated to an amino acid group independently selected from group consisting of Ser, Ala, Gly, Met, Leu, Val, Ile and Thr. In particular embodiments, the Cys residue is mutated to an amino acid group independently selected from group consisting of Ser, Ala, and Gly. In certain embodiments, the DRS polypeptide is characterized by enhanced monomer stability compared to a non cysteine modified DRS polypeptide. Certain full-length DRS polypeptides further comprise a heterologous fusion protein, for example, as described herein.

Also included are truncated aspartyl-tRNA synthetase (DRS) polypeptides, comprising an amino acid sequence at least 80% identical as any of the amino acid sequences set forth in SEQ ID NOS:57-91. In some embodiments, the truncated DRS polypeptide comprises the amino acids 11-146 of SEQ ID NO:1. In some embodiments, the truncated DRS polypeptide is characterized by enhanced stability compared to a non-truncated DRS polypeptide. Certain truncated DRS polypeptides further comprising a heterologous fusion protein.

In another aspect, the invention includes an isolated nucleic acid encoding a DRS polypeptide with an amino acid sequence at least 80% identical to any of the amino acid sequences set forth in SEQ ID NOS:1, 3-24, 29, 31, or 48-91, comprising at least one mutation at either Cys76 or Cys130. In some embodiments, the nucleic acid sequence comprises any of the polynucleotide sequences set forth in SEQ ID NOS: 2, 25-28, 30, or 92-135, or a variant thereof. In some embodiments, the DRS polypeptide is about 50-200 amino acids in length and comprises amino acid residues 1-154, 11-146, 13-146, 23-154, 1-171, or 1-174 of SEQ ID NO:1. In some embodiments, the DRS polypeptide comprises amino acid residues 1-154. In certain embodiments, the DRS polypeptide comprises amino acid residues 13-146. In some embodiments of any of these DRS polypeptides, the Cys76 residue has been mutated to another amino acid. In some embodiments of any of these DRS polypeptides, the Cys130 residue has been mutated to another amino acid. In some embodiments of any of these DRS polypeptides, both the Cys76 residue and the Cys130 residue have been mutated to another amino acid. In some embodiments of any of these DRS polypeptides, the Cys76 residue or the Cys130 residue is mutated to an amino acid group independently selected from group consisting of Ser, Ala, Gly, Met, Leu, Val, Ile and Thr. In some embodiments of any of these DRS polypeptides, the Cys76 residue or the Cys130 residue is mutated to an amino acid group independently selected from group consisting of Ser, Ala, and Gly. In some embodiments of any of these DRS polypeptides, the Cys76 residue or the Cys130 residue is mutated to an amino acid group independently selected from group consisting of Asp, Glu, Arg, Lys, Gln, and Asn. In some embodiments of any of these DRS polypeptides, the Cys76 residue or the Cys130 residue is mutated to an amino acid group independently selected from group consisting of His, Pro, Tyr, Trp and Phe. In some embodiments of any of these DRS polypeptides, the Cys76 residue or the Cys130 residue is mutated to an amino acid group independently selected from group consisting of Ser, Ala, Gly, Met, Leu, Val, Ile and Thr, and a non-naturally occurring amino acid.

In some embodiments of any of these isolated nucleic acids, the nucleic acid sequence encodes for a DRS polypeptide fused in frame to a heterologous protein. In some aspects, of any of these embodiments, the heterologous fusion protein is a host cell antigen. In some aspects, of any of these embodiments, the heterologous fusion protein is a host cell self-antigen. In some aspects, of any of these embodiments, the heterologous fusion protein is a viral antigen. In some aspects, of any of these embodiments, the heterologous fusion protein is a bacterial antigen. In some aspects, of any of these embodiments, the heterologous fusion protein is a cancer cell antigen. In some aspects, of any of these embodiments, the heterologous fusion protein is attached to the DRS polypeptide through Cys130. In some aspects, of any of these embodiments, the heterologous fusion protein is attached to the DRS polypeptide through Cys76.

In another aspect, the invention includes a recombinant vector comprising an isolated nucleic acid an isolated nucleic acid encoding a DRS polypeptide with an amino acid sequence at least 80% identical to any of the amino acid sequences set forth in SEQ ID NOS:1, 3-24, 29, 31 or 48-91, comprising at least one mutation at either Cys76 or Cys130.

In another aspect, the invention includes a host cell that comprises a nucleic acid or vector encoding a DRS polypeptide with an amino acid sequence at least 80% identical to any of the amino acid sequences set forth in SEQ ID NO:1, 3-24, 29, 31 or 48-91, comprising at least one mutation at either Cys76 or Cys130.

In another aspect, the invention includes a pharmaceutical composition comprising any of the previously disclosed DRS polypeptides, isolated nucleic acids, recombinant vectors, or host cells, and a pharmaceutically acceptable carrier or excipient. In some embodiments, the composition comprises between about 10 nM and about 100 nM arginine.

In another aspect, the invention includes a method for treating an inflammatory response in a subject, comprising administering any of the previously disclosed DRS polypeptides, nucleic acids, encoding a DRS polypeptide, or recombinant vectors to a subject in need thereof.

In another aspect, the invention includes a method for treating a TLR associated disease in a subject in need thereof, comprising administering to the subject a therapeutic dose of any of the previously disclosed DRS polypeptides, isolated nucleic acids, recombinant vectors, host cells.

In another aspect, the invention includes a method for method for modulating TLR activity in a subject, comprising administering to the subject a therapeutic dose of any of the previously disclosed DRS polypeptides, isolated nucleic acids, recombinant vectors, host cells.

In another aspect, the invention includes a method for method for killing cancer cells, comprising administering a vaccine or immunogenic composition comprising any of the previously disclosed DRS polypeptides, or vectors comprising a nucleic acid encoding a DRS polypeptide to a subject in need thereof.

In another aspect, the invention includes a method for treating a subject with cancer, or preventing the development of cancer in a subject, comprising administering a vaccine or immunogenic composition comprising any of the previously disclosed DRS polypeptides, or vectors comprising a nucleic acid encoding a DRS polypeptide to a subject in need thereof.

In another aspect, the invention includes a method for overcoming tolerance to an antigen in a subject, comprising any of the previously disclosed DRS polypeptides, or vectors comprising a nucleic acid encoding a DRS polypeptide to a subject in need thereof.

DETAILED DESCRIPTION OF THE INVENTION

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* ($3^{rd}$ Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, $5^{th}$ Ed. Hoboken N.J., John Wiley & Sons; B. Perbal, *A Practical Guide to Molecular Cloning* ($3^{rd}$ Edition 2010); Farrell, R., *RNA Methodologies: A Laboratory Guide for Isolation and Characterization* ($3^{rd}$ Edition 2005). All publications, patents and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element. By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

As used herein, "associated with" means mixed with, dispersed within, coupled to, covering, or surrounding.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "half maximal effective concentration" or "$EC_{50}$" refers to the concentration of a DRS polypeptide agent described herein at which it induces a response halfway between the baseline and maximum after some specified exposure time; the $EC_{50}$ of a graded dose response curve therefore represents the concentration of a compound at which 50% of its maximal effect is observed. In certain embodiments, the $EC_{50}$ of an agent provided herein is indicated in relation to a "non-canonical" activity, as noted above. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of a DRS protein is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, or 100 nM. Preferably, a biotherapeutic composition will have an $EC_{50}$ value of about 10 nM or less.

The term "modulating" includes "increasing," "enhancing" or "stimulating," as well as "decreasing" or "reducing," typically in a statistically significant or a physiologically significant amount as compared to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., in the absence of any of the DRS polypeptides of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between.

"Non-canonical" activity as used herein, refers generally to either i) a new activity possessed by DRS polypeptide of the invention that is not possessed to any significant degree by the intact native full length parental protein, or ii) an activity that was possessed by the by the intact native full length parental protein, where the DRS polypeptide either exhibits a significantly higher (i.e., at least 20% greater) specific activity with respect to the non-canonical activity compared to the intact native full length parental protein, or exhibits the activity in a new context; for example by isolating the activity from other activities possessed by the intact native full length parental protein. In the case of DRS polypeptides, non-limiting examples of non-canonical activities include extracellular signaling including the modulation of TLRs, RNA-binding, amino acid-binding, modulation of cell proliferation, modulation of cell migration, modulation of cell differentiation (e.g., hematopoiesis, neurogenesis, myogenesis, osteogenesis, and adipogenesis), modulation of gene transcription, modulation of apoptosis or other forms of cell death, modulation of cell signaling, modulation of cellular uptake, or secretion, modulation of angiogenesis, modulation of cell binding, modulation of cellular metabolism, modulation of cytokine production or activity, modulation of cytokine receptor activity, modulation of inflammation, immunogenicity, and the like.

In certain embodiments, the "purity" of any given agent (e.g., a DRS polypeptide) in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

The term "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA. The terms "DNA" and "polynucleotide" and "nucleic acid" refer to a DNA molecule that has been isolated free of total genomic DNA of a particular species. Therefore, an isolated DNA segment encoding a polypeptide refers to a DNA segment that contains one or more coding sequences yet is substantially isolated away from, or purified free from, total genomic DNA of the species from which the DNA segment is obtained. Also included are non-coding polynucleotides (e.g., primers, probes, oligonucleotides), which do not encode an AARS polypeptide. Included within the terms "DNA segment" and "polynucleotide" are DNA segments and smaller fragments of such segments, and also recombinant vectors, including, for example, plasmids, cosmids, phagemids, phage, viruses, and the like.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of a DRS polypeptide provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, a DRS polypeptide has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at 37° C.

A "splice junction" as used herein includes the region in a mature mRNA transcript or the encoded polypeptide where the 3' end of a first exon joins with the 5' end of a second exon. The size of the region may vary, and may include 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more (including all integers in between) nucleotide or amino acid residues on either side of the exact residues where the 3' end of one exon joins with the 5' end of another exon. An "exon" refers to a nucleic acid sequence that is represented in the mature form of an RNA molecule after either portions of a precursor RNA (introns) have been removed by cis-splicing or two or more precursor RNA molecules have been ligated by trans-splicing. The mature RNA molecule can be a messenger RNA or a functional form of a non-coding RNA such as rRNA or tRNA. Depending on the context, an exon can refer to the sequence in the DNA or its RNA transcript. An "intron" refers to a non-coding nucleic acid region within a gene, which is not translated into a protein. Non-coding intronic sections are transcribed to precursor mRNA (pre-mRNA) and some other RNAs (such as long noncoding RNAs), and subsequently removed by splicing during the processing to mature RNA.

A "splice variant" refers to a mature mRNA and its encoded protein that are produced by alternative splicing, a process by which the exons of the RNA (a primary gene transcript or pre-mRNA) are reconnected in multiple ways during RNA splicing. The resulting different mRNAs may be translated into different protein isoforms, allowing a single gene to code for multiple proteins.

A "subject," as used herein, includes any animal that exhibits a symptom, or is at risk for exhibiting a symptom, which can be treated or diagnosed with a DRS polypeptide of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95% or greater of some given quantity.

The term "therapeutically effective amount" as used herein, refers to the level or amount of agent such, as a DRS polypeptide or derivative thereof, needed to treat a condition, or reduce or prevent injury or damage without causing significant negative or adverse side effects.

The terms "treat", "treating", or "treatment" as used herein, refer to reduction or resolution or prevention of a condition, disease, disorder, injury or damage, or to promote healing of an injured or damaged tissue, and may include even minimal changes or improvements in one or more measurable markers of the disease or condition being treated. A treatment is usually effective to reduce at least one symptom of a condition, disease, disorder, injury or damage. Exemplary markers of clinical improvement will be apparent to persons skilled in the art.

Aspartyl-tRNA Synthetase Derived Polypeptides (DRS Polypeptides)

Embodiments of the present invention relate to the use of non-naturally occurring Aspartyl-tRNA synthetase derived polypeptides with altered cysteine content ("DRS polypeptides"). Aspartyl-tRNA synthetases belong to the class I tRNA synthetase family, which has two highly conserved sequence motifs at the active site, HIGH (SEQ ID NO:42) and KMSKS (SEQ ID NO:43). Class I tRNA synthetases are widely recognized as being responsible the specific attachment of an amino acid to its cognate tRNA in a 2 step reaction: the amino acid (AA) is first activated by ATP to form AA-AMP and then transferred to the acceptor end of the tRNA. The full length Aspartyl-tRNA synthetases typically exists as a homodimer; and also forms part of a multisubunit complex that typically includes the proteins AIMP1, AIMP2, EEF1A1 and the tRNA synthetases for Arg, Asp, Glu, Gln, Ile, Leu, Lys, Met and Pro.

More recently it has been established that some biological fragments, or alternatively spliced isoforms of eukaryotic aspartyl-tRNA synthetases, or in some contexts the intact synthetase, can dissociate from the multisubunit complex, and activate certain cell-signaling pathways, or act within the nucleus to modulate transcription. These activities, which are distinct from the classical role of tRNA synthetases in protein synthesis, are collectively referred to herein as "non canonical activities". These DRS polypeptides may be produced naturally by either alternative splicing or proteolysis, and can act in a cell autonomous (i.e., within the host cell), or non-cell autonomous fashion (i.e., outside the host cell) to regulate a variety of homeostatic mechanisms. For example, as provided in the present invention, the N-terminal fragment of Aspartyl-tRNA synthetase, DRS (1-154), is capable of modulating the activity of certain TLRs in vivo. In addition, certain mutations or deletions relative to the full-length DRS polypeptide sequence confer increased TLR binding or other non-canonical activities. The sequences of various exemplary DRS polypeptides and encoding nucleotides are provided in Tables D1 to D8.

TABLE D1

| Name | Amino Acid Residue Range of SEQ ID NO: 1 | Amino acid and nucleic acid sequence | SEQ ID NO: |
|---|---|---|---|
| A Exemplary DRS Polypeptides ||||
| Full length DRS sequence | Protein/ Human/1-501 | MPSASASRKSQEKPREIMDAAEDYAKERYGISSMIQSQEKP DRVLVRVRDLTIQKADEVVWVRARVHTSRAKGKQCFLVLR QQQFNVQALVAVGDHASKQMVKFAANINKESIVDVEGVVR KVNQKIGSCTQQDVELHVQKIYVISLAEPRLPLQLDDAVRPE AEGEEEGRATVNQDTRLDNRVIDLRTSTSQAVFRLQSGICHL FRETLINKGFVEIQTPKIISAASEGGANVFTVSYFKNNAYLAQ SPQLYKQMCICADFEKVFSIGPVFRAEDSNTHRHLTEFVGLD IEMAFNYHYHEVMEEIADTMVQIFKGLQERFQTEIQTVNKQ FPCEPFKFLEPTLRLEYCEALAMLREAGVEMGDEDDLSTPN EKLLGHLVKEKYDTDFYILDKYPLAVRPFYTMPDPRNPKQS NSYDMFMRGEEILSGAQRIHDPQLLTERALHHGIDLEKIKAY IDSFRFGAPPHAGGGIGLERVTMLFLGLHNVRQTSMFPRDPK RLTP | 1 |

TABLE D1-continued

| Name | Amino Acid Residue Range of SEQ ID NO: 1 | Amino acid and nucleic acid sequence | SEQ ID NO: |
|---|---|---|---|
| B Exemplary DRS Nucleic Acids | | | |
| Full length DRS sequence. Human codon usage. | DNA/Human/ 1-1506 | ATGCCCAGCGCCAGCGCCAGCCGCAAGAGTCAGGAGAAG CCGCGGGAGATCATGGACGCGGCGGAAGATTATGCTAAA GAGAGATATGGAATATCTTCAATGATACAATCACAAGAA AAACCAGATCGAGTTTTGGTTCGGGTTAGAGACTTGACA ATACAAAAAGCTGATGAAGTTGTTTGGGTACGTGCAAGA GTTCATACAAGCAGAGCTAAAGGGAAACAGTGCTTCTTA GTCCTACGTCAGCAGCAGTTTAATGTCCAGGCTCTTGTGG CGGTGGGAGACCATGCAAGCAAGCAGATGGTTAAATTTG CTGCCAACATCAACAAAGAGAGCATTGTGGATGTAGAAG GTGTTGTGAGAAAAGTGAATCAGAAAATTGGAAGCTGTA CACAGCAAGACGTTGAGTTACATGTTCAGAAGATTTATGT GATCAGTTTGGCTGAACCCCGTCTGCCCCTGCAGCTGGAT GATGCTGTTCGGCCTGAGGCAGAAGGAGAAGAGGAAGG AAGAGCTACTGTTAACCAGGATACAAGATTAGACAACAG AGTCATTGATCTTAGGACATCAACTAGTCAGGCAGTCTTC CGTCTCCAGTCTGGCATCTGCCATCTCTTCCGAGAAACTT TAATTAACAAAGGTTTTGTGGAAATCCAAACTCCTAAAAT TATTTCAGCTGCCAGTGAAGGAGGAGCCAATGTTTTTACT GTGTCATATTTTAAAAATAATGCATACCTGGCTCAGTCCC CACAGCTATATAAGCAAATGTGCATTTGTGCTGATTTTGA GAAGGTTTTCTCTATTGGACCAGTATTCAGAGCGGAAGA CTCTAATACCCATAGACATCTAACTGAGTTTGTTGGTTTG GACATTGAAATGGCTTTTAATTACCATTACCACGAAGTTA TGGAAGAAATTGCTGACACCATGGTACAAATATTCAAAG GACTTCAAGAAAGGTTTCAGACTGAAATTCAAACAGTGA ATAAACAGTTCCCATGTGAGCCATTCAAATTTTTGGAGCC AACTCTAAGACTAGAATATTGTGAAGCATTGGCTATGCTT AGGGAAGCTGGAGTCGAAATGGGAGATGAAGACGATCT GAGCACACCAAATGAAAGCTGTTGGGTCATTTGGTAAA GGAAAAGTATGATACAGATTTTTATATTCTTGATAAATAT CCATTGGCTGTAAGACCTTTCTATACCATGCCTGACCCAA GAAATCCCAAACAGTCCAACTCTTACGATATGTTCATGAG AGGAGAAGAAATATTGTCAGGAGCTCAAAGAATACATGA TCCTCAACTGCTAACAGAGAGAGCTTTACATCATGGAATT GATTTGGAGAAAATTAAGGCTTACATTGATTCCTTCCGCT TTGGAGCCCCTCCTCATGCTGGTGGAGGCATTGGATTGGA ACGAGTTACTATGCTGTTTCTGGGATTGCATAATGTTCGT CAGACCTCCATGTTCCCTCGTGATCCCAAACGACTCACTC CTTAG | 2 |

TABLE D2

Exemplary N-terminal DRS polypeptide Fragments

| Name | Amino Acid Residue Range of SEQ ID NO: 1 | Amino acid sequence | SEQ ID NO: |
|---|---|---|---|
| AspRS1[N1] | Protein/ Human/1-154 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPL | 3 |
| AspRS1[N11] | Protein/ Human/1-171 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGR | 4 |
| AspRS1[N12] | Protein/ Human/1-174 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATV | 5 |
| AspRS1[N13] | Protein/ Human/1-182 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV | 6 |

TABLE D2-continued

Exemplary N-terminal DRS polypeptide Fragments

| Name | Amino Acid Residue Range of SEQ ID NO: 1 | Amino acid sequence | SEQ ID NO: |
|---|---|---|---|
| | | EGVVRKVNQKIGSCTQQDVELHVQKIYVISLAEPRLPLQL DDAVRPEAEGEEEGRATVNQDTRLDN | |
| AspRS1$^{N4}$ | Protein/ Human/1-184 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRV | 7 |
| AspRS1$^{N2}$ | Protein/ Human/1-274 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRA | 8 |
| AspRS1$^{N3}$ | Protein/ Human/1-224 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGICHLFRETLINKGFVEIQTPKII | 9 |
| DRS 1-182 | 1-182 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDN | 57 |
| DRS 1-180 | 1-180 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRL | 58 |
| DRS 1-178 | 1-178 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDT | 59 |
| DRS 1-176 | 1-176 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQ | 60 |
| DRS 1-174 | 1-174 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATV | 61 |
| DRS 1-172 | 1-172 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRA | 62 |
| DRS 1-170 | 1-170 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEG | 63 |
| DRS 1-168 | 1-168 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEE | 64 |
| DRS 1-166 | 1-166 | MPSASASRKSQEKPREIMDAAEDYAKERYGISSMIQSQEK PDRVLVRVRDLTIQKADEVVWVRARVHTSRAKGKQCFL | 65 |

TABLE D2-continued

Exemplary N-terminal DRS polypeptide Fragments

| Name | Amino Acid Residue Range of SEQ ID NO: 1 | Amino acid sequence | SEQ ID NO: |
|---|---|---|---|
| | | VLRQQQFNVQALVAVGDHASKQMVKFAANINKESIVDV EGVVRKVNQKIGSCTQQDVELHVQKIYVISLAEPRLPLQL DDAVRPEAEG | |
| DRS 1-164 | 1-164 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEA | 66 |
| DRS 1-162 | 1-162 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRP | 67 |
| DRS 1-160 | 1-160 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAV | 68 |
| DRS 1-158 | 1-158 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DD | 69 |
| DRS 1-156 | 1-156 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL | 70 |
| DRS 1-154 | 1-154 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPL | 71 |
| DRS 1-152 | 1-152 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRL | 72 |
| DRS 1-150 | 1-150 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEP | 73 |
| DRS 1-148 | 148 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLA | 74 |
| DRS 1-146 | 1-146 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVIS | 75 |
| DRS 3-154 | 3-154 | ASASRKSQEKPREIMDAAEDYAKERYGISSMIQSQEKPDR VLVRVRDLTIQKADEVVWVRARVHTSRAKGKQCFLVLR QQQFNVQALVAVGDHASKQMVKFAANINKESIVDVEGV VRKVNQKIGSCTQQDVELHVQKIYVISLAEPRLPL | 76 |
| DRS 5-154 | 5-154 | ASRKSQEKPREIMDAAEDYAKERYGISSMIQSQEKPDRVL VRVRDLTIQKADEVVWVRARVHTSRAKGKQCFLVLRQQ QFNVQALVAVGDHASKQMVKFAANINKESIVDVEGVVR KVNQKIGSCTQQDVELHVQKIYVISLAEPRLPL | 77 |
| DRS 7-154 | 7-154 | RKSQEKPREIMDAAEDYAKERYGISSMIQSQEKPDRVLVR VRDLTIQKADEVVWVRARVHTSRAKGKQCFLVERQQQF NVQALVAVGDHASKQMVKFAANINKESIVDVEGVVRKV NQKIGSCTQQDVELHVQKIYVISLAEPRLPL | 78 |

TABLE D2-continued

Exemplary N-terminal DRS polypeptide Fragments

| Name | Amino Acid Residue Range of SEQ ID NO: 1 | Amino acid sequence | SEQ ID NO: |
|---|---|---|---|
| DRS 9-154 | 9-154 | SQEKPREIMDAAEDYAKERYGISSMIQSQEKPDRVLVRVR DLTIQKADEVVWVRARVHTSRAKGKQCFLVLRQQQFNV QALVAVGDHASKQMVKFAANINKESIVDVEGVVRKVNQ KIGSCTQQDVELHVQKIYVISLAEPRLPL | 79 |
| DRS 11-154 | 11-154 | EKPREIMDAAEDYAKERYGISSMIQSQEKPDRVLVRVRDL TIQKADEVVWVRARVHTSRAKGKQCFLVERQQQFNVQA LVAVGDHASKQMVKFAANINKESIVDVEGVVRKVNQKIG SCTQQDVELHVQKIYVISLAEPRLPL | 80 |
| DRS 13-154 | 13-154 | PREIMDAAEDYAKERYGISSMIQSQEKPDRVLVRVRDLTI QKADEVVWVRARVHTSRAKGKQCFLVLRQQQFNVQALV AVGDHASKQMVKFAANINKESIVDVEGVVRKVNQKIGSC TQQDVELHVQKIYVISLAEPRLPL | 81 |
| DRS15-154 | 15-154 | EIMDAAEDYAKERYGISSMIQSQEKPDRVLVRVRDLTIQK ADEVVWVRARVHTSRAKGKQCFLVLRQQQFNVQALVAV GDHASKQMVKFAANINKESIVDVEGVVRKVNQKIGSCTQ QDVELHVQKIYVISLAEPRLPL | 82 |
| DRS 17-154 | 17-154 | MDAAEDYAKERYGISSMIQSQEKPDRVLVRVRDLTIQKA DEVVWVRARVHTSRAKGKQCFLVLRQQQFNVQALVAVG DHASKQMVKFAANINKESIVDVEGVVRKVNQKIGSCTQQ DVELHVQKIYVISLAEPRLPL | 83 |
| DRS 19-154 | 19-154 | MDAAEDYAKERYGISSMIQSQEKPDRVLVRVRDLTIQKA DEVVWVRARVHTSRAKGKQCFLVLRQQQFNVQALVAVG DHASKQMVKFAANINKESIVDVEGVVRKVNQKIGSCTQQ DVELHVQKIYVISLAEPRL | 84 |
| DRS 21-154 | 21-154 | MDAAEDYAKERYGISSMIQSQEKPDRVLVRVRDLTIQKA DEVVWVRARVHTSRAKGKQCFLVLRQQQFNVQALVAVG DHASKQMVKFAANINKESIVDVEGVVRKVNQKIGSCTQQ DVELHVQKIYVISLAEPRL | 85 |
| DRS 23-154 | 23-154 | AAEDYAKERYGISSMIQSQEKPDRVLVRVRDLTIQKADEV VWVRARVHTSRAKGKQCFLVLRQQQFNVQALVAVGDH ASKQMVKFAANINKESIVDVEGVVRKVNQKIGSCTQQDV ELHVQKIYVISLAEPRL | 86 |
| DRS 11-146 | 11-146 | MQEKPREIMDAAEDYAKERYGISSMIQSQEKPDRVLVRV RDLTIQKADEVVWVRARVHTSRAKGKQCFLVERQQQFN VQALVAVGDHASKQMVKFACNINKESIVDVEGVVRKVN QKIGSCTQQDVELHVQKIYVIS | 87 |
| DRS 13-146 | 13-146 | MKPREIMDAAEDYAKERYGISSMIQSQEKPDRVLVRVRD LTIQKADEVVWVRARVHTSRAKGKQCFLVERQQQFNVQ ALVAVGDHASKQMVKFACNINKESIVDVEGVVRKVNQKI GSCTQQDVELHVQKIYVIS | 88 |
| DRS 13-146/A106C | 13-146 | MKPREIMDAAEDYAKERYGISSMIQSQEKPDRVLVRVRD LTIQKADEVVWVRARVHTSRAKGKQCFLVERQQQFNVQ ALVAVGDHASKQMVKFACNINKESIVDVEGVVRKVNQKI GSCTQQDVELHVQKIYVIS | 89 |
| DRS 17-146 | 17-146 | MIMDAAEDYAKERYGISSMIQSQEKPDRVLVRVRDLTIQK ADEVVWVRARVHTSRAKGKQCFLVLRQQQFNVQALVAV GDHASKQMVKFACNINKESIVDVEGVVRKVNQKIGSCTQ QDVELHVQKIYVIS | 90 |
| DRS 21-146 | 21-146 | MAEDYAKERYGISSMIQSQEKPDRVLVRVRDLTIQKADE VVWVRARVHTSRAKGKQCFLVLRQQQFNVQALVAVGD HASKQMVKFACNINKESIVDVEGVVRKVNQKIGSCTQQD VELHVQKIYVIS | 91 |

TABLE D3

Exemplary Internal DRS polypeptide Fragments

| Name | Amino Acid Residue Range of SEQ ID NO: 1 | Amino acid sequence | SEQ ID NO: |
|---|---|---|---|
| AspRS1[I1] | Protein/ Human/38-292 | QEKPDRVLVRVRDLTIQKADEVVWVRARVHTSRAKGKQ CFLVLRQQQFNVQALVAVGDHASKQMVKFAANINKESIV DVEGVVRKVNQKIGSCTQQDVELHVQKIYVISLAEPRLPL QLDDAVRPEAEGEEEGRATVNQDTRLDNRVIDLRTSTSQ AVFRLQSGICHLFRETLINKGFVEIQTPKIISAASEGGANVF TVSYFKNNAYLAQSPQLYKQMCICADFEKVFSIGPVFRAE DSNTHRHLTEFVGLDIE | 10 |
| AspRS1[I2] | Protein/ Human/23-154 | DYAKERYGISSMIQSQEKPDRVLVRVRDLTIQKADEVVW VRARVHTSRAKGKQCFLVLRQQQFNVQALVAVGDHASK QMVKFAANINKESIVDVEGVVRKVNQKIGSCTQQDVELH VQKIYVISLAEPRLPL | 11 |
| AspRS1[I3] | Protein/ Human/33-154 | SMIQSQEKPDRVLVRVRDLTIQKADEVVWVRARVHTSRA KGKQCFLVLRQQQFNVQALVAVGDHASKQMVKFAANIN KESIVDVEGVVRKVNQKIGSCTQQDVELHVQKIYVISLAE PRLPL | 12 |

TABLE D4

Exemplary C-Terminal DRS polypeptide Fragments

| Name | Amino Acid Residue Range of SEQ ID NO: 1 | Amino acid sequence | SEQ ID NO: |
|---|---|---|---|
| AspRS1[C1] | Protein/ Human/ 297-501 | YHYHEVMEEIADTMVQIFKGLQERFQTEIQTVNKQFPCEP FKFLEPTLRLEYCEALAMLREAGVEMGDEDDLSTPNEKLL GHLVKEKYDTDFYILDKYPLAVRPFYTMPDPRNPKQSNS YDMFMRGEEILSGAQRIHDPQLLTERALHHGIDLEKIKAYI DSFRFGAPPHAGGGIGLERVTMLFLGLHNVRQTSMFPRDP KRLTP | 13 |
| AspRS1[C2] | Protein/ Human/ 101-501 | MVKFAANINKESIVDVEGVVRKVNQKIGSCTQQDVELHV QKIYVISLAEPRLPLQLDDAVRPEAEGEEEGRATVNQDTR LDNRVIDLRTSTSQAVFRLQSGICHLFRETLINKGFVEIQTP KIISAASEGGANVFTVSYFKNNAYLAQSPQLYKQMCICAD FEKVFSIGPVFRAEDSNTHRHLTEFVGLDIEMAFNYHYHE VMEEIADTMVQIFKGLQERFQTEIQTVNKQFPCEPFKFLEP TLRLEYCEALAMLREAGVEMGDEDDLSTPNEKLLGHLVK EKYDTDFYILDKYPLAVRPFYTMPDPRNPKQSNSYDMFM RGEEILSGAQRIHDPQLLTERALHHGIDLEKIKAYIDSFRFG APPHAGGGIGLERVTMLFLGLHNVRQTSMFPRDPKRLTP | 14 |

TABLE D5

Exemplary Alternatively Spliced DRS polypeptide Variants

| Name | Amino Acid Residue Range of SEQ ID NO: 1 | Amino acid sequence | SEQ ID NO: |
|---|---|---|---|
| AspRS1[N6] | Protein/ Human/1-41 + 73-501 | MPSASASRKSQEKPREIMDAAEDYAKERYGISSMIQSQEK PGKQCFLVLRQQQFNVQALVAVGDHASKQMVKFAANIN KESIVDVEGVVRKVNQKIGSCTQQDVELHVQKIYVISLAE PRLPLQLDDAVRPEAEGEEEGRATVNQDTRLDNRVIDLRT STSQAVFRLQSGICHLFRETLINKGFVEIQTPKIISAASEGG ANVFTVSYFKNNAYLAQSPQLYKQMCICADFEKVFSIGPV FRAEDSNTHRHLTEFVGLDIEMAFNYHYHEVMEEIADTM VQIFKGLQERFQTEIQTVNKQFPCEPFKFLEPTLRLEYCEA LAMLREAGVEMGDEDDLSTPNEKLLGHLVKEKYDTDFYI LDKYPLAVRPFYTMPDPRNPKQSNSYDMFMRGEEILSGA QRIHDPQLLTERALHHGIDLEKIKAYIDSFRFGAPPHAGGG IGLERVTMLFLGLHNVRQTSMFPRDPKRLTP | 15 |
| AspRS1[N7] | Protein/ Human/1-141 + | MPSASASRKSQEKPREIMDAAEDYAKERYGISSMIQSQEK PDRVLVRVRDLTIQKADEVVWVRARVHTSRAKGKQCFL | 16 |

TABLE D5-continued

Exemplary Alternatively Spliced DRS polypeptide Variants

| Name | Amino Acid Residue Range of SEQ ID NO: 1 | Amino acid sequence | SEQ ID NO: |
|---|---|---|---|
| | 189-501 | VLRQQQFNVQALVAVGDHASKQMVKFAANINKESIVDV EGVVRKVNQKIGSCTQQDVELHVQKTSTSQAVFRLQSGIC HLFRETLINKGFVEIQTPKIISAASEGGANVFTVSYFKNNA YLAQSPQLYKQMCICADFEKVFSIGPVFRAEDSNTHRHLT EFVGLDIEMAFNYHYHEVMEEIADTMVQIFKGLQERFQTE IQTVNKQFPCEPFKFLEPTLRLEYCEALAMLREAGVEMGD EDDLSTPNEKLLGHLVKEKYDTDFYILDKYPLAVRPFYTM PDPRNPKQSNSYDMFMRGEEILSGAQRIHDPQLLTERALH HGIDLEKIKAYIDSFRFGAPPHAGGGIGLERVTMLFLGLHN VRQTSMFPRDPKRLTP | |
| AspRS1$^{N8}$ | Protein/ Human/1-319 + 369-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL QESTPNEKLLGHLVKEKYDTDFYILDKYPLAVRPFYTMPD PRNPKQSNSYDMFMRGEEILSGAQRIHDPQLLTERALHHG IDLEKIKAYIDSFRFGAPPHAGGGIGLERVTMLFLGLHNVR QTSMFPRDPKRLTP | 17 |
| AspRS1$^{N9}$ DRS (1-22 + 63 aa) | Protein/ Human/1-22 + 63 aa | MPSASASRKSQEKPREIMDAAEDWNELLCCFWDCIMFVR PPCSLVIPNDSLLKFTLCHLTPVWMTERDPASKKKKKKES HTYSFQ | 18 |
| AspRS1$^{N10}$ DRS (1-22 + 5 aa) | Protein/ Human/1-22 + 5 aa | MPSASASRKSQEKPREIMDAAEGNSAS | 19 |
| AspRS1$^{C2}$ | Protein/ Human/101-501 | MVKFAANINKESIVDVEGVVRKVNQKIGSCTQQDVELHV QKIYVISLAEPRLPLQLDDAVRPEAEGEEEGRATVNQDTR LDNRVIDLRTSTSQAVFRLQSGICHLFRETLINKGFVEIQTP KIISAASEGGANVFTVSYFKNNAYLAQSPQLYKQMCICAD FEKVFSIGPVFRAEDSNTHRHLTEFVGLDIEMAFNYHYHE VMEEIADTMVQIFKGLQERFQTEIQTVNKQFPCEPFKFLEP TLRLEYCEALAMLREAGVEMGDEDDLSTPNEKLLGHLVK EKYDTDFYILDKYPLAVRPFYTMPDPRNPKQSNSYDMFM RGEEILSGAQRIHDPQLLTERALHHGIDLEKIKAYIDSFRFG APPHAGGGIGLERVTMLFLGLHNVRQTSMFPRDPKRLTP | 20 |
| AspRS1$^{C3}$ DRS (478-501) | Protein/ Human/478-501 | MLFLGLHNVRQTSMFPRDPKRLTP | 21 |

Accordingly, the terms "DRS polypeptide" "DRS protein" or "DRS protein fragment" as used herein includes all naturally-occurring and synthetic forms of the aspartyl-tRNA synthetase that i) retain non canonical activity, and ii) comprise at least one mutation at either Cys76 or Cys130 (using the numbering of SEQ ID NO:1) which replaces the native cysteine with another amino acid. Such DRS polypeptides include the full length human protein, as well as the DRS peptides derived from the full length protein listed in Tables D1-O5, as well as naturally occurring variants, for example as disclosed in Table D6, the exemplary cysteine mutants listed in Table D7, and polypeptides encoded by the exemplary nucleic acid sequences in Table D8. Preferably, the term DRS polypeptide refers to a polypeptide sequence derived from human aspartyl-tRNA synthetase (SEQ ID NO:1 in Table D1) comprising at least one mutation at either Cys76 or Cys130.

A number of naturally occurring aspartyl-tRNA synthetase single nucleotide polymorphisms (SNPs) and naturally occurring variants of the human gene have been sequenced, and are known in the art to be at least partially functionally interchangeable. Additionally homologs and orthologs of the human gene exist in other species, and it would thus be a routine matter to select a naturally occurring variant such as a DRS polypeptide encoded by a SNP, or other naturally occurring variant in place of any of the DRS polypeptide sequences listed in Tables D1-D7. Several such variants of aspartyl-tRNA synthetase (i.e., representative aspartyl-tRNA synthetase SNPs) are shown in Table D6.

TABLE D6

Human Aspartyl-tRNA synthetase SNPs

| Gene Bank Accession Number | Nucleotide Change | Gene Bank Accession Number | Nucleotide Change |
|---|---|---|---|
| rs118100102 | C/T | rs2164332 | C/G |
| rs117859527 | C/G | rs2164331 | C/T |
| rs117847055 | A/G | rs1867632 | A/G |
| rs117843158 | A/C | rs1803167 | C/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs117754321 | A/C | rs1803166 | C/T |
| rs117605910 | C/G | rs1803165 | G/T |
| rs117587018 | A/G | rs1347442 | C/T |
| rs117448010 | A/C | rs895285 | A/G |
| rs117438984 | A/G | rs834734 | C/T |
| rs117395206 | G/T | rs689002 | A/G |
| rs117045416 | C/T | rs687670 | C/T |
| rs116899241 | C/T | rs661562 | A/C |
| rs116807764 | C/T | rs660002 | C/T |
| rs116756668 | C/T | rs640727 | A/T |
| rs116755289 | C/T | rs567363 | C/T |
| rs116723553 | A/G | rs561980 | A/G |
| rs116719241 | C/T | rs522086 | C/T |
| rs116626412 | C/T | rs309172 | C/T |
| rs116599033 | A/G | rs309171 | C/G |
| rs116528963 | C/T | rs309170 | C/T |
| rs116504104 | A/G | rs309169 | C/T |
| rs116503734 | A/T | rs309168 | C/T |
| rs116471228 | G/T | rs309167 | C/T |
| rs116460118 | A/T | rs309166 | C/T |
| rs116376572 | A/G | rs309165 | C/T |
| rs116373537 | G/T | rs309164 | A/G |
| rs116190965 | C/T | rs309163 | C/T |
| rs116114585 | A/T | rs309162 | A/T |
| rs116069651 | C/T | rs309161 | C/T |
| rs116013288 | C/T | rs309160 | A/G |
| rs115947325 | C/T | rs309159 | A/G |
| rs115876148 | C/T | rs309158 | C/T |
| rs115771261 | C/T | rs309157 | A/G |
| rs115749352 | A/G | rs309156 | C/G |
| rs115704588 | C/T | rs309155 | A/G |
| rs115691888 | A/C | rs309154 | C/T |
| rs115651129 | C/G | rs309153 | A/G |
| rs115572299 | C/T | rs309150 | A/T |
| rs115553816 | A/G | rs309149 | C/T |
| rs115530645 | C/T | rs7587285 | C/T |
| rs115475999 | C/T | rs7585928 | C/G |
| rs115469964 | A/C | rs7573555 | C/T |
| rs115332530 | A/G | rs6760465 | A/T |
| rs115330084 | C/G | rs6757965 | A/G |
| rs115316382 | A/G | rs6754311 | C/T |
| rs115306423 | C/T | rs6752967 | A/G |
| rs115253602 | A/G | rs6750549 | A/G |
| rs115249754 | C/T | rs6743537 | A/G |
| rs115248017 | C/G | rs6742701 | C/T |
| rs114986027 | C/T | rs6740254 | C/G |
| rs114977327 | C/T | rs6738266 | C/T |
| rs114851922 | C/T | rs6733398 | A/G |
| rs114841878 | A/G | rs6724595 | A/G |
| rs114832662 | A/G | rs6711493 | A/G |
| rs114830940 | A/G | rs6430594 | A/G |
| rs114489290 | C/T | rs5834455 | —/T |
| rs114428384 | C/T | rs5834454 | —/AA |
| rs114422751 | C/T | rs5834453 | —/AAAAT |
| rs114414669 | A/C | rs4954551 | A/G |
| rs114412783 | C/T | rs4597591 | A/T |
| rs114399267 | C/T | rs4538260 | A/G |
| rs114398361 | A/G | rs4278979 | C/T |
| rs114345514 | C/T | rs3820789 | C/G |
| rs114337780 | A/C | rs3768999 | C/G |
| rs114164361 | C/G | rs3768998 | A/C |
| rs114162105 | A/T | rs3768997 | A/G |
| rs114126158 | A/G | rs3768996 | C/G |
| rs114110228 | A/C | rs3112496 | C/T |
| rs114058841 | G/T | rs3098104 | A/T |
| rs113998842 | G/T | rs2839741 | A/T |
| rs113995718 | A/C | rs2556175 | C/T |
| rs113884130 | C/T | rs2322725 | C/T |
| rs113882668 | A/C | rs2307720 | —/TTAG |
| rs113853485 | G/T | rs2305101 | G/T |
| rs113759327 | C/G | rs2278683 | A/C |
| rs113676252 | C/T | rs2278682 | C/G |
| rs113641203 | G/T | rs2278681 | C/T |
| rs113342018 | G/T | rs2164333 | A/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs113328159 | –/C | rs13397074 | A/C |
| rs113316632 | A/T | rs13392680 | A/T |
| rs113200654 | A/T | rs13388887 | C/T |
| rs113155677 | A/G | rs13034773 | A/C |
| rs113148022 | AAAAAAAAAAAAAAAAAATCCAA | rs13025460 | A/T |
| rs113012086 | A/G | rs13007697 | G/T |
| rs112923773 | A/G | rs13004546 | C/T |
| rs112910626 | C/T | rs12999871 | A/C |
| rs112868187 | C/T | rs12990346 | G/T |
| rs112849402 | A/G | rs12990316 | C/T |
| rs112848056 | C/T | rs12624144 | C/T |
| rs112835147 | C/T | rs12623506 | A/G |
| rs112767522 | C/T | rs12617586 | C/T |
| rs112396243 | C/T | rs12615624 | A/G |
| rs112369881 | A/T | rs12613540 | C/T |
| rs112319042 | C/T | rs12613074 | G/T |
| rs112300736 | G/T | rs12477103 | A/C |
| rs112205661 | C/T | rs12474975 | A/T |
| rs112205423 | G/T | rs12471430 | A/T |
| rs112138368 | C/T | rs11895669 | G/T |
| rs112136466 | C/T | rs11895436 | A/G |
| rs111956746 | A/G | rs11892136 | G/T |
| rs111909933 | C/T | rs11889473 | A/C |
| rs111766943 | A/G | rs11548872 | C/G |
| rs111731189 | C/T | rs11548870 | A/G |
| rs111716305 | C/T | rs11375996 | –/A |
| rs111670530 | C/T | rs11345750 | –/A |
| rs111613855 | A/G | rs11340194 | –/A |
| rs111608134 | C/T | rs11319623 | –/A |
| rs111600480 | A/G | rs11297201 | –/T |
| rs111578911 | A/C | rs10610928 | –/CTCT |
| rs111533002 | –/T | rs10606646 | –/AAAA |
| rs111432741 | C/T | rs10598545 | –/AAAA |
| rs111346414 | C/T | rs10566195 | –/TGA |
| rs111261866 | C/T | rs10546948 | –/TT |
| rs80342688 | A/C | rs10205844 | C/G |
| rs80296238 | A/C | rs35332762 | –/C |
| rs80290607 | G/T | rs35323281 | –/A |
| rs80201497 | A/C | rs35250856 | –/C |
| rs80160510 | C/T | rs35207721 | –/C |
| rs80095420 | C/T | rs35180509 | –/A |
| rs79933222 | A/C | rs35066766 | –/T |
| rs79908186 | G/T | rs34855029 | –/A |
| rs79826902 | A/G | rs34818704 | –/G |
| rs79811988 | G/T | rs34764820 | –/T |
| rs79778906 | C/T | rs34762161 | –/T |
| rs79745746 | C/T | rs34744196 | –/A |
| rs79719188 | C/T | rs34739918 | –/T |
| rs79715594 | C/T | rs34719779 | –/T |
| rs79685879 | –/TT | rs34713850 | –/A |
| rs79613305 | A/C | rs34698626 | –/AA |
| rs79513920 | C/T | rs34675243 | –/A |
| rs79507949 | A/G | rs34613097 | –/A |
| rs79494100 | A/T | rs34442772 | –/C |
| rs79478181 | A/T | rs34398897 | –/G |
| rs79327246 | C/G | rs34215176 | –/G |
| rs79301888 | C/T | rs34180776 | –/G |
| rs79274257 | A/G | rs34142242 | –/T |
| rs79268627 | A/T | rs34050823 | –/T |
| rs79238496 | A/G | rs17718194 | C/T |
| rs79231002 | C/T | rs16832417 | C/T |
| rs79227800 | C/T | rs16832413 | A/C |
| rs79173488 | A/G | rs16832394 | A/C |
| rs79161420 | –/A | rs16832326 | A/G |
| rs79139071 | A/G | rs16832275 | C/G |
| rs79137850 | C/T | rs16832274 | C/T |
| rs79121686 | C/T | rs16832248 | C/G |
| rs79078468 | G/T | rs16832243 | C/T |
| rs79018926 | C/T | rs16832221 | C/T |
| rs78993580 | A/G | rs16832205 | A/G |
| rs78943662 | –/A | rs16832200 | C/T |
| rs78919277 | G/T | rs16832172 | C/T |
| rs78915112 | A/C | rs16832162 | A/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs78898735 | A/T | rs13404551 | C/T |
| rs78793088 | A/G | rs13399128 | A/G |
| rs78784878 | G/T | rs71417582 | C/T |
| rs78770570 | C/T | rs71417581 | C/G |
| rs78700806 | C/G | rs71400535 | —/A |
| rs78638278 | C/T | rs67636722 | —/A |
| rs78629157 | A/G | rs67591467 | —/A |
| rs78628013 | C/T | rs66527494 | —/A |
| rs78577601 | A/T | rs66508408 | —/AA |
| rs78537103 | C/T | rs62159056 | A/C |
| rs78518056 | A/C | rs62159055 | A/T |
| rs78512447 | A/T | rs61569739 | —/AA |
| rs78497838 | —/TTT | rs61297566 | —/AAATA |
| rs78383997 | A/T | rs61222539 | C/T |
| rs78283445 | C/G | rs61133344 | C/T |
| rs78275586 | G/T | rs60878223 | —/T |
| rs78274583 | C/T | rs60538468 | A/C |
| rs78258066 | A/G | rs60485095 | —/TT |
| rs78168253 | C/T | rs60318326 | C/T |
| rs78143716 | A/G | rs59584448 | —/A |
| rs78130363 | A/G | rs59505882 | —/A |
| rs78083497 | A/C | rs59464486 | G/T |
| rs78081965 | G/T | rs59199326 | —/TT |
| rs78076875 | C/T | rs58805013 | A/C |
| rs78026280 | A/G | rs58799551 | —/G |
| rs78015725 | G/T | rs58666594 | G/T |
| rs77987440 | C/T | rs57046249 | —/A |
| rs77972711 | A/G | rs56721192 | —/AA |
| rs77930020 | A/C | rs56100046 | A/T |
| rs77902883 | C/T | rs55951873 | A/G |
| rs77883526 | A/T | rs55815289 | —/A |
| rs77862927 | —/TT | rs55759471 | G/T |
| rs77837755 | A/C | rs55641281 | A/G |
| rs77793053 | C/T | rs41269823 | A/G |
| rs77774340 | A/C | rs41269821 | A/G |
| rs77753457 | C/T | rs36023868 | —/T |
| rs77752694 | A/T | rs35921927 | A/G |
| rs77743403 | G/T | rs35814998 | —/C |
| rs77707512 | C/T | rs35760856 | —/C |
| rs77697045 | C/T | rs35460584 | —/C |
| rs77694994 | A/G | rs35363362 | C/G |
| rs77654242 | G/T | rs74661004 | C/T |
| rs77546304 | C/T | rs74527665 | C/T |
| rs77516029 | C/T | rs74479926 | C/T |
| rs77511888 | A/C | rs74462337 | G/T |
| rs77507602 | A/T | rs74399174 | A/C |
| rs77390314 | A/G | rs74398392 | C/T |
| rs77341293 | A/C | rs74266318 | G/T |
| rs77340433 | C/T | rs73957079 | C/T |
| rs77244692 | A/G | rs73957078 | C/T |
| rs77241600 | C/T | rs73957074 | A/C |
| rs77194466 | A/T | rs73957073 | A/G |
| rs77182879 | A/G | rs73957072 | A/G |
| rs77177301 | G/T | rs73957071 | A/G |
| rs77147958 | A/G | rs73957070 | A/G |
| rs77144439 | A/T | rs73957069 | C/G |
| rs77113180 | A/G | rs73957068 | C/T |
| rs77092452 | A/G | rs72974121 | A/G |
| rs77052188 | G/T | rs72974120 | C/G |
| rs77051588 | C/T | rs72974119 | A/G |
| rs76986930 | A/C | rs72974109 | A/G |
| rs76946722 | —/AA | rs72423998 | —/A |
| rs76862952 | A/C | rs72366475 | —/T |
| rs76856516 | G/T | rs72355283 | —/A |
| rs76798249 | A/C | rs72313616 | —/TT |
| rs76793136 | A/G | rs72270342 | —/A |
| rs76792531 | A/G | rs72268157 | —/A |
| rs76732000 | G/T | rs72097458 | —/A |
| rs76729798 | C/T | rs71937749 | —/AA |
| rs76677887 | C/T | rs71930676 | —/A |
| rs76672039 | C/T | rs71746189 | —/A |
| rs76496496 | A/G | rs71701797 | —/AAAA |
| rs76460134 | A/C | rs71697066 | —/A |
| rs76456107 | A/G | rs71535212 | A/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs76448970 | A/G | rs71535211 | C/T |
| rs76433055 | C/T | rs71417587 | A/C |
| rs76392392 | A/G | rs71417586 | A/C |
| rs76357426 | C/T | rs71417585 | C/G |
| rs76350348 | A/G | rs71417584 | C/G |
| rs76337990 | C/T | rs71417583 | A/C |
| rs76306255 | G/T | rs309148 | C/T |
| rs76302219 | C/T | rs309147 | C/T |
| rs76296777 | A/G | rs309146 | A/G |
| rs76285313 | A/T | rs309145 | A/G |
| rs76189476 | A/G | rs309144 | C/T |
| rs76089705 | G/T | rs309143 | A/G |
| rs76047098 | C/T | rs309142 | C/T |
| rs75999734 | C/T | rs309141 | A/C |
| rs75990169 | A/G | rs309140 | A/C |
| rs75935955 | C/T | rs309120 | C/G |
| rs75874749 | C/T | rs309119 | A/G |
| rs75843843 | C/G | rs309115 | C/T |
| rs75843510 | C/T | rs309114 | A/T |
| rs75842188 | A/G | rs309113 | A/C |
| rs75800473 | G/T | rs309112 | G/T |
| rs75794936 | A/C | rs192822 | A/T |

TABLE D6-continued

Human Aspartyl-tRNA synthetase SNPs

| Gene Bank Accession Number | Nucleotide Change | Gene Bank Accession Number | Nucleotide Change |
|---|---|---|---|
| rs75753154 | C/T | rs177917 | C/T |
| rs75732042 | C/G | rs167442 | G/T |
| rs75683158 | G/T | rs71518151 | ACTTTTTGATGGGGTTGT(SEQ ID NO: 44)/CCTTTTTCATGGGCTTGTTTTTTTCTTGTAAATTTGTTT(SEQ ID NO: 45) |
| rs75667274 | C/T | rs75123144 | —/AG |
| rs75657010 | A/T | rs75071131 | A/T |
| rs75647121 | C/T | rs74959174 | C/T |
| rs75572938 | A/T | rs74833182 | A/T |
| rs75560320 | A/G | rs74777619 | C/T |
| rs75524146 | C/T | rs74771413 | C/G |
| rs75437018 | C/G | rs74674565 | C/T |
| rs75402079 | A/C | rs75346069 | C/T |
| rs75394224 | C/G | rs75298650 | A/G |
| rs75365510 | A/G | rs75214175 | A/G |

Thus all such homologues, orthologs, and naturally-occurring, or synthetic isoforms of aspartyl-tRNA synthetase (e.g., any of the proteins or nucleic acids listed in Tables D1 to D8) are included in any of the methods, kits and pharmaceutical compositions of the invention, as long as they encode for proteins that i) retain detectable non canonical activity, and ii) comprise, or have been modified to comprise at least one mutation at either Cys76 or Cys130 (using the numbering of SEQ ID NO:1) which replaces the native cysteine with another amino acid. Several exemplary DRS polypeptides are shown for illustration in Table D7.

TABLE D7

Exemplary Variants with reduced cysteine content

| Name | Amino Acid Residue Range of SEQ ID NO: 1 | Amino acid sequence | SEQ ID NO: |
|---|---|---|---|
| AspRS1^N1(C76S) | 1-154 | MPSASASRKSQEKPREIMDAAEDYAKERYGISSMIQSQEKPDRVLVRVRDLTIQKADEVVWVRARVHTSRAKGKQSFLVLRQQQFNVQALVAVGDHASKQMVKFAANINKESIVDVEGVVRKVNQKIGSCTQQDVELHVQKIYVISLAEPRLPL | 22 |
| AspRS1^N1(C130S) | 1-154 | MPSASASRKSQEKPREIMDAAEDYAKERYGISSMIQSQEKPDRVLVRVRDLTIQKADEVVWVRARVHTSRAKGKQCFLVLRQQQFNVQALVAVGDHASKQMVKFAANINKESIVDVEGVVRKVNQKIGSSTQQDVELHVQKIYVISLAEPRLPL | 23 |
| AspRS1^N1(C76S, C130S) | 1-154 | MPSASASRKSQEKPREIMDAAEDYAKERYGISSMIQSQEKPDRVLVRVRDLTIQKADEVVWVRARVHTSRAKGKQSFLVLRQQQFNVQALVAVGDHASKQMVKFAANINKESIVDVEGVVRKVNQKIGSSTQQDVELHVQKIYVISLAEPRLPL | 24 |
| DRS C334S | 1-501 | MPSASASRKSQEKPREIMDAAEDYAKERYGISSMIQSQEKPDRVLVRVRDLTIQKADEVVWVRARVHTSRAKGKQCFLVLRQQQFNVQALVAVGDHASKQMVKFAANINKESIVDVEGVVRKVNQKIGSCTQQDVELHVQKIYVISLAEPRLPLQL | 48 |

TABLE D7-continued

Exemplary Variants with reduced cysteine content

| Name | Amino Acid Residue Range of SEQ ID NO: 1 | Amino acid sequence | SEQ ID NO: |
|---|---|---|---|
| | | DDAVRPEAEGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL QERFQTEIQTVNKQFPSEPFKFLEPTLRLEYCEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | |
| DRS C349S | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL QERFQTEIQTVNKQFPCEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 49 |
| DRS C334S/C349S | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGICHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL QERFQTEIQTVNKQFPSEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 50 |
| DRS C203A | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGIAHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL QERFQTEIQTVNKQFPCEPFKFLEPTLRLEYCEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 51 |
| DRS C203V | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKIYVISLAEPRLPLQL DDAVRPEAEGEEEGRATVNQDTRLDNRVIDLRTSTSQAVF RLQSGIVHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL QERFQTEIQTVNKQFPCEPFKFLEPTLRLEYCEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 52 |
| DRS C334S/C349S/ C203A | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKTYVISLAEPRLPLQL DDAVRPEAEGEEEGRATVNQDTRLDNRVIDLRTSTSQAVF RLQSGIAHLFRETLINKGFVEIQTPKIISAASEGGANVFTVS YFKNNAYLAQSPQLYKQMCICADFEKVFSIGPVFRAEDSN THRHLTEFVGLDIEMAFNYHYHEVMEEIADTMVQIFKGL | 53 |

TABLE D7-continued

Exemplary Variants with reduced cysteine content

| Name | Amino Acid Residue Range of SEQ ID NO: 1 | Amino acid sequence | SEQ ID NO: |
|---|---|---|---|
| | | QERFQTEIQTVNKQFPSEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | |
| DRS C334S/C349S/ C203V | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKTYVISLAEPRLPLQL DDAVRPEAEGEEEGRATVNQDTRLDNRVIDLRTSTSQAVF RLQSGIVHLFRETLINKGFVEIQTPKIISAASEGGANVFTVS YFKNNAYLAQSPQLYKQMCIAADFEKVFSIGPVFRAEDSN THRHLTEFVGLDIEMAFNYHYHEVMEEIADTMVQIFKGL QERFQTEIQTVNKQFPSEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 54 |
| DRS C334S/C349S/ C259A/C203A | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKTYVISLAEPRLPLQL DDAVRPEAEGEEEGRATVNQDTRLDNRVIDLRTSTSQAVF RLQSGIAHLFRETLINKGFVEIQTPKIISAASEGGANVFTVS YFKNNAYLAQSPQLYKQMCIAADFEKVFSIGPVFRAEDSN THRHLTEFVGLDIEMAFNYHYHEVMEEIADTMVQIFKGL QERFQTEIQTVNKQFPSEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 55 |
| DRS C334S/C349S/ C259A/C203V | 1-501 | MPSASASRKSQEKPREIMDAAEDYAKERYGISSMIQSQEK PDRVLVRVRDLTIQKADEVVWVRARVHTSRAKGKQCFL VLRQQQFNVQALVAVGDHASKQMVKFAANINKESIVDV EGVVRKVNQKIGSCTQQDVELHVQKTYVISLAEPRLPLQL DDAVRPEAEGEEEGRATVNQDTRLDNRVIDLRTSTSQAVF RLQSGIVHLFRETLINKGFVEIQTPKIISAASEGGANVFTVS YFKNNAYLAQSPQLYKQMCIAADFEKVFSIGPVFRAEDSN THRHLTEFVGLDIEMAFNYHYHEVMEEIADTMVQIFKGL QERFQTEIQTVNKQFPSEPFKFLEPTLRLEYSEALAMLREA GVEMGDEDDLSTPNEKLLGHLVKEKYDTDFYILDKYPLA VRPFYTMPDPRNPKQSNSYDMFMRGEEILSGAQRIHDPQL LTERALHHGIDLEKIKAYIDSFRFGAPPHAGGGIGLERVTM LFLGLHNVRQTSMFPRDPKRLTP | 56 |

In one embodiment of any of these methods, compositions and kits, the DRS polypeptide is AspRS1$^{N1}$/DRS (1-154) comprising at least one mutation at either Cys76 or Cys130.

In one embodiment of any of these methods, compositions and kits, the DRS polypeptide is DRS (11-146) comprising at least one mutation at either Cys76 or Cys130.

In one embodiment of any of these methods, compositions and kits, the DRS polypeptide is DRS (13-146) comprising at least one mutation at either Cys76 or Cys130.

In one embodiment of any of these methods, compositions and kits, the DRS polypeptide is full-length DRS (SEQ ID NO:1) comprising at least one mutation at either Cys76 or Cys130.

In some embodiments, the DRS polypeptide may comprise at mutation at Cys76 and/or Cys130, wherein the substituted amino acid is independently selected from the group consisting of all 19 alternative naturally occurring amino acids except Cys, or a non-naturally occurring amino acid.

In some embodiments, the DRS polypeptide may comprise at mutation at Cys76 and/or Cys130, wherein the substituted amino acid is independently selected from the group consisting of Ser, Ala, Gly, Met, Leu, Val, Ile and Thr.

In some embodiments, the DRS polypeptide may comprise at mutation at Cys76 and/or Cys130 wherein the substituted amino acid is independently selected from the group consisting of Ser and Ala.

In some embodiments, the DRS polypeptide may comprise at mutation at Cys76 and/or Cys130 wherein the substituted amino acid is independently selected from the group consisting of Asp, Glu, Arg, Lys, Gln, and Asn.

In some embodiments the DRS polypeptide may comprise at mutation at Cys76 and/or Cys130 wherein the substituted amino acid is independently selected from the group consisting of His, Pro, Tyr, Trp and Phe.

In some embodiments, the DRS polypeptide may comprise at mutation at Cys76 and/or Cys130 wherein the substitution is a independently selected from Ser, Ala, Gly, Met, Leu, Val, Ile and Thr, and a non-naturally occurring amino acid.

In any of these various embodiments, Cys76 may be selectively modified, while Cys130 remains unmodified. Conversely, in some embodiments, Cys130 may be selectively modified, while Cys76 remains unmodified. In some embodiments both Cys76 and Cys130 may be independently modified using any combination of the sub-groupings listed above.

In some embodiments, Cys76 may be selectively modified, and then the remaining free cysteine at position 130 used to selectively chemically couple another molecule. Exemplary coupled molecules include for example water soluble polymers such as PEG, as well as heterologous proteins.

In particular embodiments, non-naturally occurring amino acids include, without limitation, any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by the following formula:

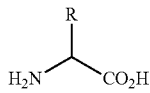

A non-natural amino acid is typically any structure having the foregoing formula wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids. For example, R in foregoing formula optionally comprises an alkyl-, aryl-, aryl halide, vinyl halide, alkyl halide, acetyl, ketone, aziridine, nitrile, nitro, halide, acyl-, keto-, azido-, hydroxyl-, hydrazine, cyano-, halo-, hydrazide, alkenyl, alkynyl, ether, thio ether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as a cyclooctyne, thio ester, enone, imine, aldehyde, ester, thioacid, hydroxylamine, amino, carboxylic acid, alpha-keto carboxylic acid, alpha or beta unsaturated acids and amides, glyoxyl amide, or organosilane group, or the like or any combination thereof.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, β-O-GlcNAc-L-serine, a tri-O-acetyl-GalNAc-α-threonine, an α-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, those listed below, or elsewhere herein, and the like.

Non-natural amino acids, once selected, can either be purchased from vendors, or chemically synthesized.

In certain aspects, the use of non-natural amino acids can be utilized to modify (e.g., increase) a selected non-canonical activity of a DRS polypeptide, or to alter the in vivo or in vitro half-life of the protein, or other properties of the protein. Non-natural amino acids can also be used to facilitate (selective) chemical modifications (e.g., pegylation) of a DRS protein, as described elsewhere herein. For instance, certain non-natural amino acids allow selective attachment of polymers such as PEG to a given protein, and thereby improve their pharmacokinetic properties.

Specific examples of amino acid analogs and mimetics can be found described in, for example, Roberts and Vellaccio, The Peptides: Analysis, Synthesis, Biology, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, Combinatorial Chemistry, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or *carbo* cycle. See, for instance, Burger's Medicinal Chemistry and Drug Discovery, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420,109; M. Bodanzsky, Principles of Peptide Synthesis (1st ed. & 2d rev. ed.), Springer-Verlag, New York, N.Y. (1984 & 1993), see Chapter 7; Stewart and Young, Solid Phase Peptide Synthesis, (2d ed.), Pierce Chemical Co., Rockford, Ill. (1984), each of which is incorporated herein by reference). Accordingly, the DRS polypeptides of the present invention may be composed of naturally occurring and non-naturally occurring amino acids as well as amino acid analogs and mimetics.

In any of these various embodiments, Cys76 may be selectively modified, while Cys130 remains unmodified. Conversely, in some embodiments, Cys130 may be selectively modified, while Cys76 remains unmodified. In some embodiments both Cys76 and Cys130 may be independently modified using any combination of the sub-groupings listed above.

The DRS polypeptides may be in their native form, i.e., as different variants as they appear in nature in different species which may be viewed as functionally equivalent variants of human aspartyl-tRNA synthetase, or they may be functionally equivalent natural derivatives thereof, which may differ in their amino acid sequence, e.g., by truncation (e.g., from the N- or C-terminus or both) or other amino acid deletions, additions, insertions, substitutions, or post-translational modifications. Naturally-occurring chemical derivatives, including post-translational modifications and degradation products of any DRS polypeptide, are also specifically included in any of the methods and pharmaceutical compositions of the invention including, e.g., pyroglutamyl, isoaspartyl, proteolytic, phosphorylated, glycosylated, oxidatized, isomerized, and deaminated variants of a DRS polypeptide.

It is known in the art to synthetically modify the sequences of proteins or peptides, while retaining their useful activity, and this may be achieved using techniques which are standard in the art and widely described in the literature, e.g., random or site-directed mutagenesis, cleavage, and ligation of nucleic acids, or via the chemical synthesis or modification of amino acids or polypeptide chains. Similarly it is within the skill in the art to address and/or mitigate immunogenicity concerns if they arise using a DRS polypeptide or variant thereof, e.g., by the use of automated computer recognition programs to identify potential T cell epitopes, and directed evolution approaches to identify less immunogenic forms.

Polynucleotides

Certain embodiments relate to polynucleotides that encode a DRS polypeptide. Among other uses, these embodiments may be utilized to recombinantly produce a desired DRS polypeptide or variant thereof, or to express the DRS polypeptide in a selected cell or subject. It will be appreciated by those of ordinary skill in the art that, as a result of the degeneracy of the genetic code, there are many nucleotide sequences that encode a DRS polypeptide as described herein. Some of these polynucleotides may bear minimal homology to the nucleotide sequence of any native gene. Nonetheless, polynucleotides that vary due to differences in codon usage are specifically contemplated by the present invention, for example polynucleotides that are optimized for human, yeast or bacterial codon selection.

Therefore, multiple polynucleotides can encode the DRS polypeptides of the invention. Moreover, the polynucleotide sequence can be manipulated for various reasons. Examples include but are not limited to the incorporation of preferred codons to enhance the expression of the polynucleotide in various organisms (see generally Nakamura et al., Nuc. Acid. Res. (2000) 28 (1): 292). In addition, silent mutations can be incorporated in order to introduce, or eliminate restriction sites, decrease the density of CpG dinucleotide motifs (see for example, Kameda et al., Biochem. Biophys. Res. Commun (2006) 349(4): 1269-1277) or reduce the ability of single stranded sequences to form stem-loop structures: (see, e.g., Zuker M., Nucl. Acid Res. (2003); 31(13): 3406-3415). In addition, mammalian expression can be further optimized by including a Kozak consensus sequence [i.e., (a/g)cc(a/g)ccATGg] at the start codon. Kozak consensus sequences useful for this purpose are known in the art (Mantyh et al. PNAS 92: 2662-2666 (1995); Mantyh et al. Prot. Exp. & Purif. 6,124 (1995)). Exemplary codon optimized versions of the wild type full length DRS polypeptide and AspRS1$^{N1}$ are provided in Table D8, below, as are other exemplary DRS coding sequences.

TABLE D8

DRS DNA Sequences

| Name | Amino Acid Residue Range of SEQ ID NO: 1 | Nucleic acid sequence | SEQ ID NO: |
|---|---|---|---|
| AspRS1$^{N1}$ | DNA/Synthetic/ Codon optimized 1-462 | ATGCCGAGCGCGAGCGCCAGCCGTAAGAGCCAGGAAA AACCACGTGAGATTATGGATGCCGCAGAGGACTATGCG AAAGAACGTTACGGTATTTCCAGCATGATCCAATCTCA GGAGAAACCGGACCGCGTTCTGGTTCGTGTTCGCGATC TGACCATTCAGAAGGCGGACGAGGTGGTTTGGGTGCGT GCGCGCGTGCACACCAGCCGTGCAAAAGGCAAACAGT GCTTTCTGGTCCTGCGTCAGCAGCAATTCAACGTCCAG GCGCTGGTGGCAGTGGGTGACCACGCCAGCAAACAAAT GGTGAAGTTCGCTGCTAACATCAATAAAGAATCCATTG TTGATGTTGAAGGCGTCGTTCGCAAGGTCAATCAAAAG ATCGGCTCGTGTACGCAACAAGATGTCGAGCTGCATGT GCAGAAGATTTACGTCATCAGCCTGGCGGAGCCGCGTT TGCCGCTG | 25 |
| AspRS1$^{N1}$ (C76S) | DNA/Synthetic/ Codon optimized 1-462 | ATGCCGAGCGCGAGCGCCAGCCGTAAGAGCCAGGAAA AACCACGTGAGATTATGGATGCCGCAGAGGACTATGCG AAAGAACGTTACGGTATTTCCAGCATGATCCAATCTCA GGAGAAACCGGACCGCGTTCTGGTTCGTGTTCGCGATC TGACCATTCAGAAGGCGGACGAGGTGGTTTGGGTGCGT GCGCGCGTGCACACCAGCCGTGCAAAAGGCAAACAGA GCTTTCTGGTCCTGCGTCAGCAGCAATTCAACGTCCAG GCGCTGGTGGCAGTGGGTGACCACGCCAGCAAACAAAT GGTGAAGTTCGCTGCTAACATCAATAAAGAATCCATTG TTGATGTTGAAGGCGTCGTTCGCAAGGTCAATCAAAAG ATCGGCTCGTGTACGCAACAAGATGTCGAGCTGCATGT GCAGAAGATTTACGTCATCAGCCTGGCGGAGCCGCGTT TGCCGCTGGGTAAGCCGATCCCTAACCCGCTGTTGGGT CTGGACAGCACGCATCACCATCACCACCACTAA | 26 |
| Full length AspRS sequence | DNA/Synthetic/ Codon optimized 1-1503 | ATGCCATCAGCCTCAGCATCTCGTAAAAGCCAGGAAAA ACCGCGCGAAATCATGGACGCTGCCGAAGATTATGCCA AAGAGCGCTATGGTATCAGTTCGATGATCCAGTCACAA GAGAAACCAGATCGTGTGCTGGTCCGTGTTCGTGACCT GACCATCCAGAAAGCGGATGAAGTTGTTTGGGTCCGTG CTCGTGTTCATACAAGCCGTGCCAAAGGCAAACAGTGC TTCCTGGTTCTGCGTCAACAGCAGTTTAACGTTCAGGCC CTGGTAGCCGTTGGTGATCACGCCTCAAAACAAATGGT GAAATTCGCCGCCAACATCAACAAAGAGAGCATCGTCG ACGTTGAAGGTGTCGTCCGTAAAGTGAATCAGAAAATC | 27 |

TABLE D8-continued

DRS DNA Sequences

| Name | Amino Acid Residue Range of SEQ ID NO: 1 | Nucleic acid sequence | SEQ ID NO: |
|---|---|---|---|
| | | GGCTCCTGTACACAGCAAGATGTGGAGCTGCATGTCCA AAAAATCTATGTCATCTCACTGGCCGAACCTCGTCTGCC TCTGCAACTGGATGATGCTGTACGCCCTGAAGCTGAAG GCGAAGAAGAAGGTCGTGCTACGGTTAATCAGGATACT CGCCTGGACAACCGTGTCATTGATCTGCGCACCTCAAC CTCTCAAGCGGTATTCCGCCTGCAATCCGGCATCTGTCA CCTGTTCCGTGAAACGCTGATCAACAAAGGGTTTGTGG AGATTCAGACCCCGAAAATCATTAGTGCCGCCAGCGAA GGTGGAGCAAATGTGTTTACCGTGTCCTATTTCAAAAA CAATGCCTATCTGGCACAGTCTCCTCAGCTGTATAAAC AAATGTGTATCTGTGCTGACTTCGAGAAAGTGTTCTCA ATCGGGCCGGTATTCCGTGCAGAGGATAGCAACACACA CCGCCATCTGACCGAATTTGTAGGCCTGGACATCGAAA TGGCCTTCAACTATCATTATCACGAGGTGATGGAAGAA ATCGCTGATACAATGGTACAGATCTTTAAAGGGCTGCA AGAACGCTTTCAAACAGAGATTCAAACCGTCAATAAAC AGTTCCCGTGTGAACCGTTCAAATTTCTGGAACCGACC CTGCGTCTGGAATATTGTGAAGCACTGGCTATGCTGCG CGAAGCTGGTGTCGAAATGGGTGATGAGGATGACCTGT CTACCCCTAACGAAAAACTGCTGGGCCACCTGGTAAAA GAAAAATATGACACAGACTTCTATATCCTGGACAAATA TCCGCTGGCAGTTCGTCCGTTTTATACGATGCCTGATCC TCGTAATCCGAAACAAAGCAACTCCTATGACATGTTCA TGCGTGGTGAAGAGATCCTGTCTGGTGCTCAACGTATC CATGATCCACAGCTGCTGACAGAACGTGCACTGCATCA CGGTATTGATCTGGAGAAAATCAAAGCCTATATCGACT CCTTTCGCTTTGGTGCCCCTCCACATGCCGGTGGTGGAA TTGGGCTGGAGCGTGTAACAATGCTGTTCCTGGGACTG CACAACGTCCGTCAAACCTCAATGTTTCCACGTGACCCT AAACGTCTGACACCT | |
| DRS-C334S | 1-1503/Reduced cysteine content | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAACAGAGTCATTGATCTTAGGACAT CAACTAGTCAGGCAGTCTTCCGTCTCCAGTCTGGCATCT GCCATCTCTTCCGAGAAACTTTAATTAACAAAGGTTTTG TGGAAATCCAAACTCCTAAAATTATTTCAGCTGCCAGT GAAGGAGGAGCCAATGTTTTTACTGTGTCATATTTTAA AAATAATGCATACCTGGCTCAGTCCCCACAGCTATATA AGCAAATGTGCATTTGTGCTGATTTTGAGAAGGTTTTCT CTATTGGACCAGTATTCAGAGCGGAAGACTCTAATACC CATAGACATCTAACTGAGTTTGTTGGTTTGGACATTGAA ATGGCTTTTAATTACCATTACCACGAAGTTATGGAAGA AATTGCTGACACCATGGTACAAATATTCAAAGGACTTC AAGAAAGGTTTCAGACTGAAATTCAAACAGTGAATAAA CAGTTCCCCATCTGAGCCATTCAAATTTTTGGAGCCAACT CTAAGACTAGAATATTGTGAAGCATTGGCTATGCTTAG GGAAGCTGGAGTCGAAATGGGAGATGAAGACGATCTG AGCACACCAAATGAAAAGCTGTTGGGTCATTTGGTAAA GGAAAAGTATGATACAGATTTTTATATTCTTGATAAAT ATCCATTGGCTGTAAGACCTTTCTATACCATGCCTGACC CAAGAAATCCCAAACAGTCCAACTCTTACGATATGTTC ATGAGAGGAGAAGAAATATTGTCAGGAGCTCAAAGAA TACATGATCCTCAACTGCTAACAGAGAGAGCTTTACAT CATGGAATTGATTTGGAGAAAATTAAGGCTTACATTGA TTCCTTCCGCTTTGGAGCCCCTCCTCATGCTGGTGGAGG CATTGGATTGGAACGAGTTACTATGCTGTTTCTGGGATT GCATAATGTTCGTCAGACCTCCATGTTCCCTCGTGATCC CAAACGACTCACTCCT | 92 |
| DRS-C349S | 1-1503/Reduced cysteine content | ATGCCCAGCGCCAGCGCCAGCCGCAAGAGTCAGGAGA AGCCGCGGGAGATCATGGACGCGGCGGAAGATTATGCT | 93 |

TABLE D8-continued

DRS DNA Sequences

| Name | Amino Acid Residue Range of SEQ ID NO: 1 | Nucleic acid sequence | SEQ ID NO: |
|---|---|---|---|
| | | AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCT<br>GCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGGCTCAGTCCCCACAGCTATATA<br>AGCAAATGTGCATTTGTGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATGTGAGCCATTCAAATTTTTGGAGCCAACT<br>CTAAGACTAGAATATTCTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT<br>GCATAATGTTCGTCAGACCTCCATGTTCCCTCGTGATCC<br>CAAACGACTCACTCCT | |
| DRS C334S/C349S | 1-1503/Reduced cysteine content | ATGCCCAGCGCCAGCGCCAGCCGCAAGAGTCAGGAGA<br>AGCCGCGGGAGATCATGGACGCGGCGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCT<br>GCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGGCTCAGTCCCCACAGCTATATA<br>AGCAAATGTGCATTTGTGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATCTGAGCCATTCAAATTTTTGGAGCCAACT<br>CTAAGACTAGAATATTCTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT | 94 |

TABLE D8-continued

DRS DNA Sequences

| Name | Amino Acid Residue Range of SEQ ID NO: 1 | Nucleic acid sequence | SEQ ID NO: |
|------|------------------------------------------|------------------------|------------|
| | | CATGGAATTGATTTGGAGAAAATTAAGGCTTACATTGA TTCCTTCCGCTTTGGAGCCCCTCCTCATGCTGGTGGAGG CATTGGATTGGAACGAGTTACTATGCTGTTTCTGGGATT GCATAATGTTCGTCAGACCTCCATGTTCCCTCGTGATCC CAAACGACTCACTCCT | |
| DRS C203A | 1-501/Reduced cysteine content | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAACAGAGTCATTGATCTTAGGACAT CAACTAGTCAGGCAGTCTTCCGTCTCCAGTCTGGCATCG CCCATCTCTTCCGAGAAACTTTAATTAACAAAGGTTTTG TGGAAATCCAAACTCCTAAAATTATTTCAGCTGCCAGT GAAGGAGGAGCCAATGTTTTTACTGTGTCATATTTTAA AAATAATGCATACCTGGCTCAGTCCCCACAGCTATATA AGCAAATGCATTTGTGCTGATTTTGAGAAGGTTTTCT CTATTGGACCAGTATTCAGAGCGGAAGACTCTAATACC CATAGACATCTAACTGAGTTTGTTGGTTTGGACATTGAA ATGGCTTTTAATTACCATTACCACGAAGTTATGGAAGA AATTGCTGACACCATGGTACAAATATTCAAAGGACTTC AAGAAAGGTTTCAGACTGAAATTCAAACAGTGAATAAA CAGTTCCCATGTGAGCCATTCAAATTTTTGGAGCCAACT CTAAGACTAGAATATTGTGAAGCATTGGCTATGCTTAG GGAAGCTGGAGTCGAAATGGGAGATGAAGACGATCTG AGCACACCAAATGAAAAGCTGTTGGGTCATTTGGTAAA GGAAAAGTATGATACAGATTTTTATATTCTTGATAAAT ATCCATTGGCTGTAAGACCTTTCTATACCATGCCTGACC CAAGAAATCCCAAACAGTCCAACTCTTACGATATGTTC ATGAGAGGAGAAGAAATATTGTCAGGAGCTCAAAGAA TACATGATCCTCAACTGCTAACAGAGAGAGCTTTACAT CATGGAATTGATTTGGAGAAAATTAAGGCTTACATTGA TTCCTTCCGCTTTGGAGCCCCTCCTCATGCTGGTGGAGG CATTGGATTGGAACGAGTTACTATGCTGTTTCTGGGATT GCATAATGTTCGTCAGACCTCCATGTTCCCTCGTGATCC CAAACGACTCACTCCT | 95 |
| DRS C203V | 1-1503/Reduced cysteine content | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAGGA TACAAGATTAGACAACAGAGTCATTGATCTTAGGACAT CAACTAGTCAGGCAGTCTTCCGTCTCCAGTCTGGCATCG TCCATCTCTTCCGAGAAACTTTAATTAACAAAGGTTTTG TGGAAATCCAAACTCCTAAAATTATTTCAGCTGCCAGT GAAGGAGGAGCCAATGTTTTTACTGTGTCATATTTTAA AAATAATGCATACCTGGCTCAGTCCCCACAGCTATATA AGCAAATGCATTTGTGCTGATTTTGAGAAGGTTTTCT CTATTGGACCAGTATTCAGAGCGGAAGACTCTAATACC CATAGACATCTAACTGAGTTTGTTGGTTTGGACATTGAA ATGGCTTTTAATTACCATTACCACGAAGTTATGGAAGA AATTGCTGACACCATGGTACAAATATTCAAAGGACTTC AAGAAAGGTTTCAGACTGAAATTCAAACAGTGAATAAA CAGTTCCCATGTGAGCCATTCAAATTTTTGGAGCCAACT | 96 |

TABLE D8-continued

DRS DNA Sequences

| Name | Amino Acid Residue Range of SEQ ID NO: 1 | Nucleic acid sequence | SEQ ID NO: |
|---|---|---|---|
| | | CTAAGACTAGAATATTGTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT<br>GCATAATGTTCGTCAGACCTCCATGTTCCCTCGTGATCC<br>CAAACGACTCACTCCT | |
| DRS C334S/C349S/ C203A | 1-1503/Reduced cysteine content | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCG<br>CCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGGCTCAGTCCCCACAGCTATATA<br>AGCAAATGTGCATTTGTGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATCTGAGCCATTCAAATTTTTGGAGCCAACT<br>CTAAGACTAGAATATTCTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT<br>GCATAATGTTCGTCAGACCTCCATGTTCCCTCGTGATCC<br>CAAACGACTCACTCCT | 97 |
| DRS C334S/C349S/ C203V | 1-501/Reduced cysteine content | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCG<br>TCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA | 98 |

TABLE D8-continued

DRS DNA Sequences

| Name | Amino Acid Residue Range of SEQ ID NO: 1 | Nucleic acid sequence | SEQ ID NO: |
|---|---|---|---|
| | | AAATAATGCATACCTGGCTCAGTCCCCACAGCTATATA<br>AGCAAATGTGCATTTGTGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATCTGAGCCATTCAAATTTTTGGAGCCAACT<br>CTAAGACTAGAATATTCTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT<br>GCATAATGTTCGTCAGACCTCCATGTTCCCTCGTGATCC<br>CAAACGACTCACTCCT | |
| DRS C334S/C349S/ C259A/C203A | 1-1503/Reduced cysteine content | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCG<br>CCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGGCTCAGTCCCCACAGCTATATA<br>AGCAAATGTGCATTGCGGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATCTGAGCCATTCAAATTTTTGGAGCCAACT<br>CTAAGACTAGAATATTCTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT<br>GCATAATGTTCGTCAGACCTCCATGTTCCCTCGTGATCC<br>CAAACGACTCACTCCT | 99 |
| DRS C334S/C349S/ C259A/C203V | 1-1503/Reduced cysteine content | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT | 100 |

TABLE D8-continued

DRS DNA Sequences

| Name | Amino Acid Residue Range of SEQ ID NO: 1 | Nucleic acid sequence | SEQ ID NO: |
|---|---|---|---|
| | | TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAACAGAGTCATTGATCTTAGGACAT<br>CAACTAGTCAGGCAGTCTTCCGTCTCCAGTCTGGCATCG<br>TCCATCTCTTCCGAGAAACTTTAATTAACAAAGGTTTTG<br>TGGAAATCCAAACTCCTAAAATTATTTCAGCTGCCAGT<br>GAAGGAGGAGCCAATGTTTTTACTGTGTCATATTTTAA<br>AAATAATGCATACCTGGCTCAGTCCCCACAGCTATATA<br>AGCAAATGTGCATTGCGGCTGATTTTGAGAAGGTTTTCT<br>CTATTGGACCAGTATTCAGAGCGGAAGACTCTAATACC<br>CATAGACATCTAACTGAGTTTGTTGGTTTGGACATTGAA<br>ATGGCTTTTAATTACCATTACCACGAAGTTATGGAAGA<br>AATTGCTGACACCATGGTACAAATATTCAAAGGACTTC<br>AAGAAAGGTTTCAGACTGAAATTCAAACAGTGAATAAA<br>CAGTTCCCATCTGAGCCATTCAAATTTTTGGAGCCAACT<br>CTAAGACTAGAATATTCTGAAGCATTGGCTATGCTTAG<br>GGAAGCTGGAGTCGAAATGGGAGATGAAGACGATCTG<br>AGCACACCAAATGAAAAGCTGTTGGGTCATTTGGTAAA<br>GGAAAAGTATGATACAGATTTTTATATTCTTGATAAAT<br>ATCCATTGGCTGTAAGACCTTTCTATACCATGCCTGACC<br>CAAGAAATCCCAAACAGTCCAACTCTTACGATATGTTC<br>ATGAGAGGAGAAGAAATATTGTCAGGAGCTCAAAGAA<br>TACATGATCCTCAACTGCTAACAGAGAGAGCTTTACAT<br>CATGGAATTGATTTGGAGAAAATTAAGGCTTACATTGA<br>TTCCTTCCGCTTTGGAGCCCCTCCTCATGCTGGTGGAGG<br>CATTGGATTGGAACGAGTTACTATGCTGTTTCTGGGATT<br>GCATAATGTTCGTCAGACCTCCATGTTCCCTCGTGATCC<br>CAAACGACTCACTCCT | |
| DRS 1-182 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTAGACAAC | 101 |
| DRS 1-180 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAGGAAGGAAGAGCTACTGTTAACCAGGA<br>TACAAGATTA | 102 |
| DRS 1-178 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT | 103 |

TABLE D8-continued

DRS DNA Sequences

| Name | Amino Acid Residue Range of SEQ ID NO: 1 | Nucleic acid sequence | SEQ ID NO: |
|---|---|---|---|
| | | GCCCCTGCAGCTGGATGATGCTGTTCGGCCTGAGGCAG AAGGAGAAGAGGAAGGAAGAGCTACTGTTAACCAGGA TACA | |
| DRS 1-176 | | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTTAACCAG | 104 |
| DRS 1-174 | | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCTACTGTT | 105 |
| DRS 1-172 | | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGAAGAGCT | 106 |
| DRS 1-170 | | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGTTTGGCTGAACCCCGTCT GCCCCTGCAGCTGGATGATGCTGTTCGGCCTGAGGCAG AAGGAGAAGAGGAAGGA | 107 |
| DRS 1-168 | | ATGCCCAGCGCCAGCGCCAGCCGCAAGAGTCAGGAGA AGCCGCGGGAGATCATGGACGCGGCGGAAGATTATGCT AAAGAGAGATATGGAATATCTTCAATGATACAATCACA AGAAAAACCAGATCGAGTTTTGGTTCGGGTTAGAGACT TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA | 108 |

TABLE D8-continued

DRS DNA Sequences

| Name | Amino Acid Residue Range of SEQ ID NO: 1 | Nucleic acid sequence | SEQ ID NO: |
|---|---|---|---|
| | | ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGAGAAGAG | |
| DRS 1-166 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCAG<br>AAGGA | 109 |
| DRS 1-164 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCTGAGGCA | 110 |
| DRS 1-162 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTTCGGCCT | 111 |
| DRS 1-160 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTGGATGATGCTGTT | 112 |
| DRS 1-158 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT | 113 |

TABLE D8-continued

DRS DNA Sequences

| Name | Amino Acid Residue Range of SEQ ID NO: 1 | Nucleic acid sequence | SEQ ID NO: |
|---|---|---|---|
| | | TCAGAAGATTTATGTGATCAGTTTGGCTGAACCCCGTCT<br>GCCCCTGCAGCTGGATGAT | |
| DRS 1-156 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTGCAGCTG | 114 |
| DRS 1-154 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCT<br>GCCCCTG | 115 |
| DRS 1-152 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCCCGTCTG | 116 |
| DRS 1-150 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCTGAACCC | 117 |
| DRS 1-148 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT<br>TGACAATACAAAAAGCTGATGAAGTTGTTTGGGTACGT<br>GCAAGAGTTCATACAAGCAGAGCTAAAGGGAAACAGT<br>GCTTCTTAGTCCTACGTCAGCAGCAGTTTAATGTCCAGG<br>CTCTTGTGGCGGTGGGAGACCATGCAAGCAAGCAGATG<br>GTTAAATTTGCTGCCAACATCAACAAAGAGAGCATTGT<br>GGATGTAGAAGGTGTTGTGAGAAAAGTGAATCAGAAA<br>ATTGGAAGCTGTACACAGCAAGACGTTGAGTTACATGT<br>TCAGAAGATTTATGTGATCAGTTTGGCT | 118 |
| DRS 1-146 | | ATGCCCAGCGCCAGCGCCAGCCGCAAGAGTCAGGAGA<br>AGCCGCGGGAGATCATGGACGCGGCGGAAGATTATGCT<br>AAAGAGAGATATGGAATATCTTCAATGATACAATCACA<br>AGAAAAACCAGATCGAGTTTTGGTTCGGGTTAGAGACT | 119 |

TABLE D8-continued

DRS DNA Sequences

| Name | Amino Acid Residue Range of SEQ ID NO: 1 | Nucleic acid sequence | SEQ ID NO: |
|---|---|---|---|
| | | TGACAATACAAAAAGCTGATGAAGTTGTTTGGGTACGT GCAAGAGTTCATACAAGCAGAGCTAAAGGGAAACAGT GCTTCTTAGTCCTACGTCAGCAGCAGTTTAATGTCCAGG CTCTTGTGGCGGTGGGAGACCATGCAAGCAAGCAGATG GTTAAATTTGCTGCCAACATCAACAAAGAGAGCATTGT GGATGTAGAAGGTGTTGTGAGAAAAGTGAATCAGAAA ATTGGAAGCTGTACACAGCAAGACGTTGAGTTACATGT TCAGAAGATTTATGTGATCAGT | |
| DRS 3-154 | | GCCAGCGCCAGCCGCAAGAGTCAGGAGAAGCCGCGGG AGATCATGGACGCGGCGGAAGATTATGCTAAAGAGAG ATATGGAATATCTTCAATGATACAATCACAAGAAAAAC CAGATCGAGTTTTGGTTCGGGTTAGAGACTTGACAATA CAAAAAGCTGATGAAGTTGTTTGGGTACGTGCAAGAGT TCATACAAGCAGAGCTAAAGGGAAACAGTGCTTCTTAG TCCTACGTCAGCAGCAGTTTAATGTCCAGGCTCTTGTGG CGGTGGGAGACCATGCAAGCAAGCAGATGGTTAAATTT GCTGCCAACATCAACAAAGAGAGCATTGTGGATGTAGA AGGTGTTGTGAGAAAAGTGAATCAGAAAATTGGAAGCT GTACACAGCAAGACGTTGAGTTACATGTTCAGAAGATT TATGTGATCAGTTTGGCTGAACCCCGTCTGCCCCTG | 120 |
| DRS 5-154 | | GCCAGCCGCAAGAGTCAGGAGAAGCCGCGGGAGATCA TGGACGCGGCGGAAGATTATGCTAAAGAGAGATATGG AATATCTTCAATGATACAATCACAAGAAAAACCAGATC GAGTTTTGGTTCGGGTTAGAGACTTGACAATACAAAAA GCTGATGAAGTTGTTTGGGTACGTGCAAGAGTTCATAC AAGCAGAGCTAAAGGGAAACAGTGCTTCTTAGTCCTAC GTCAGCAGCAGTTTAATGTCCAGGCTCTTGTGGCGGTG GGAGACCATGCAAGCAAGCAGATGGTTAAATTTGCTGC CAACATCAACAAAGAGAGCATTGTGGATGTAGAAGGT GTTGTGAGAAAAGTGAATCAGAAAATTGGAAGCTGTAC ACAGCAAGACGTTGAGTTACATGTTCAGAAGATTTATG TGATCAGTTTGGCTGAACCCCGTCTGCCCCTG | 121 |
| DRS 7-154 | | CGCAAGAGTCAGGAGAAGCCGCGGGAGATCATGGACG CGGCGGAAGATTATGCTAAAGAGAGATATGGAATATCT TCAATGATACAATCACAAGAAAAACCAGATCGAGTTTT GGTTCGGGTTAGAGACTTGACAATACAAAAAGCTGATG AAGTTGTTTGGGTACGTGCAAGAGTTCATACAAGCAGA GCTAAAGGGAAACAGTGCTTCTTAGTCCTACGTCAGCA GCAGTTTAATGTCCAGGCTCTTGTGGCGGTGGGAGACC ATGCAAGCAAGCAGATGGTTAAATTTGCTGCCAACATC AACAAAGAGAGCATTGTGGATGTAGAAGGTGTTGTGAG AAAAGTGAATCAGAAAATTGGAAGCTGTACACAGCAA GACGTTGAGTTACATGTTCAGAAGATTTATGTGATCAG TTTGGCTGAACCCCGTCTGCCCCTG | 122 |
| DRS 9-154 | | AGTCAGGAGAAGCCGCGGGAGATCATGGACGCGGCGG AAGATTATGCTAAAGAGAGATATGGAATATCTTCAATG ATACAATCACAAGAAAAACCAGATCGAGTTTTGGTTCG GGTTAGAGACTTGACAATACAAAAAGCTGATGAAGTTG TTTGGGTACGTGCAAGAGTTCATACAAGCAGAGCTAAA GGGAAACAGTGCTTCTTAGTCCTACGTCAGCAGCAGTT TAATGTCCAGGCTCTTGTGGCGGTGGGAGACCATGCAA GCAAGCAGATGGTTAAATTTGCTGCCAACATCAACAAA GAGAGCATTGTGGATGTAGAAGGTGTTGTGAGAAAAGT GAATCAGAAAATTGGAAGCTGTACACAGCAAGACGTTG AGTTACATGTTCAGAAGATTTATGTGATCAGTTTGGCTG AACCCCGTCTGCCCCTG | 123 |
| DRS 11-154 | | GAGAAGCCGCGGGAGATCATGGACGCGGCGGAAGATT ATGCTAAAGAGAGATATGGAATATCTTCAATGATACAA TCACAAGAAAAACCAGATCGAGTTTTGGTTCGGGTTAG AGACTTGACAATACAAAAAGCTGATGAAGTTGTTTGGG TACGTGCAAGAGTTCATACAAGCAGAGCTAAAGGGAA ACAGTGCTTCTTAGTCCTACGTCAGCAGCAGTTTAATGT CCAGGCTCTTGTGGCGGTGGGAGACCATGCAAGCAAGC AGATGGTTAAATTTGCTGCCAACATCAACAAAGAGAGC ATTGTGGATGTAGAAGGTGTTGTGAGAAAAGTGAATCA GAAAATTGGAAGCTGTACACAGCAAGACGTTGAGTTAC ATGTTCAGAAGATTTATGTGATCAGTTTGGCTGAACCCC GTCTGCCCCTG | 124 |

TABLE D8-continued

DRS DNA Sequences

| Name | Amino Acid Residue Range of SEQ ID NO: 1 | Nucleic acid sequence | SEQ ID NO: |
|---|---|---|---|
| DRS 13-154 | | CCGCGGGAGATCATGGACGCGGCGGAAGATTATGCTAA AGAGAGATATGGAATATCTTCAATGATACAATCACAAG AAAAACCAGATCGAGTTTTGGTTCGGGTTAGAGACTTG ACAATACAAAAAGCTGATGAAGTTGTTTGGGTACGTGC AAGAGTTCATACAAGCAGAGCTAAAGGGAAACAGTGC TTCTTAGTCCTACGTCAGCAGCAGTTTAATGTCCAGGCT CTTGTGGCGGTGGGAGACCATGCAAGCAAGCAGATGGT TAAATTTGCTGCCAACATCAACAAAGAGAGCATTGTGG ATGTAGAAGGTGTTGTGAGAAAAGTGAATCAGAAAATT GGAAGCTGTACACAGCAAGACGTTGAGTTACATGTTCA GAAGATTTATGTGATCAGTTTGGCTGAACCCCGTCTGCC CCTG | 125 |
| DRS15-154 | | GAGATCATGGACGCGGCGGAAGATTATGCTAAAGAGA GATATGGAATATCTTCAATGATACAATCACAAGAAAAA CCAGATCGAGTTTTGGTTCGGGTTAGAGACTTGACAAT ACAAAAAGCTGATGAAGTTGTTTGGGTACGTGCAAGAG TTCATACAAGCAGAGCTAAAGGGAAACAGTGCTTCTTA GTCCTACGTCAGCAGCAGTTTAATGTCCAGGCTCTTGTG GCGGTGGGAGACCATGCAAGCAAGCAGATGGTTAAATT TGCTGCCAACATCAACAAAGAGAGCATTGTGGATGTAG AAGGTGTTGTGAGAAAAGTGAATCAGAAAATTGGAAG CTGTACACAGCAAGACGTTGAGTTACATGTTCAGAAGA TTTATGTGATCAGTTTGGCTGAACCCCGTCTGCCCCTG | 126 |
| DRS 17-154 | | ATGGACGCGGCGGAAGATTATGCTAAAGAGAGATATG GAATATCTTCAATGATACAATCACAAGAAAAACCAGAT CGAGTTTTGGTTCGGGTTAGAGACTTGACAATACAAAA AGCTGATGAAGTTGTTTGGGTACGTGCAAGAGTTCATA CAAGCAGAGCTAAAGGGAAACAGTGCTTCTTAGTCCTA CGTCAGCAGCAGTTTAATGTCCAGGCTCTTGTGGCGGT GGGAGACCATGCAAGCAAGCAGATGGTTAAATTTGCTG CCAACATCAACAAAGAGAGCATTGTGGATGTAGAAGGT GTTGTGAGAAAAGTGAATCAGAAAATTGGAAGCTGTAC ACAGCAAGACGTTGAGTTACATGTTCAGAAGATTTATG TGATCAGTTTGGCTGAACCCCGTCTGCCCCTG | 127 |
| DRS 19-154 | | GCGGCGGAAGATTATGCTAAAGAGAGATATGGAATATC TTCAATGATACAATCACAAGAAAAACCAGATCGAGTTT TGGTTCGGGTTAGAGACTTGACAATACAAAAAGCTGAT GAAGTTGTTTGGGTACGTGCAAGAGTTCATACAAGCAG AGCTAAAGGGAAACAGTGCTTCTTAGTCCTACGTCAGC AGCAGTTTAATGTCCAGGCTCTTGTGGCGGTGGGAGAC CATGCAAGCAAGCAGATGGTTAAATTTGCTGCCAACAT CAACAAAGAGAGCATTGTGGATGTAGAAGGTGTTGTGA GAAAAGTGAATCAGAAAATTGGAAGCTGTACACAGCA AGACGTTGAGTTACATGTTCAGAAGATTTATGTGATCA GTTTGGCTGAACCCCGTCTGCCCCTG | 128 |
| DRS 21-154 | | GCGGCGGAAGATTATGCTAAAGAGAGATATGGAATATC TTCAATGATACAATCACAAGAAAAACCAGATCGAGTTT TGGTTCGGGTTAGAGACTTGACAATACAAAAAGCTGAT GAAGTTGTTTGGGTACGTGCAAGAGTTCATACAAGCAG AGCTAAAGGGAAACAGTGCTTCTTAGTCCTACGTCAGC AGCAGTTTAATGTCCAGGCTCTTGTGGCGGTGGGAGAC CATGCAAGCAAGCAGATGGTTAAATTTGCTGCCAACAT CAACAAAGAGAGCATTGTGGATGTAGAAGGTGTTGTGA GAAAAGTGAATCAGAAAATTGGAAGCTGTACACAGCA AGACGTTGAGTTACATGTTCAGAAGATTTATGTGATCA GTTTGGCTGAACCCCGTCTG | 129 |
| DRS 23-154 | | GCGGCGGAAGATTATGCTAAAGAGAGATATGGAATATC TTCAATGATACAATCACAAGAAAAACCAGATCGAGTTT TGGTTCGGGTTAGAGACTTGACAATACAAAAAGCTGAT GAAGTTGTTTGGGTACGTGCAAGAGTTCATACAAGCAG AGCTAAAGGGAAACAGTGCTTCTTAGTCCTACGTCAGC AGCAGTTTAATGTCCAGGCTCTTGTGGCGGTGGGAGAC CATGCAAGCAAGCAGATGGTTAAATTTGCTGCCAACAT CAACAAAGAGAGCATTGTGGATGTAGAAGGTGTTGTGA GAAAAGTGAATCAGAAAATTGGAAGCTGTACACAGCA AGACGTTGAGTTACATGTTCAGAAGATTTATGTGATCA GTTTGGCTGAACCC | 130 |

TABLE D8-continued

DRS DNA Sequences

| Name | Amino Acid Residue Range of SEQ ID NO: 1 | Nucleic acid sequence | SEQ ID NO: |
|---|---|---|---|
| DRS 11-146 | | ATGCAGGAGAAGCCGCGGGAGATCATGGACGCGGCGG AAGATTATGCTAAAGAGAGATATGGAATATCTTCAATG ATACAATCACAAGAAAAACCAGATCGAGTTTTGGTTCG GGTTAGAGACTTGACAATACAAAAAGCTGATGAAGTTG TTTGGGTACGTGCAAGAGTTCATACAAGCAGAGCTAAA GGGAAACAGTGCTTCTTAGTCCTACGTCAGCAGCAGTT TAATGTCCAGGCTCTTGTGGCGGTGGGAGACCATGCAA GCAAGCAGATGGTTAAATTTGCTTGCAACATCAACAAA GAGAGCATTGTGGATGTAGAAGGTGTTGTGAGAAAAGT GAATCAGAAAATTGGAAGCTGTACACAGCAAGACGTTG AGTTACATGTTCAGAAGATTTATGTGATCAGT | 131 |
| DRS 13-146 | | ATGAAGCCGCGGGAGATCATGGACGCGGCGGAAGATT ATGCTAAAGAGAGATATGGAATATCTTCAATGATACAA TCACAAGAAAAACCAGATCGAGTTTTGGTTCGGGTTAG AGACTTGACAATACAAAAAGCTGATGAAGTTGTTTGGG TACGTGCAAGAGTTCATACAAGCAGAGCTAAAGGGAAA ACAGTGCTTCTTAGTCCTACGTCAGCAGCAGTTTAATGT CCAGGCTCTTGTGGCGGTGGGAGACCATGCAAGCAAGC AGATGGTTAAATTTGCTTGCAACATCAACAAAGAGAGC ATTGTGGATGTAGAAGGTGTTGTGAGAAAAGTGAATCA GAAAATTGGAAGCTGTACACAGCAAGACGTTGAGTTAC ATGTTCAGAAGATTTATGTGATCAGT | 132 |
| DRS 13-146/A106C | | ATGAAGCCGCGGGAGATCATGGACGCGGCGGAAGATT ATGCTAAAGAGAGATATGGAATATCTTCAATGATACAA TCACAAGAAAAACCAGATCGAGTTTTGGTTCGGGTTAG AGACTTGACAATACAAAAAGCTGATGAAGTTGTTTGGG TACGTGCAAGAGTTCATACAAGCAGAGCTAAAGGGAAA ACAGTGCTTCTTAGTCCTACGTCAGCAGCAGTTTAATGT CCAGGCTCTTGTGGCGGTGGGAGACCATGCAAGCAAGC AGATGGTTAAATTTGCTTGCAACATCAACAAAGAGAGC ATTGTGGATGTAGAAGGTGTTGTGAGAAAAGTGAATCA GAAAATTGGAAGCTGTACACAGCAAGACGTTGAGTTAC ATGTTCAGAAGATTTATGTGATCAGT | 133 |
| DRS 17-146 | | ATGATCATGGACGCGGCGGAAGATTATGCTAAAGAGA GATATGGAATATCTTCAATGATACAATCACAAGAAAAA CCAGATCGAGTTTTGGTTCGGGTTAGAGACTTGACAAT ACAAAAAGCTGATGAAGTTGTTTGGGTACGTGCAAGAG TTCATACAAGCAGAGCTAAAGGGAAACAGTGCTTCTTA GTCCTACGTCAGCAGCAGTTTAATGTCCAGGCTCTTGTG GCGGTGGGAGACCATGCAAGCAAGCAGATGGTTAAATT TGCTTGCAACATCAACAAAGAGAGCATTGTGGATGTAG AAGGTGTTGTGAGAAAAGTGAATCAGAAAATTGGAAG CTGTACACAGCAAGACGTTGAGTTACATGTTCAGAAGA TTTATGTGATCAGT | 134 |
| DRS 21-146 | | ATGGCGGAAGATTATGCTAAAGAGAGATATGGAATATC TTCAATGATACAATCACAAGAAAAACCAGATCGAGTTT TGGTTCGGGTTAGAGACTTGACAATACAAAAAGCTGAT GAAGTTGTTTGGGTACGTGCAAGAGTTCATACAAGCAG AGCTAAAGGGAAACAGTGCTTCTTAGTCCTACGTCAGC AGCAGTTTAATGTCCAGGCTCTTGTGGCGGTGGGAGAC CATGCAAGCAAGCAGATGGTTAAATTTGCTTGCAACAT CAACAAAGAGAGCATTGTGGATGTAGAAGGTGTTGTGA GAAAAGTGAATCAGAAAATTGGAAGCTGTACACAGCA AGACGTTGAGTTACATGTTCAGAAGATTTATGTGATCA GT | 135 |

Additional coding or non-coding sequences may, but need not, be present within a polynucleotide of the present invention, and a polynucleotide may, but need not, be linked to other molecules and/or support materials. Hence, the polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably.

It is therefore contemplated that a polynucleotide fragment of almost any length may be employed; with the total length preferably being limited by the ease of preparation and use in the intended recombinant DNA protocol. Included are polynucleotides of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 43, 44, 45, 46, 47, 48, 49, 50, 60, 70, 80, 90, 100, 110, 120, 130, 140, 150, 160, 170, 180, 190, 200, 220, 240, 260, 270, 280, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000 or more (including all integers in between) bases in length, including any portion or fragment (e.g., greater than about 6, 7, 8, 9, or 10 nucleotides in length) of an AARS reference polynucleotide (e.g., base number X-Y, in which X is about 1-3000 or more and Y is about 10-3000 or more), or its complement.

Embodiments of the present invention also include "variants" of the AARS reference polynucleotide sequences. Polynucleotide "variants" may contain one or more substitutions, additions, deletions and/or insertions in relation to a reference polynucleotide. Generally, variants of an AARS reference polynucleotide sequence may have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence (Such as for example, SEQ ID NO:2, 25-28, 30, or 92-135) as determined by sequence alignment programs described elsewhere herein using default parameters. In certain embodiments, variants may differ from a reference sequence by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 43, 44, 45, 46, 47, 48, 49, 50, 60, 70, 80, 90, 100 (including all integers in between) or more bases. In certain embodiments, such as when the polynucleotide variant encodes a DRS polypeptide having a non-canonical activity, the desired activity of the encoded DRS polypeptide is not substantially diminished relative to the unmodified polypeptide. The effect on the activity of the encoded polypeptide may generally be assessed as described herein.

Certain embodiments include polynucleotides that hybridize to a reference DRS polynucleotide sequence, (such as for example, SEQ ID NO:2, 25-28, 30, or 92-135) or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C.

High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104. While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m=81.5+16.6$ ($\log_{10}$ M)$+0.41$ (% G+C)$-0.63$ (% formamide)$-(600/\text{length})$ wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m-15°$ C. for high stringency, or $T_m-30°$ C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

DRS Variants

As noted above, embodiments of the present invention include all homologues, orthologs, and naturally-occurring isoforms of aspartyl-tRNA synthetase (e.g., any of the proteins, or their corresponding nucleic acids listed in Tables D1 to D8) which i) retain detectable non canonical activity, and ii) which comprise, or can be modified to comprise, at least one mutation at either Cys76 or Cys130 (using the numbering of SEQ ID NO:1) which replaces the native cysteine with another naturally, or non-naturally, occurring amino acid.

Also included are "variants" of these DRS reference polypeptides. The recitation polypeptide "variant" refers to polypeptides that are distinguished from a reference DRS polypeptide by the addition, deletion, and/or substitution of at least one amino acid residue, and which typically retain (e.g., mimic) or modulate (e.g., antagonize) one or more non-canonical activities of a reference DRS polypeptide. The structure of human aspartyl-tRNA synthetase has been determined to a resolution of 1.7 A. (WO2010/120509) providing a detailed physical description of the protein, which in conjunction with the primary amino acid sequence provides precise insights into the roles played by specific amino acids within the protein. Accordingly it is within the skill of those in the art to identify amino acids suitable for substitution and to design variants with substantially unaltered, improved, or decreased activity with no more than routine experimentation.

In certain embodiments, a polypeptide variant is distinguished from a reference polypeptide by one or more substitutions, which may be conservative or non-conservative, as described herein and known in the art. In certain embodiments, the polypeptide variant comprises conservative substitutions and, in this regard, it is well understood in the art that some amino acids may be changed to others with broadly similar properties without changing the nature of the activity of the polypeptide.

Specific examples of DRS polypeptide variants useful in any of the methods and compositions of the invention include full-length DRS polypeptides, or truncations or splice variants thereof (e.g., any of the proteins or nucleic acids listed in Tables D1 to D8) which i) retain detectable non canonical activity, and ii) comprise, or have been modified to comprise at least one mutation at either Cys76 or Cys130 (using the numbering of SEQ ID NO:1) which replaces the native cysteine with another amino acid), and iii) have one or more additional amino acid substitutions. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to a corresponding sequence of a DRS reference polypeptide, as described herein, (e.g., any of the proteins or nucleic acids listed in Tables D1 to D8) and substantially retains the non-canonical activity of that reference polypeptide. Also included are sequences differing from the reference DRS sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of the reference DRS polypeptide. In certain embodiments, the amino acid additions or deletions occur at the C-terminal end and/or the N-terminal end of the DRS reference polypeptide. In certain embodiments, the amino acid additions include 1, 2, 3, 4, 5, 6, 7, 8, 9, 10, 11, 12, 13, 14, 15, 16, 17, 18, 19, 20, 30, 40, 50 or more wild-type residues (i.e., from the corresponding full-length DRS polypeptide) that are proximal to the C-terminal end and/or the N-terminal end of the DRS reference polypeptide.

In some embodiments, the DRS polypeptides comprise a polypeptide fragment of the full length Aspartyl-tRNA synthetase of about 50 to 250 amino acids, which comprises, or consists essentially of the amino acids 1-224, 1-184, 1-174, 1-171, 1-154, 11-146, 13-146, or 23-154 of the DRS polypeptide sequence set forth in SEQ ID NO:1, comprising at least one mutation at either Cys76 or Cys130 (using the numbering of SEQ ID NO:1), and variants thereof.

In certain embodiments, a DRS polypeptide of the invention comprises the minimal active fragment of a full-length DRS polypeptide capable of modulating TLR activity etc., in vivo or having other desirable non-canonical aspartyl-tRNA synthetase activities. In one aspect, such a minimal active fragment consists essentially of the anticodon binding domain, (i.e., about amino acids 23-154 of SEQ ID NO:1). In some aspects, the minimal active fragment consists essentially of the anticodon binding domain anticodon binding domain, and N-terminal amphiphilic helix (i.e., about amino acids 1-154 of SEQ ID NO:1. In some aspects, of either of these embodiments, the minimal active fragment consists essentially of the anticodon binding domain anticodon binding domain, and N-terminal amphiphilic helix and a variable amount of the flexible 29 amino acid linker (amino acids 154 to 182 of SEQ ID NO:1). In different embodiments, such minimal active fragments may comprise 1, 2, 3, 4, 5, 6, 7, 8, 9, 10, 11, 12, 13, 14, 15, 16, 17, 18, 19, 20, 21, 22, 23, 24, 25, 26, 27, 28, or all 29 amino acids of the flexible linker.

Without wishing to be bound by any one theory, the unique orientation, or conformation, of the anticodon-recognition domain in certain DRS polypeptides may contribute to the enhanced non canonical activities observed in these proteins. In certain embodiments, non-canonical activity may be modulated by the selective deletion, in whole or part of the Amphiphilic helix domain, anticodon-recognition domain, or the aminoacylation domain. Specific examples of splice variants that accomplish such embodiments include for example AspRS1$^{N6}$ and AspRS1$^{C2}$ (partial deletion of the anticodon binding domain), AspRS1$^{N7}$ (partial deletion of both the anticodon binding domain and aminoacylation domain), AspRS1$^{N7}$ (partial deletion of the aminoacylation domain). For the purposes of the present invention, all such DRS polypeptides comprise at least one mutation at either Cys76 or Cys130 (using the numbering of SEQ ID NO:1).

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polypeptides include "reference sequence," "comparison window," "sequence identity," "percentage of sequence identity" and "substantial identity." A "reference sequence" is at least 12 but frequently 15 to 18 and often at least 25 monomer units, inclusive of nucleotides and amino acid residues, in length. Because two polypeptides may each comprise (1) a sequence (i.e., only a portion of the complete polypeptides sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

In certain embodiments, variant polypeptides differ from the corresponding DRS reference sequences by at least 1% but less than 20%, 15%, 10% or 5% of the residues. (If this comparison requires alignment, the sequences should be aligned for maximum similarity. "Looped" out sequences from deletions or insertions, or mismatches, are considered differences.) The differences are, suitably, differences or changes at a non-essential residue or a conservative substitution. In certain embodiments, the molecular weight of a variant DRS polypeptide differs from that of the DRS reference polypeptide by about 1%, 2%, 3%, 4%, 5%, 6%, 7%, 8%, 9%, 10%, 11%, 12%, 13%, 14%, 15%, 16%, 17%, 18%, 19%, 20%, or more.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches.

The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff (1992) Proc Natl Acad Sci USA 89:10915-10919). GAP uses the algorithm of Needleman and Wunsch (1970) J Mol Biol 48:443-453, to find the alignment of two complete sequences that maximizes the number of matches and minimizes the number of gaps.

In one particular embodiment, the DRS polypeptides comprise an amino acid sequence that can be optimally aligned with a polypeptide sequence of any one of SEQ ID NOS:1, 3-24, 29, 31, or 48-91 to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1, and wherein the polypeptide optionally comprises at least one mutation at either Cys76 or Cys130.

Also included are biologically active "fragments" of the DRS reference polypeptides, i.e., biologically active fragments of the DRS protein fragments. Representative biologically active fragments generally participate in an interaction, e.g., an intramolecular or an inter-molecular interaction. An inter-molecular interaction can be a specific binding interaction or an enzymatic interaction. An inter-molecular interaction can be between a DRS polypeptide and a cellular binding partner, such as a cellular receptor or other host molecule that participates in the non-canonical activity of the DRS polypeptide.

A biologically active fragment of an DRS reference polypeptide can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 38, 359, 360, 361, 362, 363, 364, 365, 380, 400, 450, 500 or more contiguous or non-contiguous amino acids, including all integers (e.g., 101, 102, 103) and ranges (e.g., 50-100, 50-150, 50-200) in between, of the amino acid sequences set forth in any one of the DRS reference polypeptides described herein. In certain embodiments, a biologically active fragment comprises a non-canonical activity-related sequence, domain, or motif. In certain embodiments, the C-terminal or N-terminal region of any DRS reference polypeptide may be truncated by about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 160, 170, 180, 190, 200, 250, 300, 350, 400, 450, 500 or more amino acids, or by about 10-50, 20-50, 50-100, 100-150, 150-200, 200-250, 250-300, 300-350, 350-400, 400-450, 450-500 or more amino acids, including all integers and ranges in between (e.g., 101, 102, 103, 104, 105), so long as the truncated DRS polypeptide retains the non-canonical activity of the reference polypeptide. Typically, the biologically-active fragment has no less than about 1%, 10%, 25%, or 50% of an activity of the biologically-active (i.e., non-canonical activity) DRS reference polypeptide from which it is derived. Exemplary methods for measuring such non-canonical activities are described in the Examples.

In some embodiments, DRS proteins, variants, and biologically active fragments thereof, bind to one or more cellular binding partners with an affinity of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 100, or 150 nM. In some embodiments, the binding affinity of a DRS protein fragment for a selected cellular binding partner, particularly a binding partner that participates in a non-canonical activity, can be stronger than that of the corresponding full length DRS polypeptide or a specific alternatively spliced DRS polypeptide variant, by at least about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between).

As noted above, a DRS polypeptide may be altered in various ways including amino acid substitutions, deletions, truncations, and insertions. Methods for such manipulations are generally known in the art. For example, amino acid sequence variants of a DRS reference polypeptide can be prepared by mutations in the DNA. Methods for mutagenesis and nucleotide sequence alterations are well known in the art. See, for example, Kunkel (1985, Proc. Natl. Acad. Sci. USA. 82: 488-492), Kunkel et al., (1987, Methods in Enzymol, 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Biologically active truncated and/or variant DRS polypeptides may contain conservative amino acid substitutions at various locations along their sequence, as compared to a reference DRS amino acid residue, and such additional substitutions may further enhance the activity or stability of the DRS polypeptides with altered cysteine content. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science,* 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

| Amino acid sub-classification | |
|---|---|
| Sub-classes | Amino acids |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant DRS polypeptide can readily be determined by assaying its non-canonical activity, as described herein. Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE B

Exemplary Amino Acid Substitutions

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm.C. Brown Publishers (1993).

Thus, a predicted non-essential amino acid residue in a truncated and/or variant DRS polypeptide is typically replaced with another amino acid residue from the same side chain family. Alternatively, mutations can be introduced randomly along all or part of a DRS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined A "non-essential" amino acid residue is a residue that can be altered from the reference sequence of an embodiment polypeptide without abolishing or substantially altering one or more of its non canonical activities. Suitably, the alteration does not substantially abolish one of these activities, for example, the activity is at least 20%, 40%, 60%, 70% or 80% 100%, 500%, 1000% or more of the reference DRS sequence. An "essential" amino acid residue is a residue that, when altered from the reference sequence of a DRS polypeptide, results in abolition of an activity of the parent molecule such that less than 20% of the reference activity is present. For example, such essential amino acid residues include those that are conserved in DRS polypeptides across different species, including those sequences that are conserved in the active binding site(s) or motif(s) of DRS polypeptides from various sources.

Modified DRS Polypeptides

Certain embodiments of the present invention also contemplate the use of modified DRS polypeptides, including modifications that improved the desired characteristics of a DRS polypeptide, as described herein. Modifications of DRS polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of fusion proteins, carbohydrate or lipid moieties, cofactors, and the like. Exemplary modifications also include PEGylation of a DRS polypeptide (see, e.g., Veronese and Harris, *Advanced Drug Delivery Reviews* 54: 453-456, 2002; and Pasut et al., *Expert Opinion. Ther. Patents* 14(6) 859-894 2004, both herein incorporated by reference). In some embodiments, such PEGylated DRS polypeptides comprise a mutation at position Cys76 to remove the endogenous cysteine, and the PEG moieties are coupled through Cys130 via an optional linker.

PEG is a well-known polymer having the properties of solubility in water and in many organic solvents, lack of toxicity, and lack of immunogenicity. It is also clear, colorless, odorless, and chemically stable. For these reasons and others, PEG has been selected as the preferred polymer for attachment, but it has been employed solely for purposes of illustration and not limitation. Similar products may be obtained with other water-soluble polymers, including without limitation; polyvinyl alcohol, other poly(alkylene oxides) such as polypropylene glycol) and the like, poly (oxyethylated polyols) such as poly(oxyethylated glycerol) and the like, carboxymethylcellulose, dextran, polyvinyl alcohol, polyvinyl purrolidone, poly-1,3-dioxolane, poly-1, 3,6-trioxane, ethylene/maleic anhydride, and polyaminoacids. One skilled in the art will be able to select the desired polymer based on the desired dosage, circulation time, resistance to proteolysis, and other considerations.

In particular a wide variety of PEG derivatives are both available and suitable for use in the preparation of PEG-conjugates. For example, NOF Corp.'s PEG reagents sold under the trademark SUNBRIGHT® Series provides numerous PEG derivatives, including methoxypolyethylene glycols and activated PEG derivatives such as methoxy-PEG amines, maleimides, N-hydroxysuccinimide esters, and carboxylic acids, for coupling by various methods to the N-terminal, C-terminal or any internal amino acid of the AARS polypeptide. Nektar Therapeutics' Advanced PEGylation technology also offers diverse PEG-coupling technologies to potentially improve the safety and efficacy of an DRS polypeptide based therapeutic.

Patents, published patent applications, and related publications will also provide those skilled in the art reading this disclosure with significant possible PEG-coupling technologies and PEG-derivatives. See, e.g., U.S. Pat. Nos. 6,436, 386; 5,932,462; 5,900,461; 5,824,784; and 4,904,584; the contents of which are incorporated by reference in their entirety, describe such technologies and derivatives, and methods for their manufacture.

In certain aspects, chemoselective ligation technology may be utilized to modify DRS polypeptides of the invention, such as by attaching polymers in a site-specific and controlled manner (for example to Cys130). Such technology typically relies on the incorporation of chemoselective anchors into the protein backbone by either chemical, or recombinant means, and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

In other embodiments, fusion proteins (including proteins chemically coupled through Cys130, as well as translational fusions) of DRS polypeptide to other proteins are also included, and these fusion proteins may modulate the DRS polypeptide's biological activity, secretion, antigenicity, targeting, biological life, ability to penetrate cellular membranes, or the blood brain barrier, or pharmacokinetic properties. Examples of fusion proteins that improve pharmacokinetic properties ("PK modifiers") include without limitation, fusions to human albumin (Osborn et al.: *Eur. J. Pharmacol.* 456(1-3): 149-158, (2002)), antibody Fc domains, poly Glu or poly Asp sequences, and transferrin. Additionally, fusion with conformationally disordered polypeptide sequences composed of the amino acids Pro, Ala, and Ser ('PASylation') or hydroxyethyl starch (sold under the trademark HESYLATION®) provides a simple way to increase the hydrodynamic volume of the DRS polypeptide. This additional extension adopts a bulky random structure, which significantly increases the size of the resulting fusion protein. By this means the typically rapid clearance of smaller DRS polypeptides via kidney filtration is retarded by several orders of magnitude. Additionally use of Ig G fusion proteins has also been shown to enable some fusion protein proteins to penetrate the blood brain barrier (Fu et al., (2010) Brain Res. 1352:208-13).

Examples of fusion proteins that improve penetration across cellular membranes include fusions to membrane translocating sequences. In this context, the term "membrane translocating sequences" refers to naturally occurring and synthetic amino acid sequences that are capable of membrane translocation across a cellular membrane, e.g., a nuclear or plasma membrane. Representative membrane translocating sequences include those based on the naturally occurring membrane translocating sequences derived from the Tat protein, and homeotic transcription protein Antennapedia, as well as synthetic membrane translocating sequences based in whole or part on poly Arginine and Lysine resides. Representative membrane translocating sequences include for example those disclosed in the following patents, U.S. Pat. No. 5,652,122; U.S. Pat. No. 5,670,617; U.S. Pat. No. 5,674,980; U.S. Pat. No. 5,747,641; U.S. Pat. No. 5,804,604; U.S. Pat. No. 6,316,003; U.S. Pat. No. 6,589,503; U.S. Pat. No. 7,585,834; U.S. Pat. No. 7,312,244; U.S. Pat. No. 7,279,502 U.S. Pat. No. 7,229,961; U.S. Pat. No. 7,169,814; U.S. Pat. No. 7,453,011; U.S. Pat. No. 7,235,695; U.S. Pat. No. 6,982,351; U.S. Pat. No. 6,605,115; U.S. Pat. No. 7,306,784; U.S. Pat. No. 7,306,783; U.S. Pat. No. 6,348,185; U.S. Pat. No. 6,881,825; U.S. Pat. No. 7,431,915; WO0074701A2; WO2007111993A2; WO2007106554A2; WO02069930A1; WO03049772A2; WO03106491A2; and WO2008063113A1. It will be appreciated that a flexible molecular linker (or spacer) optionally may be interposed between, and covalently join, the DRS polypeptide and any of the fusion proteins disclosed herein.

Additionally in some embodiments, the DRS polypeptide can include synthetic, or naturally occurring secretion signal sequences, derived from other well characterized secreted proteins. In some embodiments such proteins, may be processed by proteolytic cleavage to form the DRS polypeptide in situ. Such fusions proteins may also include for example fusions of DRS polypeptide to ubiquitin to provide a new N-terminal amino acid, or the use of a secretion signal to mediate high level secretion of the DRS polypeptide into the extracellular medium, or N, or C-terminal epitope tags to improve purification or detection.

Production of DRS Polypeptides

DRS polypeptide may be prepared by any suitable procedure known to those of skill in the art for example, by using standard solid-phase peptide synthesis (Merrifield, *J. Am. Chem. Soc.* 85:2149-2154 (1963)), or by recombinant technology using a genetically modified host. Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

DRS polypeptides can also be produced by expressing a DNA sequence encoding the DRS polypeptide in question) in a suitable host cell by well-known techniques. The polynucleotide sequence coding for the DRS polypeptide may be prepared synthetically by established standard methods, e.g., the phosphoamidite method described by Beaucage et al. (1981) *Tetrahedron Letters* 22:1859-1869, or the method described by Matthes et al. (1984) *EMBO Journal* 3:801-805. According to the phosphoramidite method, oligonucleotides are synthesized, e.g., in an automatic DNA synthesizer, purified, duplexed and ligated to form the synthetic DNA construct. Alternatively the DNA construct can be constructed using standard recombinant molecular biological techniques including restriction enzyme mediated cloning and PCR based gene amplification.

The polynucleotide sequences may also be of mixed genomic, cDNA, and synthetic origin. For example, a genomic or cDNA sequence encoding a leader peptide may be joined to a genomic or cDNA sequence encoding the DRS polypeptide, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides. In some embodiments a signal sequence can be included before the coding sequence. This sequence encodes a signal peptide N-terminal to the coding sequence which communicates to the host cell to direct the polypeptide to the cell surface or secrete the polypeptide into the media. Typically the signal peptide is clipped off by the host cell before the protein leaves the cell. Signal peptides can be found in variety of proteins in prokaryotes and eukaryotes.

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems transformed with viral, plasmid, episomal or integrating expression vectors.

The "control elements" or "regulatory sequences" present in an expression vector are non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

Certain embodiments may employ *E. coli*-based expression systems (see, e.g., Structural Genomics Consortium et al., *Nature Methods*. 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series). These and related embodiments may utilize the expression host strain BL21 (DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as ROSETTA™ (DE3) and Rosetta 2 (DE3) strains. Cell lysis and sample handling may also be improved using reagents sold under the trademarks BENZONASE® nuclease and BUGBUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG.

Particular embodiments employ hexahistidine tags (such as those sold under the trademark HIS•TAG® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology*. 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L. In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987). Also included are *Pichia pandoris* expression systems (see, e.g., Li et al., *Nature Biotechnology*. 24, 210-215, 2006; and Hamilton et al., *Science*, 301:1244, 2003). Certain embodiments include yeast systems that are engineered to selectively glycosylate proteins, including yeast that have humanized N-glycosylation pathways, among others (see, e.g., Hamilton et al., *Science*. 313:1441-1443, 2006; Wildt et al., *Nature Reviews Microbiol*. 3:119-28, 2005; and Gerngross et al., *Nature-Biotechnology*. 22:1409-1414, 2004; U.S. Pat. Nos. 7,629,163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., *Proc. Natl. Acad. Sci. U.S.A.* 91:3224-3227 (1994)). Also included are baculovirus expression systems, including those that utilize SF9, SF21, and *T. ni* cells (see, e.g., Murphy and Piwnica-Worms, *Curr Protoc Protein Sci*. Chapter 5:Unit5.4, 2001). Insect systems can provide post-translation modifications that are similar to mammalian systems.

In mammalian host cells, a number of expression systems are well known in the art and commercially available. Exemplary mammalian vector systems include for example, pCEP4, pREP4, and pREP7 from Invitrogen, the PerC6 system from Crucell, and Lentiviral based systems such as pLP1 from Invitrogen, and others. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Vivol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS USA* 77:4216 (1980)); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included is cell-free expression of proteins. These and related embodiments typically utilize purified RNA polymerase, ribosomes, tRNA and ribonucleotides; these reagents may be produced by extraction from cells or from a cell-based expression system.

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation, or the insertion of non-naturally occurring amino acids (see generally U.S. Pat. No. 7,939,496; U.S. Pat. No. 7,816,320; U.S. Pat. No. 7,947,473; U.S. Pat. No. 7,883,866; U.S. Pat. No. 7,838,265; U.S. Pat. No. 7,829,310; U.S. Pat. No. 7,820,766; U.S. Pat. No. 7,820,766; U.S. Pat. No. 7,737,226, U.S. Pat. No. 7,736,872; U.S. Pat. No. 7,638,299; U.S. Pat. No. 7,632,924; and U.S. Pat. No. 7,230,068). In some embodiments, such non-naturally occurring amino acids may be inserted at position Cys130. Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

The DRS polypeptides produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art. Several exemplary methods are also disclosed in the Examples sections.

Recombinant Vectors

Another embodiment of the invention provides for recombinant vectors and recombinant viral vectors comprising a polynucleotide whose sequence comprises a nucleotide sequence which encodes for any of the DRS polypeptides disclosed herein.

The selection of recombinant vectors suitable for expressing the DRS polypeptides of the invention, methods for inserting nucleic acid sequences for expressing the DRS polypeptides into the vector, and methods of delivering the recombinant vector to the cells of interest are within the skill in the art. See, for example Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; Paul C P et al. (2002), Nat. Biotechnol. 20: 505-508, Conese et al., Gene Therapy 11: 1735-1742 (2004), and Fjord-Larsen et al., (2005) Exp Neurol 195:49-60 the entire disclosures of which are herein incorporated by reference.

Representative commercially available recombinant expression vectors include, for example, pREP4, pCEP4, pREP7 and pcDNA3.1 and pcDNA™5/FRT from Invitrogen, and pBK-CMV and pExchange-6 Core Vectors from Stratagene.

Recombinant vectors can be administered to a patient directly or in conjunction with a suitable delivery reagent, including the Minis Transit LT1 lipophilic reagent; lipofectin; lipofectamine; cellfectin; polycations (e.g., polylysine) or liposomes. Selection of recombinant viral vectors suitable for use in the invention, methods for inserting nucleic acid sequences for expressing the DRS polypeptides into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; and Anderson W F (1998), *Nature* 392: 25-30, the entire disclosures of which are herein incorporated by reference.

Representative commercially available viral expression vectors include, but are not limited to, the adenovirus-based systems, such as the Per.C6 system available from Crucell, Inc., lentiviral-based systems such as pLP1 from Invitrogen, and retroviral vectors such as Retroviral Vectors pFB-ERV and pCFB-EGSH from Stratagene (US). In general, any viral vector capable of accepting the coding sequences for the DRS polypeptides to be expressed can be used, for example vectors derived from adenovirus (AV); adeno-associated virus (AAV); retroviruses (e.g., lentiviruses (LV), Rhabdoviruses, murine leukemia virus); herpes virus, papillomavirus (U.S. Pat. Nos. 6,399,383, & 7,205,126) and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like. Non infectious pseudovirions, for example of Papillomavirus, may also be used to enable the efficient delivery of genes to mucosal membranes (U.S. Pat. No. 7,205,126, Peng et al., Gene Ther. 2010 Jul. 29 epub).

In one aspect, viral vectors derived from AV and AAV may be used in the present invention. Suitable AAV vectors for expressing the DRS polypeptides of the invention, methods for constructing the recombinant AAV vector, and methods for delivering the vectors into target cells are described in Samulski R et al. (1987), J. Virol. 61: 3096-3101; Fisher K J et al. (1996), J. Virol., 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

Typically the recombinant vectors and recombinant viral vectors include expression control sequences that direct the expression of the polynucleotide of the invention in various systems, both in vitro and in vivo. For instance, one set of regulatory elements will direct expression in certain mammalian cells or tissues and another set of regulatory elements will direct expression to bacterial cells and yet a third set of regulatory elements will direct expression in baculovirus systems. Some vectors are hybrid vectors that contain regulatory elements necessary for expression in more than one system. Vectors containing these various regulatory systems are commercially available and one skilled in the art will readily be able to clone the polynucleotides of the invention into such vectors.

In some instances, the vectors will possess promoters for expression in a wide variety of cells. In other instances, the vectors will possess promoters that are tissue specific. For example, the promoters direct expression only in neurons. In one aspect, the vector of the invention comprises a polynucleotide whose nucleotide sequence encodes, or comprises, any of SEQ ID NOS:2, 25-28, 30, or 92-135, where the encoded protein i) retains detectable non canonical activity, and ii) comprises at least one mutation at either Cys76 or Cys130 (using the numbering of SEQ ID NO:1) which replaces the native cysteine with another amino acid.

Host Cells

In another embodiment, the invention provides a host cell transformed with a vector of the invention. In one aspect, the DRS polypeptides of the invention are expressed by the host cell in order to produce or manufacture a DRS polypeptide as described previously. Such host cells include bacteria, insect cells, yeast cells or mammalian cells.

In another aspect, the host cells may be used to express and deliver a DRS polypeptide via cell therapy. Accordingly in another aspect, the current invention includes a cell therapy for treating a disease or disorder, comprising administering a host cell expressing, or capable of expressing, a DRS polypeptide of the invention. In one aspect the disease or disorder is selected from a TLR associated disease.

Cell therapy involves the administration of cells which have been selected, multiplied and pharmacologically treated or altered (i.e., genetically modified) outside of the body (Bordignon, C. et al, Cell Therapy: Achievements and Perspectives (1999), Haematologica, 84, pp. 1110-1149). Such host cells include for example, primary cells, including macrophages, and stem cells which have been genetically modified to express a DRS polypeptide of the invention. The aim of cell therapy is to replace, repair or enhance the biological function of damaged tissues or organs (Bordignon, C. et al, (1999), Haematologica, 84, pp. 1110-1149).

Methods for Use

Embodiments of the present invention relate to the discovery that aspartyl-tRNA synthetase (DRS polypeptides), and fragments and variants thereof, with altered cysteine content offer improved methods of modulating Toll like receptors (TLRs) in a variety of useful ways, both in vitro and in vivo. The compositions of the invention may thus be useful, for example, as immunomodulators for treating anti- or pro-inflammatory indications, and inflammatory responses, by modulating the cells that mediate, either directly or indirectly, autoimmune and/or inflammatory disease, conditions and disorders. The utility of the compositions of the invention as immunomodulators can be monitored using any of a number of known and available techniques in the art including, for example, migration assays (e.g., using leukocytes or lymphocytes), cytokine production assays, or cell viability assays (e.g., using B-cells, T-cells, monocytes or NK cells).

Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art. Ideally, inflammation is a protective attempt by the body to both remove the injurious stimuli and initiate the healing process for the affected tissue or tissues. In the absence of inflammation, wounds and infections would never heal, creating a situation in which progressive destruction of the tissue would threaten survival. On the other hand, excessive or chronic inflammation may associate with a variety of diseases, such as hay fever, atherosclerosis, and rheumatoid arthritis, among others described herein and known in the art.

Clinical signs of chronic inflammation are dependent upon duration of the illness, inflammatory lesions, cause and anatomical area affected, (see, e.g., Kumar et al., Robbins Basic Pathology-8 ft Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, gout and gout flares, pancreatitis, hepatitis, stroke, surgical complications, acetaminophen-induced liver toxicity, inflammatory lung disease, inflammatory bowel diseases including Crohn's disease (CD), necrotizing enterocolitis, and ulcerative colitis (UC), atherosclerosis, neurological disorders, (neuro)inflammatory disorders, diabetes, metabolic disorders, obesity, graft versus host disease, myositis, emphysema/COPD and psoriasis, among others described herein and known in the art. Hence, DRS polypeptide compositions may be used to treat or manage chronic inflammation, modulate any of one or more of the individual chronic inflammatory responses, or treat any one or more diseases or conditions associated with chronic inflammation.

Certain specific inflammatory responses include cytokine production and activity, and related pathways. For instance, certain exemplary embodiments relate to modulating cell-signaling through nuclear factor-kB (NF-kB), such as by increasing the downstream activities of this transcription factor. In certain instances, increases in NF-kB activity can lead to increases in cytokine signaling or activity, such as pro-inflammatory cytokines {e.g., TNF-alpha or beta), and anti-inflammatory cytokines (e.g., IL-10).

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, 16th edition, Merck and Co., Rahway, N.J., 1992; Goodman et al., eds., Goodman and Gilman's The Pharmacological Basis of Therapeutics, 10th edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, 18th edition, Mack Publishing Co., Easton, Pa. (1990); Katzung, Basic and Clinical Pharmacology, Appleton and Lange, Norwalk, Conn. (1992).

Also included are methods of modulating an immune response, such as an innate immune response. As used herein, the term "immune response" includes a measurable or observable reaction to an antigen, vaccine composition, or immunomodulatory molecule mediated by one or more cells of the immune system. An immune response typically begins with an antigen or immunomodulatory molecule binding to an immune system cell. A reaction to an antigen or immunomodulatory molecule may be mediated by many cell types, including a cell that initially binds to an antigen or immunomodulatory molecule and cells that participate in mediating an innate, humoral, cell-mediated immune response.

An "innate immune response," as used herein, may involve binding of pathogen-associated molecular patterns (PAMPs) or damage-associated molecular pattern molecules, (DAMPS) or a DRS polypeptide to cell surface receptors, such as toll-like receptors. Activation of toll-like receptors and Ipaf-signaling pathways in response to PAMPs or other signals leads to the production of immunomodulatory molecules, such as cytokines and co-stimulatory molecules, which induce and/or enhance an immune response. Cells involved in the innate immune response include, for example, dendritic cells, macrophages, natural killer cells, and neutrophils, among others.

Certain embodiments relate to increasing an innate immune response. Other embodiments relate to decreasing an innate immune response. In certain aspects, an innate immune response is mediated by one or more toll-like receptors (TLRs), such as TLR2 and/or TLR4. Certain DRS polypeptides of the invention bind to TLRS such as TLR2 and/or TLR4. More generally, DRS polypeptides are capable of selectively modulating host immune responses via specific interactions with Toll like receptors, and may therefore be used to modulate host immune responses and thereby to manage diseases and conditions associated with the same, as described herein and known in the art. Exemplary uses for the DRS polypeptides of the invention therefore include both methods for the treatment and prevention of TLR associated diseases, as well as for use in the breakdown of immune tolerance, for example for the development of vaccines, and in the development of immune therapies.

Exemplary "TLR associated diseases" include for example, inflammatory conditions, and diseases and disorders associated with the dysfunction of the innate immune response, including for example, autoimmunity, cancer, allergy, autoimmunity, radiation induced toxicity, (neuro) inflammation, depression, and the treatment and prevention of bacterial and viral infections. Accordingly in one embodiment the present invention includes a method for treating a TLR associated disease in a subject in need thereof, comprising administering to the subject a therapeutic dose of a DRS polypeptide (e.g., any of the proteins or nucleic acids listed in Tables D1 to D8) which i) retain detectable non canonical activity, and ii) which comprise, or have been modified to comprise at least one mutation at either Cys76 or Cys130 (using the numbering of SEQ ID NO:1) which replaces the native cysteine with another naturally, or non-naturally, occurring amino acid.

Exemplary uses associated with the breakdown of immune tolerance include for example the development of vaccines and adjutants comprising DRS polypeptides mixed with antigens, or comprising DRS fusion proteins with antigens, which exhibit enhanced immunogenicity. In some embodiments the antigen is a self-antigen. DRS polypeptide compositions that stimulate innate immunity (e.g., via TLR2 and/r TLR4) can be useful in the treatment of a wide variety of conditions, either alone or in combination with other therapies. Specific examples of such conditions include infectious diseases, such as bacterial, viral, and parasitic infectious diseases. DRS polypeptide compositions that stimulate innate immunity can also be useful as vaccine adjuvants, to enhance a subject's immune response to the primary antigen, whether in a live, attenuated, or other type of vaccine.

Examples of viral infectious diseases or agents (and their corresponding vaccines) include, but are not limited to, Hepatitis A, Hepatitis B, Hepatitis C, Hepatitis E, Caliciviruses associated diarrhoea, Rotavirus diarrhoea, *Haemophilus influenzae* B pneumonia and invasive disease, influenza, measles, mumps, *rubella*, Parainfluenza associated pneumonia, Respiratory syncytial virus (RSV) pneumonia, Severe Acute Respiratory Syndrome (SARS), Human papillomavirus, Herpes simplex type 2 genital ulcers, HIV/AIDS, Dengue Fever, Japanese encephalitis, Tick-borne encephalitis, West-Nile virus associated disease, Yellow Fever, Epstein-Barr virus, Lassa fever, Crimean-Congo haemorrhagic fever, Ebola haemorrhagic fever, Marburg haemorrhagic fever, Rabies, Rift Valley fever, Smallpox, leprosy, upper and lower respiratory infections, poliomyelitis, among others described elsewhere herein.

Examples of bacterial infections disease or agents include, but are not limited to, *Bacillus antracis, Borellia burgdorferi, Brucella abortus, Brucella canus, Brucella melitensis, Brucella suis, Campylobacter jejuni, Chlamydia pneumoniae, Chlamydia psitacci, Chlamydia trachomatis, Clostridium botulinum, C. difficile, C. perfringens, C. tetani, Corynebacterium diphtheriae* (i.e., diphtheria), *Enterococcus, Escherichia coli, Haemophilus influenza, Helicobacter pylori, Legionella pneumophila, Leptospira, Listeria monocytogenes, Mycobacterium leprae, M. tuberculosis, Mycoplasma pneumoniae, Neisseria gonorrhea, N. meningitidis, Pseudomonas aeruginosa, Rickettsia recketisii, Salmonella typhi, S. typhimurium, Shigella sonnei, Staphylococcus aureus, S. epidermidis, S. saprophytics, Streptococcus agalactiae, S. pneumoniae, S. pyogenes, Treponema pallidum, Vibrio cholera, Yersinia pestis, Bordatella pertussis*, and otitis media (e.g., often caused by *Streptococcus pneumoniae, Haemophilus influenzae*, or *Moraxella catarrhalis*), among others described elsewhere herein.

Examples of parasitic infectious diseases include, but are not limited to, Amoebiasis (e.g., *Entemoeba histolytica*), Hookworm Disease (e.g., nematode parasites such as *Necator americanus* and *Ancylostoma duodenale*), Leishmaniasis, Malaria (four species of the protozoan parasite *Plasmodium; P. falciparum, P. vivax, P. ovale,* and *P. malariae*), Schistosomiasis (parasitic *Schistosoma; S. mansoni, S. haematobium,* and *S. japonicum*), *Onchocerca volvulus* (River blindness), *Trypanosoma cruzi* (Chagas disease/American sleeping sickness), and *Dracunculus medinensis,* lymphatic filariasis. Certain DRS polypeptide compositions may be useful in the treatment or reduction of endotoxic shock, which often results from exposure to foreign antigens, such as lipopolysacchande (LPS). Because endotoxic shock can be mediated by TLR signaling, and naturally-occurring endogenous DRS polypeptide fragments may stimulate TLRs, certain of the binding agents, antisense agents, or RNAi agents provided herein may render a subject more resistant to endotoxic shock by antagonizing or otherwise reducing the endogenous DRS polypeptide fragment-mediated stimulation of TLR2 and/or TLR4.

Also included are methods of treating immune diseases. Illustrative immune system diseases, disorders or conditions that may be treated according to the present invention include, but are not limited to, primary immunodeficiencies, immune-mediated thrombocytopenia, Kawasaki syndrome, bone marrow transplant (for example, recent bone marrow transplant in adults or children), chronic B cell lymphocytic leukemia, HIV infection (for example, adult or pediatric HIV infection), chronic inflammatory demyelinating polyneuropathy, necrotizing enterocolitis, post-transfusion purpura, and the like.

Additionally, further diseases, disorders and conditions include Guillain-Barre syndrome, anemia (for example, anemia associated with parvovirus B19, patients with stable multiple myeloma who are at high risk for infection (for example, recurrent infection), autoimmune hemolytic anemia (for example, warm-type autoimmune hemolytic anemia), thrombocytopenia (for example, neonatal thrombocytopenia), and immune-mediated neutropenia), transplantation (for example, cytomegalovirus (CMV)-negative recipients of CMV-positive organs), hypogammaglobulinemia (for example, hypogammaglobulinemic neonates with risk factor for infection or morbidity), epilepsy (for example, intractable epilepsy), systemic vasculitic syndromes, myasthenia gravis (for example, decompensation in myasthenia gravis), dermatomyositis, and polymyositis.

Further autoimmune diseases, disorders and conditions include but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (for example, IgA nephropathy), multiple sclerosis, neuritis, uveitis ophthalmia, polyendochnopathies, purpura (for example, Henloch-Scoenlein purpura), Reiter's disease, stiff-man syndrome, autoimmune pulmonary inflammation, Guillain-Barre Syndrome, insulin dependent diabetes mellitus, and autoimmune inflammatory eye disease.

Additional autoimmune diseases, disorders or conditions include, but are not limited to, autoimmune thyroiditis; hypothyroidism, including Hashimoto's thyroiditis and thyroiditis characterized, for example, by cell-mediated and humoral thyroid cytotoxicity; SLE (which is often characterized, for example, by circulating and locally generated immune complexes); Goodpasture's syndrome (which is often characterized, for example, by anti-basement membrane antibodies); pemphigus (which is often characterized, for example, by epidermal acantholytic antibodies); receptor autoimmunities such as, for example, Graves' disease (which is often characterized, for example, by antibodies to a thyroid stimulating hormone receptor; myasthenia gravis, which is often characterized, for example, by acetylcholine receptor antibodies); insulin resistance (which is often characterized, for example, by insulin receptor antibodies); autoimmune hemolytic anemia (which is often characterized, for example, by phagocytosis of antibody-sensitized red blood cells); and autoimmune thrombocytopenic purpura (which is often characterized, for example, by phagocytosis of antibody-sensitized platelets).

Further autoimmune diseases, disorders or conditions include, but are not limited to, rheumatoid arthritis (which is often characterized, for example, by immune complexes in joints); scleroderma with anti-collagen antibodies (which is often characterized, for example, by nucleolar and other nuclear antibodies); mixed connective tissue disease, (which is often characterized, for example, by antibodies to extractable nuclear antigens, for example, ribonucleoprotein); polymyositis/dermatomyositis (which is often characterized, for example, by nonhistone anti-nuclear antibodies); pernicious anemia (which is often characterized, for example, by antiparietal cell, antimicrosome, and anti-intrinsic factor antibodies); idiopathic Addison's disease (which is often characterized, for example, by humoral and cell-mediated adrenal cytotoxicity); infertility (which is often characterized, for example, by antispennatozoal antibodies); glomerulonephritis (which is often characterized, for example, by glomerular basement membrane antibodies or immune complexes); by primary glomerulonephritis, by IgA nephropathy; bullous pemphigoid (which is often characterized, for example, by IgG and complement in the basement membrane); Sjogren's syndrome (which is often characterized, for example, by multiple tissue antibodies and/or the specific nonhistone antinuclear antibody (SS-B)); diabetes mellitus (which is often characterized, for example, by cell-mediated and humoral islet cell antibodies); and adrenergic drug resistance, including adrenergic drug resistance with asthma or cystic fibrosis (which is often characterized, for example, by beta-adrenergic receptor antibodies).

Still further autoimmune diseases, disorders or conditions include, but are not limited to chronic active hepatitis (which is often characterized, for example by smooth muscle antibodies); primary biliary cirrhosis (which is often characterized, for example, by anti-mitochondrial antibodies); other endocrine gland failure (which is characterized, for example, by specific tissue antibodies in some cases); vitiligo (which is often characterized, for example, by anti-melanocyte antibodies); vasculitis (which is often characterized, for example, by immunoglobulin and complement in vessel walls and/or low serum complement); post-myocardial infarction conditions (which are often characterized, for example, by anti-myocardial antibodies); cardiotomy syndrome (which is often characterized, for example, by anti-myocardial antibodies); urticaria (which is often characterized, for example, by IgG and IgM antibodies to IgE); atopic dermatitis (which is often characterized, for example, by IgG and IgM antibodies to IgE); asthma (which is often characterized, for example, by IgG and IgM antibodies to IgE); inflammatory myopathies; and other inflammatory, granulomatous, degenerative, and atrophic disorders.

Further embodiments the present invention include methods for killing cancer cells, comprising administering a vaccine or immunogenic composition comprising a DRS polypeptide of the invention fused to, or associated with an antigen, or vector comprising a nucleic acid encoding a DRS polypeptide fused to an antigen, to a subject in need thereof. Such DRS polypeptides may comprise any of the proteins or nucleic acids listed in Tables D1 to D8) which i) retain detectable non canonical activity, and ii) which comprise, or have been modified to comprise at least one mutation at either Cys76 or Cys130 (using the numbering of SEQ ID NO:1) which replaces the native cysteine with another naturally, or non-naturally, occurring amino acid). In some embodiments the antigen is a self-antigen, in some embodiments the antigen is a tumor derived antigen. In some embodiments, the antigen is a pathogen derived antigen. In some embodiments the pathogen derived antigen is derived from a virus, bacteria or prion. In some embodiments, the antigen is fused to the DRS polypeptide through conjugation at Cys130. In some embodiments the antigen and DRS polypeptide are mixed together.

In some embodiments the present invention includes a method for treating a subject with cancer, or preventing the development of cancer in a subject, comprising administering a vaccine or immunogenic composition comprising a DRS polypeptide of the invention fused to an antigen, or vector comprising a nucleic acid encoding a DRS polypeptide fused to an antigen, wherein the vaccine elicits an immune response to the cancer. Such DRS polypeptides may comprise any of the proteins or nucleic acids listed in Tables D1 to D8) which i) retain detectable non canonical activity, and ii) which comprise, or have been modified to comprise at least one mutation at either Cys76 or Cys130 (using the numbering of SEQ ID NO:1) which replaces the native cysteine with another naturally, or non-naturally, occurring amino acid). In some embodiments the antigen is a self-antigen, in some embodiments the antigen is a tumor derived antigen. In some embodiments, the antigen is a pathogen derived antigen. In some embodiments the pathogen derived antigen is derived from a virus, bacteria or prion. In some embodiments, the antigen is fused to the DRS polypeptide through conjugation at Cys130.

In some embodiments the present invention includes a method for overcoming tolerance of a subject to an antigen, comprising administering a vaccine or immunogenic composition comprising a DRS polypeptide of the invention fused to the antigen, or vector comprising a nucleic acid encoding a DRS polypeptide fused to the antigen. In different embodiments, the antigen may be selected self-antigens, tumor derived antigens, pathogen derived antigens. In some embodiments the pathogen derived antigen is derived from a virus, bacteria or prion. In some embodiments, the antigen is fused to the DRS polypeptide through conjugation at Cys130.

Pharmaceutical Formulations, Administration, and Kits

Embodiments of the present invention include compositions comprising DRS polypeptides formulated in pharmaceutically-acceptable or physiologically-acceptable solutions for administration to a cell, subject, or an animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the modulatory or other effects desired to be achieved.

For pharmaceutical production, DRS polypeptide therapeutic compositions will typically be substantially endotoxin free. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Endotoxins can be detected using routine techniques known in the art. For example, the Limulus Ameobocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA).

To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of protein. Typically, 1 ng lipopolysaccharide (LPS) corresponds to about 1-10 EU.

In certain embodiments, as noted herein, the DRS polypeptide compositions have an endotoxin content of less than about 10 EU/mg of DRS polypeptide, or less than about 5 EU/mg of DRS polypeptide, less than about 3 EU/mg of DRS polypeptide, or less than about 1 EU/mg of DRS polypeptide, or less than about 0.1 EU/mg of DRS polypeptide, or less than about 0.01 EU/mg of DRS polypeptide. In certain embodiments, as noted above, the DRS polypeptide pharmaceutical compositions are about 95% endotoxin free, preferably about 99% endotoxin free, and more preferably about 99.99% endotoxin free on wt/wt protein basis.

Pharmaceutical compositions comprising a therapeutic dose of a DRS polypeptide include all homologues, orthologs, and naturally-occurring isoforms of aspartyl-tRNA synthetase (e.g., any of the proteins or nucleic acids listed in Tables D1 to D8 which i) retain detectable non canonical activity, and ii) which comprise, or have been modified to comprise, at least one mutation at either Cys76 or Cys130 (using the numbering of SEQ ID NO:1) which replaces the native cysteine with another amino acid.

In some embodiments such pharmaceutical compositions may comprise an arginine buffer, which may be present in any of the pharmaceutical compositions within the range of about 1 mM to about 100 mM. In different embodiments, the arginine buffer may be present at a concentration of about 1 mM, about 10 mM, about 20 mM, about 40 mM, about 50 mM, about 60 mM, about 70 mM, about 80 mM, about 90 mM, or about 100 mM.

In one aspect such compositions may comprises DRS polypeptides that are substantially monodisperse, meaning that the DRS polypeptide compositions exist primarily (i.e., at least about 90%, or greater) in one apparent molecular weight form when assessed for example, by size exclusion chromatography, dynamic light scattering, or analytical ultracentrifugation.

In another aspect, such compositions have a purity (on a protein basis) of at least about 90%, or in some aspects at least about 95% purity, or in some embodiments, at least 98% purity. Purity may be determined via any routine analytical method as known in the art.

In another aspect, such compositions have a high molecular weight aggregate content of less than about 10%, compared to the total amount of protein present, or in some embodiments such compositions have a high molecular weight aggregate content of less than about 5%, or in some aspects such compositions have a high molecular weight aggregate content of less than about 3%, or in some embodiments a high molecular weight aggregate content of less than about 1%. High molecular weight aggregate content may be determined via a variety of analytical techniques including for example, by size exclusion chromatography, dynamic light scattering, or analytical ultracentrifugation.

Pharmaceutical compositions may include pharmaceutically acceptable salts of a DRS polypeptide. For a review on suitable salts, see *Handbook of Pharmaceutical Salts: Properties, Selection, and Use* by Stahl and Wermuth (Wiley-VCH, 2002). Suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. Compositions to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo(2.2.2)-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In particular embodiments, the carrier may include water. In some embodiments, the carrier may be an aqueous solution of saline, for example, water containing physiological concentrations of sodium, potassium, calcium, magnesium, and chloride at a physiological pH. In some embodiments, the carrier may be water and the formulation may further include NaCl. In some embodiments, the formulation may be isotonic. In some embodiments, the formulation may be hypotonic. In other embodiments, the formulation may be hypertonic. In some embodiments, the formulation may be isomostic. In some embodiments, the formulation is substantially free of polymers (e.g., gel-forming polymers, polymeric viscosity-enhancing agents, etc.). In some embodiments, the formulation is substantially free of viscosity-increasing agents (e.g., carboxymethylcellulose, polyanionic polymers, etc.). In some embodiments, the formulation is substantially free of gel-forming polymers. In some embodiments, the viscosity of the formulation is about the same as the viscosity of a saline solution containing the same concentration of a DRS polypeptide (or a pharmaceutically acceptable salt thereof).

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain embodiments, the DRS polypeptides have a solubility that is desirable for the particular mode of administration, such intravenous administration. Examples of desirable solubilities include at least about 1 mg/ml, at least about 10 mg/ml, at least about 25 mg/ml, and at least about 50 mg/ml.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

Pharmaceutical compositions suitable for the delivery of DRS polypeptides and methods for their preparation will be readily apparent to those skilled in the art. Such compositions and methods for their preparation may be found, e.g., in *Remington's Pharmaceutical Sciences*, 19th Edition (Mack Publishing Company, 1995).

Administration of a therapeutic dose of a DRS polypeptide may be by any suitable method known in the medicinal arts, including for example, oral, intranasal, parenteral administration include intravitreal, subconjuctival, subtenon, retrobulbar, suprachoroidal intravenous, intra-arterial, intraperitoneal, intrathecal, intraventricular, intraurethral, intrasternal, intracranial, intramuscular, intrasynovial, intraocular, topical and subcutaneous. Suitable devices for parenteral administration include needle (including microneedle) injectors, needle-free injectors, and infusion techniques.

Parenteral formulations are typically aqueous solutions which may contain excipients such as salts, carbohydrates, and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, e.g., by lyophilization, may readily be accomplished using standard pharmaceutical techniques well-known to those skilled in the art.

Formulations for parenteral administration may be formulated to be immediate and/or sustained release. Sustained release compositions include delayed, modified, pulsed, controlled, targeted and programmed release. Thus a DRS polypeptide may be formulated as a suspension or as a solid, semi-solid, or thixotropic liquid for administration as an implanted depot providing sustained release of DRS polypeptides. Examples of such formulations include without limitation, drug-coated stents and semi-solids and suspensions comprising drug-loaded poly(DL-lactic-co-glycolic) acid (PGLA), poly(DL-lactide-co-glycolide) (PLG) or poly (lactide) (PLA) lamellar vesicles or microparticles, hydrogels (Hoffman A S: *Ann. N.Y. Acad. Sci.* 944: 62-73 (2001)), poly-amino acid nanoparticles systems, such as the Medusa system developed by Flamel Technologies Inc., non aequous gel systems such as Atrigel developed by Atrix, Inc., and SABER (Sucrose Acetate Isobutyrate Extended Release) developed by Durect Corporation, and lipid-based systems such as DepoFoam developed by SkyePharma.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

DRS polypeptides for use in the present invention may also be administered topically, (intra)dermally, or transdermally to the skin, mucosa, or surface of the eye, either alone or in combination with one or more antihistamines, one or more antibiotics, one or more antifungal agents, one or more beta blockers, one or more anti-inflammatory Agents, one or more antineoplastic agents, one or more immunosuppressive agents, one or more antiviral agents, one or more antioxidant agents, or other active agents. Formulations for topical and ocular administration may be formulated to be immediate and/or modified release. Modified release formulations include delayed, sustained, pulsed, controlled, targeted and programmed release.

Typical formulations for this purpose include gels, hydrogels, lotions, solutions, eye drops, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol, and propylene glycol. Penetration enhancers may be incorporated—see, e.g., Finnin and Morgan: J. Pharm. Sci. 88(10): 955-958, (1999). Other means of topical administration include delivery by electroporation, iontophoresis, phonophoresis, sonophoresis, and microneedle or needle-free injection (e.g., the systems sold under the trademarks POWDERJECT™, BIOJECT™).

Examples of antihistamines include, but are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include, but are not limited to: Aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefmetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). 2.4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibornol).

Examples of antifungal agents include, but are not limited to Polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin), Allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Examples of beta blockers include but are not limited to acebutolol, atenolol, labetalol, metoprolol, propranolol, timolol, and derivatives thereof.

Examples of antineoplastic agents include, but are not limited to Antibiotics and analogs (e.g., aclacinomycins, actinomycin $f_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g., folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Examples of anti-inflammatory agents include but are not Limited to steroidal anti-inflammatory agents and non-steroidal anti-inflammatory agents. Exemplary steroidal anti-inflammatory agents include acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Exemplary non-steroidal anti-inflammatory agents include, but are not limited to, aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), ε-acetamidocaproic acid, s-adenosylmethionine, 3-amino-4-hydroxybutyric acid, amixetrine, bendazac, benzydamine, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Examples of antiviral agents include interferon gamma, zidovudine, amantadine hydrochloride, ribavirin, acyclovir, valciclovir, dideoxycytidine, phosphonoformic acid, ganciclovir, and derivatives thereof Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof. Other therapeutic agents include squalamine, carbonic anhydrase inhibitors, alpha-2 adrenergic receptor agonists, antiparasitics, antifungals, and derivatives thereof.

The exact dose of each component administered will, of course, differ depending on the specific components prescribed, on the subject being treated, on the severity of the disease, e.g., severity of the inflammatory reaction, on the manner of administration and on the judgment of the prescribing physician. Thus, because of patient-to-patient variability, the dosages given above are a guideline and the physician may adjust doses of the compounds to achieve the treatment that the physician considers appropriate.

As will be understood by the skilled artisan, for DRS polypeptide ocular formulations where the carrier includes a gel-forming polymer, in certain formulations the inclusion of salt(s), in particular saline solution, is contraindicated as inclusion of salt may either cause the solution to gel prior to topical administration, as with certain in situ gel-forming polymers (e.g., gellan gel), or the inclusion of salts may inhibit the gelling properties of the gel-forming polymer. The skilled artisan will be able to select appropriate combinations based on the desired properties of the formulation and characteristics of gel-forming polymers known in the art.

Suitable aqueous saline solutions will be understood by those of skill in the art and may include, for example, solutions at a pH of from about pH 4.5 to about pH 8.0. In further variations of aqueous solutions (where water is included in the carrier), the pH of the formulation is between any of about 6 and about 8.0; between about 6 and about 7.5; between about 6 and about 7.0; between about 6.2 and about 8; between about 6.2 and about 7.5; between about 7 and about 8; between about 6.2 and about 7.2; between about 5.0 and about 8.0; between about 5 and about 7.5; between about 5.5 and about 8.0; between about 6.1 and about 7.7; between about 6.2 and about 7.6; between about 7.3 and about 7.4; about 6.0; about 7.1; about 6.2; about 7.3; about 6.4; about 6.5; about 6.6; about 6.7; about 6.8; about 6.9; about 7.0; about 7.1; about 7.2; about 7.3; about 7.4; about 7.5; about 7.6; or about 8.0. In some variations, the DRS polypeptide formulation has a pH of about 6.0 to about 7.0. In some variations, the formulation has a pH of about 7.4. In particular variations, the formulation has a pH of about 6.2 to about 7.5.

In certain embodiments the concentration of the salt (e.g., NaCl) will be, for example, from about 0% to about 0.9% (w/v). For example, the concentration of salt may be from about 0.01 to about 0.9%, from about 0.02% to about 0.9%, from about 0.03% to about 9%, from about 0.05% to about 0.9% from about 0.07% to about 0.9%, from about 0.09% to about 0.9%, from about 0.1% to about 0.9% from about 0.2% to about 0.9%, from about 0.3% to about 0.9%, from about 0.4% to about 0.9% from about 0.5% to about 0.9%, from about 0.6% to about 0.9%, from about 0.7% to about 0.9%, from about 0.8% to about 0.9%, about 0.9%, about 0%, about 0.05%, about 0.01%, about 0.09%, about 0.1%, about 0.2%, about 0.3%, about 0.4%, about 0.5%, about 0.6%, about 0.7%, or about 0.8%. In certain embodiments, the aqueous saline solution will be isotonic (e.g., NaCl concentration of about 0.9% NaCl (w/v)). In certain embodiments, the aqueous solution will contain a NaCl concentration of about 0.5%, about 0.7%, about 0.8%, about 0.85, or about 0.75%. As will be appreciated the skilled artisan, depending on the concentrations of other components, for example where the DRS polypeptides are present as salts of, the concentration of NaCl or other salt needed to achieve an formulation suitable for administration may vary.

In some embodiments, where the ocular formulation is substantially free of viscosity-increasing agents, the formulation may be substantially free of viscosity-increasing agents such as, but not limited to polyanionic polymers, water soluble cellulose derivatives (e.g., hypromellose (also known as HPMC, hydroxypropylmethyl cellulose, and hydroxypropylcellulose), hydroxyethylcellulose, carboxmethylcellulose, etc.), polyvinyl alcohol, polyvinyl pyrrolidone, chondroitin sulfate, hyaluronic acid, soluble starches, etc. In some variations, the formulation does not incorporate a hydrogel or other retention agent (e.g., such as those disclosed in U.S. Pat. Pub. No. 2005/0255144 (incorporated by reference herein in its entirety)), e.g., where they hydrogel may include, hydrogels incorporating homopolymers; copolymers (e.g., tetrapolymers of hydroxymethylmethacrylate, ethylene glycol, dimethylmethacrylate, and methacrylic acid), copolymers of trimethylene carbonate and polyglycolicacid, polyglactin 910, glyconate, poly-p-dioxanone, polyglycolic acid, polyglycolic acid felt, poly-4-hydroxybutyrate, a combination of poly(L-lactide) and poly(L-lactide-co-glycolide), glycol methacrylate, poly-DL-lactide, or Primacryl); composites of oxidized regenerated cellulose, polypropylene, and polydioxanone or a composite of polypropylene and poligelcaprone; etc. In some variations, the formulations do not include one or more of polyvinyl alcohol, hydroxypropyl methylcellulose, polyethylene glycol 400 castor oil emulsion, carboxymethylcellulose sodium, propylene glycol, hydroxypropyl guar, carboxymethylcelluose sodium, white petrolatum, mineral oil, dextran 70, glycerin, hypromellose, flaxseed oil, fish oils, omega 3 and omega 6 fatty acids, lutein, or primrose oil. In some variations, the formulations do not include one or more of the carriers described in U.S. Pat. No. 4,888,354 (incorporated by reference herein in its entirety), e.g., such as one or more of oleic acid, ethanol, isopropanol, glycerol monooleate, glycerol dioleate, methyl laurate, propylene glycol, propanol or dimethyl sulfoxide. In some variations, the formulations are substantially free of glycerol diooleate and isopropanol.

In particular embodiments, the gel-forming polymer may be, for example, a polysaccharide. In certain embodiments, the polysaccharide is gellan gum. Gellan gum refers to a heteropolysaccharide elaborated by the bacterium *Pseudomonas elodea*, though the name "gellan gum" is more commonly used in the field. Gellan gum, in particular the formulation GELRITE® is described in detail in U.S. Pat. No. 4,861,760 (hereby incorporated by reference in its entirety), in particular in its use in formulation of timolol. GELRITE®, a low acetyl clarified grade of gellan gum, is commercially available from Merck & Co (Rahway, N.J.) and gellan gum can be commercially obtained from, among others CPKelco (Atlanta, Ga.). The preparation of polysaccharides such as gellan gum is described in, for example, U.S. Pat. Nos. 4,326,053 and 4,326,052, which are hereby incorporated by reference in their entirety.

In certain embodiments, the gel-forming polymer is present at a concentration of from about 0.03% to about 2% (w/v). In some embodiments, the gel-forming polymer is present at a concentration from about 0.03% to about 1.75%; from about 0.03% to about 1.5%, from about 0.03% to about 1.25%, from about 0.03% to about 1%, from about 0.03% to about 0.9%, from about 0.03% to about 0.8%, from about 0.03% to about 0.7%, from about 0.03% to about 0.6%, from about 0.03% to about 0.5%, from about 0.05% to about 2%, from about 0.05% to about 1.75%; from about 0.05% to about 1.5%, from about 0.05% to about 1.25%, from about 0.05% to about 1%, from about 0.05% to about 0.9%, from about 0.05% to about 0.8%, from about 0.05% to about 0.7%, from about 0.05% to about 0.6%, from about 0.05% to about 0.5%, from about 0.1% to about 2%, from about 0.1% to about 1.75%; from about 0.1% to about 1.5%, from about 0.1% to about 1.25%, from about 0.1% to about 1%, from about 0.1% to about 0.9%, from about 0.1% to about 0.8%, from about 0.1% to about 0.7%, from about 0.1% to about 0.6%, from about 0.1% to about 0.5%, from about 0.2% to about 2%, from about 0.2% to about 1.75%; from about 0.2% to about 1.5%, from about 0.2% to about 1.25%, from about 0.2% to about 1%, from about 0.2% to about 0.9%, from about 0.2% to about 0.8%, from about 0.2% to about 0.7%, from about 0.2% to, about 0.6%, from about 0.2% to about 0.5%, or from about 0.5% to about 1.5%. In some embodiments, the concentration of gel-forming polymer is about 0.1%, about 0.2%, about 0.4%, about 0.6%, about 0.8%, about 1%.

In particular embodiments, the gel-forming polymer is gellan gum at a concentration of from about 0.05% to about 2% (w/v), from about 0.1% to about 2% (w/v), from about 0.1% to about 1% (w/v), from about 0.05% to about 1% (w/v) or from about 0.1% to about 0.6% (w/v). In some embodiments, the concentration of gellan gum is about 0.1%, about 0.2%, about 0.4%, about 0.6%, about 0.8%, about 1%.

In some embodiments of the ocular formulations, the formulation may include additional components such as one or more preservatives, one or more surfactants, or one or more pharmaceutical agents In particular embodiments, the formulation may include additional components such as one or more preservatives, one or more surfactants, one or more tonicity agents, one or more buffering agents, one or more chelating agents, one or more viscosity-increasing agents, one or more salts, or one or more pharmaceutical agents. In certain of these embodiments, the formulation may include (in addition to a DRS polypeptide (or a pharmaceutically acceptable salt thereof) and carrier): one or more preservatives, one or more buffering agents (e.g., one, two, three, etc.), one or more chelating agents, and one or more salts. In some embodiments, the formulation may include (in addition to a DRS polypeptide (or a pharmaceutically acceptable salt thereof) and carrier): one or more preservatives, one or more tonicity agents, one or more buffering agents, one or more chelating agents, and one or more viscosity-increasing agents.

In some embodiments, the viscosity of the formulation is about the same as the viscosity of a saline solution containing the same concentration of a DRS polypeptide (or a pharmaceutically acceptable salt thereof). In some embodiments, the formulation is substantially free of gel-forming polymers. In certain embodiments, where the carrier is water, the formulation may additionally include one or more chelating agents (e.g., EDTA disodium (EDTA), one or more preservatives (e.g., benzalkonium chloride, benzethonium chloride, chlorhexidine, chlorobutanol, methylparaben, phenylethyl alcohol, propylparaben, thimerosal, phenylmercuric nitrate, phenylmercuric borate, phenylmercuric acetate, or combinations of two or more of the foregoing), salt (e.g., NaCl) and one or more buffering agents (e.g., one or more phosphate buffers (e.g., dibasic sodium phosphate, monobasic sodium phosphate, combinations thereof, etc.), citrate buffers, maleate buffers, borate buffers, and combination of two or more of the foregoing.).

In particular embodiments, the chelating agent is EDTA disodium, the preservative is benzalkonium chloride, the salt is NaCl, and the buffering agents are dibasic sodium phosphate and monobasic sodium phosphate. In certain of these embodiments, the formulation is substantially free of polymer. In some embodiments, the formulation is substantially free of substantially viscosity-increasing agent(s) (e.g., carboxymethylcellulose, polyanionic polymers, etc.). In some embodiments, the viscosity of the formulation is about the same as the viscosity of a saline solution containing the same concentration of a DRS polypeptide (or a pharmaceutically acceptable salt thereof). In some of these embodiments, the concentration of a DRS polypeptide (or a pharmaceutically acceptable salt thereof) if from about 0.02% to about 3%, from about 0.02% to about 2%, from about 0.02% to about 1% (w/v). In certain embodiments, the concentration of a DRS polypeptide (or a pharmaceutically acceptable salt thereof), is about 0.01%, about 0.02%, about 0.03%, about 0.05%, about 0.07%, about 0.1%, about 0.3%, about 0.4%, about 0.5%, about 0.6%, about 0.8% or about 1% (w/v).

In certain embodiments, where the carrier includes water, a viscosity-increasing agent may also be included in the formulation. The skilled artisan will be familiar with viscosity-increasing agents that are suitable (e.g., water-soluble cellulose derivatives (e.g., hypromellose (also known as HPMC, hydroxypropylmethyl cellulose, and hydroxypropylcellulose), hydroxyethylcellulose, carboxymethylcellulose, etc.), polyvinyl alcohol, polyvinyl pyrrolidone, chondroitin sulfate, hyaluronic acid, and soluble starches. It is intended that when viscosity-increasing agents are used, they are not included in high enough concentrations such that the formulation would form a gel prior to or after administration (e.g., wherein the concentration of the viscosity-increasing agent is not sufficient to induce gel formation).

While exact concentrations of viscosity-increasing agents will depend upon the selection and concentration of other components in the formulation as well as the particular viscosity-increasing agent(s) selected, in general, viscosity-increasing agents may be present in a concentration such that the viscosity of the resulting solution is less than about 1000 centipoise. In certain embodiments, the viscosity of the formulation is less than about 900, less than about 800, less than about 700, less than about 600, less than about 500, less than about 400, less than about 300, less than about 200, less than about 150, less than about 100, less than about 50 centipoise. In some embodiments, the viscosity of the formulation is about 200, about 150, about 100, about 50 centipoise. In particular embodiments, the viscosity is less than about 200 centipoise. In others, less than about 120 centipoise or less than about 100 centipoise. In some embodiments, the viscosity is about 100 centipoise. In others about 50 centipoise. In still other embodiments the viscosity is about 200 centipoise. Methods for measuring viscosity are well known to the skilled artisan. For example, as described in United States Pharmacopoeia 29 (Chapter 911) Viscosity, page 2785 (which is herein incorporated by reference in its entirety). As is well known to the skilled artisan, formulations commonly considered "gels" will have viscosity significantly greater than 1000 centipoise, for example, greater than about 2000 centipoise, greater than about 5000 centipoise.

In some embodiments, including (but not limited to) where the use of salts is contraindicated as described above, the ocular formulation may further include one or more tonicity agents. As used herein, the term "tonicity agent" and its cognates refers to agents that adjust the tonicity of the formulation, but are not salts (e.g., not NaCl), which, as will be appreciated by the skill artisan in view of the teaching provided herein, are contraindicated for some formulations due to the presence of certain of the gel-forming polymers or viscosity-increasing agents. These agents may be used to prepare formulations that are isotonic or near isotonic (e.g., somewhat hyper- or hypo-isotonic; e.g., within about ±20%, about ±15%, about ±10%, about ±5% of being isotonic). Tonicity agent(s) may also be used in formulations where the use of salts is not contraindicated.

Tonicity agents that may be used to adjust the tonicity of formulation the formulations described herein and are known to the skilled artisan and can be selected based on the teaching provided herein. For example, tonicity agents include polyols (e.g., sugar alcohols (e.g., mannitol, etc.), trihydroxy alcohols (e.g., glycerin, etc.), propylene glycol or polyethylene glycol, etc.), or combinations of two or more polyols. Likewise, the concentration of the tonicity agent(s) will depend upon the identity and concentrations of the other components in the formulation and can be readily determined by the skilled artisan in view of the teaching provided herein.

In certain embodiments, the tonicity agent is glycerin or mannitol. In some embodiments, the tonicity agent is glycerin. In other embodiments it is, mannitol. In still others a combination of mannitol and glycerin may be used. Exemplary concentrations of tonicity agents include, for example from about 0.001 to about 3%. In some embodiments, the concentration of the tonicity agent (e.g., mannitol or glycerin) is, for example, about 0.001% to about 2.7%, about 0.001% to about 2.5%, about 0.001% to about 2%, about 0.001% to about 1.5%, about 0.001% to about 1%, about 0.01% to about 3%, about 0.01% to about 2.7%, about 0.01% to about 2.5%, about 0.01% to about 2%, about 0.01% to about 1.5%, about 0.01% to about 1%, about 0.1% to about 3%, about 0.1% to about 2.7%, about 0.1% to about 2.5%, about 0.1% to about 2%, about 0.1% to about 1.5%, about 0.1% to about 1%, about 0.01% about 1% to about 3%; about 1% to about 2.5%; about 1% to about 2%; about 1% to about 1.8%; about 1% to about 1.5%; or about 0.001%, about 0.01%, about 0.05%, about 0.08%, about 0.1%, about 0.2%, about 0.5%, about 0.8%, about 1%, about 1.5%, about 1.8%, about 2%, about 2.2%, about 2.5%, about 2.8%, or about 3% (w/v). In certain embodiments, the tonicity agent is mannitol. In some of these embodiments, the carrier includes a gel-forming agent (e.g., gellan gum).

In some embodiments, the tonicity agent is mannitol. In certain of these embodiments, the carrier includes a viscosity-increasing agent (e.g., water soluble cellulose derivatives (e.g., hypromellose), polyvinyl alcohol, polyvinyl pyrrolidone, chondroitin sulfate, hyaluronic acid, or soluble starches).

In some embodiments, the ocular formulation may additionally include a preservative (e.g., benzalkonium chloride, benzethonium chloride, chlorhexidine, chlorobutanol, methylparaben, Phenylethyl alcohol, propylparaben, thimerosal, phenylmercuric nitrate, phenylmercuric borate, or phenylmercuric acetate, peroxides), or a combination of two or more of the foregoing preservatives. In certain embodiments, the preservative is benzalkonium chloride.

As will be appreciated by the skilled artisan, preservatives may be present in concentrations of from about 0.001% to about 0.7% (w/v). In particular embodiments, the preservative(s) may be present in a concentration of from about 0.001% to about 0.5% (w/v); from about 0.001% to about 0.05% (w/v), from about 0.001% to about 0.02% (w/v), from about 0.001% to about 0.015% (w/v), from about 0.001% to about 0.005% (w/v), from about 0.01% to about 0.02%, from about 0.002% to about 0.01%, from about 0.015% to about 0.05%, less than about <0.5%, from about 0.005% to about 0.01%, from about 0.001% to about 0.15%, from about 0.002% to about 0.004%, from about 0.001% to about 0.002%. In some embodiments the concentration of the preservative may be, for example, about 0.001%, about 0.005%, about 0.01%, about 0.02%, about 0.03%, about 0.05%, about 0.1%, about 0.2%, about 0.5%, or about 0.7% (w/v). Typical concentrations (w/v) for various commonly used preservatives are listed in Table C below.

TABLE C

| Preservative | Approximate Concentration Range (w/v) |
| --- | --- |
| Benzalkonium chloride | 0.01-0.02% |
| Benzethonium chloride | 0.01-0.02% |
| Chlorhexidine | 0.002-0.01% |
| Chlorobutanol | <0.5% |
| Methylparaben | 0.015-0.05% |
| Phenylethyl alcohol | <0.5% |
| Propylparaben | 0.005-0.01% |
| Thimerosal | 0.001-0.15% |
| Phenylmercuric nitrate | 0.002-0.004% |
| Phenylmercuric borate | 0.002-0.004 |
| Phenylmercuric acetate | 0.001-0.002 |

In certain embodiments, the formulation may additionally include a surfactant, or combinations of two or more surfactants. In particular embodiments, the formulation is substantially free of surfactant. As used herein, the term "substantially free" is intended to refer to levels of a particular component that are undetectable using routine detection methods and protocols known to the skilled artisan. For example, HPLC (including chiral HPLC, chiral HPLC/MS, LC/MS/MS etc.), thin layer chromatography, mass spectrometry, polarimetry measurements, Gas-chromatography-mass spectrometry, or others.

In particular embodiments, the ocular formulation may further include a chelating agent (e.g., EDTA disodium (EDTA) (e.g., EDTAEDTA disodium (dihydrate), etc.) citrates, etc.). In some embodiments, a combination of chelating agents may be present. As will be appreciated by those of skill in the field, chelating agents can be used to hinder degradation of the formulation components and thereby increase the shelf life of ocular formulations. As will be appreciated by the skilled artisan, use of EDTA in combination with gellan gum formulation may be contraindicated as the EDTA can cause gel formation prior to administration of the gellan gum formulation.

Typical concentrations for chelating agents are from about 0.005% to 0.1% (w/v). For example, from about 0.005% to about 0.09%, from about 0.005% to about 0.08%, from about 0.005% to about 07%, from about 0.005%, to about 0.06%, from about 0.005% to about 0.05%, from about 0.005 to about 0.04%, from about 0.005% to about 0.03%, from about 0.01% to about 0.1%, from about 0.01% to about 0.09%, from about 0.01% to about 0.08%, from about 0.01% to about 0.07%, from about 0.01% to about 0.06%, from about 0.01% to about 0.05%, from about 0.01% to about 0.04%, etc. In certain embodiments, the concentration of chelating agent(s) is about 0.005%, about 0.01%, about 0.02%, about 0.03%, about 0.05%, about 0.06%, about 0.07%, about 0.08%, about 0.09%, or about 0.1%.

In particular embodiments, the chelating agent is EDTA disodium. In certain embodiments, the chelating agent is EDTA disodium (dihydrate). In some of these embodiments, the EDTA disodium dihydrate is present at a concentration of about 0.01% (w/v).

In some embodiments, the ocular formulation may additionally include one or more buffering agents (e.g., phosphate buffer(s) (e.g., sodium phosphate buffers (e.g., dibasic sodium phosphate, monobasic sodium phosphate, etc.), citrate buffers, maleate buffers, borate buffers, etc.). As will be appreciated by the skilled artisan, the one or more buffering agent(s) should be selected in combination with the other components of a given formulation to achieve a pH suitable for use (e.g., pH of about 4.5 to about 8).

In certain embodiments, the buffering agent is a phosphate buffer or combination of two or more phosphate buffers. In certain embodiments, the buffering agents are dibasic sodium phosphate and monobasic sodium phosphate.

Typical concentrations for buffering agent(s) for example, phosphate buffering agent(s) may be from about 0.005 molar to 0.1 molar. In some embodiments, the buffering agent(s) may be at a concentration of about 0.01 to about 0.1, from about 0.01 to about 0.08, from about 0.01 to about 0.05, from about 0.01 to about 0.04, from about 0.02 to about 0.1, from about 0.02 to about 0.08, from about 0.02 to about 0.06, from about 0.02 to about 0.05, from about 0.02 to about 0.04 molar, etc. In particular embodiments, there are two buffering agents. Exemplary buffering agents include a combination of dibasic sodium phosphate (e.g., dibasic sodium phosphate.$7H_2O$) and monobasic sodium phosphate (e.g., monobasic sodium phosphate anhydrous). In some embodiments, the concentration of the buffering agent(s) is about 0.005 molar, about 0.01 molar, about 0.02 molar, about 0.03 molar, about 0.04 molar, about 0.05 molar, about 0.06 molar, about 0.07 molar, or about 0.1 molar.

An additional aspect of the invention includes use of the formulations as described herein in the manufacture of a medicament. Particularly, the manufacture of a medicament for use in the treatment and/or prevention of conditions as described herein. Further, the formulations, variously described herein, are also intended for use in the manufacture of a medicament for use in treatment and/or prevention of the conditions and, in accordance with the methods, described herein, unless otherwise noted.

Methods of formulation are well known in the art and are disclosed, for example, in Remington: The Science and Practice of Pharmacy, Mack Publishing Company, Easton, Pa., 19th Edition (1995). The compositions and agents provided herein may be administered according to the methods of the present invention in any therapeutically effective dosing regime. The dosage amount and frequency are selected to create an effective level of the agent without harmful effects. The effective amount of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidylglycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In certain embodiments, the agents provided herein may be attached to a pharmaceutically acceptable solid substrate, including biocompatible and biodegradable substrates such as polymers and matrices. Examples of such solid substrates include, without limitation, polyesters, hydrogels (for example, poly(2-hydroxyethyl-methacrylate), or poly(vinyl-alcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as poly(lactic-co-glycolic acid) (PLGA) and the LUPRON DEPOT™ (injectable microspheres composed of lactic acid-glycolic acid copolymer and leuprolide acetate), poly-D-(−)-3-hydroxybutyric acid, collagen, metal, hydroxyapatite, bioglass, aluminate, bioceramic materials, and purified proteins.

In one particular embodiment, the solid substrate comprises ATRIGEL™ (QLT, Inc., Vancouver, B.C.). The ATRIGEL® drug delivery system consists of biodegradable polymers dissolved in biocompatible carriers. Pharmaceuticals may be blended into this liquid delivery system at the time of manufacturing or, depending upon the product, may be added later by the physician at the time of use. When the liquid product is injected into the subcutaneous space through a small gauge needle or placed into accessible tissue sites through a cannula, water in the tissue fluids causes the polymer to precipitate and trap the drug in a solid implant. The drug encapsulated within the implant is then released in a controlled manner as the polymer matrix biodegrades with time.

In particular embodiments, the amount of a DRS composition the agent administered will generally range from a dosage of from about 0.1 to about 100 mg/kg/day, and typically from about 0.1 to 10 mg/kg where administered orally or intravenously. In particular embodiments, a dosage is 5 mg/kg or 7.5 mg/kg. For humans, the daily dosage used may range from, about 0.1 mg/kg to 0.5 mg/kg, about 1 mg/kg to 5 mg/kg, about 5 mg/kg to 10 mg/kg, about 10 mg/kg to 20 mg/kg, about 20 mg/kg to 30 mg/kg, about 30 mg/kg to 50 mg/kg, and about 50 mg/kg to 100 mg/kg/24 hours.

In certain embodiments, a composition or agent is administered in a single dosage of 0.1 to 10 mg/kg or 0.5 to 5 mg/kg. In other embodiments, a composition or agent is administered in a dosage of 0.1 to 50 mg/kg/day, 0.5 to 20 mg/kg/day, or 5 to 20 mg/kg/day.

In various embodiments, the dosage is about 50-2500 mg per day, 100-2500 mg/day, 300-1800 mg/day, or 500-1800 mg/day. In one embodiment, the dosage is between about 100 to 600 mg/day. In another embodiment, the dosage is between about 300 and 1200 mg/day. In particular embodiments, the composition or agent is administered at a dosage of 100 mg/day, 240 mg/day 300 mg/day, 600 mg/day, 1000 mg/day, 1200 mg/day, or 1800 mg/day, in one or more doses per day (i.e., where the combined doses achieve the desired daily dosage). In related embodiments, a dosage is 100 mg bid, 150 mg bid, 240 mg bid, 300 mg bid, 500 mg bid, or 600 mg bid. In various embodiments, the composition or agent is administered in single or repeat dosing. The initial dosage and subsequent dosages may be the same or different.

In some embodiments, total daily dose may be about 0.001 mg, about 0.005 mg, about 0.01 mg, about 0.05 mg, about 0.1 mg, 0.5 mg, 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg or about 100 mg/24 hours. For repeated administrations over several days or longer, depending on the condition, the treatment is sustained until a desired suppression of disease symptoms occurs. The progress of these and other therapies (e.g., ex vivo therapies) can be readily monitored by conventional methods and assays and based on criteria known to the physician or other persons of skill in the art.

It will be further appreciated that for sustained delivery devices and compositions the total dose of DRS contained in such delivery system will be correspondingly larger depending upon the release profile of the sustained release system. Thus, a sustained release composition or device that is intended to deliver DRS polypeptide over a period of 5 days will typically comprise at least about 5 to 10 times the daily dose of DRS polypeptide; a sustained release composition or device that is intended to deliver a DRS peptide over a period of 365 days will typically comprise at least about 400 to 800 times the daily dose of the DRS polypeptide (depending upon the stability and bioavailability of the DRS polypeptide when administered using the sustained release system).

In certain embodiments, a composition or agent is administered orally or intravenously, e.g., by infusion over a period of time of about, e.g., 10 minutes to 90 minutes. In other related embodiments, a composition or agent is administered by continuous infusion, e.g., at a dosage of between about 0.1 to about 10 mg/kg/hr over a time period. While the time period can vary, in certain embodiments the time period may be between about 10 minutes to about 24 hours or between about 10 minutes to about three days.

In particular embodiments, an effective amount or therapeutically effective amount is an amount sufficient to achieve a total concentration of the composition or agent in the blood plasma of a subject with a $C_{max}$ of between about 0.1 µg/ml and about 20 µg/ml or between about 0.3 µg/ml and about 20 µg/ml. In certain embodiments, an oral dosage is an amount sufficient to achieve a blood plasma concentration ($C_{max}$) of between about 0.1 µg/ml to about 5 µg/ml or between about 0.3 µg/ml to about 3 µg/ml. In certain embodiments, an intravenous dosage is an amount sufficient to achieve a blood plasma concentration ($C_{max}$) of between about 1 µg/ml to about 10 µg/ml or between about 2 µg/ml and about 6 µg/ml. In a related embodiment, the total concentration of an agent in the blood plasma of the subject has a mean trough concentration of less than about 20 µg/ml and/or a steady state concentration of less than about 20 µg/ml. In a further embodiment, the total concentration of an agent in the blood plasma of the subject has a mean trough concentration of less than about 10 µg/ml and/or a steady state concentration of less than about 10 µg/ml.

In yet another embodiment, the total concentration of an agent in the blood plasma of the subject has a mean trough concentration of between about 1 ng/ml and about 10 µg/ml and/or a steady state concentration of between about 1 ng/ml and about 10 µg/ml. In one embodiment, the total concentration of an agent in the blood plasma of the subject has a mean trough concentration of between about 0.3 µg/ml and about 3 µg/ml and/or a steady state concentration of between about 0.3 µg/ml and about 3 µg/ml.

In particular embodiments, a composition or agent is administered in an amount sufficient to achieve in the mammal a blood plasma concentration having a mean trough concentration of between about 1 ng/ml and about 10 µg/ml and/or a steady state concentration of between about 1 ng/ml and about 10 µg/ml. In related embodiments, the total concentration of the agent in the blood plasma of the mammal has a mean trough concentration of between about 0.3 µg/ml and about 3 µg/ml and/or a steady state concentration of between about 0.3 µg/ml and about 3 µg/ml.

In particular embodiments of the present invention, the effective amount of a composition or agent, or the blood plasma concentration of composition or agent is achieved or maintained, e.g., for at least 15 minutes, at least 30 minutes, at least 45 minutes, at least 60 minutes, at least 90 minutes, at least 2 hours, at least 3 hours, at least 4 hours, at least 8 hours, at least 12 hours, at least 24 hours, at least 48 hours, at least 3 days, at least 4 days, at least 5 days, at least 6 days, at least one week, at least 2 weeks, at least one month, at least 2 months, at least 4 months, at least 6 months, at least one year, at least 2 years, or greater than 2 years.

In certain DRS polypeptide-based embodiments, the amount of polypeptide administered will typically be in the range of about 0.1 µg/kg to about 0.1 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 0.1 µg/kg to about 1 µg/kg to 100 mg/kg or more, depending on the factors mentioned above. For repeated administrations over several days or longer, depending on the condition, the treatment is sustained until a desired suppression of disease symptoms occurs.

In particular embodiments, the effective dosage achieves the blood plasma levels or mean trough concentration of a composition or agent described herein. These may be readily determined using routine procedures.

Embodiments of the present invention, in other aspects, provide kits comprising one or more containers filled with one or more of the polypeptides, polynucleotides, antibodies, multiunit complexes, compositions thereof, etc., of the invention, as described herein. The kits can include written instructions on how to use such compositions (e.g., to modulate cellular signaling, angiogenesis, cancer, inflammatory conditions, diagnosis etc.).

The kits herein may also include a one or more additional therapeutic agents or other components suitable or desired for the indication being treated, or for the desired diagnostic application. An additional therapeutic agent may be contained in a second container, if desired. Examples of additional therapeutic agents include, but are not limited to anti-neoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

Kits

In another aspect of the invention, kits, comprising: a) a container comprising a DRS polypeptide component; and b) instructions for use. Instructions may include steps of how to handle the DRS polypeptides, how to store the DRS polypeptides, and what to expect from using the DRS polypeptides.

In another aspect of the invention, kits, comprising: a) a container comprising a recombinant vector comprising a nucleic acid encoding a DRS polypeptide component; and b) instructions for use. Instructions may include steps of how to handle the vectors, how to store the vectors, or how to construct DRS polypeptide fusion proteins.

In another aspect of the invention, kits for treating a disease or disorder are provided, comprising: a) a container comprising a pharmaceutical composition comprising a DRS polypeptide component in a pharmaceutically acceptable formulation and b) instructions, and/or a product insert or label. In one aspect, the instructions include a dosing regimen for administration of the DRS polypeptide.

The present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

Production of AspRS1$^{N1}$ Comprising the Mutation Cys76→Ser in *E. coli*

Codon Optimization and Gene Synthesis:

An *E. coli* codon optimized nucleic acid sequence encoding the DRS polypeptide AspRS1$^{N1}$ (C76S) (comprising amino acids 1-154, and a cysteine→serine mutation at position 76) was designed for optimal *E. coli* expression using the algorithm developed by DNA2.0 (Menlo Park, Calif.). The gene was synthesized with a C-terminal V5His tag and subcloned into pJExpress411 vector where the T7 promoter was used to drive the transcription and the kanamycin resistance was used for antibiotic selection. The codon-optimized DNA sequence is as follows:

```
                                        (SEQ ID NO: 28)
ATGCCGAGCGCGAGCGCCAGCCGTAAGAGCCAGGAAAAACCACGTGAGAT

TATGGATGCCGCAGAGGACTATGCGAAAGAACGTTACGGTATTTCCAGCA

TGATCCAATCTCAGGAGAAACCGGACCGCGTTCTGGTTCGTGTTCGCGAT

CTGACCATTCAGAAGGCGGACGAGGTGGTTTGGGTGCGTGCGCGCGTGCA

CACCAGCCGTGCAAAAGGCAAACAGAGCTTTCTGGTCCTGCGTCAGCAGC

AATTCAACGTCCAGGCGCTGGTGGCAGTGGGTGACCACGCCAGCAAACAA
```

-continued

```
ATGGTGAAGTTCGCTGCTAACATCAATAAAGAATCCATTGTTGATGTTGA

AGGCGTCGTTCGCAAGGTCAATCAAAAGATCGGCTCGTGTACGCAACAAG

ATGTCGAGCTGCATGTGCAGAAGATTTACGTCATCAGCCTGGCGGAGCCG

CGTTTGCCGCTGGGTAAGCCGATCCCTAACCCGCTGTTGGGTCTGGACAG

CACGCATCACCATCACCACCACTAA
```

The corresponding translated protein sequence is:

(SEQ ID NO: 29)
MPSASASRKSQEKPREIMDAAEDYAKERYGISSMIQSQEKPDRVLVRVRD

LTIQKADEVVWVRARVHTSRAKGKQSFLVLRQQQFNVQALVAVGDHASKQ

MVKFAANINKESIVDVEGVVRKVNQKIGSCTQQDVELHVQKIYVISLAEP

RLPLGKPIPNPLLGLDSTHHHHHH

As a control, the non-mutated AspRS1$^{N1}$ protein was also prepared, using wild type (human codon usage), and cloned into the identical expression cassette. The nucleic acid sequence of the native AspRS1$^{N1}$ is as follows:

(SEQ ID NO: 30)
```
ATGCCCAGCGCCAGCGCCAGCCGCAAGAGTCAGGAGAAGCCGCGGGAGAT

CATGGACGCGGCGGAAGATTATGCTAAAGAGAGATATGGAATATCTTCAA

TGATACAATCACAAGAAAAACCAGATCGAGTTTTGGTTCGGGTTAGAGAC

TTGACAATACAAAAAGCTGATGAAGTTGTTTGGGTACGTGCAAGAGTTCA

TACAAGCAGAGCTAAAGGGAAACAGTGCTTCTTAGTCCTACGTCAGCAGC

AGTTTAATGTCCAGGCTCTTGTGGCGGTGGGAGACCATGCAAGCAAGCAG

ATGGTTAAATTTGCTGCCAACATCAACAAAGAGAGCATTGTGGATGTAGA

AGGTGTTGTGAGAAAGTGAATCAGAAAATTGGAAGCTGTACACAGCAAG

ACGTTGAGTTACATGTTCAGAAGATTTATGTGATCAGTTTGGCTGAACCC

CGTCTGCCCCTGGGTAAGCCTATCCCTAACCCTCTCCTCGGTCTCGATTC

TACGCACCACCACCACCACCACTGA
```

The encoding protein, containing the identical C-terminal tag, but the wild type Cys76 is shown below:

(SEQ ID NO: 31)
MPSASASRKSQEKPREIMDAAEDYAKERYGISSMIQSQEKPDRVLVRVRD

LTIQKADEVVWVRARVHTSRAKGKQCFLVLRQQQFNVQALVAVGDHASKQ

MVKFAANINKESIVDVEGVVRKVNQKIGSCTQQDVELHVQKIYVISLAEP

RLPLGKPIPNPLLGLDSTHHHHHH

Expression Strains:

BL21-CodonPlus (DE3)-RIPL competent cells (Agilent cat. no. 230280) were transformed with the non-mutated AspRS1$^{N1}$ expression construct. BL21 (DE3) competent cells (Novagen, cat. no. 69450) were transformed with the AspRS1$^{N1}$ (C76S) expression construct. Briefly, the plasmid (1 μL) was added into 50 μL of the competent cells. The reaction was mixed and incubated on ice for 30 minutes. The reaction was heat-shocked for at 42° C. for 30 sec followed by a cold-shock on ice for 2 minutes. Then the SOC medium (500 μL) was added and the tube was incubated at 37° C., 250 rpm for 1 hour. Finally, an aliquot of the culture (50 μL) was spread on the Kanamycin plate (Teknova 59641) and incubated at 37° C. overnight. Single colony was picked and used for expression scale-up.

Fed-Batch Fermentation Production of Proteins:

M9YE medium was prepared by mixing 200 mL sterile M9 minimal salt 5× (BD248510), 778 mL 30 g/L yeast extract in sterile purified water (BD212750), 20 mL sterilized 20% glucose (Sigma G7021) and 2 mL sterile 1.0 M MgSO$_4$ (Sigma M7506). The feeding solution contains 5% yeast extract, 50% glucose, trace elements and 2 g/L magnesium sulfate. Kanamycin sulfate (Invitrogen 15160) was added to a final concentration of 100 μg/mL in both M9YE and feeding solution.

A 4 L fermentor (Sartorius Biostat B plus) with MFCS/DA software was used for the fed-batch fermentation of both proteins. The agitation was set at 1000 rpm. The pH value was controlled at 7.0 automatically by the addition of 30% ammonium hydroxide (Sigma 221228) and 30% phosphoric acid (Sigma P5811). The air was provided at a flow rate of 4 L/min with an oil-free diaphragm air compressor (Cole-Parmer). The air was passed through a 0.2 μm Midisart 2000 filter (Sartorius 17805). The pure oxygen (West Air) was supplied automatically to control the dissolved oxygen level at 70%. The temperature was controlled at 30° C. with a Neslab RTE7 circulator (Thermo Scientific). The foaming was controlled by addition of the antifoam 204 (Sigma A8311). The initial volume of M9YE medium in the fermentor was 3 L. The fermentor was inoculated with 150 mL of the seed culture grown overnight at 30° C. and 250 rpm. When the glucose was depleted in the vessel, the concentrated feeding solution was introduced into the vessel by a peristaltic pump set at 0.9 ml/min. When the optical density of the cells at 600 nm reached about 30, the culture was induced with 0.5 mM IPTG (Fisher Scientific BP1755). The culture was run overnight (about 18-hour fed-batch phase) and harvested by centrifugation at 6,000 g for 1 hour. The cell pellet was stored at −20° C. until purification. The expression of each protein was confirmed by SDS-PAGE analysis (data not shown).

Purification of Proteins:

Frozen cell pellets from each production run were resuspended in 4 volumes (i.e., 4 mL/g cell pellet) of Lysis Buffer (50 mM Tris, 300 mM NaCl, 25 mM Imidazole, 14 mM β-ME, pH 8.0). Complete EDTA-FREE protease inhibitor cocktail tablets (Roche Cat. #05 056 489 001) were added to the suspension at a ratio of 1 tablet/50 mL. The suspension was passed through a microfluidizer (Microfluidics) twice at 14,000 psi with cooling by ice. The lysate was centrifuged at 35,000×g for 45 min at 4° C. The supernatant was filtered through 0.45+0.22 nm Sartobran capsule filters (Sartorius).

The clarified lysate was bound to the Ni-NTA resin (Qiagen), pre-equilibrated with Ni-NTA Binding Buffer (50 mM Tris, 300 mM NaCl, 25 mM Imidazole, pH 8.0). The column was washed with 300 column volumes of Ni-NTA Binding Buffer+0.1% Triton X-114 followed by 33 column volumes of the Ni-NTA Binding Buffer. The bound protein, D1-C76S, was eluted with 5 column volumes of Ni-NTA Elution Buffer (50 mM Tris, 300 mM NaCl, 300 mM Imidazole, pH 8.0).

The purified proteins were dialyzed into a buffer containing 20 mM sodium phosphate, 200 mM Arginine, at pH 7.3. The dialyzed protein was passed through a Q membrane filter (Sartobind-Q from Sartorius or Mustang-Q from Pall) or a Q-Sepharose column (GE Healthcare) for further endotoxin removal, and then filtered through a 0.22 μm sterile filter.

Comparison of Production Yield, Purity and Endotoxin Content of AspRS1$^{N1}$ (C76S) with AspRS1$^{N1}$.

A direct comparison of the yields of soluble proteins from the AspRS1$^{N1}$ (C76S) and non-mutated AspRS1$^{N1}$ constructs, over several independent production runs, (Table E1) reveals that the AspRS1$^{N1}$ (C76S) variant has a consistently higher yield compared to the non-mutated parent protein. Table E1 lists the average purification yield of AspRS1$^{N1}$ (C76S) and non-mutated AspRS1$^{N1}$.

TABLE E1

Production yields for different AspRS1$^{N1}$ variants

| DRS polypeptide form | Purified protein yield (mg/g cell pellet) |
|---|---|
| AspRS1$^{N1}$(C76S) | 1.72 ± 0.25 (n = 8) |
| AspRS1$^{N1}$ | 1.38 ± 0.57 (n = 7) |

An analysis of representative proteins by SDS-gel is shown in FIG. 1. The gel demonstrates that the purified AspRS1$^{N1}$ (C76S) has less low molecular weight impurities, and contains less disulfide cross-linked dimer species, compared to comparable batches of AspRS1$^{N1}$ prepared under identical conditions.

Moreover an analysis of the proteins endotoxin content reveals that the AspRS1$^{N1}$ (C76S) proteins exhibited a significantly reduced endotoxin content compared to the non-mutated AspRS1$^{N1}$. (Table E2).

TABLE E2

Endotoxin Content

| DRS polypeptide form | Average Endotoxin level in purified protein (EU/mg) |
|---|---|
| AspRS1$^{N1}$ (C76S) | 7.3 (n = 8) |
| AspRS1$^{N1}$ | 43.5 (n = 7) |

Accordingly it is concluded that the DRS polypeptides comprising a reduced a cysteine content, specifically AspRS1$^{N1}$ (C76S) exhibits improved manufacturability, improved production yields and significantly less endotoxin contamination compared to the corresponding non mutated protein.

Example 2

Production of DRS Polypeptides in Mammalian Cells

As an alternative production system, exemplary DRS polypeptides were prepared using a mammalian expression system. This approach has the potential advantage of eliminating any potential contamination of the DRS polypeptides with *E. coli* derived endotoxins.

Cloning:

The AspRS1$^{N1}$ fragment (amino acid 1-154 of human cytoplasmic Aspartyl-tRNA synthetase) was amplified by polymerase chain reaction (PCR) using the following primer pairs synthesized at Integrated DNA Technologies to create either cytoplasmic, or secreted versions of the AspRS1$^{N1}$.

Primer Pair 1

(SEQ ID NO: 32)
AGTCTTGCACTTGTCACGAATTCGATGCCCAGCGCCAGCGCCAGC (SEQ ID NO: 33)
CGGTGGGCATGTGTGAGTTTTGTCTCACTTGTCGTCATCGTCTTTGTAGT
CCGTAGAATCGAGACCGAGGAGAGG

Primer Pair 2

(SEQ ID NO: 34)
GATCACCGGCGAAGGAGGGCCACCATGCCCAGCGCCAGCGCCAGC (SEQ ID NO: 35)
CGGTGGGCATGTGTGAGTTTTGTCTCACTTGTCGTCATCGTCTTTGTAGT
CCGTAGAATCGAGACCGAGGAGAGG

The primers were mixed with the template (AspRS1$^{N1}$ nucleic acid fragment in the pET28 vector)(see above), Accuprime pfx supermix (Invitrogen cat. no. 12344-040) and denatured for 5 minutes at 95° C. The amplification was done in the Eppendorf thermal cycler for 35 cycles of 95° C. for 30 seconds, 52° C. for 30 seconds and 68° C. for 40 seconds. The amplified fragments were purified with QIAquick PCR Purification Kit (Qiagen cat. no. 28104). The fragment size, quantity and purity were confirmed on the 1% agarose gel in the TAE buffer (Invitrogen cat. no. 15558). The fragment was inserted into the pFUSE-hIgG1-Fc2 (Invivogen cat. no. pfuse-hg1fc2) by mutagenesis using the QuikChange Lightning Site-Directed Mutagenesis Kit (Agilent, cat. no. 210518). Eighteen thermal cycles were performed at 95° C. for 30 seconds, 52° C. for 30 seconds and 68° C. for 4 minutes. After mutagenesis, the sample was treated with Dpn I enzyme at 37° C. and transformed into XL10 gold competent cells. The heat shock was done at 42° C. for 30 seconds followed by 2 minutes on ice. The XL10 gold transformants were resuspended in SOC medium and incubated at 37° C. for 1 hour and then were spread onto zeocin agar and incubated at 37° C. overnight. Multiple colonies were grown in terrific broth overnight at 37° C. and the plasmids were purified with QIAprep Spin Miniprep Kit (Qiagen cat. no. 27106). The plasmids were sequenced to confirm the DNA identity. The correct clones were transformed into NovaBlue competent cells (Novagen cat. no. 70181) and grown in 250 ml M9YE medium at 37° C. overnight. The maxiprep was performed using the HiSpeed Plasmid Maxi Kit (Qiagen cat. no. 12663). The concentration and purity were determined by measuring A260, A280 and A230. The purified plasmids were stored at −20° C. before transfection.

The secretory AspRS1$^{N1}$ sequence is as follows:

(SEQ ID NO: 36)
ATGTACAGGATGCAACTCCTGTCTTGCATTGCACTAAGTCTTGCACTTGT

CACGAATTCGATGCCCAGCGCCAGCGCCAGCCGCAAGAGTCAGGAGAAGC

CGCGGGAGATCATGGACGCGGCGGAAGATTATGCTAAAGAGAGATATGGA

ATATCTTCAATGATACAATCACAAGAAAAACCAGATCGAGTTTTGGTTCG

GGTTAGAGACTTGACAATACAAAAAGCTGATGAAGTTGTTTGGGTACGTG

CAAGAGTTCATACAAGCAGAGCTAAAGGGAAACAGTGCTTCTTAGTCCTA

CGTCAGCAGCAGTTTAATGTCCAGGCTCTTGTGGCGGTGGGAGACCATGC

AAGCAAGCAGATGGTTAAATTTGCTGCCAACATCAACAAAGAGAGCATTG

TGGATGTAGAAGGTGTTGTGAGAAAAGTGAATCAGAAAATTGGAAGCTGT

ACACAGCAAGACGTTGAGTTACATGTTCAGAAGATTTATGTGATCAGTTT

-continued

```
GGCTGAACCCCGTCTGCCCCTGGGTAAGCCTATCCCTAACCCTCTCCTCG

GTCTCGATTCTACGGACTACAAAGACGATGACGACAAGTGA
```

The intracellular AspRS1$^{N1}$ sequence is as follows:

(SEQ ID NO: 37)
```
ATGCCCAGCGCCAGCGCCAGCCGCAAGAGTCAGGAGAAGCCGCGGGAGAT

CATGGACGCGGCGGAAGATTATGCTAAAGAGAGATATGGAATATCTTCAA

TGATACAATCACAAGAAAAACCAGATCGAGTTTTGGTTCGGGTTAGAGAC

TTGACAATACAAAAAGCTGATGAAGTTGTTTGGGTACGTGCAAGAGTTCA

TACAAGCAGAGCTAAAGGGAAACAGTGCTTCTTAGTCCTACGTCAGCAGC

AGTTTAATGTCCAGGCTCTTGTGGCGGTGGGAGACCATGCAAGCAAGCAG

ATGGTTAAATTTGCTGCCAACATCAACAAAGAGAGCATTGTGGATGTAGA

AGGTGTTGTGAGAAAAGTGAATCAGAAAATTGGAAGCTGTACACAGCAAG

ACGTTGAGTTACATGTTCAGAAGATTTATGTGATCAGTTTGGCTGAACCC

CGTCTGCCCCTGGGTAAGCCTATCCCTAACCCTCTCCTCGGTCTCGATTC

TACGGACTACAAAGACGATGACGACAAGTGA
```

The hEF1-HTLV promoter comprising the Elongation Factor-1α (EF-1α) core promoter and the R segment and part of the U5 sequence of the Human T-Cell Leukemia Virus (HTLV) Type 1 Long Terminal Repeat was used to drive the transcription. The V5 (GKPIPNPLLGLDST) (SEQ ID NO:46) and Flag (DYKDDDDK) (SEQ ID NO:47) tags were added to the C-terminus of the D1 fragments for detection and purification purpose. The Sh ble gene from *Streptoalloteichus hindustanus* was used for antibiotic resistance. The Simian Virus 40 late polyadenylation signal enables the cleavage and polyadenylation resulting in stable mRNA.

Expression:

The FREESTYLE™ MAX CHO Expression System (Invitrogen cat. no. K9000-20) was used for expression of the secretory form of AspRS1$^{N1}$. The CHO-S cells were thawed from liquid nitrogen and grown in the serum-free medium (FREESTYLE™ CHO Expression Medium) supplemented with 8 mM L-Glutamine in a 37° C. incubator containing a humidified atmosphere of 8% $CO_2$ in air on an orbital shaker platform rotating at 125 rpm. The cells were diluted to 2-3×10$^5$ cells/ml when the density reached about 10$^6$ cells/ml and were repeated a few passages. The DNA was mixed 1:1 with the Freestyle Max reagent in the Optipro SFM and incubated 10 minutes at room temperature. The complex was added slowly into the cells at the density about 10$^6$ cells/ml. The cell density and viability were monitored daily until harvest.

The FREESTYLE™ 293 Expression (Invitrogen cat. no. K9000-01) was used for expression of the intracellular form of AspRS1$^{N1}$. The 293-F cells were thawed from liquid nitrogen and grown in the serum-free medium (FREESTYLE™ 293 Expression Medium) supplemented with Glutamax-I in a 37° C. incubator containing a humidified atmosphere of 8% $CO_2$ in air on an orbital shaker platform rotating at 125 rpm. The cells were diluted to 2-3×10$^5$ cells/ml when the density reached about 10$^6$ cells/ml and were repeated for a few passages. The DNA was mixed 1:2 with the 293 transfectin reagent in the Opti-MEM I and incubated 20-30 minutes at room temperature. The complex was added slowly into the cells at the density about 10$^6$ cells/ml. The cell density and viability were monitored daily until harvest.

Purification:

In the case of secretory form of AspRS1$^{N1}$, the supernatant of the cell culture was separated from the cells by centrifugation. The clarified sample was loaded onto M2 agarose (Sigma cat. no. A2220) in a gravity column. The resin was then washed with TBS (50 mM Tris HCl, with 150 mM NaCl, pH 7.4). The bound protein was eluted with 0.1 M glycine HCl, pH 3.0 and neutralized immediately with 1M Tris buffer at pH8.0.

In the case of intracellular form of AspRS1$^{N1}$, the cells were recovered by centrifugation. The cells were lysed using M-PER Mammalian Protein Extraction Reagent (Pierce cat. no. 78501) and then centrifuged to remove the insoluble debris. The clarified lysate was loaded onto M2 agarose (Sigma cat. no. A2220) in a gravity column. The resin was then washed with TBS (50 mM Tris HCl, with 150 mM NaCl, pH 7.4). The bound protein was eluted with 0.1 M glycine HCl, pH 3.0 and neutralized immediately with 1M Tris buffer at pH8.0. The purified protein was analyzed by SDS-PAGE and Western blot. Purified proteins may be evaluated for binding to TLRs as described in Example 3 below.

Example 3

Evaluation of Biological Activity

To evaluate the binding of the DRS polypeptides to human toll like receptors a series of studies were conducted with commercially available reporter HEK 293 and THP-1 cell lines over expressing the TLR 2 and TLR 4 receptors.

Genetically modified Human HEK293 cells sold under the trademark HEK-Blue™ TLR cells (Invivogen) selectively express the TLR2 or TLR4 receptors and include a secreted embryonic alkaline phosphatase (SEAP) reporter gene under the control of an IFN-beta minimal promoter which is fused to five NF-kB and AP-1 transcription factors binding sites. With the use of specific TLR 2 or 4 agonists (respectively), HEK-BLUE™ TLR2 and HEK-BLUE™ TLR4 cells activate NF-kB and/or AP-1 leading to the secretion of SEAP which is measurable when using SEAP detection reagent. The HEK-BLUE™ TLR2 cells are co-transfected with the LPS co-receptor protein CD14 to enhance TLR2 responsiveness and improve signal quality. The parent cell expresses endogenous levels of TLR1, 3, 5, 6 and also NOD1. The THP-1 monocyte reporter cells (Invivogen THP1-XBlue™ cells). Stably express CD14, MD-2, & and also include a secreted embryonic alkaline phosphatase (SEAP) reporter gene under the control of NF-kB and AP-1 promoter elements as described above.

Methods.

HEK-BLUE™-TLR2 or HEK-BLUE™-TLR4 cells were washed twice with PBS, trypsinized and resuspended in fresh Growth Medium (Growth Medium: DMEM, 4.5 g/L glucose, 10% heat-inactivated fetal bovine serum (30 minutes at 56° C.), 100 mg/mL ZEOCIN™, 2 mM L-glutamine). Cells were plated at a concentration of 50,000 cells/well in a 96 well plate in a total volume of 100 µL, and DRS polypeptides, (AspRS1$^{N1}$ or AspRS1$^{N1}$ (C76S)), were added to each well at the concentrations shown for 16 hours. On the next day, SEAP detection medium (QUANTI-BLUE™) (Invivogen Catalog code: rep-qb1) was prepared following the manufacturer's instructions and 120 µL was added per well to a clear flat-bottom 96-well plate, followed by (20 μL) of cell supernatant. Samples were incubated at 37° C. for 24 hours. SEAP levels were determined using a spectrophotometer and reading absorbance at 650 nM.

Results.

Figure 2:
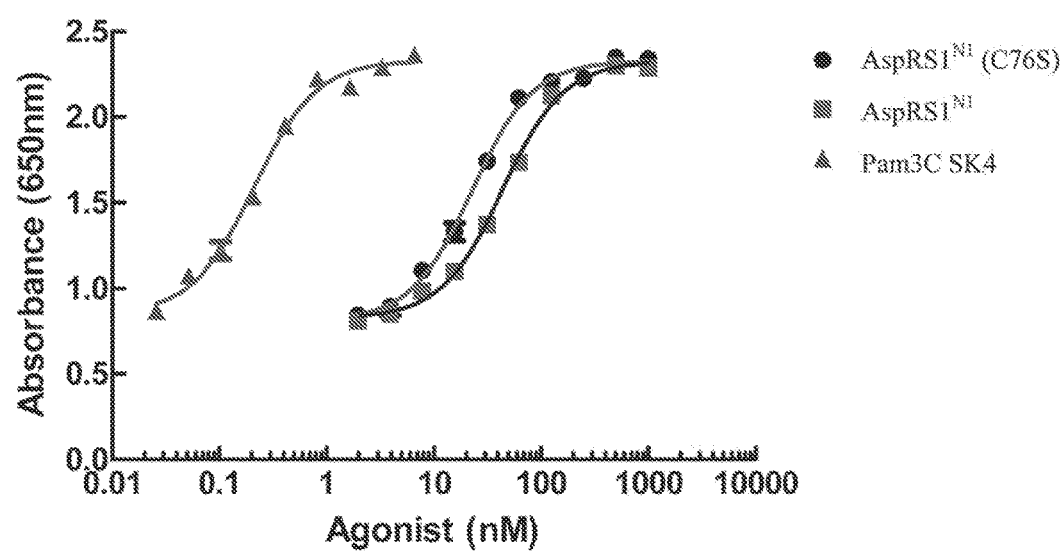
FIG. 2 shows a direct comparison of AspRS1$^{N1}$ and AspRS1$^{N1}$ (C76S) on their ability to stimulate reporter gene activity mediated by the TLR2 receptor in HEK-Blue 2 cells.
Figure 3:
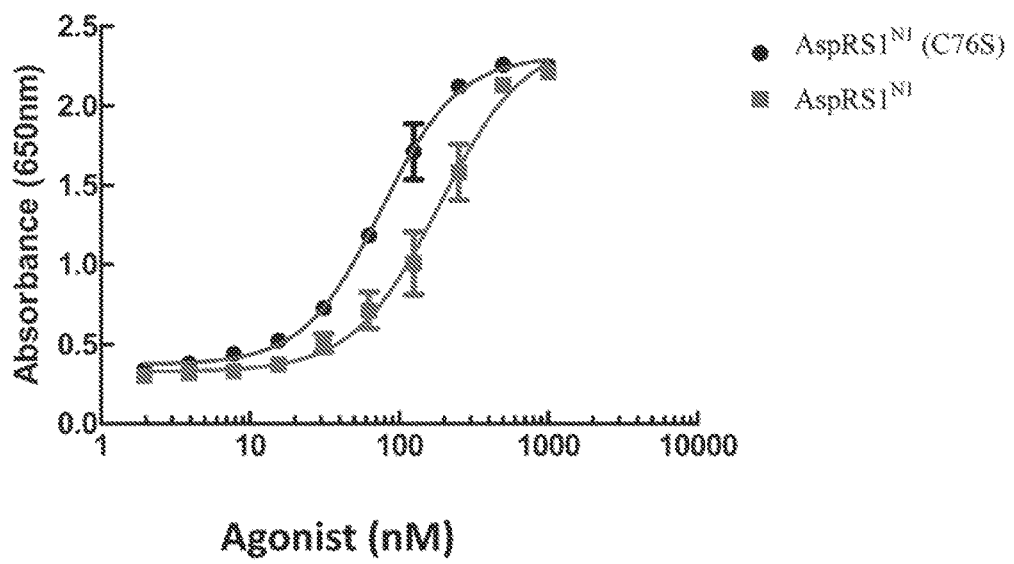
FIG. 3 shows a direct comparison of AspRS1$^{N1}$ and AspRS1$^{N1}$ (C76S) on their ability to stimulate reporter gene activity mediated by the TLR4 receptor in HEK-Blue 4 cells.

The results shown in FIGS. 2 and 3, demonstrate that the DRS polypeptide AspRS1$^{N1}$ (C76S) exhibited significantly more activity, and displayed an apparent EC$_{50}$ which was significantly higher compared to the non-mutated AspRS1$^{N1}$ parent molecule with respect to both TLR2 and TLR4 receptor binding (Table E3).

TABLE E3

Activity of AspRS1$^{N1}$ variant C76S on TLR2 and TLR4 receptors

| DRS polypeptide form | Fold increase in activity over AspRS1$^{N1}$ |
|---|---|
| TLR2 Activity | |
| AspRS1$^{N1}$ (C76S) | 3.2 ± 0.14 (n = 2) |
| TLR4 Activity | |
| AspRS1$^{N1}$ (C76S) | 3.6 ± 0.17 (n = 2) |

In conclusion these results demonstrate the DRS polypeptides with altered cysteine content, and in particular DRS mutants comprising the mutation of cysteine 76 to another amino acid, result in the creation of new product forms which surprisingly exhibit enhanced activities, improved production yields and further surprisingly demonstrate reduced endotoxin content.

Example 4

Mutation of C76 and C130 to Other Amino Acids

To determine whether other favorable mutations in addition to Cys76→Ser could be identified, both cysteine residues (i.e., those at either Cys76 or Cys130) were mutated to all 19 alternative naturally occurring amino acid residues. To accomplish this in either the native human codon usage DRS polypeptides, or the *E. coli* optimized DRS polypeptides, the following primers were used:

TABLE E4

Mutagenesis Primer Sequences

| Name | Amino Acid Residue Range of SEQ ID NO: 1 | Nucleic acid sequence | SEQ ID NO: |
|---|---|---|---|
| Human C76X Primer | 211-247 | GCTAAAGGGAAACAGNNNTTCTTAGTCCT ACGTCAGC (NNN = AGC) | 38 |
| Human C130X Primer | 367-403 | GTGAATCAGAAAATTGGAAGCNNNACACA GCAAGACG (NNN = AGC) | 39 |
| *E. coli* codon optimized C76X Primer | 208-247 | CGTGCAAAAGGCAAACAGNNNTTTCTGGT CCTGCGTCAGC (NNN = AGC) | 40 |
| *E. coli* codon optimized C130X Primer | 369-409 | CAATCAAAAGATCGGCTCGNNNACGCAAC AAGATGTCGAGC (NNN = AGC) | 41 |

Mutations at either position were introduced by mutagenesis using the QuikChange Lightning Site-Directed Mutagenesis Kit (Agilent, cat. no. 210518) as described above. After mutagenesis, the sample was treated with Dpn I enzyme at 37° C. and transformed into XL10 gold competent cells as described in Example 2. Multiple colonies were grown in terrific broth overnight at 37° C. and the resulting plasmids were purified with QIAprep Spin Miniprep Kit (Qiagen cat. no. 27106). The plasmids were sequenced to confirm the identity of the amino acid substitution of each clone. The representative clones were transformed into NovaBlue competent cells (Novagen cat. no. 70181) and grown in 250 ml M9YE medium at 37° C. overnight. A maxiprep was performed using the HiSpeed Plasmid Maxi Kit (Qiagen cat. no. 12663) to create a plasmid stock of mutant for further analysis. The concentration and purity were determined by measuring A260, A280 and A230. The purified plasmids were stored at −20° C. before transfection into *E. coli* or mammalian cells using the methods described above in Examples 1 and 2.

To assess the impact of the mutation of Cys76 or Cys130, representative clones were transformed into *E. coli*, or mammalian cells, and the production yields, endotoxin contents were compared. Also, the relative activity of the purified proteins are compared in the HEK293-TLR2 and HEK293-TLR4 expressing cell lines as described above. The optimal substitutions are identified based on the results obtained. Representative results are shown in Table E5.

TABLE E5

| Variant | Yield + <1.2 mg, ++ >1.2 mg, +++ >1.4 mg, ++++ >2.0 mg | EU/mg + <1 EU/mg, ++ <5 EU/mg, +++ <10 EU/mg, ++++ <20 EU/mg, +++++ >20 EU/mg |
|---|---|---|
| C76A | ++++ | +++++ |
| C76I | +++ | +++ |
| C76L | + | +++ |
| C76T | ++ | +++ |
| C76V | + | + |
| C130F | ++ | + |
| C130L | +++ | ++++ |
| C130T | + | +++ |
| C130V | + | +++++ |

The results show that C76V, C76L, and C76T show enhanced yields and reduced endotoxin content. Additionally the results show that C130T and C130V demonstrate enhanced yields and reduced endotoxin content.

Example 5

Production of DRS Cysteine Mutants

Creation of DRS Cysteine Mutants:

To improve the stability of full length DRS and reduce the impact of non-specific disulfide bond mediated aggregation formation, potential problematic cysteines were identified based on the crystal structure (see, e.g., commonly owned U.S. application Ser. No. 12/751,358), and mutated into Ser or Ala or Val. In particular cysteines C334, C349, C203 and C259 in wild type DRS were initially targeted for mutagenesis. To systematically assess the impact of each cysteine in mediating protein aggregation, mini libraries were created in which each DRS cysteine mutant could contain either a mutation on one cysteine position or multiple positions. To make DRS mutants C334S, C349S, C334S/C349S, C334S/C349S/C259A/C203A, C334S/C349S/C259A/C203V, C334S/C349S/C203A, C334S/C349S/C203V, C203A and C203V, the following primers were used as listed in Table E6:

TABLE E6

| Mutation | Oligo sequence | SEQ ID NO: |
|---|---|---|
| C334S | CAGTTCCCATCTGAGCCATTC | 136 |
| C349S | GACTAGAATATTCTGAAGCATTGGC | 137 |

TABLE E6-continued

| Mutation | Oligo sequence | SEQ ID NO: |
|---|---|---|
| C203A | CCAGTCTGGCATCGCCCATCTCTTCC | 138 |
| C203V | CCAGTCTGGCATCGTCCATCTCTTCC | 139 |
| C259A | CCACAGCTATATAAGCAAATGTGCATTGCGGCTGATTTTGAG | 140 |

Mutations at cysteine positions were introduced by mutagenesis using the QuickChange Lightning Site-Directed Mutagenesis Kit (Agilent, cat. no. 210518) following the manufacturer's instructions. After mutagenesis, the sample was treated with Dpn I enzyme at 37° C. and transformed into XL10 gold competent cells using routine procedures. Multiple colonies were grown in LB media overnight at 37° C. and the resulting plasmids are purified with QIAprep Spin Miniprep Kit (Qiagen cat. no. 27106). The plasmids were sequenced to confirm the identity of the amino acid substitution of each clone.

The DRS cysteine mutant DNA sequences are as follows:

1. DRS-C334S:

(SEQ ID NO: 92)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAACAGAGT
CATTGATCTTAGGACATCAACTAGTCAGGCAGTCTTCCGTCTCCAGTCTGGCATCTGCCATCT
CTTCCGAGAAACTTTAATTAACAAAGGTTTTGTGGAAATCCAAACTCCTAAAATTATTTCAG
CTGCCAGTGAAGGAGGAGCCAATGTTTTTACTGTGTCATATTTTAAAAATAATGCATACCTG
GCTCAGTCCCCACAGCTATATAAGCAAATGTGCATTTGTGCTGATTTTGAGAAGGTTTTCTCT
ATTGGACCAGTATTCAGAGCGGAAGACTCTAATACCCATAGACATCTAACTGAGTTTGTTGG
TTTGGACATTGAAATGGCTTTTAATTACCATTACCACGAAGTTATGGAAGAAATTGCTGACA
CCATGGTACAAATATTCAAAGGACTTCAAGAAAGGTTTCAGACTGAAATTCAAACAGTGAA
TAAACAGTTCCCATCTGAGCCATTCAAATTTTTGGAGCCAACTCTAAGACTAGAATATTGTG
AAGCATTGGCTATGCTTAGGGAAGCTGGAGTCGAAATGGGAGATGAAGACGATCTGAGCAC
ACCAAATGAAAAGCTGTTGGGTCATTTGGTAAAGGAAAAGTATGATACAGATTTTTATATTC
TTGATAAATATCCATTGGCTGTAAGACCTTTCTATACCATGCCTGACCCAAGAAATCCCAAA
CAGTCCAACTCTTACGATATGTTCATGAGAGGAGAAGAAATATTGTCAGGAGCTCAAAGAA
TACATGATCCTCAACTGCTAACAGAGAGCTTTACATCATGGAATTGATTTGGAGAAAATT
AAGGCTTACATTGATTCCTTCCGCTTTGGAGCCCCTCCTCATGCTGGTGGAGGCATTGGATTG
GAACGAGTTACTATGCTGTTTCTGGGATTGCATAATGTTCGTCAGACCTCCATGTTCCCTCGT
GATCCCAAACGACTCACTCCT

2. DRS-C349S:

(SEQ ID NO: 93)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAACAGAGT
CATTGATCTTAGGACATCAACTAGTCAGGCAGTCTTCCGTCTCCAGTCTGGCATCTGCCATCT
CTTCCGAGAAACTTTAATTAACAAAGGTTTTGTGGAAATCCAAACTCCTAAAATTATTTCAG
CTGCCAGTGAAGGAGGAGCCAATGTTTTTACTGTGTCATATTTTAAAAATAATGCATACCTG
GCTCAGTCCCCACAGCTATATAAGCAAATGTGCATTTGTGCTGATTTTGAGAAGGTTTTCTCT
ATTGGACCAGTATTCAGAGCGGAAGACTCTAATACCCATAGACATCTAACTGAGTTTGTTGG
TTTGGACATTGAAATGGCTTTTAATTACCATTACCACGAAGTTATGGAAGAAATTGCTGACA

-continued

CCATGGTACAAATATTCAAAGGACTTCAAGAAAGGTTTCAGACTGAAATTCAAACAGTGAA
TAAACAGTTCCCATGTGAGCCATTCAAATTTTTGGAGCCAACTCTAAGACTAGAATATTCTG
AAGCATTGGCTATGCTTAGGGAAGCTGGAGTCGAAATGGGAGATGAAGACGATCTGAGCAC
ACCAAATGAAAAGCTGTTGGGTCATTTGGTAAAGGAAAAGTATGATACAGATTTTTATATTC
TTGATAAATATCCATTGGCTGTAAGACCTTTCTATACCATGCCTGACCCAAGAAATCCCAAA
CAGTCCAACTCTTACGATATGTTCATGAGAGGAGAAGAAATATTGTCAGGAGCTCAAAGAA
TACATGATCCTCAACTGCTAACAGAGAGAGCTTTACATCATGGAATTGATTTGGAGAAAATT
AAGGCTTACATTGATTCCTTCCGCTTTGGAGCCCCTCCTCATGCTGGTGGAGGCATTGGATTG
GAACGAGTTACTATGCTGTTTCTGGGATTGCATAATGTTCGTCAGACCTCCATGTTCCCTCGT
GATCCCAAACGACTCACTCCT

3. DRS C334S/C349S:
(SEQ ID NO: 94)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAACAGAGT
CATTGATCTTAGGACATCAACTAGTCAGGCAGTCTTCCGTCTCCAGTCTGGCATCTGCCATCT
CTTCCGAGAAACTTTAATTAACAAAGGTTTTGTGGAAATCCAAACTCCTAAAATTATTTCAG
CTGCCAGTGAAGGAGGAGCCAATGTTTTTACTGTGTCATATTTTAAAAATAATGCATACCTG
GCTCAGTCCCCACAGCTATATAAGCAAATGTGCATTTGTGCTGATTTTGAGAAGGTTTTCTCT
ATTGGACCAGTATTCAGAGCGGAAGACTCTAATACCCATAGACATCTAACTGAGTTTGTTGG
TTTGGACATTGAAATGGCTTTTAATTACCATTACCACGAAGTTATGGAAGAAATTGCTGACA
CCATGGTACAAATATTCAAAGGACTTCAAGAAAGGTTTCAGACTGAAATTCAAACAGTGAA
TAAACAGTTCCCATCTGAGCCATTCAAATTTTTGGAGCCAACTCTAAGACTAGAATATTCTG
AAGCATTGGCTATGCTTAGGGAAGCTGGAGTCGAAATGGGAGATGAAGACGATCTGAGCAC
ACCAAATGAAAAGCTGTTGGGTCATTTGGTAAAGGAAAAGTATGATACAGATTTTTATATTC
TTGATAAATATCCATTGGCTGTAAGACCTTTCTATACCATGCCTGACCCAAGAAATCCCAAA
CAGTCCAACTCTTACGATATGTTCATGAGAGGAGAAGAAATATTGTCAGGAGCTCAAAGAA
TACATGATCCTCAACTGCTAACAGAGAGAGCTTTACATCATGGAATTGATTTGGAGAAAATT
AAGGCTTACATTGATTCCTTCCGCTTTGGAGCCCCTCCTCATGCTGGTGGAGGCATTGGATTG
GAACGAGTTACTATGCTGTTTCTGGGATTGCATAATGTTCGTCAGACCTCCATGTTCCCTCGT
GATCCCAAACGACTCACTCCT

4. DRS C203A:
(SEQ ID NO: 95)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAACAGAGT
CATTGATCTTAGGACATCAACTAGTCAGGCAGTCTTCCGTCTCCAGTCTGGCATCGCCCATCT
CTTCCGAGAAACTTTAATTAACAAAGGTTTTGTGGAAATCCAAACTCCTAAAATTATTTCAG
CTGCCAGTGAAGGAGGAGCCAATGTTTTTACTGTGTCATATTTTAAAAATAATGCATACCTG
GCTCAGTCCCCACAGCTATATAAGCAAATGTGCATTTGTGCTGATTTTGAGAAGGTTTTCTCT
ATTGGACCAGTATTCAGAGCGGAAGACTCTAATACCCATAGACATCTAACTGAGTTTGTTGG
TTTGGACATTGAAATGGCTTTTAATTACCATTACCACGAAGTTATGGAAGAAATTGCTGACA
CCATGGTACAAATATTCAAAGGACTTCAAGAAAGGTTTCAGACTGAAATTCAAACAGTGAA
TAAACAGTTCCCATGTGAGCCATTCAAATTTTTGGAGCCAACTCTAAGACTAGAATATTGTG
AAGCATTGGCTATGCTTAGGGAAGCTGGAGTCGAAATGGGAGATGAAGACGATCTGAGCAC
ACCAAATGAAAAGCTGTTGGGTCATTTGGTAAAGGAAAAGTATGATACAGATTTTTATATTC
TTGATAAATATCCATTGGCTGTAAGACCTTTCTATACCATGCCTGACCCAAGAAATCCCAAA
CAGTCCAACTCTTACGATATGTTCATGAGAGGAGAAGAAATATTGTCAGGAGCTCAAAGAA
TACATGATCCTCAACTGCTAACAGAGAGAGCTTTACATCATGGAATTGATTTGGAGAAAATT
AAGGCTTACATTGATTCCTTCCGCTTTGGAGCCCCTCCTCATGCTGGTGGAGGCATTGGATTG
GAACGAGTTACTATGCTGTTTCTGGGATTGCATAATGTTCGTCAGACCTCCATGTTCCCTCGT
GATCCCAAACGACTCACTCCT

5. DRS C203V:
(SEQ ID NO: 96)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAACAGAGT
CATTGATCTTAGGACATCAACTAGTCAGGCAGTCTTCCGTCTCCAGTCTGGCATCGTCCATCT
CTTCCGAGAAACTTTAATTAACAAAGGTTTTGTGGAAATCCAAACTCCTAAAATTATTTCAG
CTGCCAGTGAAGGAGGAGCCAATGTTTTTACTGTGTCATATTTTAAAAATAATGCATACCTG

-continued

```
GCTCAGTCCCCACAGCTATATAAGCAAATGTGCATTTGTGCTGATTTTGAGAAGGTTTTCTCT
ATTGGACCAGTATTCAGAGCGGAAGACTCTAATACCCATAGACATCTAACTGAGTTTGTTGG
TTTGGACATTGAAATGGCTTTTAATTACCATTACCACGAAGTTATGGAAGAAATTGCTGACA
CCATGGTACAAATATTCAAAGGACTTCAAGAAAGGTTTCAGACTGAAATTCAAACAGTGAA
TAAACAGTTCCCATGTGAGCCATTCAAATTTTTGGAGCCAACTCTAAGACTAGAATATTGTG
AAGCATTGGCTATGCTTAGGGAAGCTGGAGTCGAAATGGGAGATGAAGACGATCTGAGCAC
ACCAAATGAAAAGCTGTTGGGTCATTTGGTAAAGGAAAAGTATGATACAGATTTTTATATTC
TTGATAAATATCCATTGGCTGTAAGACCTTTCTATACCATGCCTGACCCAAGAAATCCCAAA
CAGTCCAACTCTTACGATATGTTCATGAGAGGAAGAAGAAATATTGTCAGGAGCTCAAAGAA
TACATGATCCTCAACTGCTAACAGAGAGAGCTTTACATCATGGAATTGATTTGGAGAAAATT
AAGGCTTACATTGATTCCTTCGCTTTGGAGCCCCTCCTCATGCTGGTGGAGGCATTGGATTG
GAACGAGTTACTATGCTGTTTCTGGGATTGCATAATGTTCGTCAGACCTCCATGTTCCCTCGT
GATCCCAAACGACTCACTCCT
```

6. DRS C334S/C349S/C203A:

(SEQ ID NO: 97)
```
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAACAGAGT
CATTGATCTTAGGACATCAACTAGTCAGGCAGTCTTCCGTCTCCAGTCTGGCATCGTCCATCT
CTTCCGAGAAACTTTAATTAACAAAGGTTTTGTGGAAATCCAAACTCCTAAAATTATTTCAG
CTGCCAGTGAAGGAGGAGCCAATGTTTTTACTGTGTCATATTTTAAAAATAATGCATACCTG
GCTCAGTCCCCACAGCTATATAAGCAAATGTGCATTTGTGCTGATTTTGAGAAGGTTTTCTCT
ATTGGACCAGTATTCAGAGCGGAAGACTCTAATACCCATAGACATCTAACTGAGTTTGTTGG
TTTGGACATTGAAATGGCTTTTAATTACCATTACCACGAAGTTATGGAAGAAATTGCTGACA
CCATGGTACAAATATTCAAAGGACTTCAAGAAAGGTTTCAGACTGAAATTCAAACAGTGAA
TAAACAGTTCCCATCTGAGCCATTCAAATTTTTGGAGCCAACTCTAAGACTAGAATATTCTG
AAGCATTGGCTATGCTTAGGGAAGCTGGAGTCGAAATGGGAGATGAAGACGATCTGAGCAC
ACCAAATGAAAAGCTGTTGGGTCATTTGGTAAAGGAAAAGTATGATACAGATTTTTATATTC
TTGATAAATATCCATTGGCTGTAAGACCTTTCTATACCATGCCTGACCCAAGAAATCCCAAA
CAGTCCAACTCTTACGATATGTTCATGAGAGGAGAAGAAATATTGTCAGGAGCTCAAAGAA
TACATGATCCTCAACTGCTAACAGAGAGAGCTTTACATCATGGAATTGATTTGGAGAAAATT
AAGGCTTACATTGATTCCTTCGCTTTGGAGCCCCTCCTCATGCTGGTGGAGGCATTGGATTG
GAACGAGTTACTATGCTGTTTCTGGGATTGCATAATGTTCGTCAGACCTCCATGTTCCCTCGT
GATCCCAAACGACTCACTCCT
```

7. DRS C334S/C349S/C203V:

(SEQ ID NO: 98)
```
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAACAGAGT
CATTGATCTTAGGACATCAACTAGTCAGGCAGTCTTCCGTCTCCAGTCTGGCATCGTCCATCT
CTTCCGAGAAACTTTAATTAACAAAGGTTTTGTGGAAATCCAAACTCCTAAAATTATTTCAG
CTGCCAGTGAAGGAGGAGCCAATGTTTTTACTGTGTCATATTTTAAAAATAATGCATACCTG
GCTCAGTCCCCACAGCTATATAAGCAAATGTGCATTTGTGCTGATTTTGAGAAGGTTTTCTCT
ATTGGACCAGTATTCAGAGCGGAAGACTCTAATACCCATAGACATCTAACTGAGTTTGTTGG
TTTGGACATTGAAATGGCTTTTAATTACCATTACCACGAAGTTATGGAAGAAATTGCTGACA
CCATGGTACAAATATTCAAAGGACTTCAAGAAAGGTTTCAGACTGAAATTCAAACAGTGAA
TAAACAGTTCCCATCTGAGCCATTCAAATTTTTGGAGCCAACTCTAAGACTAGAATATTCTG
AAGCATTGGCTATGCTTAGGGAAGCTGGAGTCGAAATGGGAGATGAAGACGATCTGAGCAC
ACCAAATGAAAAGCTGTTGGGTCATTTGGTAAAGGAAAAGTATGATACAGATTTTTATATTC
TTGATAAATATCCATTGGCTGTAAGACCTTTCTATACCATGCCTGACCCAAGAAATCCCAAA
CAGTCCAACTCTTACGATATGTTCATGAGAGGAGAAGAAATATTGTCAGGAGCTCAAAGAA
TACATGATCCTCAACTGCTAACAGAGAGAGCTTTACATCATGGAATTGATTTGGAGAAAATT
AAGGCTTACATTGATTCCTTCGCTTTGGAGCCCCTCCTCATGCTGGTGGAGGCATTGGATTG
GAACGAGTTACTATGCTGTTTCTGGGATTGCATAATGTTCGTCAGACCTCCATGTTCCCTCGT
GATCCCAAACGACTCACTCCT
```

8. DRS C334S/C349S/C259A/C203A:

(SEQ ID NO: 99)
```
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAACAGAGT
```

-continued
```
CATTGATCTTAGGACATCAACTAGTCAGGCAGTCTTCCGTCTCCAGTCTGGCATCGCCCATCT
CTTCCGAGAAACTTTAATTAACAAAGGTTTTGTGGAAATCCAAACTCCTAAAATTATTTCAG
CTGCCAGTGAAGGAGGAGCCAATGTTTTTACTGTGTCATATTTTAAAAATAATGCATACCTG
GCTCAGTCCCCACAGCTATATAAGCAAATGTGCATTGCGGCTGATTTTGAGAAGGTTTTCTCT
ATTGGACCAGTATTCAGAGCGGAAGACTCTAATACCCATAGACATCTAACTGAGTTTGTTGG
TTTGGACATTGAAATGGCTTTTAATTACCATTACCACGAAGTTATGGAAGAAATTGCTGACA
CCATGGTACAAATATTCAAAGGACTTCAAGAAAGGTTTCAGACTGAAATTCAAACAGTGAA
TAAACAGTTCCCATCTGAGCCATTCAAATTTTTGGAGCCAACTCTAAGACTAGAATATTCTG
AAGCATTGGCTATGCTTAGGGAAGCTGGAGTCGAAATGGGAGATGAAGACGATCTGAGCAC
ACCAAATGAAAAGCTGTTGGGTCATTTGGTAAAGGAAAAGTATGATACAGATTTTTATATTC
TTGATAAATATCCATTGGCTGTAAGACCTTTCTATACCATGCCTGACCCAAGAAATCCCAAA
CAGTCCAACTCTTACGATATGTTCATGAGAGGAGAAGAAATATTGTCAGGAGCTCAAAGAA
TACATGATCCTCAACTGCTAACAGAGAGAGCTTTACATCATGGAATTGATTTGGAGAAAATT
AAGGCTTACATTGATTCCTTCCGCTTTGGAGCCCCTCCTCATGCTGGTGGAGGCATTGGATTG
GAACGAGTTACTATGCTGTTTCTGGGATTGCATAATGTTCGTCAGACCTCCATGTTCCCTCGT
GATCCCAAACGACTCACTCCT 9. DRS C334S/C349S/C259A/C203V:
                                              (SEQ ID NO: 100)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAACAGAGT
CATTGATCTTAGGACATCAACTAGTCAGGCAGTCTTCCGTCTCCAGTCTGGCATCGTCCATCT
CTTCCGAGAAACTTTAATTAACAAAGGTTTTGTGGAAATCCAAACTCCTAAAATTATTTCAG
CTGCCAGTGAAGGAGGAGCCAATGTTTTTACTGTGTCATATTTTAAAAATAATGCATACCTG
GCTCAGTCCCCACAGCTATATAAGCAAATGTGCATTGCGGCTGATTTTGAGAAGGTTTTCTCT
ATTGGACCAGTATTCAGAGCGGAAGACTCTAATACCCATAGACATCTAACTGAGTTTGTTGG
TTTGGACATTGAAATGGCTTTTAATTACCATTACCACGAAGTTATGGAAGAAATTGCTGACA
CCATGGTACAAATATTCAAAGGACTTCAAGAAAGGTTTCAGACTGAAATTCAAACAGTGAA
TAAACAGTTCCCATCTGAGCCATTCAAATTTTTGGAGCCAACTCTAAGACTAGAATATTCTG
AAGCATTGGCTATGCTTAGGGAAGCTGGAGTCGAAATGGGAGATGAAGACGATCTGAGCAC
ACCAAATGAAAAGCTGTTGGGTCATTTGGTAAAGGAAAAGTATGATACAGATTTTTATATTC
TTGATAAATATCCATTGGCTGTAAGACCTTTCTATACCATGCCTGACCCAAGAAATCCCAAA
CAGTCCAACTCTTACGATATGTTCATGAGAGGAGAAGAAATATTGTCAGGAGCTCAAAGAA
TACATGATCCTCAACTGCTAACAGAGAGAGCTTTACATCATGGAATTGATTTGGAGAAAATT
AAGGCTTACATTGATTCCTTCCGCTTTGGAGCCCCTCCTCATGCTGGTGGAGGCATTGGATTG
GAACGAGTTACTATGCTGTTTCTGGGATTGCATAATGTTCGTCAGACCTCCATGTTCCCTCGT
GATCCCAAACGACTCACTCCT
```

The corresponding translated protein sequences are:

1. DRS C334S:
   (SEQ ID NO: 48)
   MPSASASRKSQEKPREIMDAAEDYAKERYGISSMIQSQEKPDRVLVR
   VRDLTIQKADEVVWVRARVHTSRAKGKQCFLVLRQQQFNVQALVAVG
   DHASKQMVKFAANINKESIVDVEGVVRKVNQKIGSCTQQDVELHVQK
   IYVISLAEPRLPLQLDDAVRPEAEGEEEGRATVNQDTRLDNRVIDLR
   TSTSQAVFRLQSGICHLFRETLINKGFVEIQTPKIISAASEGGANVF
   TVSYFKNNAYLAQSPQLYKQMCICADFEKVFSIGPVFRAEDSNTHRH
   LTEFVGLDIEMAFNYHYHEVMEEIADTMVQIFKGLQERFQTEIQTVN
   KQFPSEPPFKFLEPTLRLEYCEALAMLREAGVEMGDEDDLSTPNEKLL
   GHLVKEKYDTDFYILDKYPLAVRPFYTMPDPRNPKQSNSYDMFMRGE
   EILSGAQRIHDPQLLTERALHHGIDLEKIKAYIDSFRFGAPPHAGGG
   IGLERVTMLFLGLHNVRQTSMFPRDPKRLTP

2. DRS C349S:
   (SEQ ID NO: 49)
   MPSASASRKSQEKPREIMDAAEDYAKERYGISSMIQSQEKPDRVLVR
   VRDLTIQKADEVVWVRARVHTSRAKGKQCFLVLRQQQFNVQALVAVG
   DHASKQMVKFAANINKESIVDVEGVVRKVNQKIGSCTQQDVELHVQK
   IYVISLAEPRLPLQLDDAVRPEAEGEEEGRATVNQDTRLDNRVIDLR
   TSTSQAVFRLQSGICHLFRETLINKGFVEIQTPKIISAASEGGANVF
   TVSYFKNNAYLAQSPQLYKQMCICADFEKVFSIGPVFRAEDSNTHRH
   LTEFVGLDIEMAFNYHYHEVMEEIADTMVQIFKGLQERFQTEIQTVN
   KQFPCEPPFKFLEPTLRLEYSEALAMLREAGVEMGDEDDLSTPNEKLL
   GHLVKEKYDTDFYILDKYPLAVRPFYTMPDPRNPKQSNSYDMFMRGE
   EILSGAQRIHDPQLLTERALHHGIDLEKIKAYIDSFRFGAPPHAGGG
   IGLERVTMLFLGLHNVRQTSMFPRDPKRLTP

3. DRS C334S/C349S:
   (SEQ ID NO: 50)
   MPSASASRKSQEKPREIMDAAEDYAKERYGISSMIQSQEKPDRVLVR
   VRDLTIQKADEVVWVRARVHTSRAKGKQCFLVLRQQQFNVQALVAVG
   DHASKQMVKFAANINKESIVDVEGWRKVNQKIGSCTQQDVELHVQKI
   YVISLAEPRLPLQLDDAVRPEAEGEEEGRATVNQDTRLDNRVIDLRT
   STSQAVFRLQSGICHLFRETLINKGFVEIQTPKIISAASEGGANVFT
   VSYFKNNAYLAQSPQLYKQMCICADFEKVFSIGPVFRAEDSNTHRHL
   TEFVGLDIEMAFNYHYHEVMEEIADTMVQIFKGLQERFQTEIQTVNK

```
QFPSEPFKFLEPTLRLEYSEALAMLREAGVEMGDEDDLSTPNEKLLG

HLVKEKYDTDFYILDKYPLAVRPFYTMPDPRNPKQSNSYDMFMRGEE

ILSGAQRIHDPQLLTERALHHGIDLEKIKAYIDSFRFGAPPHAGGGI

GLERVTMLFLGLHNVRQTSMFPRDPKRLTP
```

4. DRS C203A:
(SEQ ID NO: 51)
```
MPSASASRKSQEKPREIMDAAEDYAKERYGISSMIQSQEKPDRVLVR

VRDLTIQKADEWWVRARVHTSRAKGKQCFLVLRQQQFNVQALVAVGD

HASKQMVKFAANINKESIVDVEGWRKVNQKIGSCTQQDVELHVQKIY

VISLAEPRLPLQLDDAVRPEAEGEEEGRATVNQDTRLDNRVIDLRTS

TSQAVFRLQSGIAHLFRETLINKGFVEIQTPKIISAASEGGANVFTV

SYFKNNAYLAQSPQLYKQMCICADFEKVFSIGPVFRAEDSNTHRHLT

EFVGLDIEMAFNYHYHEVMEEIADTMVQIFKGLQERFQTEIQTVNKQ

FPCEPPFKFLEPTLRLEYCEALAMLREAGVEMGDEDDLSTPNEKLLGH

LVKEKYDTDFYILDKYPLAVRPFYTMPDPRNPKQSNSYDMFMRGEEI

LSGAQRIHDPQLLTERALHHGIDLEKDCAYIDSFRFGAPPHAGGGIG

LERVTMLFLGLHNVRQTSMFPRDPKRLTP
```

5. DRS C203V:
(SEQ ID NO: 52)
```
MPSASASRKSQEKPREIMDAAEDYAKERYGISSMIQSQEKPDRVLVR

VRDLTIQKADEWWVRARVHTSRAKGKQCFLVLRQQQFNVQALVAVGD

HASKQMVKFAANINKESIVDVEGWRKVNQKIGSCTQQDVELHVQKIY

VISLAEPRLPLQLDDAVRPEAEGEEEGRATVNQDTRLDNRVIDLRTS

TSQAVFRLQSGIVHLFRETLINKGFVEIQTPKIISAASEGGANVFTV

SYFKNNAYLAQSPQLYKQMCICADFEKVFSIGPVFRAEDSNTHRHLT

EFVGLDIEMAFNYHYHEVMEEIADTMVQIFKGLQERFQTEIQTVNKQ

FPCEPPFKFLEPTLRLEYCEALAMLREAGVEMGDEDDLSTPNEKLLGH

LVKEKYDTDFYILDKYPLAVRPFYTMPDPRNPKQSNSYDMFMRGEEI

LSGAQRIHDPQLLTERALHHGIDLEKIKAYIDSFRFGAPPHAGGGIG

LERVTMLFLGLHNVRQTSMFPRDPKRLTP
```

6. DRS C334S/C349S/C203A:
(SEQ ID NO: 53)
```
MPSASASRKSQEKPREIMDAAEDYAKERYGISSMIQSQEKPDRVLVR

VRDLTIQKADEVVWVRARVHTSRAKGKQCFLVLRQQQFNVQALVAVG

DHASKQMVKFAANINKESIVDVEGVVRKVNQKIGSCTQQDVELHVQK

IYVISLAEPRLPLQLDDAVRPEAEGEEEGRATVNQDTRLDNRVIDLR

TSTSQAVFRLQSGIAHLFRETLINKGFVEIQTPKIISAASEGGANVF

TVSYFKNNAYLAQSPQLYKQMCIAADFEKVFSIGPVFRAEDSNTHRH

LTEFVGLDIEMAFNYHYHEVMEEIADTMVQIFKGLQERFQTEIQTVNK

QFPSEPFKFLEPTLRLEYSEALAMLREAGVEMGDEDDLSTPNEKLLG

HLVKEKYDTDFYILDKYPLAVRPFYTMPDPRNPKQSNSYDMFMRGEE

ILSGAQRIHDPQLLTERALHHGIDLEKIKAYIDSFRFGAPPHAGGGI

GLERVTMLFLGLHNVRQTSMFPRDPKRLTP
```

7. DRS C334S/C349S/C203V
(SEQ ID NO: 54)
```
MPSASASRKSQEKPREIMDAAEDYAKERYGISSMIQSQEKPDRVLVR

VRDLTIQKADEVVWVRARVHTSRAKGKQCFLVLRQQQFNVQALVAVG

DHASKQMVKFAANINKESIVDVEGVVRKVNQKIGSCTQQDVELHVQK

IYVISLAEPRLPLQLDDAVRPEAEGEEEGRATVNQDTRLDNRVIDLR

TSTSQAVFRLQSGIVHLFRETLINKGFVEIQTPKIISAASEGGANVF

TVSYFKNNAYLAQSPQLYKQMCIAADFEKVFSIGPVFRAEDSNTHRH

LTEFVGLDIEMAFNYHYHEVMEEIADTMVQIFKGLQERFQTEIQTVN

KQFPSEPFKFLEPTLRLEYSEALAMLREAGVEMGDEDDLSTPNEKLL

GHLVKEKYDTDFYILDKYPLAVRPFYTMPDPRNPKQSNSYDMFMRGE

EILSGAQRIHDPQLLTERALHHGIDLEKIKAYIDSFRFGAPPHAGGG

IGLERVTMLFLGLHNVRQTSMFPRDPKRLTP
```

8. DRS C334S/C349S/C259A/C203A:
(SEQ ID NO: 55)
```
MPSASASRKSQEKPREIMDAAEDYAKERYGISSMIQSQEKPDRVLVR

VRDLTIQKADEVVWVRARVHTSRAKGKQCFLVLRQQQFNVQALVAVG

DHASKQMVKFAANINKESIVDVEGVVRKVNQKIGSCTQQDVELHVQK

IYVISLAEPRLPLQLDDAVRPEAEGEEEGRATVNQDTRLDNRVIDLR

TSTSQAVFRLQSGIAHLFRETLINKGFVEIQTPKIISAASEGGANVF

TVSYFKNNAYLAQSPQLYKQMCIAADFEKVFSIGPVFRAEDSNTHRH

LTEFVGLDIEMAFNYHYHEVMEEIADTMVQIFKGLQERFQTEIQTVN

KQFPSEPFKFLEPTLRLEYSEALAMLREAGVEMGDEDDLSTPNEKLL

GHLVKEKYDTDFYILDKYPLAVRPFYTMPDPRNPKQSNSYDMFMRGE

EILSGAQRIHDPQLLTERALHHGIDLEKIKAYIDSFRFGAPPHAGGG

IGLERVTMLFLGLHNVRQTSMFPRDPKRLTP
```

9. DRS C334S/C349S/C259A/C203V:
(SEQ ID NO: 56)
```
MPSASASRKSQEKPREIMDAAEDYAKERYGISSMIQSQEKPDRVLVR

VRDLTIQKADEVVWVRARVHTSRAKGKQCFLVLRQQQFNVQALVAVG

DHASKQMVKFAANINKESIVDVEGVVRKVNQKIGSCTQQDVELHVQK

IYVISLAEPRLPLQLDDAVRPEAEGEEEGRATVNQDTRLDNRVIDLR

TSTSQAVFRLQSGIVHLFRETLINKGFVEIQTPKIISAASEGGANVF

TVSYFKNNAYLAQSPQLYKQMCIAADFEKVFSIGPVFRAEDSNTHRH

LTEFVGLDIEMAFNYHYHEVMEEIADTMVQIFKGLQERFQTEIQTVN

KQFPSEPFKFLEPTLRLEYSEALAMLREAGVEMGDEDDLSTPNEKLL

GHLVKEKYDTDFYILDKYPLAVRPFYTMPDPRNPKQSNSYDMFMRGE

EILSGAQRIHDPQLLTERALHHGIDLEKIKAYIDSFRFGAPPHAGGG

IGLERVTMLFLGLHNVRQTSMFPRDPKRLTP
```

Expression of DRS Cysteine Mutants:

DRS cysteine mutant constructs were transformed into BL21 (DE3) competent cells (Novagen, cat. N. 69450-4) and expressed in LB media in flask at 30° C. for 16 hrs.

Purification of DRS Cysteine Mutants:

Frozen cell pellets were resuspended in lysis buffer (50 mM Tris, 300 mM NaCl, 25 mM Imidazole, 5 mM DTT, pH 8.0 with complete EDTA-FREE protease inhibitor cocktail tablets (Roche cat. no: 05 056 489 001) and the then rotated for 30 mins at 4° C. with 300 mg chicken egg lysozyme. The suspension was sonicated for two cycles 50% and 75% for 60 seconds each with 10 second on and 5 second off. The lysate was centrifuged at 35,000×g for 45 min at 4° C. The supernatant was filtered through 0.22 μm Sartobran capsule filters (Sartorius). The clarified lysate was bound to the Ni-NTA resin (Qiagen), pre-equilibrated with Ni-NTA Binding Buffer (50 mM Tris, 300 mM NaCl, 25 mM Imidazole, 5 mM DTT, pH 8.0). The column was washed with 1000 column volumes of Ni-NTA Binding Buffer plus 0.1% Triton X-114 and 5 mM DTT followed by 50 column volumes of the Ni-NTA Binding Buffer. The bound protein was eluted with 5 column volumes of Ni-NTA Elution Buffer (50 mM Tris, 300 mM NaCl, 300 mM Imidazole, 1 mM DTT pH 8.0).

The purified proteins were dialyzed into a PBS. The dialyzed protein was passed through a Q membrane filter (Sartobind-Q from Sartorius or Mustang-Q from Pall) or a Q-Sepharose column (GE Healthcare) for further endotoxin removal when endotoxin level is detectable using Charles River endotoxin detection kit (product code: PTS20), and then filtered through a 0.22 μm sterile filter.

Testing of the relative activity of the purified proteins compared in the HEK293-TLR2 and HEK293-TLR4 expressing cell lines as described above confirmed that the proteins were active (data not shown).

Comparison of Production Yield and Stability of Purified DRS Cysteine Mutants:

Purification yield of each DRS cysteine mutant is summarized in Table E7. Tm of these mutants is measured by DSF (differential scanning fluorimetry) using Protein Thermo Shift Dye Kit from Life Technologies (cat. no. 4461146) following the manufacturer's instructions. Stability was assessed by incubating 50 μl of each of thr DRS cysteine mutants in PBS at 1 mg/ml at 37° C. for 1 hrs, and then by running an analytical SEC column (YMC America, Inc, cat. no. YMC-Pack Diol-300) using 200 mM phosphate, 100 mM NaCl pH7.0 as running buffer to compare monomer loss with samples before incubation.

TABLE E7

| Variant | Yield (mg/L) | Tm (° C., in PBS) | % monomer loss* |
|---|---|---|---|
| wild type | 6.8 | 47.7 | + |
| C334S | 6.5 | 53.2 | +++++ |
| C349S | 16.9 | 53.8 | ++ |
| C334S/C349S | 11.9 | 53.8 | +++ |
| C203A | 9.3 | 53.1 | NA |
| C203V | 10.2 | 53.5 | NA |
| C334S/C349S/C203A | 12.7 | 53.8 | + |
| C3334S/C349S/C203V | 13.9 | 53.4 | + |
| C334S/C3349S/C259A/C203A | 16.8 | 50.8 | + |
| C334S/C349S/C259A/C203V | 11.1 | 51 | + |

*monomer loss after 1 hr incubation at 37° C.
+: >5%;
++: >50%;
+++: 75%;
+++++: >90%;
NA: no loss The results demonstrate that the cysteine mutants at position 203 display enhanced stability, and reduced tendency for aggregation formation. Surprisingly the C203 mutants also enhanced stability in the context of mutations at position C334, C349 and C259, even if these mutations alone did not themselves confer significantly enhanced stability alone. The results thus demonstrate that C203 represents a key residue in the non specific cysteine dependent aggregation of DRS.

Example 6

Construction and Production of Truncated Homeokine (DRS) Mutants

To systematically evaluate the minimal active, and most stable N-terminal DRS polypeptide fragment, a series of N-terminal, C-terminal and double truncated Homeokine (DRS 1-154) variants were made using the primers listed in Table E8. The corresponding DNA and protein sequences for the constructs are listed below. Briefly, the N-terminal truncated form variants of Homeokine (DRS) were designed by truncating two amino acids at a time from the N- or C terminus of the Homeokine (DRS 1-154) sequence. Additionally a series of C-terminal extension variants was created to extend the C-terminal of the Homeokine sequence from amino acid 154 to 182 by 2 amino acid additions. Double truncated Homeokine variants were designed based on the DRS structure in order to define a minimally active core domain of Homeokine.

TABLE E8

| HK variants | Primers | SEQ ID NO: |
|---|---|---|
| C-terminal truncation variant | Reverse primers | |
| 1-148 | 5'-GGG TTA GGG ATA GGC TTA CCA GCC AAA CTG ATC ACA TAA ATC-3' | 141 |
| 1-150 | 5'-GGG TTA GGG ATA GGC TTA CCG GGT TCA GCC AAA CTG ATC AC-3' | 142 |
| 1-152 | 5'-GGG TTA GGG ATA GGC TTA CCC AGA CGG GGT TCA GCC AAA C-3' | 143 |
| 1-156 | 5'-GGG TTA GGG ATA GGC TTA CCC AGC TGC AGG GGC AGA CGG GG-3' | 144 |
| 1-158 | 5'-GGG TTA GGG ATA GGC TTA CCA TCA TCC AGC TGC AGG GGC AG-3' | 145 |
| 1-160 | 5'-GGG TTA GGG ATA GGC TTA CCA ACA GCA TCA TCC AGC TGC AGG-3' | 146 |
| 1-162 | 5'-GGG TTA GGG ATA GGC TTA CCA GGC CGA ACA GCA TCA TCC AG-3' | 147 |

TABLE E8-continued

| HK variants | Primers | SEQ ID NO: |
|---|---|---|
| 1-164 | 5'-GGG TTA GGG ATA GGC TTA CCT GCC TCA GGC CGA ACA GCA TC-3' | 148 |
| 1-166 | 5'-GGG TTA GGG ATA GGC TTA CCT CCT TCT GCC TCA GGC CGA AC-3' | 149 |
| 1-168 | 5'-GGG TTA GGG ATA GGC TTA CCC TCT TCT CCT TCT GCC TCA GG-3' | 150 |
| 1-170 | 5'-GGG TTA GGG ATA GGC TTA CCT CCT TCC TCT TCT CCT TCT GC-3' | 151 |
| 1-172 | 5'-GGG TTA GGG ATA GGC TTA CCA GCT CTT CCT TCC TCT TCT CC-3' | 152 |
| 1-176 | 5'-GGG TTA GGG ATA GGC TTA CCC TGG TTA ACA GTA GCT CTT CC-3' | 153 |
| 1-178 | 5'-GGG TTA GGG ATA GGC TTA CCT GTA TCC TGG TTA ACA GTA GC-3' | 154 |
| 1-180 | 5'-GGG TTA GGG ATA GGC TTA CCT AAT CTT GTA TCC TGG TTA AC-3' | 155 |
| 1-182 | 5'-GGG TTA GGG ATA GGC TTA CCG TTG TCT AAT CTT GTA TCC TGG-3' | 156 |

| N-terminal truncation variant | Forward primers | |
|---|---|---|
| 3-154 | 5'-GAA GGA GAT ATA CCATGA GCG CCA GCG CCA GCC G-3' | 157 |
| 5-154 | 5'-GAA GGA GAT ATA CCATGA GCG CCA GCC GCA AGA G-3' | 158 |
| 7-154 | 5'-GAA GGA GAT ATA CCATGA GCC GCA AGA GTC AGG AG-3' | 159 |
| 9-154 | 5'-GAA GGA GAT ATA CCATGA AGA GTC AGG AGA AGC C-3' | 160 |
| 11-154 | 5'-GAAGGAGATATCATATGCAGGAGAAGCCGCGGGAG-3' | 161 |
| 13-154 | 5'-GAAGGAGATATCATATGAAGCCGCGGGAGATCATG-3' | 162 |
| 15-154 | 5'-GAAGGAGATATCATATGCGGGAGATCATGGACGCGG-3' | 163 |
| 17-154 | 5'-GAAGGAGATATCATATGATCATGGACGCGGCGG-3' | 164 |
| 21-154 | 5'-GAAGGAGATATCATATGGCGGAAGATTATGCTAAAG-3' | 165 |
| 23-154 | 5'-GAAGGAGATATCATATGGATTATGCTAAAG-3' | 166 |

| double truncated HK variant | Forward primers | |
|---|---|---|
| 11-146-F | 5'-ACC GAT CAC ATA TGC AGG AGA AGC CGC GGG AGA TCA TGG A-3' | 167 |
| 13-146-F | 5'-AAG CTT ACG CAT ATG AAG CCG CGG GAG ATC ATG GAC GCG-3' | 168 |
| 17-146-F | 5'-AAC TGT TAC CAT ATG ATC ATG GAC GCG GCG GAA GAT TAT G-3' | 169 |
| 21-146-F | 5'-AAC TGT CAT CAT ATG GCG GAA GAT TAT GCT AAA GAG AGA TAT-3' | 170 |

| | Reverse primer | |
|---|---|---|
| X-146-R | 5'-TGA CGG CTC GAG ACT GAT CAC ATA AAT CTT CTG-3' | 171 |

| | Forward primers | |
|---|---|---|
| A106C-F | 5'-GCA GAT GGT TAA ATT TGC TTG CAA CAT CAA CAA AGA GAG CAT TGT GG-3' | 172 |

The truncated Homeokine (DRS) DNA sequences are as follows

DRS 1-182

(SEQ ID NO: 101)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTAGACAAC

DRS 1-180

(SEQ ID NO: 102)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACAAGATTA

DRS 1-178

(SEQ ID NO: 103)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAGGATACA

DRS 1-176

(SEQ ID NO: 104)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTTAACCAG

DRS 1-174

(SEQ ID NO: 105)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCTACTGTT

DRS 1-172

(SEQ ID NO: 106)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGAAGAGCT

DRS 1-170

(SEQ ID NO: 107)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA

```
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAGGAAGGA

DRS 1-168
                                                       (SEQ ID NO: 108)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGAGAAGAG

DRS 1-166
                                                       (SEQ ID NO: 109)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGC
AGAAGGA

DRS 1-164
                                                       (SEQ ID NO: 110)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCTGAGGCA

DRS 1-162
                                                       (SEQ ID NO: 111)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTTCGGCCT

DRS 1-160
                                                       (SEQ ID NO: 112)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGATGCTGTT

DRS 1-158
                                                       (SEQ ID NO: 113)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTGGATGAT

DRS 1-156
                                                       (SEQ ID NO: 114)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
```

```
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTGCAGCTG

DRS 1-154
                                                   (SEQ ID NO: 115)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTGCCCCTG

DRS 1-152
                                                   (SEQ ID NO: 116)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCCCGTCTG

DRS 1-150
                                                   (SEQ ID NO: 117)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCTGAACCC

DRS 1-148
                                                   (SEQ ID NO: 118)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGTTTGGCT

DRS 1-146
                                                   (SEQ ID NO: 119)
ATGCCCAGCGCCAGCGCCAGCCGCAAGAGTCAGGAGAAGCCGCGGGAGATCATGGACGCG
GCGGAAGATTATGCTAAAGAGAGATATGGAATATCTTCAATGATACAATCACAAGAAAAAC
CAGATCGAGTTTTGGTTCGGGTTAGAGACTTGACAATACAAAAAGCTGATGAAGTTGTTTGG
GTACGTGCAAGAGTTCATACAAGCAGAGCTAAAGGGAAACAGTGCTTCTTAGTCCTACGTCA
GCAGCAGTTTAATGTCCAGGCTCTTGTGGCGGTGGGAGACCATGCAAGCAAGCAGATGGTT
AAATTTGCTGCCAACATCAACAAAGAGAGCATTGTGGATGTAGAAGGTGTTGTGAGAAAAG
TGAATCAGAAAATTGGAAGCTGTACACAGCAAGACGTTGAGTTACATGTTCAGAAGATTTAT
GTGATCAGT

DRS 3-154
                                                   (SEQ ID NO: 120)
GCCAGCGCCAGCCGCAAGAGTCAGGAGAAGCCGCGGGAGATCATGGACGCGGCGGAAGAT
TATGCTAAAGAGAGATATGGAATATCTTCAATGATACAATCACAAGAAAAACCAGATCGAG
TTTTGGTTCGGGTTAGAGACTTGACAATACAAAAAGCTGATGAAGTTGTTTGGGTACGTGCA
AGAGTTCATACAAGCAGAGCTAAAGGGAAACAGTGCTTCTTAGTCCTACGTCAGCAGCAGTT
TAATGTCCAGGCTCTTGTGGCGGTGGGAGACCATGCAAGCAAGCAGATGGTTAAATTTGCTG
CCAACATCAACAAAGAGAGCATTGTGGATGTAGAAGGTGTTGTGAGAAAAGTGAATCAGAA
AATTGGAAGCTGTACACAGCAAGACGTTGAGTTACATGTTCAGAAGATTTATGTGATCAGTT
TGGCTGAACCCCGTCTGCCCCTG

DRS 5-154
                                                   (SEQ ID NO: 121)
GCCAGCCGCAAGAGTCAGGAGAAGCCGCGGGAGATCATGGACGCGGCGGAAGATTATGCTA
AAGAGAGATATGGAATATCTTCAATGATACAATCACAAGAAAAACCAGATCGAGTTTTGGT
TCGGGTTAGAGACTTGACAATACAAAAAGCTGATGAAGTTGTTTGGGTACGTGCAAGAGTTC
ATACAAGCAGAGCTAAAGGGAAACAGTGCTTCTTAGTCCTACGTCAGCAGCAGTTTAATGTC
CAGGCTCTTGTGGCGGTGGGAGACCATGCAAGCAAGCAGATGGTTAAATTTGCTGCCAACAT
CAACAAAGAGAGCATTGTGGATGTAGAAGGTGTTGTGAGAAAAGTGAATCAGAAAATTGGA
AGCTGTACACAGCAAGACGTTGAGTTACATGTTCAGAAGATTTATGTGATCAGTTTGGCTGA
ACCCCGTCTGCCCCTG
```

-continued

DRS 7-154
(SEQ ID NO: 122)
CGCAAGAGTCAGGAGAAGCCGCGGGAGATCATGGACGCGGCGGAAGATTATGCTAAAGAG
AGATATGGAATATCTTCAATGATACAATCACAAGAAAAACCAGATCGAGTTTTGGTTCGGGT
TAGAGACTTGACAATACAAAAAGCTGATGAAGTTGTTTGGGTACGTGCAAGAGTTCATACA
AGCAGAGCTAAAGGGAAACAGTGCTTCTTAGTCCTACGTCAGCAGCAGTTTAATGTCCAGGC
TCTTGTGGCGGTGGGAGACCATGCAAGCAAGCAGATGGTTAAATTTGCTGCCAACATCAACA
AAGAGAGCATTGTGGATGTAGAAGGTGTTGTGAGAAAAGTGAATCAGAAAATTGGAAGCTG
TACACAGCAAGACGTTGAGTTACATGTTCAGAAGATTTATGTGATCAGTTTGGCTGAACCCC
GTCTGCCCCTG

DRS 9-154
(SEQ ID NO: 123)
AGTCAGGAGAAGCCGCGGGAGATCATGGACGCGGCGGAAGATTATGCTAAAGAGAGATAT
GGAATATCTTCAATGATACAATCACAAGAAAAACCAGATCGAGTTTTGGTTCGGGTTAGAGA
CTTGACAATACAAAAAGCTGATGAAGTTGTTTGGGTACGTGCAAGAGTTCATACAAGCAGA
GCTAAAGGGAAACAGTGCTTCTTAGTCCTACGTCAGCAGCAGTTTAATGTCCAGGCTCTTGT
GGCGGTGGGAGACCATGCAAGCAAGCAGATGGTTAAATTTGCTGCCAACATCAACAAAGAG
AGCATTGTGGATGTAGAAGGTGTTGTGAGAAAAGTGAATCAGAAAATTGGAAGCTGTACAC
AGCAAGACGTTGAGTTACATGTTCAGAAGATTTATGTGATCAGTTTGGCTGAACCCCGTCTG
CCCCTG

DRS 11-154
(SEQ ID NO: 124)
GAGAAGCCGCGGGAGATCATGGACGCGGCGGAAGATTATGCTAAAGAGAGATATGGAATAT
CTTCAATGATACAATCACAAGAAAAACCAGATCGAGTTTTGGTTCGGGTTAGAGACTTGACA
ATACAAAAAGCTGATGAAGTTGTTTGGGTACGTGCAAGAGTTCATACAAGCAGAGCTAAAG
GGAAACAGTGCTTCTTAGTCCTACGTCAGCAGCAGTTTAATGTCCAGGCTCTTGTGGCGGTG
GGAGACCATGCAAGCAAGCAGATGGTTAAATTTGCTGCCAACATCAACAAAGAGAGCATTG
TGGATGTAGAAGGTGTTGTGAGAAAAGTGAATCAGAAAATTGGAAGCTGTACACAGCAAGA
CGTTGAGTTACATGTTCAGAAGATTTATGTGATCAGTTTGGCTGAACCCCGTCTGCCCCTG

DRS 13-154
(SEQ ID NO: 125)
CCGCGGGAGATCATGGACGCGGCGGAAGATTATGCTAAAGAGAGATATGGAATATCTTCAA
TGATACAATCACAAGAAAAACCAGATCGAGTTTTGGTTCGGGTTAGAGACTTGACAATACA
AAAAGCTGATGAAGTTGTTTGGGTACGTGCAAGAGTTCATACAAGCAGAGCTAAAGGGAAA
CAGTGCTTCTTAGTCCTACGTCAGCAGCAGTTTAATGTCCAGGCTCTTGTGGCGGTGGGAGA
CCATGCAAGCAAGCAGATGGTTAAATTTGCTGCCAACATCAACAAAGAGAGCATTGTGGAT
GTAGAAGGTGTTGTGAGAAAAGTGAATCAGAAAATTGGAAGCTGTACACAGCAAGACGTTG
AGTTACATGTTCAGAAGATTTATGTGATCAGTTTGGCTGAACCCCGTCTGCCCCTG

DRS 15-154
(SEQ ID NO: 126)
GAGATCATGGACGCGGCGGAAGATTATGCTAAAGAGAGATATGGAATATCTTCAATGATAC
AATCACAAGAAAAACCAGATCGAGTTTTGGTTCGGGTTAGAGACTTGACAATACAAAAAGC
TGATGAAGTTGTTTGGGTACGTGCAAGAGTTCATACAAGCAGAGCTAAAGGGAAACAGTGC
TTCTTAGTCCTACGTCAGCAGCAGTTTAATGTCCAGGCTCTTGTGGCGGTGGGAGACCATGC
AAGCAAGCAGATGGTTAAATTTGCTGCCAACATCAACAAAGAGAGCATTGTGGATGTAGAA
GGTGTTGTGAGAAAAGTGAATCAGAAAATTGGAAGCTGTACACAGCAAGACGTTGAGTTAC
ATGTTCAGAAGATTTATGTGATCAGTTTGGCTGAACCCCGTCTGCCCCTG

DRS 17-154
(SEQ ID NO: 127)
ATGGACGCGGCGGAAGATTATGCTAAAGAGAGATATGGAATATCTTCAATGATACAATCAC
AAGAAAAACCAGATCGAGTTTTGGTTCGGGTTAGAGACTTGACAATACAAAAAGCTGATGA
AGTTGTTTGGGTACGTGCAAGAGTTCATACAAGCAGAGCTAAAGGGAAACAGTGCTTCTTAG
TCCTACGTCAGCAGCAGTTTAATGTCCAGGCTCTTGTGGCGGTGGGAGACCATGCAAGCAAG
CAGATGGTTAAATTTGCTGCCAACATCAACAAAGAGAGCATTGTGGATGTAGAAGGTGTTGT
GAGAAAAGTGAATCAGAAAATTGGAAGCTGTACACAGCAAGACGTTGAGTTACATGTTCAG
AAGATTTATGTGATCAGTTTGGCTGAACCCCGTCTGCCCCTG

DRS 19-154
(SEQ ID NO: 128)
GCGGCGGAAGATTATGCTAAAGAGAGATATGGAATATCTTCAATGATACAATCACAAGAAA
AACCAGATCGAGTTTTGGTTCGGGTTAGAGACTTGACAATACAAAAAGCTGATGAAGTTGTT
TGGGTACGTGCAAGAGTTCATACAAGCAGAGCTAAAGGGAAACAGTGCTTCTTAGTCCTAC
GTCAGCAGCAGTTTAATGTCCAGGCTCTTGTGGCGGTGGGAGACCATGCAAGCAAGCAGAT
GGTTAAATTTGCTGCCAACATCAACAAAGAGAGCATTGTGGATGTAGAAGGTGTTGTGAGA
AAAGTGAATCAGAAAATTGGAAGCTGTACACAGCAAGACGTTGAGTTACATGTTCAGAAGA
TTTATGTGATCAGTTTGGCTGAACCCCGTCTGCCCCTG

DRS 21-154
(SEQ ID NO: 129)
GCGGCGGAAGATTATGCTAAAGAGAGATATGGAATATCTTCAATGATACAATCACAAGAAA
AACCAGATCGAGTTTTGGTTCGGGTTAGAGACTTGACAATACAAAAAGCTGATGAAGTTGTT
TGGGTACGTGCAAGAGTTCATACAAGCAGAGCTAAAGGGAAACAGTGCTTCTTAGTCCTAC
GTCAGCAGCAGTTTAATGTCCAGGCTCTTGTGGCGGTGGGAGACCATGCAAGCAAGCAGAT
GGTTAAATTTGCTGCCAACATCAACAAAGAGAGCATTGTGGATGTAGAAGGTGTTGTGAGA
AAAGTGAATCAGAAAATTGGAAGCTGTACACAGCAAGACGTTGAGTTACATGTTCAGAAGA
TTTATGTGATCAGTTTGGCTGAACCCCGTCTG

-continued

DRS 23-154
(SEQ ID NO: 130)
GCGGCGGAAGATTATGCTAAAGAGAGATATGGAATATCTTCAATGATACAATCACAAGAAA
AACCAGATCGAGTTTTGGTTCGGGTTAGAGACTTGACAATACAAAAAGCTGATGAAGTTGTT
TGGGTACGTGCAAGAGTTCATACAAGCAGAGCTAAAGGGAAACAGTGCTTCTTAGTCCTAC
GTCAGCAGCAGTTTAATGTCCAGGCTCTTGTGGCGGTGGGAGACCATGCAAGCAAGCAGAT
GGTTAAATTTGCTGCCAACATCAACAAAGAGAGCATTGTGGATGTAGAAGGTGTTGTGAGA
AAAGTGAATCAGAAAATTGGAAGCTGTACACAGCAAGACGTTGAGTTACATGTTCAGAAGA
TTTATGTGATCAGTTTGGCTGAACCC

Double truncated coding sequences are as follows:

DRS 11-146:
(SEQ ID NO: 131)
ATGCAGGAGAAGCCGCGGGAGATCATGGACGCGGCGGAAGATTATGCTAAAGAGAGATAT
GGAATATCTTCAATGATACAATCACAAGAAAAACCAGATCGAGTTTTGGTTCGGGTTAGAGA
CTTGACAATACAAAAAGCTGATGAAGTTGTTTGGGTACGTGCAAGAGTTCATACAAGCAGA
GCTAAAGGGAAACAGTGCTTCTTAGTCCTACGTCAGCAGCAGTTTAATGTCCAGGCTCTTGT
GGCGGTGGGAGACCATGCAAGCAAGCAGATGGTTAAATTTGCTTGCAACATCAACAAAGAG
AGCATTGTGGATGTAGAAGGTGTTGTGAGAAAAGTGAATCAGAAAATTGGAAGCTGTACAC
AGCAAGACGTTGAGTTACATGTTCAGAAGATTTATGTGATCAGT

DRS 13-146:
(SEQ ID NO: 132)
ATGAAGCCGCGGGAGATCATGGACGCGGCGGAAGATTATGCTAAAGAGAGATATGGAATAT
CTTCAATGATACAATCACAAGAAAAACCAGATCGAGTTTTGGTTCGGGTTAGAGACTTGACA
ATACAAAAAGCTGATGAAGTTGTTTGGGTACGTGCAAGAGTTCATACAAGCAGAGCTAAAG
GGAAACAGTGCTTCTTAGTCCTACGTCAGCAGCAGTTTAATGTCCAGGCTCTTGTGGCGGTG
GGAGACCATGCAAGCAAGCAGATGGTTAAATTTGCTTGCAACATCAACAAAGAGAGCATTG
TGGATGTAGAAGGTGTTGTGAGAAAAGTGAATCAGAAAATTGGAAGCTGTACACAGCAAGA
CGTTGAGTTACATGTTCAGAAGATTTATGTGATCAGT

DRS 13-146/A106C:
(SEQ ID NO: 133)
ATGAAGCCGCGGGAGATCATGGACGCGGCGGAAGATTATGCTAAAGAGAGATATGGAATAT
CTTCAATGATACAATCACAAGAAAAACCAGATCGAGTTTTGGTTCGGGTTAGAGACTTGACA
ATACAAAAAGCTGATGAAGTTGTTTGGGTACGTGCAAGAGTTCATACAAGCAGAGCTAAAG
GGAAACAGTGCTTCTTAGTCCTACGTCAGCAGCAGTTTAATGTCCAGGCTCTTGTGGCGGTG
GGAGACCATGCAAGCAAGCAGATGGTTAAATTTGCTTGCAACATCAACAAAGAGAGCATTG
TGGATGTAGAAGGTGTTGTGAGAAAAGTGAATCAGAAAATTGGAAGCTGTACACAGCAAGA
CGTTGAGTTACATGTTCAGAAGATTTATGTGATCAGT

DRS 17-146:
(SEQ ID NO: 134)
ATGATCATGGACGCGGCGGAAGATTATGCTAAAGAGAGATATGGAATATCTTCAATGATAC
AATCACAAGAAAAACCAGATCGAGTTTTGGTTCGGGTTAGAGACTTGACAATACAAAAAGC
TGATGAAGTTGTTTGGGTACGTGCAAGAGTTCATACAAGCAGAGCTAAAGGGAAACAGTGC
TTCTTAGTCCTACGTCAGCAGCAGTTTAATGTCCAGGCTCTTGTGGCGGTGGGAGACCATGC
AAGCAAGCAGATGGTTAAATTTGCTTGCAACATCAACAAAGAGAGCATTGTGGATGTAGAA
GGTGTTGTGAGAAAAGTGAATCAGAAAATTGGAAGCTGTACACAGCAAGACGTTGAGTTAC
ATGTTCAGAAGATTTATGTGATCAGT

DRS 21-146:
(SEQ ID NO: 135)
ATGGCGGAAGATTATGCTAAAGAGAGATATGGAATATCTTCAATGATACAATCACAAGAAA
AACCAGATCGAGTTTTGGTTCGGGTTAGAGACTTGACAATACAAAAAGCTGATGAAGTTGTT
TGGGTACGTGCAAGAGTTCATACAAGCAGAGCTAAAGGGAAACAGTGCTTCTTAGTCCTAC
GTCAGCAGCAGTTTAATGTCCAGGCTCTTGTGGCGGTGGGAGACCATGCAAGCAAGCAGAT
GGTTAAATTTGCTTGCAACATCAACAAAGAGAGCATTGTGGATGTAGAAGGTGTTGTGAGA
AAAGTGAATCAGAAAATTGGAAGCTGTACACAGCAAGACGTTGAGTTACATGTTCAGAAGA
TTTATGTGATCAGT

The corresponding protein sequences of the DRS truncations are as follows:

DRS 1-182
(SEQ ID NO: 57)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEAEGEEEGRATVNQDTRLDN

```
DRS 1-180
                                                   (SEQ ID NO: 58)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEAEGEEEGRATVNQDTRL

DRS 1-178
                                                   (SEQ ID NO: 59)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEAEGEEEGRATVNQDT

DRS 1-176
                                                   (SEQ ID NO: 60)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEAEGEEEGRATVNQ

DRS 1-174
                                                   (SEQ ID NO: 61)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEAEGEEEGRATV

DRS 1-172
                                                   (SEQ ID NO: 62)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEAEGEEEGRA

DRS 1-170
                                                   (SEQ ID NO: 63)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEAEGEEEG

DRS 1-168
                                                   (SEQ ID NO: 64)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEAEGEE

DRS 1-166
                                                   (SEQ ID NO: 65)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEAEG

DRS 1-164
                                                   (SEQ ID NO: 66)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRPEA

DRS 1-162
                                                   (SEQ ID NO: 67)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAVRP

DRS 1-160
                                                   (SEQ ID NO: 68)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDDAV

DRS 1-158
                                                   (SEQ ID NO: 69)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQLDD

DRS 1-156
                                                   (SEQ ID NO: 70)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPLQL
```

-continued

DRS 1-154
(SEQ ID NO: 71)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRLPL

DRS 1-152
(SEQ ID NO: 72)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEPRL

DRS 1-150
(SEQ ID NO: 73)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLAEP

DRS 1-148
(SEQ ID NO: 74)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVISLA

DRS 1-146
(SEQ ID NO: 75)
MPSASASRKSQEKPREIMDAAEDYAKERYGISSMIQSQEKPDRVLVRVRDLTIQKADEVVWVRA
RVHTSRAKGKQCFLVLRQQQFNVQALVAVGDHASKQMVKFAANINKESIVDVEGVVRKVNQK
IGSCTQQDVELHVQKIYVIS

DRS 3-154
(SEQ ID NO: 76)
ASASRKSQEKPREIMDAAEDYAKERYGISSMIQSQEKPDRVLVRVRDLTIQKADEVVWVRARVH
TSRAKGKQCFLVLRQQQFNVQALVAVGDHASKQMVKFAANINKESIVDVEGVVRKVNQKIGSC
TQQDVELHVQKIYVISLAEPRLPL

DRS 5-154
(SEQ ID NO: 77)
ASRKSQEKPREIMDAAEDYAKERYGISSMIQSQEKPDRVLVRVRDLTIQKADEVVWVRARVHTS
RAKGKQCFLVLRQQQFNVQALVAVGDHASKQMVKFAANINKESIVDVEGVVRKVNQKIGSCT
QQDVELHVQKIYVISLAEPRLPL

DRS 7-154
(SEQ ID NO: 78)
RKSQEKPREIMDAAEDYAKERYGISSMIQSQEKPDRVLVRVRDLTIQKADEVVWVRARVHTSRA
KGKQCFLVLRQQQFNVQALVAVGDHASKQMVKFAANINKESIVDVEGVVRKVNQKIGSCTQQ
DVELHVQKIYVISLAEPRLPL

DRS 9-154
(SEQ ID NO: 79)
SQEKPREIMDAAEDYAKERYGISSMIQSQEKPDRVLVRVRDLTIQKADEVVWVRARVHTSRAKG
KQCFLVLRQQQFNVQALVAVGDHASKQMVKFAANINKESIVDVEGVVRKVNQKIGSCTQQDVE
LHVQKIYVISLAEPRLPL

DRS 11-154
(SEQ ID NO: 80)
EKPREIMDAAEDYAKERYGISSMIQSQEKPDRVLVRVRDLTIQKADEVVWVRARVHTSRAKGK
QCFLVLRQQQFNVQALVAVGDHASKQMVKFAANINKESIVDVEGVVRKVNQKIGSCTQQDVEL
HVQKIYVISLAEPRLPL

DRS 13-154
(SEQ ID NO: 81)
PREIMDAAEDYAKERYGISSMIQSQEKPDRVLVRVRDLTIQKADEVVWVRARVHTSRAKGKQC
FLVLRQQQFNVQALVAVGDHASKQMVKFAANINKESIVDVEGVVRKVNQKIGSCTQQDVELHV
QKIYVISLAEPRLPL

DRS 15-154
(SEQ ID NO: 82)
EIMDAAEDYAKERYGISSMIQSQEKPDRVLVRVRDLTIQKADEVVWVRARVHTSRAKGKQCFL
VLRQQQFNVQALVAVGDHASKQMVKFAANINKESIVDVEGVVRKVNQKIGSCTQQDVELHVQ
KIYVISLAEPRLPL

DRS 17-154
(SEQ ID NO: 83)
MDAAEDYAKERYGISSMIQSQEKPDRVLVRVRDLTIQKADEVVWVRARVHTSRAKGKQCFLVL
RQQQFNVQALVAVGDHASKQMVKFAANINKESIVDVEGVVRKVNQKIGSCTQQDVELHVQKIY
VISLAEPRLPL

-continued

DRS 19-154

(SEQ ID NO: 84)
MDAAEDYAKERYGISSMIQSQEKPDRVLVRVRDLTIQKADEVVWVRARVHTSRAKGKQCFLVL
RQQQFNVQALVAVGDHASKQMVKFAANINKESIVDVEGVVRKVNQKIGSCTQQDVELHVQKIY
VISLAEPRL

DRS 21-154

(SEQ ID NO: 85)
MDAAEDYAKERYGISSMIQSQEKPDRVLVRVRDLTIQKADEVVWVRARVHTSRAKGKQCFLVL
RQQQFNVQALVAVGDHASKQMVKFAANINKESIVDVEGVVRKVNQKIGSCTQQDVELHVQKIY
VISLAEPRL

DRS 23-154

(SEQ ID NO: 86)
AAEDYAKERYGISSMIQSQEKPDRVLVRVRDLTIQKADEVVWVRARVHTSRAKGKQCFLVLRQ
QQFNVQALVAVGDHASKQMVKFAANINKESIVDVEGVVRKVNQKIGSCTQQDVELHVQKIYVI
SLAEPRL

DRS 11-146:

(SEQ ID NO: 87)
MQEKPREIMDAAEDYAKERYGISSMIQSQEKPDRVLVRVRDLTIQKADEVVWVRARVHTSRAK
GKQCFLVLRQQQFNVQALVAVGDHASKQMVKFACNINKESIVDVEGVVRKVNQKIGSCTQQD
VELHVQKIYVIS

DRS 13-146:

(SEQ ID NO: 88)
MKPREIMDAAEDYAKERYGISSMIQSQEKPDRVLVRVRDLTIQKADEVVWVRARVHTSRAKGK
QCFLVLRQQQFNVQALVAVGDHASKQMVKFACNINKESIVDVEGVVRKVNQKIGSCTQQDVEL
HVQKIYVIS

DRS 13-146/A106C:

(SEQ ID NO: 89)
MKPREIMDAAEDYAKERYGISSMIQSQEKPDRVLVRVRDLTIQKADEVVWVRARVHTSRAKGK
QCFLVLRQQQFNVQALVAVGDHASKQMVKFACNINKESIVDVEGVVRKVNQKIGSCTQQDVEL
HVQKIYVIS

DRS 17-146:

(SEQ ID NO: 90)
MIMDAAEDYAKERYGISSMIQSQEKPDRVLVRVRDLTIQKADEVVWVRARVHTSRAKGKQCFL
VLRQQQFNVQALVAVGDHASKQMVKFACNINKESIVDVEGVVRKVNQKIGSCTQQDVELHVQ
KIYVIS

DRS 21-146:

(SEQ ID NO: 91)
MAEDYAKERYGISSMIQSQEKPDRVLVRVRDLTIQKADEVVWVRARVHTSRAKGKQCFLVLRQ
QQFNVQALVAVGDHASKQMVKFACNINKESIVDVEGVVRKVNQKIGSCTQQDVELHVQKIYVIS

N-terminal truncated Homeokine variants 3-154, 5-154, 7-154 and 9-154 were made by QuickChange Lightning Site-Directed Mutagenesis Kit (Agilent, cat. no. 210518) following the manufacturer's instructions using construct plasmid pET28a-C-V5/His-DRS aa1-154 as template. Homeokine variants 13-146/A106C were also made by direct mutagenesis approach using the truncated form DRS 13-146 as template.

C-terminal Homeokine variants 1-148, 1-150, 1-152, 1-156, 1-158, 1-160, 1-162, 1-164, 1-166, 1-168, 1-170, 1-172, 1-174, 1-176, 1-178 and 1-180 were made by via Kunkle mutagenesis approach using pET28a C-V5/His DRS as template. The whole process can be divided into two steps, ssDNA preparation and Kunkle mutagenesis. To prepare ssDNA, the dsDNA vector was transformed into CJ236 bacterial cells (NEB, cat no E4141S) and plated on ampicillin (100 ug/mL) and chloramphenicol (30 ug/mL) containing LB-Agar plates. Plates were incubated overnight at 37° C. A colony was used to inoculate LB medium containing ampicillin and chloramphenicol and incubated overnight at 225 rpm and 37° C. 20 mL of LB containing ampicillin and chloramphenicol was inoculated with 200 uL of the overnight culture and grown for 2 hr at 225 rpm and 37° C. The culture was infected with 5e9 pfu of M13KO7 Helper Phage (NEB, cat no N0315S). After 1 hr, kanamycin was added to the culture at a final concentration of 50 ug/mL and incubated overnight at 225 rpm and 37° C. Bacteria were separated and discarded from culture by two centrifugations at 1900×g. ssDNA was precipitated by incubation at 4° C. with final concentrations of 4% PEG-8000 and 500 mM Sodium Acetate for 2 hr. ssDNA was centrifuged at 12000×g and resuspended in 1.4 mL LB medium. Cell debris was eliminated by subsequent centrifugation at 14500×g. ssDNA was purified from the supernatant using Qiagen QIAprep M13 kit (Qiagen, cat no 27704). Kunkel mutagenesis was performed by first diluting primers to 100 ng/uL. 100 ng of the oligo was then incubated with 5 U PNK kinase (Roche, cat no 10633542001) in the presence of 1× PNK kinase buffer and 0.5 mM ATP. This reaction was incubated at 37° C. for 1 hr. 100 ng of ssDNA vector was incubated with 6.9 ng of kinased oligo in annealing buffer (20 mM Tris, pH7.4, 2 mM MgCl2, 50 mM NaCl, final concentrations) for 5 min in a heat block at 75° C. Reactions were allowed to cool to room temperature while contained in the heat block. For elongation of the plasmid, 1 U of T4 DNA Polymerase (Roche, cat no 11004786001) and 1 U T4 DNA Ligase (Roche, cat no 10481220001) was added to the reaction. Additionally, synthesis buffer was added to a final concentration of 0.45 mM dNTPs, 0.91 mM ATP, 9.1 mM Tris, pH7.4, 4.5 mM MgCl2, and 1.8 mM DTT. This reaction was incubated on ice for 5 min and then at 37° C. for 90 min. 5 uL of the elongation reaction was transformed into 200 uL DH5a cells. Transformations were plated on Ampicillin plates and incubated overnight at 37° C. Individual colonies were used to inoculate 6 mL LB medium containing ampicillin. Cultures were grown overnight at 37° C. DNA plasmids were prepared using Qiagen Spin Miniprep kit (Qiagen, cat no 27106) and sequence verified.

Double truncated Homeokine variants 11-146, 13-146, 17-146 and 21-146 were made by traditional cloning method using construct pet28a+_CtermV5His_DRS_NdeI-XhoI_revcomp as template. Briefly, the desired fragment was amplified by PCR (Invitrogen, cat no 12344-040) and double digested by NdeI (NEB, cat. no R0111S) and XhoI (NEB, cat no. R0146S) restriction enzymes. Purified double digested fragment was ligated with NdeI/XhoI double vector pet28a+_CtermV5His_DRS_NdeI-XhoI_revcomp by T4 DNA Ligase (Roche, cat no 10481220001) and transformed into DH5a competent cells (Invitrogen, cat. no 18263-012) and plated on LB-agar plates containing ampicillin (100 ug/mL). Colonies were grown individually in LB/Amp media and sequenced to confirm sequence.

Expression of Truncated Homeokine Variant:

Homeokine truncated variant constructs with correct sequences are transformed into BL21 (DE3) competent cells (Novagen, cat. no. 69450-4) and expressed at 30° C. for 16 hrs in LB media with 100 ug/ml ampicillin as described above.

Purification of truncated Homeokine variants were prepared as described in Example 5, except for the final lysis step. In which for these constructs frozen cell pellets were resuspended in lysis buffer (50 mM Tris, 300 mM NaCl, 25 mM Imidazole, 5 mM DTT, pH 8.0 with complete EDTA-FREE protease inhibitor cocktail tablets (Roche cat. no: 05 056 489 001) and the then rotated for 30 mins at 4° C. with 300 mg chicken egg lysozyme. The suspension was then sonicated for two cycles 50% and 75% for 60 seconds each with 10 second on and 5 second off. The lysate was centrifuged at 35,000×g for 45 min at 4° C., and the supernatant then filtered through 0.22 μm Sartobran capsule filters (Sartorius). The clarified lysate was bound to the Ni-NTA resin (Qiagen), pre-equilibrated with Ni-NTA Binding Buffer (50 mM Tris, 300 mM NaCl, 25 mM Imidazole, 5 mM DTT, pH 8.0). The column was washed with 1000 column volumes of Ni-NTA Binding Buffer plus 0.1% Triton X-114 and 5 mM DTT followed by 50 column volumes of the Ni-NTA Binding Buffer. The bound protein was eluted with 5 column volumes of Ni-NTA Elution Buffer (50 mM Tris, 300 mM NaCl, 300 mM Imidazole, 1 mM DTT pH 8.0).

The purified proteins were dialyzed into 20 mM sodium phosphate, 200 mM Arginine, at pH7.3. The dialyzed protein was passed through a Q membrane filter (Sartobind-Q from Sartorius or Mustang-Q from Pall) or a Q-Sepharose column (GE Healthcare) for further endotoxin removal when endotoxin level is detectable using Charles River endotoxin detection kit (product code: PTS20), and then filtered through a 0.22 μm sterile filter.

Testing of the relative activity of the purified proteins compared in the HEK293-TLR2 and HEK293-TLR4 expressing cell lines as described above confirmed that the majority of proteins were active (data not shown).

Example 7

Comparison of Stability of Purified Truncated Homeokine (DRS) Mutants

Stability was assessed by incubating 50 μl of each of the deletion mutants in PBS at 1 mg/ml at 37° C. for 1 hrs, and then by running an analytical SEC column (YMC America, Inc, cat. no. YMC-Pack Diol-300) using 200 mM phosphate, 100 mM NaCl pH7.0 as running buffer to compare the % High molecular weight (HMW) component after incubation at 37 C, and via determining turbidity as assessed via absorption at A340 nM. Results are summarized in Table E9.

TABLE E9

| Variant | % Change A340 nm after incubation after 5 hr at 37 C. +: <50%; ++: >50%; +++: >100%; ++++: >500%; | % HMW determined via SEC (Time zero) +: <7%; ++: >7%; +++: >10%; ++++: >15%; | % HMW determined via SEC after incubation after 5 hr at 37 C. +: <7%; ++: >7%; +++: >10%; ++++: >15%; |
|---|---|---|---|
| 1-148 | + | + | + |
| 1-150 | ++ | + | + |
| 1-152 | +++ | + | + |
| 1-154 | ++ | + | + |
| 1-156 | ++ | + | + |
| 1-158 | ++ | + | + |
| 1-160 | +++ | ++ | ++ |
| 1-162 | + | + | ++ |
| 1-164 | + | + | ++ |
| 1-166 | ++++ | ++++ | + |
| 1-168 | + | ++ | ++++ |
| 1-170 | + | + | +++ |
| 1-172 | + | + | ++++ |
| 1-174 | + | + | ++++ |
| 1-176 | +++ | ++++ | ++ |
| 1-178 | + | ++ | ++++ |
| 1-180 | + | + | +++ |
| 1-182 | + | ++ | ++++ |
| N-terminal mutations | | | |
| 3-154 | ++++ | ++++ | ++ |
| 5-154 | ++++ | ++++ | ++ |
| 7-154 | ++++ | ++++ | ++ |
| 9-154 | ++++ | ++++ | ++ |
| 11-154 | + | + | + |
| 13-154 | + | + | + |
| 17-154 | + | + | + |

TABLE E9-continued

| | | | |
|---|---|---|---|
| 21-154 | ++ | + | + |
| 23-154 | ++ | + | + |

| Double truncations | | | % HMW determined via SEC after incubation after 24 hr at 37 C. |
|---|---|---|---|
| 11-146 | Not determined | + | Not determined |
| 13-146 | Not determined | + | +++ |
| 17-146 | Not determined | + | Not determined |
| 21-146 | Not determined | + | Not determined |
| 13-146/A106C | Not determined | + | ++ |

These results demonstrate that C-terminal deletions from about 1-158 to about 1-146 of DRS display enhanced stability and reduced tendency for aggregation. With respect to N-terminal deletions, deletions in the range of 11-154 to 17-154 of DRS results in constructs with improved stability profiles. Additionally all of the doubly deleted constructs, including 11-146, 13-146, 17-146 and 21-146 of DRS all exhibited extremely low tendency for aggregation and enhanced stability.

Example 8

Testing of Reduced Cysteine Variants in Vivo in a Partial Body Irradiation Survival Model Methods.

Adult (10-12 week) C57BL/6 male mice were divided into 10 groups of 26. Mice were irradiated at 15:00 hours+/−1 hour with 14 Gy (five groups) or 14.5 Gy (five groups) irradiation. Irradiation was performed using a Pantak HF320 X-ray operated at 300 kV, 10 mA. The X-ray tube had additional filtration to give a radiation quality of 2.3 mm Cu half-value layer (HVL). Mice were anaesthetized and restrained in a jig and irradiation was delivered at a dose rate of 70.0 cGy/min. (Epistem, UK). Animals received partial body irradiation to the abdomen only—the head, thorax and forelimbs were lead shielded. This equates to approximately 40% bone marrow shielding. 24 hours post irradiation each group of mice was dosed i.v. (5 ml/kg) with a test item via the tail vein. The test item groups tested at each radiation dose using a PBS diluent. Mice were then dosed every 24 hours for a total of 7 days with DRS (1-154) C76S or with PBS as a control.

Mice were weighed daily and signs of diarrhea noted twice daily from day 4-10 post irradiation. Moribund mice from day 10 onwards were anaesthetized and subjected to terminal cardiac puncture to obtain a cardiac bleed. An aliquot of blood was used to perform a complete blood count, with the remainder used to isolate serum, which was then snap frozen. The small and large intestine were removed and fixed. The spleen, femur, Iliac bones and vertebrae, heart, lung and kidneys were also collected from selected mice on day 15 following 14 Gy and fixed in formalin.

Results.

Figure 4:
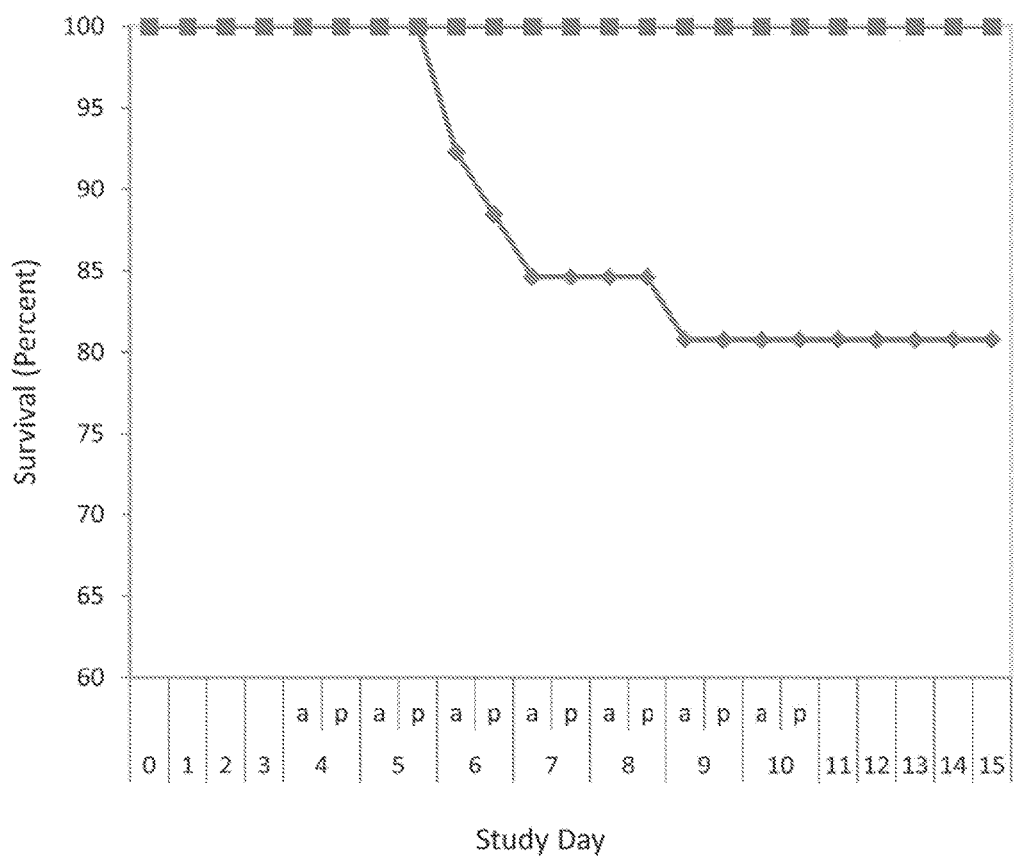
FIG. 4 shows the results of the administration of DRS1-154 comprising the C76S mutation in a partial body irradiation survival model; DRS1-154 (C76S) shown in squares and the PBS control shown as diamonds.

The survival data obtained with 14 Gy is shown in FIG. 4, and demonstrates that the cysteine variant DRS1-154 C76S displays improved survival in a radiation survival model.

Example 9

Testing of Reduced Cysteine Variants in Vivo in a MSU Induced Gout Model

Methods.

Gout like inflammation was induced in groups of 5 female C57BL/6 mice by single administration of MSU crystals into the left tarsal joint (Performed by Comparative Biosciences Inc., Sunnyvale, Calif.). One hour before the injection of the MSU crystals, mice were dosed prophylactically once by single injection of vehicle, DRS1-154 (C76S) (5 mg/kg, IV) or dexamethasone. Clinical measurements of joint inflammation severity (joint thickness, erythema and lameness) were assessed three times during the study. Mice were sacrificed one day after dosing; blood for serum was collected and the hind limbs were collected for histopathological evaluation. Throughout the study, general clinical observations were recorded daily; body weights were recorded prior to dosing and at necropsy.

Results.

Figure 5A:
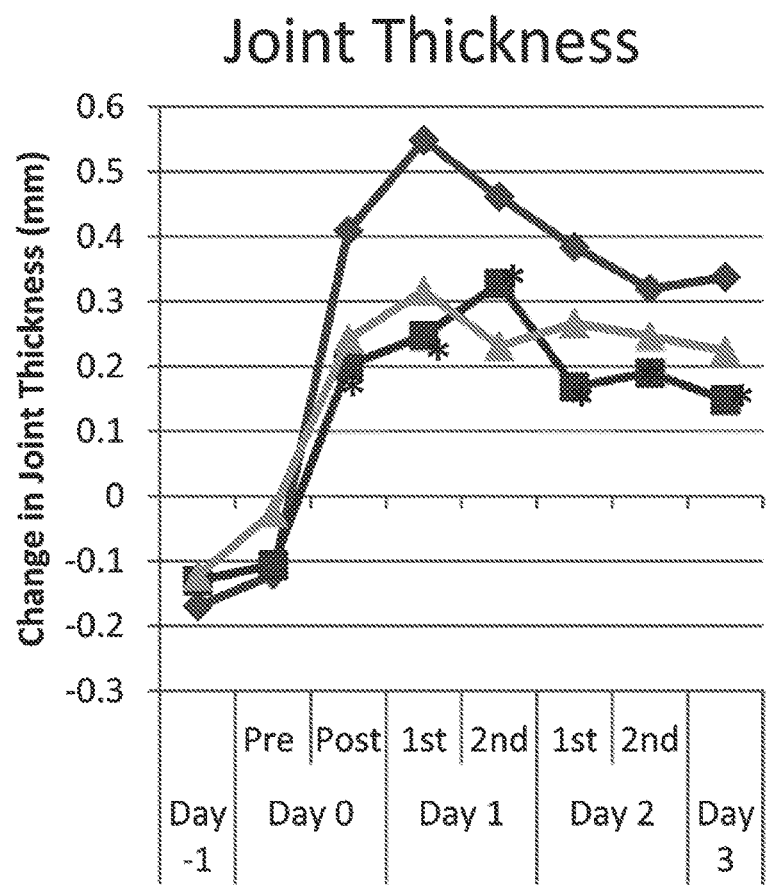
FIGS. 5A and 5B show the results of the administration of DRS1-154 comprising the C76S mutation in an MSU induced model of gout inflammation (squares), compared to vehicle control (PBS) diamonds, and a positive control dexamethasone (triangles). The insert shows the statistical significance for DRS1-154 (C76S) ("Homeokine") compared to the vehicle control.
Figure 5B:
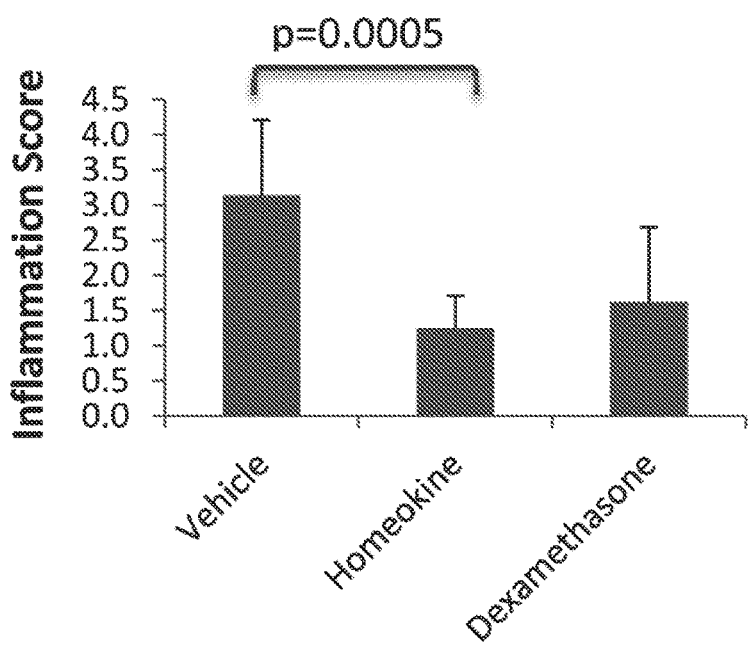

Administration of MSU induced an appropriate brisk inflammatory response characterized by joint swelling and erythema which corresponded clinically to the acute inflammation as seen by histopathology examination. Clinically, dexamethasone administration was associated with reduced swelling (attenuated severity score and mean joint diameter) compared to those treated with saline. Histopathologic examination (FIGS. 5A and 5B) of the MSU injected left tarsal joint showed that dexamethasone and DRS1-154 (C76S) induced a significant reduction in inflammation.

These results demonstrate that DRS1-154 comprising the C76S mutation exhibits enhanced anti-inflammatory activity in the MSU induced model of gout and gout flares.

Example 10

Activity of DRS (1-154) C76S in the TNBS Mouse Model

The DRS (1-154) C76S polypeptide was tested in the TNBS mouse model of colitis. In this model, colonic irritation is induced by intracolonic administration of TNBS in ethanol. This provokes an acute colitis that has a TH1-type cytokine profile, which is characterised by the expression of genes coding for TNF-α, IFN-γ and IL-12 amongst others (see Fichtner-Feigl et al., $J.$ $Clin.$ $Invest.$ 115:3057-3071, 2005). The colitis can be severe and localised to the area of the colon into which the TNBS is introduced. The inflammatory response results in localised swelling, inflammatory cell infiltration, and epithelial loss.

Methods.

A total of 62 male BDF-1 mice were used in this study. The mice were randomised into four treatment groups of 12 mice each, one treatment group of eight mice and one group of six mice each. All mice in the five largest treatment groups received 3 mg TNBS in 50% ethanol/saline by colonic instillation on study day 0, in order to induce colitis. Test items (DRS (1-154) C76S)) were first administered three hours prior to the instillation of TNBS, by i.v. injection, at a dose of 5 mg/Kg, and subsequently on study days 1-3 inclusive. Budesonide was employed as a reference test item and was dosed daily, by oral gavage, at 5 mg/kg, with the first dose being given 3 hours prior to the instillation of TNBS. Weight, faecal consistency and presence of overt blood, in faeces and around the anus, were assessed daily. All mice were euthanised on study day 4, and the large bowel taken for assessment of intestinal morphology, a small sample was also snap-frozen.

Harvesting and Preparation of Tissue for Histological Examination.

Mice were sacrificed at 09:00 by cervical dislocation on study day 4, 24 hours after receiving the last dose of test item. Blood was collected, post-sacrifice, by cardiac puncture, into EDTA-treated tubes, and immediately placed on ice. Plasma was prepared by centrifugation of blood samples at 3000 g for 10 minutes, and stored at −80° C. The large intestine was removed and flushed with PBS and its length and wet weight were recorded, prior to cutting into caecum, mid-colon and rectum and fixation in Carnoy's solution. A small sample of mid-colon was also snap-frozen in liquid nitrogen. Fixed tissue was dehydrated through a series of alcohols and xylene and embedded in paraffin, using a Leica TP1020 tissue processor and an EG1140H work station. Sections (3 nm thick) were cut using a Leica RM2125RTF microtome, and air-dried on to microscope slides, overnight at 37° C. Subsequently, slides were dewaxed in xylene and rehydrated through graded alcohols to PBS. All sections were then stained with haematoxylin and eosin (H&E), and mounted. The results are shown in Table E10 below.

TABLE E10

| | % of surviving animals | | | |
|---|---|---|---|---|
| Study Day | untreated | TNBS alone | TNBS + budesonide | TNBS + DRS (1-154)C76S |
| 0 | 100 | 100 | 100 | 100 |
| 1 | 100 | 90 | 100 | 100 |
| 2 | 100 | 90 | 100 | 100 |
| 3 | 100 | 75 | 75 | 100 |
| 4 | 100 | 45 | 75 | 75 |
| 5 | 100 | 45 | 70 | 75 |

These results demonstrate that the DRS polypeptide DRS (1-154) C76S exhibits anti-inflammatory activity in the TNBS model of inflammatory bowel disease.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An aspartyl-tRNA synthetase (DRS) polypeptide, comprising the amino acid sequence that is at least 95% identical to any of the amino acid sequences set forth in SEQ ID NO: 22-24 or a fragment thereof comprising residues 21-146 comprising at least one mutation at either Cys76 or Cys130.

2. The DRS polypeptide of claim 1, wherein the DRS polypeptide comprises residues 17-146.

3. The DRS polypeptide of claim 2, wherein the DRS polypeptide comprises amino acid residues 1-154.

4. The DRS polypeptide of claim 2, wherein the DRS polypeptide comprises amino acid residues 13-146.

5. The DRS polypeptide of claim 1, wherein the Cys76 residue has been mutated to another amino acid.

6. The DRS polypeptide of claim 1, wherein the Cys130 residue has been mutated to another amino acid.

7. The DRS polypeptide of claim 1, wherein both the Cys76 residue and the Cys130 residue have been mutated to another amino acid.

8. The DRS polypeptide of claim 1, wherein the Cys76 residue or the Cys130 residue is mutated to an amino acid group independently selected from group consisting of Ser, Ala, Gly, Met, Leu, Val, Ile and Thr.

9. The DRS polypeptide of claim 1, wherein the Cys76 residue or the Cys130 residue is mutated to an amino acid group independently selected from group consisting of Ser, Ala, and Gly.

10. The DRS polypeptide of claim 1, wherein the Cys76 residue or the Cys130 residue is mutated to an amino acid group independently selected from group consisting of Ser, Ala, Gly, Met, Leu, Val, Ile and Thr, and a non-naturally occurring amino acid.

11. The DRS polypeptide of claim 1, wherein the DRS polypeptide is characterized by an increased production yield after expression in *E. coli* compared to a non-cysteine mutated DRS polypeptide.

12. The DRS polypeptide of claim 11, wherein the DRS polypeptide is characterized by a production yield in *E. coli* of greater than about 1.5 mg/g cell pellet.

13. The DRS polypeptide of claim 1, wherein the DRS polypeptide is characterized by a decreased endotoxin content after expression in *E. coli* compared to a non-cysteine mutated DRS polypeptide.

14. The DRS polypeptide of claim 13, wherein the DRS polypeptide is characterized by an endotoxin content of less than about 10 EU/mg.

15. The DRS polypeptide of claim 1, wherein the DRS polypeptide is characterized by an increased activity and/or affinity to a TLR 2 receptor.

16. The DRS polypeptide of claim 1, wherein the DRS polypeptide is characterized by an increased activity and/or affinity to a TLR 4 receptor.

17. The DRS polypeptide of claim 1, wherein the DRS polypeptide is characterized by an apparent affinity ($EC_{50}$) to a TLR 2 receptor of greater than about 25 nM.

18. The DRS polypeptide of claim 1, wherein the DRS polypeptide is characterized by an apparent affinity ($EC_{50}$) to a TLR 4 receptor of greater than about 70 nM.

19. The DRS polypeptide of claim 1, further comprising a heterologous fusion protein.

20. The DRS polypeptide of claim 19, wherein the heterologous fusion protein is selected from a host cell antigen, a host cell self-antigen, a viral antigen, a bacterial antigen, and a cancer cell antigen.

21. The DRS polypeptide of claim 19, wherein the heterologous fusion protein is attached to the DRS polypeptide through Cys130.

22. An isolated nucleic acid encoding a DRS polypeptide of claim 1.

23. A pharmaceutical composition comprising (a) a DRS polypeptide of claim 1; (b) an isolated nucleic acid molecule encoding a DRS polypeptide of (a); a recombinant vector that comprises an isolated nucleic acid molecule of (b); and (c) a host cell that comprises an isolated nucleic acid molecule of (b) or a recombinant vector of (c), and a pharmaceutically acceptable carrier or excipient.

24. The pharmaceutical composition of claim 23, wherein the composition comprises between about 10 nM and about 100 nM arginine.

\* \* \* \* \*

SEQUENCE LISTING

```
<160> NUMBER OF SEQ ID NOS: 172

<210> SEQ ID NO 1
<211> LENGTH: 501
<212> TYPE: PRT
<213> ORGANISM: Homo sapiens

<400> SEQUENCE: 1

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175
```

```
Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Cys Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 2
<211> LENGTH: 1506
<212> TYPE: DNA
<213> ORGANISM: Homo sapiens

<400> SEQUENCE: 2
atgcccagcg ccagcgccag ccgcaagagt caggagaagc cgcgggagat catggacgcg    60
gcggaagatt atgctaaaga gagatatgga atatcttcaa tgataacaatc acaagaaaaa   120 ccagatcgag ttttggttcg ggttagagac ttgacaatac aaaaagctga tgaagttgtt   180
tgggtacgtg caagagttca tacaagcaga gctaaaggga acagtgctt cttagtccta    240
```

```
cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
gacaacagag tcattgatct taggacatca actagtcagg cagtcttccg tctccagtct    600
ggcatctgcc atctcttccg agaaacttta attaacaaag gttttgtgga aatccaaact    660
cctaaaatta tttcagctgc cagtgaagga ggagccaatg tttttactgt gtcatatttt    720
aaaaataatg catacctggc tcagtcccca cagctatata agcaaatgtg catttgtgct    780
gattttgaga aggttttctc tattggacca gtattcagag cggaagactc taatacccat    840
agacatctaa ctgagtttgt tggtttggac attgaaatgg cttttaatta ccattaccac    900
gaagttatgg aagaaattgc tgacaccatg gtacaaatat caaaggact tcaagaaagg    960 tttcagactg aaattcaaac agtgaataaa cagttcccat gtgagccatt caaattttg    1020 gagccaactc taagactaga atattgtgaa gcattggcta tgcttaggga agctggagtc    1080
gaaatgggag atgaagacga tctgagcaca ccaaatgaaa agctgttggg tcatttggta    1140
aaggaaaagt atgatacaga tttttatatt cttgataaat atccattggc tgtaagacct    1200
ttctatacca tgcctgaccc aagaaatccc aacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatcccaa acgactcact    1500
ccttag                                                               1506
```

<210> SEQ ID NO 3
<211> LENGTH: 154
<212> TYPE: PRT
<213> ORGANISM: Homo sapiens

<400> SEQUENCE: 3

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140
```

```
Ile Ser Leu Ala Glu Pro Arg Leu Pro Leu
145                 150

<210> SEQ ID NO 4
<211> LENGTH: 171
<212> TYPE: PRT
<213> ORGANISM: Homo sapiens

<400> SEQUENCE: 4

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg
                165                 170

<210> SEQ ID NO 5
<211> LENGTH: 174
<212> TYPE: PRT
<213> ORGANISM: Homo sapiens

<400> SEQUENCE: 5

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140
```

```
Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val
                165                 170
```

<210> SEQ ID NO 6
<211> LENGTH: 182
<212> TYPE: PRT
<213> ORGANISM: Homo sapiens

<400> SEQUENCE: 6

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn
                180
```

<210> SEQ ID NO 7
<211> LENGTH: 184
<212> TYPE: PRT
<213> ORGANISM: Homo sapiens

<400> SEQUENCE: 7

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110
```

```
Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val
            180

<210> SEQ ID NO 8
<211> LENGTH: 274
<212> TYPE: PRT
<213> ORGANISM: Homo sapiens

<400> SEQUENCE: 8

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala

<210> SEQ ID NO 9
<211> LENGTH: 224
```

```
<212> TYPE: PRT
<213> ORGANISM: Homo sapiens

<400> SEQUENCE: 9

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
    210                 215                 220

<210> SEQ ID NO 10
<211> LENGTH: 255
<212> TYPE: PRT
<213> ORGANISM: Homo sapiens

<400> SEQUENCE: 10

Gln Glu Lys Pro Asp Arg Val Leu Val Arg Val Arg Asp Leu Thr Ile
1               5                   10                  15

Gln Lys Ala Asp Glu Val Val Trp Val Arg Ala Arg Val His Thr Ser
            20                  25                  30

Arg Ala Lys Gly Lys Gln Cys Phe Leu Val Leu Arg Gln Gln Gln Phe
        35                  40                  45

Asn Val Gln Ala Leu Val Ala Val Gly Asp His Ala Ser Lys Gln Met
    50                  55                  60

Val Lys Phe Ala Ala Asn Ile Asn Lys Glu Ser Ile Val Asp Val Glu
65                  70                  75                  80

Gly Val Val Arg Lys Val Asn Gln Lys Ile Gly Ser Cys Thr Gln Gln
                85                  90                  95

Asp Val Glu Leu His Val Gln Lys Ile Tyr Val Ile Ser Leu Ala Glu
            100                 105                 110

Pro Arg Leu Pro Leu Gln Leu Asp Asp Ala Val Arg Pro Glu Ala Glu
        115                 120                 125
```

```
Gly Glu Glu Gly Arg Ala Thr Val Asn Gln Asp Thr Arg Leu Asp
    130             135                 140

Asn Arg Val Ile Asp Leu Arg Thr Ser Thr Ser Gln Ala Val Phe Arg
145                 150                 155                 160

Leu Gln Ser Gly Ile Cys His Leu Phe Arg Glu Thr Leu Ile Asn Lys
                165                 170                 175

Gly Phe Val Glu Ile Gln Thr Pro Lys Ile Ile Ser Ala Ala Ser Glu
            180                 185                 190

Gly Gly Ala Asn Val Phe Thr Val Ser Tyr Phe Lys Asn Asn Ala Tyr
        195                 200                 205

Leu Ala Gln Ser Pro Gln Leu Tyr Lys Gln Met Cys Ile Cys Ala Asp
210                 215                 220

Phe Glu Lys Val Phe Ser Ile Gly Pro Val Phe Arg Ala Glu Asp Ser
225                 230                 235                 240

Asn Thr His Arg His Leu Thr Glu Phe Val Gly Leu Asp Ile Glu
                245                 250                 255

<210> SEQ ID NO 11
<211> LENGTH: 132
<212> TYPE: PRT
<213> ORGANISM: Homo sapiens

<400> SEQUENCE: 11

Asp Tyr Ala Lys Glu Arg Tyr Gly Ile Ser Ser Met Ile Gln Ser Gln
1               5                   10                  15

Glu Lys Pro Asp Arg Val Leu Val Arg Val Arg Asp Leu Thr Ile Gln
            20                  25                  30

Lys Ala Asp Glu Val Val Trp Val Arg Ala Arg Val His Thr Ser Arg
        35                  40                  45

Ala Lys Gly Lys Gln Cys Phe Leu Val Leu Arg Gln Gln Gln Phe Asn
    50                  55                  60

Val Gln Ala Leu Val Ala Val Gly Asp His Ala Ser Lys Gln Met Val
65                  70                  75                  80

Lys Phe Ala Ala Asn Ile Asn Lys Glu Ser Ile Val Asp Val Glu Gly
                85                  90                  95

Val Val Arg Lys Val Asn Gln Lys Ile Gly Ser Cys Thr Gln Gln Asp
            100                 105                 110

Val Glu Leu His Val Gln Lys Ile Tyr Val Ile Ser Leu Ala Glu Pro
        115                 120                 125

Arg Leu Pro Leu
    130

<210> SEQ ID NO 12
<211> LENGTH: 122
<212> TYPE: PRT
<213> ORGANISM: Homo sapiens

<400> SEQUENCE: 12

Ser Met Ile Gln Ser Gln Glu Lys Pro Asp Arg Val Leu Val Arg Val
1               5                   10                  15

Arg Asp Leu Thr Ile Gln Lys Ala Asp Glu Val Val Trp Val Arg Ala
            20                  25                  30

Arg Val His Thr Ser Arg Ala Lys Gly Lys Gln Cys Phe Leu Val Leu
        35                  40                  45

Arg Gln Gln Gln Phe Asn Val Gln Ala Leu Val Ala Val Gly Asp His
    50                  55                  60
```

Ala Ser Lys Gln Met Val Lys Phe Ala Ala Asn Ile Asn Lys Glu Ser
 65                  70                  75                  80

Ile Val Asp Val Glu Gly Val Val Arg Lys Val Asn Gln Lys Ile Gly
                 85                  90                  95

Ser Cys Thr Gln Gln Asp Val Glu Leu His Val Gln Lys Ile Tyr Val
            100                 105                 110

Ile Ser Leu Ala Glu Pro Arg Leu Pro Leu
        115                 120

<210> SEQ ID NO 13
<211> LENGTH: 205
<212> TYPE: PRT
<213> ORGANISM: Homo sapiens

<400> SEQUENCE: 13

Tyr His Tyr His Glu Val Met Glu Glu Ile Ala Asp Thr Met Val Gln
 1               5                  10                  15

Ile Phe Lys Gly Leu Gln Glu Arg Phe Gln Thr Glu Ile Gln Thr Val
                 20                  25                  30

Asn Lys Gln Phe Pro Cys Glu Pro Phe Lys Phe Leu Glu Pro Thr Leu
            35                  40                  45

Arg Leu Glu Tyr Cys Glu Ala Leu Ala Met Leu Arg Glu Ala Gly Val
 50                  55                  60

Glu Met Gly Asp Glu Asp Asp Leu Ser Thr Pro Asn Gly Lys Leu Leu
 65                  70                  75                  80

Gly His Leu Val Lys Glu Lys Tyr Asp Thr Asp Phe Tyr Ile Leu Asp
                 85                  90                  95

Lys Tyr Pro Leu Ala Val Arg Pro Phe Tyr Thr Met Pro Asp Pro Arg
            100                 105                 110

Asn Pro Lys Gln Ser Asn Ser Tyr Asp Met Phe Met Arg Gly Glu Glu
            115                 120                 125

Ile Leu Ser Gly Ala Gln Arg Ile His Asp Pro Gln Leu Leu Thr Glu
        130                 135                 140

Arg Ala Leu His His Gly Ile Asp Leu Glu Lys Ile Lys Ala Tyr Ile
145                 150                 155                 160

Asp Ser Phe Arg Phe Gly Ala Pro Pro His Ala Gly Gly Ile Gly
                165                 170                 175

Leu Glu Arg Val Thr Met Leu Phe Leu Gly Leu His Asn Val Arg Gln
                180                 185                 190

Thr Ser Met Phe Pro Arg Asp Pro Lys Arg Leu Thr Pro
            195                 200                 205

<210> SEQ ID NO 14
<211> LENGTH: 401
<212> TYPE: PRT
<213> ORGANISM: Homo sapiens

<400> SEQUENCE: 14

Met Val Lys Phe Ala Ala Asn Ile Asn Lys Glu Ser Ile Val Asp Val
 1               5                  10                  15

Glu Gly Val Val Arg Lys Val Asn Gln Lys Ile Gly Ser Cys Thr Gln
                 20                  25                  30

Gln Asp Val Glu Leu His Val Gln Lys Ile Tyr Val Ile Ser Leu Ala
            35                  40                  45

Glu Pro Arg Leu Pro Leu Gln Leu Asp Asp Ala Val Arg Pro Glu Ala
 50                  55                  60

Glu Gly Glu Glu Glu Gly Arg Ala Thr Val Asn Gln Asp Thr Arg Leu
65                  70                  75                  80

Asp Asn Arg Val Ile Asp Leu Arg Thr Ser Thr Ser Gln Ala Val Phe
            85                  90                  95

Arg Leu Gln Ser Gly Ile Cys His Leu Phe Arg Glu Thr Leu Ile Asn
            100                 105                 110

Lys Gly Phe Val Glu Ile Gln Thr Pro Lys Ile Ile Ser Ala Ala Ser
            115                 120                 125

Glu Gly Gly Ala Asn Val Phe Thr Val Ser Tyr Phe Lys Asn Asn Ala
130                 135                 140

Tyr Leu Ala Gln Ser Pro Gln Leu Tyr Lys Gln Met Cys Ile Cys Ala
145                 150                 155                 160

Asp Phe Glu Lys Val Phe Ser Ile Gly Pro Val Phe Arg Ala Glu Asp
                165                 170                 175

Ser Asn Thr His Arg His Leu Thr Glu Phe Val Gly Leu Asp Ile Glu
                180                 185                 190

Met Ala Phe Asn Tyr His Tyr His Glu Val Met Glu Glu Ile Ala Asp
            195                 200                 205

Thr Met Val Gln Ile Phe Lys Gly Leu Gln Glu Arg Phe Gln Thr Glu
210                 215                 220

Ile Gln Thr Val Asn Lys Gln Phe Pro Cys Glu Pro Phe Lys Phe Leu
225                 230                 235                 240

Glu Pro Thr Leu Arg Leu Glu Tyr Cys Glu Ala Leu Ala Met Leu Arg
                245                 250                 255

Glu Ala Gly Val Glu Met Gly Asp Glu Asp Asp Leu Ser Thr Pro Asn
            260                 265                 270

Glu Lys Leu Leu Gly His Leu Val Lys Glu Lys Tyr Asp Thr Asp Phe
            275                 280                 285

Tyr Ile Leu Asp Lys Tyr Pro Leu Ala Val Arg Pro Phe Tyr Thr Met
290                 295                 300

Pro Asp Pro Arg Asn Pro Lys Gln Ser Asn Ser Tyr Asp Met Phe Met
305                 310                 315                 320

Arg Gly Glu Glu Ile Leu Ser Gly Ala Gln Arg Ile His Asp Pro Gln
                325                 330                 335

Leu Leu Thr Glu Arg Ala Leu His His Gly Ile Asp Leu Glu Lys Ile
            340                 345                 350

Lys Ala Tyr Ile Asp Ser Phe Arg Phe Gly Ala Pro Pro His Ala Gly
            355                 360                 365

Gly Gly Ile Gly Leu Glu Arg Val Thr Met Leu Phe Leu Gly Leu His
370                 375                 380

Asn Val Arg Gln Thr Ser Met Phe Pro Arg Asp Pro Lys Arg Leu Thr
385                 390                 395                 400

Pro

<210> SEQ ID NO 15
<211> LENGTH: 470
<212> TYPE: PRT
<213> ORGANISM: Homo sapiens

<400> SEQUENCE: 15

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

-continued

```
Ser Met Ile Gln Ser Gln Glu Lys Pro Gly Lys Gln Cys Phe Leu Val
        35                  40                  45
Leu Arg Gln Gln Gln Phe Asn Val Gln Ala Leu Val Ala Val Gly Asp
 50                  55                  60
His Ala Ser Lys Gln Met Val Lys Phe Ala Ala Asn Ile Asn Lys Glu
 65                  70                  75                  80
Ser Ile Val Asp Val Glu Gly Val Val Arg Lys Val Asn Gln Lys Ile
                 85                  90                  95
Gly Ser Cys Thr Gln Gln Asp Val Glu Leu His Val Gln Lys Ile Tyr
            100                 105                 110
Val Ile Ser Leu Ala Glu Pro Arg Leu Pro Leu Gln Leu Asp Asp Ala
            115                 120                 125
Val Arg Pro Glu Ala Glu Gly Glu Glu Gly Arg Ala Thr Val Asn
130                 135                 140
Gln Asp Thr Arg Leu Asp Asn Arg Val Ile Asp Leu Arg Thr Ser Thr
145                 150                 155                 160
Ser Gln Ala Val Phe Arg Leu Gln Ser Gly Ile Cys His Leu Phe Arg
                165                 170                 175
Glu Thr Leu Ile Asn Lys Gly Phe Val Glu Ile Gln Thr Pro Lys Ile
            180                 185                 190
Ile Ser Ala Ala Ser Glu Gly Gly Ala Asn Val Phe Thr Val Ser Tyr
            195                 200                 205
Phe Lys Asn Asn Ala Tyr Leu Ala Gln Ser Pro Gln Leu Tyr Lys Gln
            210                 215                 220
Met Cys Ile Cys Ala Asp Phe Glu Lys Val Phe Ser Ile Gly Pro Val
225                 230                 235                 240
Phe Arg Ala Glu Asp Ser Asn Thr His Arg His Leu Thr Glu Phe Val
                245                 250                 255
Gly Leu Asp Ile Glu Met Ala Phe Asn Tyr His Tyr His Glu Val Met
            260                 265                 270
Glu Glu Ile Ala Asp Thr Met Val Gln Ile Phe Lys Gly Leu Gln Glu
            275                 280                 285
Arg Phe Gln Thr Glu Ile Gln Thr Val Asn Lys Gln Phe Pro Cys Glu
290                 295                 300
Pro Phe Lys Phe Leu Glu Pro Thr Leu Arg Leu Glu Tyr Cys Glu Ala
305                 310                 315                 320
Leu Ala Met Leu Arg Glu Ala Gly Val Glu Met Gly Asp Glu Asp Asp
                325                 330                 335
Leu Ser Thr Pro Asn Glu Lys Leu Leu Gly His Leu Val Lys Glu Lys
            340                 345                 350
Tyr Asp Thr Asp Phe Tyr Ile Leu Asp Lys Tyr Pro Leu Ala Val Arg
            355                 360                 365
Pro Phe Tyr Thr Met Pro Asp Pro Arg Asn Pro Lys Gln Ser Asn Ser
370                 375                 380
Tyr Asp Met Phe Met Arg Gly Glu Glu Ile Leu Ser Gly Ala Gln Arg
385                 390                 395                 400
Ile His Asp Pro Gln Leu Leu Thr Glu Arg Ala Leu His His Gly Ile
                405                 410                 415
Asp Leu Glu Lys Ile Lys Ala Tyr Ile Asp Ser Phe Arg Phe Gly Ala
            420                 425                 430
Pro Pro His Ala Gly Gly Gly Ile Gly Leu Glu Arg Val Thr Met Leu
            435                 440                 445
Phe Leu Gly Leu His Asn Val Arg Gln Thr Ser Met Phe Pro Arg Asp
```

```
                   450                 455                 460
Pro Lys Arg Leu Thr Pro
465                 470

<210> SEQ ID NO 16
<211> LENGTH: 454
<212> TYPE: PRT
<213> ORGANISM: Homo sapiens

<400> SEQUENCE: 16

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65              70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Thr Ser Thr
130                 135                 140

Ser Gln Ala Val Phe Arg Leu Gln Ser Gly Ile Cys His Leu Phe Arg
145                 150                 155                 160

Glu Thr Leu Ile Asn Lys Gly Phe Val Glu Ile Gln Thr Pro Lys Ile
                165                 170                 175

Ile Ser Ala Ala Ser Glu Gly Gly Ala Asn Val Phe Thr Val Ser Tyr
            180                 185                 190

Phe Lys Asn Asn Ala Tyr Leu Ala Gln Ser Pro Gln Leu Tyr Lys Gln
        195                 200                 205

Met Cys Ile Cys Ala Asp Phe Glu Lys Val Phe Ser Ile Gly Pro Val
    210                 215                 220

Phe Arg Ala Glu Asp Ser Asn Thr His Arg His Leu Thr Glu Phe Val
225                 230                 235                 240

Gly Leu Asp Ile Glu Met Ala Phe Asn Tyr His Tyr His Glu Val Met
                245                 250                 255

Glu Glu Ile Ala Asp Thr Met Val Gln Ile Phe Lys Gly Leu Gln Glu
            260                 265                 270

Arg Phe Gln Thr Glu Ile Gln Thr Val Asn Lys Gln Phe Pro Cys Glu
        275                 280                 285

Pro Phe Lys Phe Leu Glu Pro Thr Leu Arg Leu Glu Tyr Cys Glu Ala
    290                 295                 300

Leu Ala Met Leu Arg Glu Ala Gly Val Glu Met Gly Asp Glu Asp Asp
305                 310                 315                 320

Leu Ser Thr Pro Asn Glu Lys Leu Leu Gly His Leu Val Lys Glu Lys
                325                 330                 335

Tyr Asp Thr Asp Phe Tyr Ile Leu Asp Lys Tyr Pro Leu Ala Val Arg
            340                 345                 350
```

```
Pro Phe Tyr Thr Met Pro Asp Pro Arg Asn Pro Lys Gln Ser Asn Ser
            355                 360                 365

Tyr Asp Met Phe Met Arg Gly Glu Glu Ile Leu Ser Gly Ala Gln Arg
370                 375                 380

Ile His Asp Pro Gln Leu Leu Thr Glu Arg Ala Leu His His Gly Ile
385                 390                 395                 400

Asp Leu Glu Lys Ile Lys Ala Tyr Ile Asp Ser Phe Arg Phe Gly Ala
                405                 410                 415

Pro Pro His Ala Gly Gly Gly Ile Gly Leu Glu Arg Val Thr Met Leu
            420                 425                 430

Phe Leu Gly Leu His Asn Val Arg Gln Thr Ser Met Phe Pro Arg Asp
            435                 440                 445

Pro Lys Arg Leu Thr Pro
    450

<210> SEQ ID NO 17
<211> LENGTH: 452
<212> TYPE: PRT
<213> ORGANISM: Homo sapiens

<400> SEQUENCE: 17

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270
```

```
Arg Ala Glu Asp Ser Asn Thr His Arg His Leu Thr Glu Phe Val Gly
            275                 280                 285

Leu Asp Ile Glu Met Ala Phe Asn Tyr His Tyr His Glu Val Met Glu
290                 295                 300

Glu Ile Ala Asp Thr Met Val Gln Ile Phe Lys Gly Leu Gln Glu Ser
305                 310                 315                 320

Thr Pro Asn Glu Lys Leu Leu Gly His Leu Val Lys Glu Lys Tyr Asp
            325                 330                 335

Thr Asp Phe Tyr Ile Leu Asp Lys Tyr Pro Leu Ala Val Arg Pro Phe
            340                 345                 350

Tyr Thr Met Pro Asp Pro Arg Asn Pro Lys Gln Ser Asn Ser Tyr Asp
            355                 360                 365

Met Phe Met Arg Gly Glu Glu Ile Leu Ser Gly Ala Gln Arg Ile His
            370                 375                 380

Asp Pro Gln Leu Leu Thr Glu Arg Ala Leu His His Gly Ile Asp Leu
385                 390                 395                 400

Glu Lys Ile Lys Ala Tyr Ile Asp Ser Phe Arg Phe Gly Ala Pro Pro
                405                 410                 415

His Ala Gly Gly Gly Ile Gly Leu Glu Arg Val Thr Met Leu Phe Leu
            420                 425                 430

Gly Leu His Asn Val Arg Gln Thr Ser Met Phe Pro Arg Asp Pro Lys
            435                 440                 445

Arg Leu Thr Pro
    450

<210> SEQ ID NO 18
<211> LENGTH: 85
<212> TYPE: PRT
<213> ORGANISM: Homo sapiens

<400> SEQUENCE: 18

Met Pro Ser Ala Ser Ala Ser Arg Lys Ser Gln Glu Lys Pro Arg Glu
1               5                   10                  15

Ile Met Asp Ala Ala Glu Asp Trp Asn Glu Leu Leu Cys Cys Phe Trp
            20                  25                  30

Asp Cys Ile Met Phe Val Arg Pro Pro Cys Ser Leu Val Ile Pro Asn
        35                  40                  45

Asp Ser Leu Leu Lys Phe Thr Leu Cys His Leu Thr Pro Val Trp Met
    50                  55                  60

Thr Glu Arg Asp Pro Ala Ser Lys Lys Lys Lys Lys Glu Ser His
65                  70                  75                  80

Thr Tyr Ser Phe Gln
                85

<210> SEQ ID NO 19
<211> LENGTH: 27
<212> TYPE: PRT
<213> ORGANISM: Homo sapiens

<400> SEQUENCE: 19

Met Pro Ser Ala Ser Ala Ser Arg Lys Ser Gln Glu Lys Pro Arg Glu
1               5                   10                  15

Ile Met Asp Ala Ala Glu Gly Asn Ser Ala Ser
            20                  25

<210> SEQ ID NO 20
```

-continued

```
<211> LENGTH: 401
<212> TYPE: PRT
<213> ORGANISM: Homo sapiens

<400> SEQUENCE: 20

Met Val Lys Phe Ala Ala Asn Ile Asn Lys Glu Ser Ile Val Asp Val
1               5                   10                  15

Glu Gly Val Val Arg Lys Val Asn Gln Lys Ile Gly Ser Cys Thr Gln
            20                  25                  30

Gln Asp Val Glu Leu His Val Gln Lys Ile Tyr Val Ile Ser Leu Ala
        35                  40                  45

Glu Pro Arg Leu Pro Leu Gln Leu Asp Asp Ala Val Arg Pro Glu Ala
    50                  55                  60

Glu Gly Glu Glu Gly Arg Ala Thr Val Asn Gln Asp Thr Arg Leu
65                  70                  75                  80

Asp Asn Arg Val Ile Asp Leu Arg Thr Ser Thr Ser Gln Ala Val Phe
                85                  90                  95

Arg Leu Gln Ser Gly Ile Cys His Leu Phe Arg Glu Thr Leu Ile Asn
            100                 105                 110

Lys Gly Phe Val Glu Ile Gln Thr Pro Lys Ile Ile Ser Ala Ala Ser
        115                 120                 125

Glu Gly Gly Ala Asn Val Phe Thr Val Ser Tyr Phe Lys Asn Asn Ala
    130                 135                 140

Tyr Leu Ala Gln Ser Pro Gln Leu Tyr Lys Gln Met Cys Ile Cys Ala
145                 150                 155                 160

Asp Phe Glu Lys Val Phe Ser Ile Gly Pro Val Phe Arg Ala Glu Asp
                165                 170                 175

Ser Asn Thr His Arg His Leu Thr Glu Phe Val Gly Leu Asp Ile Glu
            180                 185                 190

Met Ala Phe Asn Tyr His Tyr His Glu Val Met Glu Glu Ile Ala Asp
        195                 200                 205

Thr Met Val Gln Ile Phe Lys Gly Leu Gln Glu Arg Phe Gln Thr Glu
    210                 215                 220

Ile Gln Thr Val Asn Lys Gln Phe Pro Cys Glu Pro Phe Lys Phe Leu
225                 230                 235                 240

Glu Pro Thr Leu Arg Leu Glu Tyr Cys Glu Ala Leu Ala Met Leu Arg
                245                 250                 255

Glu Ala Gly Val Glu Met Gly Asp Glu Asp Leu Ser Thr Pro Asn
            260                 265                 270

Glu Lys Leu Leu Gly His Leu Val Lys Glu Lys Tyr Asp Thr Asp Phe
        275                 280                 285

Tyr Ile Leu Asp Lys Tyr Pro Leu Ala Val Arg Pro Phe Tyr Thr Met
    290                 295                 300

Pro Asp Pro Arg Asn Pro Lys Gln Ser Asn Ser Tyr Asp Met Phe Met
305                 310                 315                 320

Arg Gly Glu Glu Ile Leu Ser Gly Ala Gln Arg Ile His Asp Pro Gln
                325                 330                 335

Leu Leu Thr Glu Arg Ala Leu His His Gly Ile Asp Leu Glu Lys Ile
            340                 345                 350

Lys Ala Tyr Ile Asp Ser Phe Arg Phe Gly Ala Pro Pro His Ala Gly
        355                 360                 365

Gly Gly Ile Gly Leu Glu Arg Val Thr Met Leu Phe Leu Gly Leu His
    370                 375                 380

Asn Val Arg Gln Thr Ser Met Phe Pro Arg Asp Pro Lys Arg Leu Thr
```

```
<210> SEQ ID NO 21
<211> LENGTH: 24
<212> TYPE: PRT
<213> ORGANISM: Homo sapiens

<400> SEQUENCE: 21

Met Leu Phe Leu Gly Leu His Asn Val Arg Gln Thr Ser Met Phe Pro
1               5                   10                  15

Arg Asp Pro Lys Arg Leu Thr Pro
            20

<210> SEQ ID NO 22
<211> LENGTH: 154
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 22

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Ser Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 23
<211> LENGTH: 154
<212> TYPE: PRT
<213> ORGANISM: Artificial Sequence
<220> FEATURE:
<223> OTHER INFORMATION: DRS polypetide variant with reduced cysteine
      content

<400> SEQUENCE: 23

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45
```

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Ser Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 24
<211> LENGTH: 154
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 24

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Ser Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Ser Thr Gln Gln Asp Val Glu Leu His Val Gln Lys Ile Tyr Val
    130                 135                 140

Ile Ser Leu Ala Glu Pro Arg Leu Pro Leu
145                 150

<210> SEQ ID NO 25
<211> LENGTH: 462
<212> TYPE: DNA
<213> ORGANISM: Artificial Sequence
<220> FEATURE:
<223> OTHER INFORMATION: Codon optimizedversion of the wild type
      AspRS1N1 polypeptide

<400> SEQUENCE: 25
atgccgagcg cgagcgccag ccgtaagagc caggaaaaac cacgtgagat tatggatgcc      60
gcagaggact atgcgaaaga acgttacggt atttccagca tgatccaatc tcaggagaaa     120
ccggaccgcg ttctggttcg tgttcgcgat ctgaccattc agaaggcgga cgaggtggtt     180

| | |
|---|---|
| tgggtgcgtg cgcgcgtgca caccagccgt gcaaaaggca aacagtgctt tctggtcctg | 240 |
| cgtcagcagc aattcaacgt ccaggcgctg gtggcagtgg gtgaccacgc cagcaaacaa | 300 |
| atggtgaagt cgctgctaa catcaataaa gaatccattg ttgatgttga aggcgtcgtt | 360 |
| cgcaaggtca atcaaaagat cggctcgtgt acgcaacaag atgtcgagct gcatgtgcag | 420 |
| aagatttacg tcatcagcct ggcggagccg cgtttgccgc tg | 462 |

<210> SEQ ID NO 26
<211> LENGTH: 525
<212> TYPE: DNA
<213> ORGANISM: Artificial Sequence
<220> FEATURE:
<223> OTHER INFORMATION: Codon optimized version of the wild type AspRS1N1 polypeptide

<400> SEQUENCE: 26

| | |
|---|---|
| atgccgagcg cgagcgccag ccgtaagagc caggaaaaac cacgtgagat tatggatgcc | 60 |
| gcagaggact atgcgaaaga cgttacggt atttccagca tgatccaatc tcaggagaaa | 120 |
| ccggaccgcg ttctggttcg tgttcgcgat ctgaccattc agaaggcgga cgaggtggtt | 180 |
| tgggtgcgtg cgcgcgtgca caccagccgt gcaaaaggca aacagagctt tctggtcctg | 240 |
| cgtcagcagc aattcaacgt ccaggcgctg gtggcagtgg gtgaccacgc cagcaaacaa | 300 |
| atggtgaagt cgctgctaa catcaataaa gaatccattg ttgatgttga aggcgtcgtt | 360 |
| cgcaaggtca atcaaaagat cggctcgtgt acgcaacaag atgtcgagct gcatgtgcag | 420 |
| aagatttacg tcatcagcct ggcggagccg cgtttgccgc tgggtaagcc gatccctaac | 480 |
| ccgctgttgg gtctggacag cacgcatcac catcaccacc actaa | 525 |

<210> SEQ ID NO 27
<211> LENGTH: 1503
<212> TYPE: DNA
<213> ORGANISM: Artificial Sequence
<220> FEATURE:
<223> OTHER INFORMATION: Codon optimized version of the wild type full length DRS polypeptide

<400> SEQUENCE: 27

| | |
|---|---|
| atgccatcag cctcagcatc tcgtaaaagc caggaaaaac cgcgcgaaat catggacgct | 60 |
| gccgaagatt atgccaaaga gcgctatggt atcagttcga tgatccagtc acaagagaaa | 120 |
| ccagatcgtg tgctggtccg tgttcgtgac ctgaccatcc agaaagcgga tgaagttgtt | 180 |
| tgggtccgtg ctcgtgttca tacaagccgt gccaaaggca aacagtgctt cctggttctg | 240 |
| cgtcaacagc agtttaacgt tcaggccctg gtagccgttg gtgatcacgc tcaaaaacaa | 300 |
| atggtgaaat cgccgccaa catcaacaaa gagagcatcg tcgacgttga aggtgtcgtc | 360 |
| cgtaaagtga atcagaaaat cggctcctgt acacagcaag atgtggagct gcatgtccaa | 420 |
| aaaatctatg tcatctcact ggccgaacct cgtctgcctc tgcaactgga tgatgctgta | 480 |
| cgccctgaag ctgaaggcga agaagaaggt cgtgctacgg ttaatcagga tactcgcctg | 540 |
| gacaaccgtg tcattgatct cgcacctca acctctcaag cggtattccg cctgcaatcc | 600 |
| ggcatcgtc acctgttccg tgaaacgctg atcaacaaag gtttgtgga gattcagacc | 660 |
| ccgaaaatca ttagtgccgc cagcgaaggt ggagcaaatg tgtttaccgt gtcctatttc | 720 |
| aaaaacaatg cctatctggc acagtctcct cagctgtata acaaatgtg tatctgtgct | 780 |
| gacttcgaga aagtgttctc aatcgggccg gtattccgtg cagaggatag caacacacac | 840 |
| cgccatctga ccgaatttgt aggcctggac atcgaaatgg ccttcaacta tcattatcac | 900 |

```
gaggtgatgg aagaaatcgc tgatacaatg gtacagatct ttaaagggct gcaagaacgc    960
tttcaaacag agattcaaac cgtcaataaa cagttcccgt gtgaaccgtt caaatttctg   1020
gaaccgaccc tgcgtctgga atattgtgaa gcactggcta tgctgcgcga agctggtgtc   1080
gaaatgggtg atgaggatga cctgtctacc cctaacgaaa aactgctggg ccacctggta   1140
aaagaaaaat atgacacaga cttctatatc ctggacaaat atccgctggc agttcgtccg   1200
ttttatacga tgcctgatcc tcgtaatccg aaacaaagca actcctatga catgttcatg   1260
cgtggtgaag agatcctgtc tggtgctcaa cgtatccatg atccacagct gctgacagaa   1320
cgtgcactgc atcacggtat tgatctggag aaaatcaaag cctatatcga ctcctttcgc   1380
tttggtgccc ctccacatgc cggtggtgga attgggctgg agcgtgtaac aatgctgttc   1440
ctgggactgc acaacgtccg tcaaacctca atgtttccac gtgaccctaa acgtctgaca   1500
cct                                                                 1503

<210> SEQ ID NO 28
<211> LENGTH: 525
<212> TYPE: DNA
<213> ORGANISM: Artificial Sequence
<220> FEATURE:
<223> OTHER INFORMATION: An E.coli codon optimized nucleic acid sequence
      encoding the DRS polypeptide AspRS1N1

<400> SEQUENCE: 28
atgccgagcg cgagcgccag ccgtaagagc caggaaaaac cacgtgagat tatggatgcc     60
gcagaggact atgcgaaaga acgttacggt atttccagca tgatccaatc tcaggagaaa    120
ccggaccgcg ttctggttcg tgttcgcgat ctgaccattc agaaggcgga cgaggtggtt    180
tgggtgcgtg cgcgcgtgca caccagccgt gcaaaaggca acagagctt tctggtcctg    240 cgtcagcagc aattcaacgt ccaggcgctg gtggcagtgg gtgaccacgc cagcaaacaa    300
atggtgaagt cgctgctaa catcaataaa gaatccattg ttgatgttga aggcgtcgtt    360
cgcaaggtca atcaaaagat cggctcgtgt acgcaacaag atgtcgagct gcatgtgcag    420
aagatttacg tcatcagcct ggcggagccg cgtttgccgc tgggtaagcc gatccctaac    480
ccgctgttgg gtctggacag cacgcatcac catcaccacc actaa                    525

<210> SEQ ID NO 29
<211> LENGTH: 174
<212> TYPE: PRT
<213> ORGANISM: Artificial Sequence
<220> FEATURE:
<223> OTHER INFORMATION: Traqnslated protein of the E.coli codon
      optimized nucleic acid sequence encoding the DRS polypeptide
      AspRS1N1

<400> SEQUENCE: 29

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Ser Phe Leu Val Leu
65                  70                  75                  80
```

-continued

```
Arg Gln Gln Gln Phe Asn Val Gln Ala Leu Val Ala Val Gly Asp His
                 85                  90                  95
Ala Ser Lys Gln Met Val Lys Phe Ala Ala Asn Ile Asn Lys Glu Ser
            100                 105                 110
Ile Val Asp Val Glu Gly Val Val Arg Lys Val Asn Gln Lys Ile Gly
        115                 120                 125
Ser Cys Thr Gln Gln Asp Val Glu Leu His Val Gln Lys Ile Tyr Val
    130                 135                 140
Ile Ser Leu Ala Glu Pro Arg Leu Pro Leu Gly Lys Pro Ile Pro Asn
145                 150                 155                 160
Pro Leu Leu Gly Leu Asp Ser Thr His His His His His
                165                 170
```

<210> SEQ ID NO 30
<211> LENGTH: 525
<212> TYPE: DNA
<213> ORGANISM: Artificial Sequence
<220> FEATURE:
<223> OTHER INFORMATION: The nucleic acid sequence of the native
      AspRS1N1 cloned into the identical expression cassette

<400> SEQUENCE: 30

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgcttc cttagtccta     240
cgtcagcagc agtttaatgt ccaggctctt gtggcggtgg agaccatgc aagcaagcag      300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgggtaagcc tatccctaac     480
cctctcctcg gtctcgattc tacgcaccac caccaccacc actga                     525
```

<210> SEQ ID NO 31
<211> LENGTH: 174
<212> TYPE: PRT
<213> ORGANISM: Artificial Sequence
<220> FEATURE:
<223> OTHER INFORMATION: the non-mutated AspRS1N1 protein with
      C-terminal tag

<400> SEQUENCE: 31

```
Met Pro Ser Ala Ser Ala Ser Arg Lys Ser Gln Glu Lys Pro Arg Glu
1               5                   10                  15
Ile Met Asp Ala Ala Glu Asp Tyr Ala Lys Glu Arg Tyr Gly Ile Ser
            20                  25                  30
Ser Met Ile Gln Ser Gln Glu Lys Pro Asp Arg Val Leu Val Arg Val
        35                  40                  45
Arg Asp Leu Thr Ile Gln Lys Ala Asp Glu Val Val Trp Val Arg Ala
    50                  55                  60
Arg Val His Thr Ser Arg Ala Lys Gly Lys Gln Cys Phe Leu Val Leu
65                  70                  75                  80
Arg Gln Gln Gln Phe Asn Val Gln Ala Leu Val Ala Val Gly Asp His
                85                  90                  95
Ala Ser Lys Gln Met Val Lys Phe Ala Ala Asn Ile Asn Lys Glu Ser
            100                 105                 110
```

```
Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gly Lys Pro Ile Pro Asn
145                 150                 155                 160

Pro Leu Leu Gly Leu Asp Ser Thr His His His His His His
                165                 170

<210> SEQ ID NO 32
<211> LENGTH: 45
<212> TYPE: DNA
<213> ORGANISM: Homo sapiens
<220> FEATURE:
<221> NAME/KEY: misc_feature
<222> LOCATION: (1)..(45)
<223> OTHER INFORMATION: Primer

<400> SEQUENCE: 32
agtcttgcac ttgtcacgaa ttcgatgccc agcgccagcg ccagc              45

<210> SEQ ID NO 33
<211> LENGTH: 75
<212> TYPE: DNA
<213> ORGANISM: Homo sapiens
<220> FEATURE:
<221> NAME/KEY: misc_feature
<222> LOCATION: (1)..(75)
<223> OTHER INFORMATION: Primer

<400> SEQUENCE: 33
cggtgggcat gtgtgagttt tgtctcactt gtcgtcatcg tctttgtagt ccgtagaatc     60
gagaccgagg agagg                                                     75

<210> SEQ ID NO 34
<211> LENGTH: 45
<212> TYPE: DNA
<213> ORGANISM: Homo sapiens
<220> FEATURE:
<221> NAME/KEY: misc_feature
<222> LOCATION: (1)..(45)
<223> OTHER INFORMATION: Primer

<400> SEQUENCE: 34
gatcaccggc gaaggagggc caccatgccc agcgccagcg ccagc              45

<210> SEQ ID NO 35
<211> LENGTH: 75
<212> TYPE: DNA
<213> ORGANISM: Homo sapiens
<220> FEATURE:
<221> NAME/KEY: misc_feature
<222> LOCATION: (1)..(75)
<223> OTHER INFORMATION: Primer

<400> SEQUENCE: 35
cggtgggcat gtgtgagttt tgtctcactt gtcgtcatcg tctttgtagt ccgtagaatc     60
gagaccgagg agagg                                                     75

<210> SEQ ID NO 36
<211> LENGTH: 591
<212> TYPE: DNA
<213> ORGANISM: Artificial Sequence
<220> FEATURE:
<223> OTHER INFORMATION: secretory AspRS1N1 sequence
```

<400> SEQUENCE: 36

```
atgtacagga tgcaactcct gtcttgcatt gcactaagtc ttgcacttgt cacgaattcg    60
atgcccagcg ccagcgccag ccgcaagagt caggagaagc cgcgggagat catggacgcg   120
gcggaagatt atgctaaaga gagatatgga atatcttcaa tgatacaatc acaagaaaaa   180
ccagatcgag ttttggttcg ggttagagac ttgacaatac aaaaagctga tgaagttgtt   240
tgggtacgtg caagagttca tacaagcaga gctaaaggga aacagtgctt cttagtccta   300
cgtcagcagc agtttaatgt ccaggctctt gtggcggtgg gagaccatgc aagcaagcag   360
atggttaaat ttgctgccaa catcaacaaa gagagcattg tggatgtaga aggtgttgtg   420
agaaaagtga atcagaaaat tggaagctgt acacagcaag acgttgagtt acatgttcag   480
aagatttatg tgatcagttt ggctgaaccc cgtctgcccc tgggtaagcc tatccctaac   540
cctctcctcg gtctcgattc tacggactac aaagacgatg acgacaagtg a            591
```

<210> SEQ ID NO 37
<211> LENGTH: 531
<212> TYPE: DNA
<213> ORGANISM: Artificial Sequence
<220> FEATURE:
<223> OTHER INFORMATION: intracellular AspRS1N1 sequence

<400> SEQUENCE: 37

```
atgcccagcg ccagcgccag ccgcaagagt caggagaagc cgcgggagat catggacgcg    60
gcggaagatt atgctaaaga gagatatgga atatcttcaa tgatacaatc acaagaaaaa   120
ccagatcgag ttttggttcg ggttagagac ttgacaatac aaaaagctga tgaagttgtt   180
tgggtacgtg caagagttca tacaagcaga gctaaaggga aacagtgctt cttagtccta   240
cgtcagcagc agtttaatgt ccaggctctt gtggcggtgg gagaccatgc aagcaagcag   300
atggttaaat ttgctgccaa catcaacaaa gagagcattg tggatgtaga aggtgttgtg   360
agaaaagtga atcagaaaat tggaagctgt acacagcaag acgttgagtt acatgttcag   420
aagatttatg tgatcagttt ggctgaaccc cgtctgcccc tgggtaagcc tatccctaac   480
cctctcctcg gtctcgattc tacggactac aaagacgatg acgacaagtg a            531
```

<210> SEQ ID NO 38
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: Human C76X Primer

<400> SEQUENCE: 38

```
gctaaaggga aacagagctt cttagtccta cgtcagc                             37
```

<210> SEQ ID NO 39
<211> LENGTH: 37
<212> TYPE: DNA
<213> ORGANISM: Homo sapiens
<220> FEATURE:
<221> NAME/KEY: misc_feature
<222> LOCATION: (1)..(37)
<223> OTHER INFORMATION: Human C130X Primer

<400> SEQUENCE: 39

```
gtgaatcaga aaattggaag cagcacacag caagacg                             37
```

-continued

```
<210> SEQ ID NO 40
<211> LENGTH: 40
<212> TYPE: DNA
<213> ORGANISM: Artificial Sequence
<220> FEATURE:
<223> OTHER INFORMATION: E.coli codon optimized C76X Primer

<400> SEQUENCE: 40
cgtgcaaaag gcaaacagag ctttctggtc ctgcgtcagc                              40

<210> SEQ ID NO 41
<211> LENGTH: 41
<212> TYPE: DNA
<213> ORGANISM: Artificial Sequence
<220> FEATURE:
<223> OTHER INFORMATION: E.coli codon optimized C130X Primer

<400> SEQUENCE: 41
caatcaaaag atcggctcga gcacgcaaca agatgtcgag c                            41

<210> SEQ ID NO 42
<211> LENGTH: 4
<212> TYPE: PRT
<213> ORGANISM: Homo sapiens

<400> SEQUENCE: 42

His Ile Gly His
1

<210> SEQ ID NO 43
<211> LENGTH: 5
<212> TYPE: PRT
<213> ORGANISM: Homo sapiens

<400> SEQUENCE: 43

Lys Met Ser Lys Ser
1               5

<210> SEQ ID NO 44
<211> LENGTH: 18
<212> TYPE: DNA
<213> ORGANISM: Homo sapiens

<400> SEQUENCE: 44 acttttttgat ggggttgt                                                     18

<210> SEQ ID NO 45
<211> LENGTH: 39
<212> TYPE: DNA
<213> ORGANISM: Homo sapiens

<400> SEQUENCE: 45 ccttttttcat gggcttgttt ttttcttgta aatttgttt                              39

<210> SEQ ID NO 46
<211> LENGTH: 14
<212> TYPE: PRT
<213> ORGANISM: Artificial Sequence
<220> FEATURE:
<223> OTHER INFORMATION: V5 tag sequence

<400> SEQUENCE: 46

Gly Lys Pro Ile Pro Asn Pro Leu Leu Gly Leu Asp Ser Thr
1               5                   10
```

<210> SEQ ID NO 47
<211> LENGTH: 8
<212> TYPE: PRT
<213> ORGANISM: Artificial Sequence
<220> FEATURE:
<223> OTHER INFORMATION: Flag tag sequence

<400> SEQUENCE: 47

Asp Tyr Lys Asp Asp Asp Asp Lys
1               5

<210> SEQ ID NO 48
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 48

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu

```
                    290                 295                 300
Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Cys Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 49
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 49

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140
```

```
Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
            165                 170                 175

Asp Thr Arg Leu Asp Asn Arg Val Ile Asp Leu Arg Thr Ser Thr Ser
        180                 185                 190

Gln Ala Val Phe Arg Leu Gln Ser Gly Ile Cys His Leu Phe Arg Glu
            195                 200                 205

Thr Leu Ile Asn Lys Gly Phe Val Glu Ile Gln Thr Pro Lys Ile Ile
        210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
            245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
            275                 280                 285

Leu Asp Ile Glu Met Ala Phe Asn Tyr His Tyr His Glu Val Met Glu
        290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
            325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
            355                 360                 365

Ser Thr Pro Asn Glu Lys Leu Leu Gly His Leu Val Lys Glu Lys Tyr
        370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
            405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
            435                 440                 445

Leu Glu Lys Ile Lys Ala Tyr Ile Asp Ser Phe Arg Phe Gly Ala Pro
        450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
            485                 490                 495

Lys Arg Leu Thr Pro
            500
```

<210> SEQ ID NO 50
<211> LENGTH: 501
<212> TYPE: PRT
<213> ORGANISM: Artificial Sequence
<220> FEATURE:
<223> OTHER INFORMATION: DRS polypeptide variant with reduced cysteine content

<400> SEQUENCE: 50

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                      70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Cys His Leu Phe Arg Glu
                195                 200                 205

Thr Leu Ile Asn Lys Gly Phe Val Glu Ile Gln Thr Pro Lys Ile Ile
        210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415
```

```
Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500
```

<210> SEQ ID NO 51
<211> LENGTH: 501
<212> TYPE: PRT
<213> ORGANISM: Artificial Sequence
<220> FEATURE:
<223> OTHER INFORMATION: DRS polypeptide variant with reduced cysteine content

<400> SEQUENCE: 51

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Ala His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270
```

-continued

```
Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Cys Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 52
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 52

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
```

```
            115                 120                 125
Ser Cys Thr Gln Gln Asp Val Glu Leu His Val Gln Lys Ile Tyr Val
            130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
            165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Val His Leu Phe Arg Glu
            195                 200                 205

Thr Leu Ile Asn Lys Gly Phe Val Glu Ile Gln Thr Pro Lys Ile Ile
            210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
            275                 280                 285

Leu Asp Ile Glu Met Ala Phe Asn Tyr His Tyr His Glu Val Met Glu
            290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Cys Glu Pro
                325                 330                 335

Phe Lys Phe Leu Glu Pro Thr Leu Arg Leu Glu Tyr Cys Glu Ala Leu
            340                 345                 350

Ala Met Leu Arg Glu Ala Gly Val Glu Met Gly Asp Glu Asp Asp Leu
            355                 360                 365

Ser Thr Pro Asn Glu Lys Leu Leu Gly His Leu Val Lys Glu Lys Tyr
            370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
            435                 440                 445

Leu Glu Lys Ile Lys Ala Tyr Ile Asp Ser Phe Arg Phe Gly Ala Pro
            450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 53
<211> LENGTH: 501
<212> TYPE: PRT
<213> ORGANISM: Artificial Sequence
```

<220> FEATURE:
<223> OTHER INFORMATION: DRS polypeptide variant with reduced cysteine
      content

<400> SEQUENCE: 53

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Ala His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Cys Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
```

```
                385                 390                 395                 400
        Phe Tyr Thr Met Pro Asp Pro Arg Asn Pro Lys Gln Ser Asn Ser Tyr
                        405                 410                 415

Asp Met Phe Met Arg Gly Glu Glu Ile Leu Ser Gly Ala Gln Arg Ile
                        420                 425                 430

His Asp Pro Gln Leu Leu Thr Glu Arg Ala Leu His His Gly Ile Asp
                        435                 440                 445

Leu Glu Lys Ile Lys Ala Tyr Ile Asp Ser Phe Arg Phe Gly Ala Pro
        450                 455                 460

Pro His Ala Gly Gly Gly Ile Gly Leu Glu Arg Val Thr Met Leu Phe
        465                 470                 475                 480

Leu Gly Leu His Asn Val Arg Gln Thr Ser Met Phe Pro Arg Asp Pro
                        485                 490                 495

Lys Arg Leu Thr Pro
                        500

<210> SEQ ID NO 54
<211> LENGTH: 501
<212> TYPE: PRT
<213> ORGANISM: Artificial Sequence
<220> FEATURE:
<223> OTHER INFORMATION: DRS polypeptide variant with reduced cysteine
      content

<400> SEQUENCE: 54

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Val His Leu Phe Arg Glu
        195                 200                 205

Thr Leu Ile Asn Lys Gly Phe Val Glu Ile Gln Thr Pro Lys Ile Ile
        210                 215                 220

Ser Ala Ala Ser Glu Gly Gly Ala Asn Val Phe Thr Val Ser Tyr Phe
225                 230                 235                 240
```

```
Lys Asn Asn Ala Tyr Leu Ala Gln Ser Pro Gln Leu Tyr Lys Gln Met
                    245                 250                 255

Cys Ile Ala Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Leu
        355                 360                 365

Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
            420                 425                 430

His Asp Pro Gln Leu Leu Thr Glu Arg Ala Leu His His Gly Ile Asp
        435                 440                 445

Leu Glu Lys Ile Lys Ala Tyr Ile Asp Ser Phe Arg Phe Gly Ala Pro
    450                 455                 460

Pro His Ala Gly Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
                500
```

<210> SEQ ID NO 55
<211> LENGTH: 501
<212> TYPE: PRT
<213> ORGANISM: Artificial Sequence
<220> FEATURE:
<223> OTHER INFORMATION: DRS polypeptide variant with reduced cysteine content

<400> SEQUENCE: 55

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95
```

```
Ala Ser Lys Gln Met Val Lys Phe Ala Ala Asn Ile Asn Lys Glu Ser
            100                 105                 110
Ile Val Asp Val Glu Gly Val Val Arg Lys Val Asn Gln Lys Ile Gly
            115                 120                 125
Ser Cys Thr Gln Gln Asp Val Glu Leu His Val Gln Lys Ile Tyr Val
130                 135                 140
Ile Ser Leu Ala Glu Pro Arg Leu Pro Leu Gln Leu Asp Asp Ala Val
145                 150                 155                 160
Arg Pro Glu Ala Glu Gly Glu Glu Gly Arg Ala Thr Val Asn Gln
            165                 170                 175
Asp Thr Arg Leu Asp Asn Arg Val Ile Asp Leu Arg Thr Ser Thr Ser
            180                 185                 190
Gln Ala Val Phe Arg Leu Gln Ser Gly Ile Ala His Leu Phe Arg Glu
            195                 200                 205
Thr Leu Ile Asn Lys Gly Phe Val Glu Ile Gln Thr Pro Lys Ile Ile
            210                 215                 220
Ser Ala Ala Ser Glu Gly Gly Ala Asn Val Phe Thr Val Ser Tyr Phe
225                 230                 235                 240
Lys Asn Asn Ala Tyr Leu Ala Gln Ser Pro Gln Leu Tyr Lys Gln Met
            245                 250                 255
Cys Ile Ala Ala Asp Phe Glu Lys Val Phe Ser Ile Gly Pro Val Phe
            260                 265                 270
Arg Ala Glu Asp Ser Asn Thr His Arg His Leu Thr Glu Phe Val Gly
            275                 280                 285
Leu Asp Ile Glu Met Ala Phe Asn Tyr His Tyr His Glu Val Met Glu
            290                 295                 300
Glu Ile Ala Asp Thr Met Val Gln Ile Phe Lys Gly Leu Gln Glu Arg
305                 310                 315                 320
Phe Gln Thr Glu Ile Gln Thr Val Asn Lys Gln Phe Pro Ser Glu Pro
            325                 330                 335
Phe Lys Phe Leu Glu Pro Thr Leu Arg Leu Glu Tyr Ser Glu Ala Leu
            340                 345                 350
Ala Met Leu Arg Glu Ala Gly Val Glu Met Gly Asp Glu Asp Leu
            355                 360                 365
Ser Thr Pro Asn Glu Lys Leu Leu Gly His Leu Val Lys Glu Lys Tyr
            370                 375                 380
Asp Thr Asp Phe Tyr Ile Leu Asp Lys Tyr Pro Leu Ala Val Arg Pro
385                 390                 395                 400
Phe Tyr Thr Met Pro Asp Pro Arg Asn Pro Lys Gln Ser Asn Ser Tyr
            405                 410                 415
Asp Met Phe Met Arg Gly Glu Glu Ile Leu Ser Gly Ala Gln Arg Ile
            420                 425                 430
His Asp Pro Gln Leu Leu Thr Glu Arg Ala Leu His His Gly Ile Asp
            435                 440                 445
Leu Glu Lys Ile Lys Ala Tyr Ile Asp Ser Phe Arg Phe Gly Ala Pro
            450                 455                 460
Pro His Ala Gly Gly Gly Ile Gly Leu Glu Arg Val Thr Met Leu Phe
465                 470                 475                 480
Leu Gly Leu His Asn Val Arg Gln Thr Ser Met Phe Pro Arg Asp Pro
            485                 490                 495
Lys Arg Leu Thr Pro
            500
```

<210> SEQ ID NO 56
<211> LENGTH: 501
<212> TYPE: PRT
<213> ORGANISM: Artificial Sequence
<220> FEATURE:
<223> OTHER INFORMATION: RS polypeptide variant with reduced cysteine content

<400> SEQUENCE: 56

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn Arg Val Ile Asp Leu Arg Thr Ser Thr Ser
            180                 185                 190

Gln Ala Val Phe Arg Leu Gln Ser Gly Ile Val His Leu Phe Arg Glu
        195                 200                 205

Thr Leu Ile Asn Lys Gly Phe Val Glu Ile Gln Thr Pro Lys Ile Ile
    210                 215                 220

Ser Ala Ala Ser Glu Gly Gly Ala Asn Val Phe Thr Val Ser Tyr Phe
225                 230                 235                 240

Lys Asn Asn Ala Tyr Leu Ala Gln Ser Pro Gln Leu Tyr Lys Gln Met
                245                 250                 255

Cys Ile Ala Ala Asp Phe Glu Lys Val Phe Ser Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Met Glu
    290                 295                 300

Glu Ile Ala Asp Thr Met Val Gln Ile Phe Lys Gly Leu Gln Glu Arg
305                 310                 315                 320

Phe Gln Thr Glu Ile Gln Thr Val Asn Lys Gln Phe Pro Ser Glu Pro
                325                 330                 335

Phe Lys Phe Leu Glu Pro Thr Leu Arg Leu Glu Tyr Ser Glu Ala Leu
            340                 345                 350

Ala Met Leu Arg Glu Ala Gly Val Glu Met Gly Asp Glu Asp Leu
        355                 360                 365
```

```
Ser Thr Pro Asn Glu Lys Leu Leu Gly His Leu Val Lys Glu Lys Tyr
    370                 375                 380

Asp Thr Asp Phe Tyr Ile Leu Asp Lys Tyr Pro Leu Ala Val Arg Pro
385                 390                 395                 400

Phe Tyr Thr Met Pro Asp Pro Arg Asn Pro Lys Gln Ser Asn Ser Tyr
                405                 410                 415

Asp Met Phe Met Arg Gly Glu Glu Ile Leu Ser Gly Ala Gln Arg Ile
                420                 425                 430

His Asp Pro Gln Leu Leu Thr Glu Arg Ala Leu His His Gly Ile Asp
            435                 440                 445

Leu Glu Lys Ile Lys Ala Tyr Ile Asp Ser Phe Arg Phe Gly Ala Pro
450                 455                 460

Pro His Ala Gly Gly Ile Gly Leu Glu Arg Val Thr Met Leu Phe
465                 470                 475                 480

Leu Gly Leu His Asn Val Arg Gln Thr Ser Met Phe Pro Arg Asp Pro
                485                 490                 495

Lys Arg Leu Thr Pro
            500

<210> SEQ ID NO 57
<211> LENGTH: 182
<212> TYPE: PRT
<213> ORGANISM: Homo sapiens

<400> SEQUENCE: 57

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu Asp Asn
            180

<210> SEQ ID NO 58
<211> LENGTH: 180
<212> TYPE: PRT
<213> ORGANISM: Homo sapiens

<400> SEQUENCE: 58
```

-continued

```
Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr Arg Leu
            180

<210> SEQ ID NO 59
<211> LENGTH: 178
<212> TYPE: PRT
<213> ORGANISM: Homo sapiens

<400> SEQUENCE: 59

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

Asp Thr
```

<210> SEQ ID NO 60
<211> LENGTH: 176
<212> TYPE: PRT
<213> ORGANISM: Homo sapiens

<400> SEQUENCE: 60

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val Asn Gln
                165                 170                 175

<210> SEQ ID NO 61
<211> LENGTH: 174
<212> TYPE: PRT
<213> ORGANISM: Homo sapiens

<400> SEQUENCE: 61

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala Thr Val
                165                 170

<210> SEQ ID NO 62
<211> LENGTH: 172
<212> TYPE: PRT
<213> ORGANISM: Homo sapiens

<400> SEQUENCE: 62

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu Gly Arg Ala
                165                 170

<210> SEQ ID NO 63
<211> LENGTH: 170
<212> TYPE: PRT
<213> ORGANISM: Homo sapiens

<400> SEQUENCE: 63

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
130                 135                 140

```
Ile Ser Leu Ala Glu Pro Arg Leu Pro Leu Gln Leu Asp Asp Ala Val
145                 150                 155                 160

Arg Pro Glu Ala Glu Gly Glu Glu Gly
                165                 170

<210> SEQ ID NO 64
<211> LENGTH: 168
<212> TYPE: PRT
<213> ORGANISM: Homo sapiens

<400> SEQUENCE: 64

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Val
145                 150                 155                 160

Arg Pro Glu Ala Glu Gly Glu Glu
                165

<210> SEQ ID NO 65
<211> LENGTH: 166
<212> TYPE: PRT
<213> ORGANISM: Homo sapiens

<400> SEQUENCE: 65

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125
```

```
Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala Glu Gly
                165

<210> SEQ ID NO 66
<211> LENGTH: 164
<212> TYPE: PRT
<213> ORGANISM: Homo sapiens

<400> SEQUENCE: 66

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro Glu Ala

<210> SEQ ID NO 67
<211> LENGTH: 162
<212> TYPE: PRT
<213> ORGANISM: Homo sapiens

<400> SEQUENCE: 67

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110
```

Ile Val Asp Val Glu Gly Val Val Arg Lys Val Asn Gln Lys Ile Gly
115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

Arg Pro

<210> SEQ ID NO 68
<211> LENGTH: 160
<212> TYPE: PRT
<213> ORGANISM: Homo sapiens

<400> SEQUENCE: 68

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu Asp Asp Ala Val
145                 150                 155                 160

<210> SEQ ID NO 69
<211> LENGTH: 158
<212> TYPE: PRT
<213> ORGANISM: Homo sapiens

<400> SEQUENCE: 69

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly

```
                    115                 120                 125

Ser Cys Thr Gln Gln Asp Val Glu Leu His Val Gln Lys Ile Tyr Val
        130                 135                 140

Ile Ser Leu Ala Glu Pro Arg Leu Pro Leu Gln Leu Asp Asp
145                 150                 155

<210> SEQ ID NO 70
<211> LENGTH: 156
<212> TYPE: PRT
<213> ORGANISM: Homo sapiens

<400> SEQUENCE: 70

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala Glu Pro Arg Leu Pro Leu Gln Leu
145                 150                 155

<210> SEQ ID NO 71
<211> LENGTH: 154
<212> TYPE: PRT
<213> ORGANISM: Homo sapiens

<400> SEQUENCE: 71

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
            20                  25                  30

Ser Met Ile Gln Ser Gln Glu Lys Pro Asp Arg Val Leu Val Arg Val
        35                  40                  45

Arg Asp Leu Thr Ile Gln Lys Ala Asp Glu Val Val Trp Val Arg Ala
    50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
```

Ile Ser Leu Ala Glu Pro Arg Leu Pro Leu
145                 150

<210> SEQ ID NO 72
<211> LENGTH: 152
<212> TYPE: PRT
<213> ORGANISM: Homo sapiens

<400> SEQUENCE: 72

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro Arg Leu
145                 150

<210> SEQ ID NO 73
<211> LENGTH: 150
<212> TYPE: PRT
<213> ORGANISM: Homo sapiens

<400> SEQUENCE: 73

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
                100                 105                 110

Ile Val Asp Val Glu Gly Val Val Arg Lys Val Asn Gln Lys Ile Gly
            115                 120                 125

Ser Cys Thr Gln Gln Asp Val Glu Leu His Val Gln Lys Ile Tyr Val
        130                 135                 140

Ile Ser Leu Ala Glu Pro

```
145                 150

<210> SEQ ID NO 74
<211> LENGTH: 148
<212> TYPE: PRT
<213> ORGANISM: Homo sapiens

<400> SEQUENCE: 74

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser Leu Ala
145

<210> SEQ ID NO 75
<211> LENGTH: 146
<212> TYPE: PRT
<213> ORGANISM: Homo sapiens

<400> SEQUENCE: 75

Met Pro Ser Ala Ser Ala Ser Arg Lys Ser Gln Glu Lys Pro Arg Glu
1               5                   10                  15

Ile Met Asp Ala Ala Glu Asp Tyr Ala Lys Glu Arg Tyr Gly Ile Ser
                20                  25                  30

Ser Met Ile Gln Ser Gln Glu Lys Pro Asp Arg Val Leu Val Arg Val
            35                  40                  45

Arg Asp Leu Thr Ile Gln Lys Ala Asp Glu Val Val Trp Val Arg Ala
        50                  55                  60

Arg Val His Thr Ser Arg Ala Lys Gly Lys Gln Cys Phe Leu Val Leu
65                  70                  75                  80

Arg Gln Gln Gln Phe Asn Val Gln Ala Leu Val Ala Val Gly Asp His
                85                  90                  95

Ala Ser Lys Gln Met Val Lys Phe Ala Ala Asn Ile Asn Lys Glu Ser
            100                 105                 110

Ile Val Asp Val Glu Gly Val Val Arg Lys Val Asn Gln Lys Ile Gly
        115                 120                 125

Ser Cys Thr Gln Gln Asp Val Glu Leu His Val Gln Lys Ile Tyr Val
    130                 135                 140

Ile Ser
145
```

```
<210> SEQ ID NO 76
<211> LENGTH: 151
<212> TYPE: PRT
<213> ORGANISM: Homo sapiens

<400> SEQUENCE: 76

Ala Ser Ala Ser Arg Lys Ser Gln Glu Lys Pro Arg Glu Ile Met Asp
1               5                   10                  15

Ala Ala Glu Asp Tyr Ala Lys Glu Arg Tyr Gly Ile Ser Ser Met Ile
            20                  25                  30

Gln Ser Gln Glu Lys Pro Asp Arg Val Leu Val Arg Val Arg Asp Leu
        35                  40                  45

Thr Ile Gln Lys Ala Asp Glu Val Val Trp Val Arg Ala Arg Val His
50                  55                  60

Thr Ser Arg Ala Lys Gly Lys Gln Cys Phe Leu Val Leu Arg Gln Gln
65                  70                  75                  80

Gln Phe Asn Val Gln Ala Leu Val Ala Val Gly Asp His Ala Ser Lys
                85                  90                  95

Gln Met Val Lys Phe Ala Ala Asn Ile Asn Lys Glu Ser Ile Val Asp
            100                 105                 110

Val Glu Gly Val Val Arg Lys Val Asn Gln Lys Ile Gly Ser Cys Thr
        115                 120                 125

Gln Gln Asp Val Glu Leu His Val Gln Lys Ile Tyr Val Ile Ser Leu
    130                 135                 140

Ala Glu Pro Arg Leu Pro Leu
145                 150

<210> SEQ ID NO 77
<211> LENGTH: 149
<212> TYPE: PRT
<213> ORGANISM: Homo sapiens

<400> SEQUENCE: 77

Ala Ser Arg Lys Ser Gln Glu Lys Pro Arg Glu Ile Met Asp Ala Ala
1               5                   10                  15

Glu Asp Tyr Ala Lys Glu Arg Tyr Gly Ile Ser Ser Met Ile Gln Ser
            20                  25                  30

Gln Glu Lys Pro Asp Arg Val Leu Val Arg Val Arg Asp Leu Thr Ile
        35                  40                  45

Gln Lys Ala Asp Glu Val Val Trp Val Arg Ala Arg Val His Thr Ser
50                  55                  60

Arg Ala Lys Gly Lys Gln Cys Phe Leu Val Leu Arg Gln Gln Gln Phe
65                  70                  75                  80

Asn Val Gln Ala Leu Val Ala Val Gly Asp His Ala Ser Lys Gln Met
                85                  90                  95

Val Lys Phe Ala Ala Asn Ile Asn Lys Glu Ser Ile Val Asp Val Glu
            100                 105                 110

Gly Val Val Arg Lys Val Asn Gln Lys Ile Gly Ser Cys Thr Gln Gln
        115                 120                 125

Asp Val Glu Leu His Val Gln Lys Ile Tyr Val Ile Ser Leu Ala Glu
    130                 135                 140

Pro Arg Leu Pro Leu
145

<210> SEQ ID NO 78
<211> LENGTH: 147
<212> TYPE: PRT
```

<213> ORGANISM: Homo sapiens

<400> SEQUENCE: 78

Arg Lys Ser Gln Glu Lys Pro Arg Glu Ile Met Asp Ala Ala Glu Asp
1               5                   10                  15

Tyr Ala Lys Glu Arg Tyr Gly Ile Ser Ser Met Ile Gln Ser Gln Glu
            20                  25                  30

Lys Pro Asp Arg Val Leu Val Arg Val Arg Asp Leu Thr Ile Gln Lys
        35                  40                  45

Ala Asp Glu Val Val Trp Val Arg Ala Arg Val His Thr Ser Arg Ala
    50                  55                  60

Lys Gly Lys Gln Cys Phe Leu Val Leu Arg Gln Gln Gln Phe Asn Val
65                  70                  75                  80

Gln Ala Leu Val Ala Val Gly Asp His Ala Ser Lys Gln Met Val Lys
                85                  90                  95

Phe Ala Ala Asn Ile Asn Lys Glu Ser Ile Val Asp Val Glu Gly Val
            100                 105                 110

Val Arg Lys Val Asn Gln Lys Ile Gly Ser Cys Thr Gln Gln Asp Val
        115                 120                 125

Glu Leu His Val Gln Lys Ile Tyr Val Ile Ser Leu Ala Glu Pro Arg
    130                 135                 140

Leu Pro Leu
145

<210> SEQ ID NO 79
<211> LENGTH: 145
<212> TYPE: PRT
<213> ORGANISM: Homo sapiens

<400> SEQUENCE: 79

Ser Gln Glu Lys Pro Arg Glu Ile Met Asp Ala Ala Glu Asp Tyr Ala
1               5                   10                  15

Lys Glu Arg Tyr Gly Ile Ser Ser Met Ile Gln Ser Gln Glu Lys Pro
            20                  25                  30

Asp Arg Val Leu Val Arg Val Arg Asp Leu Thr Ile Gln Lys Ala Asp
        35                  40                  45

Glu Val Val Trp Val Arg Ala Arg Val His Thr Ser Arg Ala Lys Gly
    50                  55                  60

Lys Gln Cys Phe Leu Val Leu Arg Gln Gln Gln Phe Asn Val Gln Ala
65                  70                  75                  80

Leu Val Ala Val Gly Asp His Ala Ser Lys Gln Met Val Lys Phe Ala
                85                  90                  95

Ala Asn Ile Asn Lys Glu Ser Ile Val Asp Val Glu Gly Val Val Arg
            100                 105                 110

Lys Val Asn Gln Lys Ile Gly Ser Cys Thr Gln Gln Asp Val Glu Leu
        115                 120                 125

His Val Gln Lys Ile Tyr Val Ile Ser Leu Ala Glu Pro Arg Leu Pro
    130                 135                 140

Leu
145

<210> SEQ ID NO 80
<211> LENGTH: 143
<212> TYPE: PRT
<213> ORGANISM: Homo sapiens

<400> SEQUENCE: 80

```
Glu Lys Pro Arg Glu Ile Met Asp Ala Ala Glu Asp Tyr Ala Lys Glu
1               5                   10                  15

Arg Tyr Gly Ile Ser Ser Met Ile Gln Ser Gln Glu Lys Pro Asp Arg
            20                  25                  30

Val Leu Val Arg Val Arg Asp Leu Thr Ile Gln Lys Ala Asp Glu Val
            35                  40                  45

Val Trp Val Arg Ala Arg Val His Thr Ser Arg Ala Lys Gly Lys Gln
50                  55                  60

Cys Phe Leu Val Leu Arg Gln Gln Gln Phe Asn Val Gln Ala Leu Val
65                  70                  75                  80

Ala Val Gly Asp His Ala Ser Lys Gln Met Val Lys Phe Ala Ala Asn
            85                  90                  95

Ile Asn Lys Glu Ser Ile Val Asp Val Glu Gly Val Val Arg Lys Val
            100                 105                 110

Asn Gln Lys Ile Gly Ser Cys Thr Gln Gln Asp Val Glu Leu His Val
            115                 120                 125

Gln Lys Ile Tyr Val Ile Ser Leu Ala Glu Pro Arg Leu Pro Leu
            130                 135                 140

<210> SEQ ID NO 81
<211> LENGTH: 141
<212> TYPE: PRT
<213> ORGANISM: Homo sapiens

<400> SEQUENCE: 81

Pro Arg Glu Ile Met Asp Ala Ala Glu Asp Tyr Ala Lys Glu Arg Tyr
1               5                   10                  15

Gly Ile Ser Ser Met Ile Gln Ser Gln Glu Lys Pro Asp Arg Val Leu
            20                  25                  30

Val Arg Val Arg Asp Leu Thr Ile Gln Lys Ala Asp Glu Val Val Trp
            35                  40                  45

Val Arg Ala Arg Val His Thr Ser Arg Ala Lys Gly Lys Gln Cys Phe
50                  55                  60

Leu Val Leu Arg Gln Gln Gln Phe Asn Val Gln Ala Leu Val Ala Val
65                  70                  75                  80

Gly Asp His Ala Ser Lys Gln Met Val Lys Phe Ala Ala Asn Ile Asn
            85                  90                  95

Lys Glu Ser Ile Val Asp Val Glu Gly Val Val Arg Lys Val Asn Gln
            100                 105                 110

Lys Ile Gly Ser Cys Thr Gln Gln Asp Val Glu Leu His Val Gln Lys
            115                 120                 125

Ile Tyr Val Ile Ser Leu Ala Glu Pro Arg Leu Pro Leu
            130                 135                 140

<210> SEQ ID NO 82
<211> LENGTH: 139
<212> TYPE: PRT
<213> ORGANISM: Homo sapiens

<400> SEQUENCE: 82

Glu Ile Met Asp Ala Ala Glu Asp Tyr Ala Lys Glu Arg Tyr Gly Ile
1               5                   10                  15

Ser Ser Met Ile Gln Ser Gln Glu Lys Pro Asp Arg Val Leu Val Arg
            20                  25                  30

Val Arg Asp Leu Thr Ile Gln Lys Ala Asp Glu Val Val Trp Val Arg
            35                  40                  45
```

-continued

Ala Arg Val His Thr Ser Arg Ala Lys Gly Lys Gln Cys Phe Leu Val
        50                  55                  60

Leu Arg Gln Gln Gln Phe Asn Val Gln Ala Leu Val Ala Val Gly Asp
65                  70                  75                  80

His Ala Ser Lys Gln Met Val Lys Phe Ala Ala Asn Ile Asn Lys Glu
                85                  90                  95

Ser Ile Val Asp Val Glu Gly Val Val Arg Lys Val Asn Gln Lys Ile
            100                 105                 110

Gly Ser Cys Thr Gln Gln Asp Val Glu Leu His Val Gln Lys Ile Tyr
        115                 120                 125

Val Ile Ser Leu Ala Glu Pro Arg Leu Pro Leu
    130                 135

<210> SEQ ID NO 83
<211> LENGTH: 137
<212> TYPE: PRT
<213> ORGANISM: Homo sapiens

<400> SEQUENCE: 83

Met Asp Ala Ala Glu Asp Tyr Ala Lys Glu Arg Tyr Gly Ile Ser Ser
1               5                   10                  15

Met Ile Gln Ser Gln Glu Lys Pro Asp Arg Val Leu Val Arg Val Arg
                20                  25                  30

Asp Leu Thr Ile Gln Lys Ala Asp Glu Val Val Trp Val Arg Ala Arg
            35                  40                  45

Val His Thr Ser Arg Ala Lys Gly Lys Gln Cys Phe Leu Val Leu Arg
        50                  55                  60

Gln Gln Gln Phe Asn Val Gln Ala Leu Val Ala Val Gly Asp His Ala
65                  70                  75                  80

Ser Lys Gln Met Val Lys Phe Ala Ala Asn Ile Asn Lys Glu Ser Ile
                85                  90                  95

Val Asp Val Glu Gly Val Val Arg Lys Val Asn Gln Lys Ile Gly Ser
            100                 105                 110

Cys Thr Gln Gln Asp Val Glu Leu His Val Gln Lys Ile Tyr Val Ile
        115                 120                 125

Ser Leu Ala Glu Pro Arg Leu Pro Leu
    130                 135

<210> SEQ ID NO 84
<211> LENGTH: 135
<212> TYPE: PRT
<213> ORGANISM: Homo sapiens

<400> SEQUENCE: 84

Met Asp Ala Ala Glu Asp Tyr Ala Lys Glu Arg Tyr Gly Ile Ser Ser
1               5                   10                  15

Met Ile Gln Ser Gln Glu Lys Pro Asp Arg Val Leu Val Arg Val Arg
                20                  25                  30

Asp Leu Thr Ile Gln Lys Ala Asp Glu Val Val Trp Val Arg Ala Arg
            35                  40                  45

Val His Thr Ser Arg Ala Lys Gly Lys Gln Cys Phe Leu Val Leu Arg
        50                  55                  60

Gln Gln Gln Phe Asn Val Gln Ala Leu Val Ala Val Gly Asp His Ala
65                  70                  75                  80

Ser Lys Gln Met Val Lys Phe Ala Ala Asn Ile Asn Lys Glu Ser Ile
                85                  90                  95

```
Val Asp Val Glu Gly Val Val Arg Lys Val Asn Gln Lys Ile Gly Ser
            100                 105                 110

Cys Thr Gln Gln Asp Val Glu Leu His Val Gln Lys Ile Tyr Val Ile
            115                 120                 125

Ser Leu Ala Glu Pro Arg Leu
            130             135

<210> SEQ ID NO 85
<211> LENGTH: 135
<212> TYPE: PRT
<213> ORGANISM: Homo sapiens

<400> SEQUENCE: 85

Met Asp Ala Ala Glu Asp Tyr Ala Lys Glu Arg Tyr Gly Ile Ser Ser
1               5                   10                  15

Met Ile Gln Ser Gln Glu Lys Pro Asp Arg Val Leu Val Arg Val Arg
                20                  25                  30

Asp Leu Thr Ile Gln Lys Ala Asp Glu Val Val Trp Val Arg Ala Arg
            35                  40                  45

Val His Thr Ser Arg Ala Lys Gly Lys Gln Cys Phe Leu Val Leu Arg
        50                  55                  60

Gln Gln Gln Phe Asn Val Gln Ala Leu Val Ala Val Gly Asp His Ala
65                  70                  75                  80

Ser Lys Gln Met Val Lys Phe Ala Ala Asn Ile Asn Lys Glu Ser Ile
                85                  90                  95

Val Asp Val Glu Gly Val Val Arg Lys Val Asn Gln Lys Ile Gly Ser
            100                 105                 110

Cys Thr Gln Gln Asp Val Glu Leu His Val Gln Lys Ile Tyr Val Ile
            115                 120                 125

Ser Leu Ala Glu Pro Arg Leu
            130             135

<210> SEQ ID NO 86
<211> LENGTH: 133
<212> TYPE: PRT
<213> ORGANISM: Homo sapiens

<400> SEQUENCE: 86

Ala Ala Glu Asp Tyr Ala Lys Glu Arg Tyr Gly Ile Ser Ser Met Ile
1               5                   10                  15

Gln Ser Gln Glu Lys Pro Asp Arg Val Leu Val Arg Val Arg Asp Leu
                20                  25                  30

Thr Ile Gln Lys Ala Asp Glu Val Val Trp Val Arg Ala Arg Val His
            35                  40                  45

Thr Ser Arg Ala Lys Gly Lys Gln Cys Phe Leu Val Leu Arg Gln Gln
        50                  55                  60

Gln Phe Asn Val Gln Ala Leu Val Ala Val Gly Asp His Ala Ser Lys
65                  70                  75                  80

Gln Met Val Lys Phe Ala Ala Asn Ile Asn Lys Glu Ser Ile Val Asp
                85                  90                  95

Val Glu Gly Val Val Arg Lys Val Asn Gln Lys Ile Gly Ser Cys Thr
            100                 105                 110

Gln Gln Asp Val Glu Leu His Val Gln Lys Ile Tyr Val Ile Ser Leu
            115                 120                 125

Ala Glu Pro Arg Leu
            130
```

<210> SEQ ID NO 87
<211> LENGTH: 137
<212> TYPE: PRT
<213> ORGANISM: Homo sapiens

<400> SEQUENCE: 87

Met Gln Glu Lys Pro Arg Glu Ile Met Asp Ala Ala Glu Asp Tyr Ala
1               5                   10                  15

Lys Glu Arg Tyr Gly Ile Ser Ser Met Ile Gln Ser Gln Glu Lys Pro
                20                  25                  30

Asp Arg Val Leu Val Arg Val Arg Asp Leu Thr Ile Gln Lys Ala Asp
            35                  40                  45

Glu Val Val Trp Val Arg Ala Arg Val His Thr Ser Arg Ala Lys Gly
    50                  55                  60

Lys Gln Cys Phe Leu Val Leu Arg Gln Gln Gln Phe Asn Val Gln Ala
65                  70                  75                  80

Leu Val Ala Val Gly Asp His Ala Ser Lys Gln Met Val Lys Phe Ala
                85                  90                  95

Cys Asn Ile Asn Lys Glu Ser Ile Val Asp Val Glu Gly Val Val Arg
            100                 105                 110

Lys Val Asn Gln Lys Ile Gly Ser Cys Thr Gln Gln Asp Val Glu Leu
        115                 120                 125

His Val Gln Lys Ile Tyr Val Ile Ser
    130                 135

<210> SEQ ID NO 88
<211> LENGTH: 135
<212> TYPE: PRT
<213> ORGANISM: Homo sapiens

<400> SEQUENCE: 88

Met Lys Pro Arg Glu Ile Met Asp Ala Ala Glu Asp Tyr Ala Lys Glu
1               5                   10                  15

Arg Tyr Gly Ile Ser Ser Met Ile Gln Ser Gln Glu Lys Pro Asp Arg
                20                  25                  30

Val Leu Val Arg Val Arg Asp Leu Thr Ile Gln Lys Ala Asp Glu Val
            35                  40                  45

Val Trp Val Arg Ala Arg Val His Thr Ser Arg Ala Lys Gly Lys Gln
    50                  55                  60

Cys Phe Leu Val Leu Arg Gln Gln Gln Phe Asn Val Gln Ala Leu Val
65                  70                  75                  80

Ala Val Gly Asp His Ala Ser Lys Gln Met Val Lys Phe Ala Cys Asn
                85                  90                  95

Ile Asn Lys Glu Ser Ile Val Asp Val Glu Gly Val Val Arg Lys Val
            100                 105                 110

Asn Gln Lys Ile Gly Ser Cys Thr Gln Gln Asp Val Glu Leu His Val
        115                 120                 125

Gln Lys Ile Tyr Val Ile Ser
    130                 135

<210> SEQ ID NO 89
<211> LENGTH: 135
<212> TYPE: PRT
<213> ORGANISM: Homo sapiens

<400> SEQUENCE: 89

```
Met Lys Pro Arg Glu Ile Met Asp Ala Ala Glu Asp Tyr Ala Lys Glu
1               5                   10                  15

Arg Tyr Gly Ile Ser Ser Met Ile Gln Ser Gln Glu Lys Pro Asp Arg
            20                  25                  30

Val Leu Val Arg Val Arg Asp Leu Thr Ile Gln Lys Ala Asp Glu Val
            35                  40                  45

Val Trp Val Arg Ala Arg Val His Thr Ser Arg Ala Lys Gly Lys Gln
50                  55                  60

Cys Phe Leu Val Leu Arg Gln Gln Gln Phe Asn Val Gln Ala Leu Val
65                  70                  75                  80

Ala Val Gly Asp His Ala Ser Lys Gln Met Val Lys Phe Ala Cys Asn
                85                  90                  95

Ile Asn Lys Glu Ser Ile Val Asp Val Glu Gly Val Val Arg Lys Val
            100                 105                 110

Asn Gln Lys Ile Gly Ser Cys Thr Gln Gln Asp Val Glu Leu His Val
            115                 120                 125

Gln Lys Ile Tyr Val Ile Ser
            130                 135

<210> SEQ ID NO 90
<211> LENGTH: 131
<212> TYPE: PRT
<213> ORGANISM: Homo sapiens

<400> SEQUENCE: 90

Met Ile Met Asp Ala Ala Glu Asp Tyr Ala Lys Glu Arg Tyr Gly Ile
1               5                   10                  15

Ser Ser Met Ile Gln Ser Gln Glu Lys Pro Asp Arg Val Leu Val Arg
            20                  25                  30

Val Arg Asp Leu Thr Ile Gln Lys Ala Asp Glu Val Val Trp Val Arg
            35                  40                  45

Ala Arg Val His Thr Ser Arg Ala Lys Gly Lys Gln Cys Phe Leu Val
50                  55                  60

Leu Arg Gln Gln Gln Phe Asn Val Gln Ala Leu Val Ala Val Gly Asp
65                  70                  75                  80

His Ala Ser Lys Gln Met Val Lys Phe Ala Cys Asn Ile Asn Lys Glu
                85                  90                  95

Ser Ile Val Asp Val Glu Gly Val Val Arg Lys Val Asn Gln Lys Ile
            100                 105                 110

Gly Ser Cys Thr Gln Gln Asp Val Glu Leu His Val Gln Lys Ile Tyr
            115                 120                 125

Val Ile Ser
130

<210> SEQ ID NO 91
<211> LENGTH: 127
<212> TYPE: PRT
<213> ORGANISM: Homo sapiens

<400> SEQUENCE: 91

Met Ala Glu Asp Tyr Ala Lys Glu Arg Tyr Gly Ile Ser Ser Met Ile
1               5                   10                  15

Gln Ser Gln Glu Lys Pro Asp Arg Val Leu Val Arg Val Arg Asp Leu
            20                  25                  30

Thr Ile Gln Lys Ala Asp Glu Val Val Trp Val Arg Ala Arg Val His
            35                  40                  45
```

```
Thr Ser Arg Ala Lys Gly Lys Gln Cys Phe Leu Val Leu Arg Gln Gln
    50                  55                  60

Gln Phe Asn Val Gln Ala Leu Val Ala Val Gly Asp His Ala Ser Lys
65                  70                  75                  80

Gln Met Val Lys Phe Ala Cys Asn Ile Asn Lys Glu Ser Ile Val Asp
                85                  90                  95

Val Glu Gly Val Val Arg Lys Val Asn Gln Lys Ile Gly Ser Cys Thr
                100                 105                 110

Gln Gln Asp Val Glu Leu His Val Gln Lys Ile Tyr Val Ile Ser
                115                 120                 125
```

<210> SEQ ID NO 92
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 92

| | | |
|---|---|---|
| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggga acagtgcttc cttagtccta | 240 |
| cgtcagcagc agtttaatgt ccaggctctt gtggcggtgg agaccatgca agcaagcag | 300 |
| atggttaaat ttgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctgcccc tgcagctgga tgatgctgtt | 480 |
| cggcctgagg cagaaggaga agaggaagga agagctactg ttaaccagga tacaagatta | 540 |
| gacaacagag tcattgatct taggacatca actagtcagg cagtcttccg tctccagtct | 600 |
| ggcatctgcc atctcttccg agaaactta attaacaaag ttttgtgga atccaaact | 660 |
| cctaaaatta tttcagctgc cagtgaagga ggagccaatg ttttactgt gtcatatttt | 720 |
| aaaaataatg catacctggc tcagtcccca cagctatata agcaaatgtg catttgtgct | 780 |
| gattttgaga aggttttctc tattggacca gtattcagag cggaagactc taatacccat | 840 |
| agacatctaa ctgagtttgt tggtttggac attgaaatgg cttttaatta ccattaccac | 900 |
| gaagttatgg aagaaattgc tgacaccatg gtacaaatat caaaggact tcaagaaagg | 960 |
| tttcagactg aaattcaaac agtgaataaa cagttcccat ctgagccatt caaatttttg | 1020 |
| gagccaactc taagactaga atattgtgaa gcattggcta tgcttaggga agctggagtc | 1080 |
| gaaatgggag atgaagacga tctgagcaca ccaaatgaaa agctgttggg tcatttggta | 1140 |
| aaggaaaagt atgatacaga tttttatatt cttgataaat atccattggc tgtaagacct | 1200 |
| ttctatacca tgcctgaccc aagaaatccc aacagtcca actcttacga tatgttcatg | 1260 |
| agaggagaag aaatattgtc aggagctcaa gaatacatg atcctcaact gctaacagag | 1320 |
| agagctttac atcatggaat tgatttggag aaaattaagg cttacattga ttccttccgc | 1380 |
| tttggagccc ctcctcatgc tggtggaggc attggattgg aacgagttac tatgctgttt | 1440 |
| ctgggattgc ataatgttcg tcagacctcc atgttccctc gtgatcccaa acgactcact | 1500 |
| cct | 1503 |

```
<210> SEQ ID NO 93
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 93
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt  cttagtccta     240 cgtcagcagc agtttaatgt ccaggctctt gtggcggtgg agaccatgc  aagcaagcag     300 atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tgcagctgga tgatgctgtt     480
cggcctgagg cagaaggaga agaggaagga agagctactg ttaaccagga tacaagatta     540
gacaacagag tcattgatct taggacatca actagtcagg cagtcttccg tctccagtct     600
ggcatctgcc atctcttccg agaaacttta attaacaaag ttttgtgga  atccaaact      660 cctaaaatta tttcagctgc cagtgaagga ggagccaatg ttttactgt  gtcatatttt     720 aaaaataatg catacctggc tcagtcccca cagctatata agcaaatgtg catttgtgct     780
gattttgaga aggttttctc tattggacca gtattcagag cggaagactc taatacccat     840
agacatctaa ctgagtttgt tggtttggac attgaaatgg cttttaatta ccattaccac     900
gaagttatgg aagaaattgc tgacaccatg gtacaaatat caaaggact  caagaaagg      960 tttcagactg aaattcaaac agtgaataaa cagttcccat gtgagccatt caaattttg     1020 gagccaactc taagactaga atattctgaa gcattggcta tgcttaggga agctggagtc    1080
gaaatgggag atgaagacga tctgagcaca ccaaatgaaa agctgttggg tcatttggta    1140 aggaaaagt  atgatacaga tttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttcctc  gtgatcccaa acgactcact    1500
cct                                                                  1503

<210> SEQ ID NO 94
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 94
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
```

```
tgggtacgtg caagagttca tacaagcaga gctaaaggga aacagtgctt cttagtccta    240
cgtcagcagc agtttaatgt ccaggctctt gtggcggtgg agaccatgc aagcaagcag     300 atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta   540
gacaacagag tcattgatct taggacatca actagtcagg cagtcttccg tctccagtct    600
ggcatctgcc atctcttccg agaaacttta attaacaaag gttttgtgga aatccaaact   660
cctaaaatta tttcagctgc cagtgaagga ggagccaatg ttttttactgt gtcatatttt  720 aaaaataatg catacctggc tcagtcccca cagctatata agcaaatgtg catttgtgct   780
gattttgaga aggttttctc tattggacca gtattcagag cggaagactc taatacccat    840
agacatctaa ctgagtttgt tggtttggac attgaaatgg cttttaatta ccattaccac    900
gaagttatgg aagaaattgc tgacaccatg gtacaaatat tcaaaggact tcaagaaagg    960
tttcagactg aaattcaaac agtgaataaa cagttcccat ctgagccatt caaattttg    1020 gagccaactc taagactaga atattctgaa gcattggcta tgcttaggga agctggagtc   1080
gaaatgggag atgaagacga tctgagcaca ccaaatgaaa agctgtggg tcatttggta    1140 aaggaaaagt atgatacaga tttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag   1320
agagctttac atcatggaat tgatttggag aaaattaagg cttacattga ttccttccgc   1380
tttggagccc ctcctcatgc tggtggaggc attggattgg aacgagttac tatgctgttt   1440
ctgggattgc ataatgttcg tcagacctcc atgttccctc gtgatcccaa acgactcact   1500
cct                                                                   1503

<210> SEQ ID NO 95
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 95
atgcccagcg ccagcgccag ccgcaagagt caggagaagc cgcgggagat catggacgcg     60
gcggaagatt atgctaaaga gagatatgga atatcttcaa tgatacaatc acaagaaaaa   120
ccagatcgag ttttggttcg ggttagagac ttgacaatac aaaaagctga tgaagttgtt    180
tgggtacgtg caagagttca tacaagcaga gctaaaggga aacagtgctt cttagtccta    240
cgtcagcagc agtttaatgt ccaggctctt gtggcggtgg agaccatgc aagcaagcag     300 atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta   540
gacaacagag tcattgatct taggacatca actagtcagg cagtcttccg tctccagtct    600
ggcatcgccc atctcttccg agaaacttta attaacaaag gttttgtgga aatccaaact   660
```

-continued

```
cctaaaatta tttcagctgc cagtgaagga ggagccaatg ttttactgt gtcatatttt      720 aaaaataatg catacctggc tcagtcccca cagctatata agcaaatgtg catttgtgct     780
gattttgaga aggttttctc tattggacca gtattcagag cggaagactc taatacccat    840
agacatctaa ctgagtttgt tggtttggac attgaaatgg cttttaatta ccattaccac     900
gaagttatgg aagaaattgc tgacaccatg gtacaaatat tcaaaggact tcaagaaagg    960
tttcagactg aaattcaaac agtgaataaa cagttcccat gtgagccatt caaattttg    1020 gagccaactc taagactaga atattgtgaa gcattggcta tgcttaggga agctggagtc   1080
gaaatgggag atgaagacga tctgagcaca ccaaatgaaa agctgttggg tcatttggta   1140
aaggaaaagt atgatacaga tttttatatt cttgataaat atccattggc tgtaagacct   1200
ttctatacca tgcctgaccc aagaaatccc aaacagtcca actcttacga tatgttcatg   1260
agaggagaag aaatattgtc aggagctcaa agaatacatg atcctcaact gctaacagag   1320
agagctttac atcatggaat tgatttggag aaaattaagg cttacattga ttccttccgc   1380
tttggagccc ctcctcatgc tggtggaggc attggattgg aacgagttac tatgctgttt   1440
ctgggattgc ataatgttcg tcagacctcc atgttccctc gtgatcccaa acgactcact   1500
cct                                                                  1503
```

<210> SEQ ID NO 96
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 96

```
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta    240 cgtcagcagc agtttaatgt ccaggctctt gtggcggtgg agaccatgc aagcaagcag    300 atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
gacaacagag tcattgatct taggacatca actagtcagg cagtcttccg tctccagtct    600
ggcatcgtcc atctcttccg agaaacttta attaacaaag ttttgtgga atccaaact    660 cctaaaatta tttcagctgc cagtgaagga ggagccaatg ttttactgt gtcatatttt    720 aaaaataatg catacctggc tcagtcccca cagctatata agcaaatgtg catttgtgct    780
gattttgaga aggttttctc tattggacca gtattcagag cggaagactc taatacccat    840
agacatctaa ctgagtttgt tggtttggac attgaaatgg cttttaatta ccattaccac    900
gaagttatgg aagaaattgc tgacaccatg gtacaaatat tcaaaggact tcaagaaagg    960
tttcagactg aaattcaaac agtgaataaa cagttcccat gtgagccatt caaattttg    1020 gagccaactc taagactaga atattgtgaa gcattggcta tgcttaggga agctggagtc   1080
gaaatgggag atgaagacga tctgagcaca ccaaatgaaa agctgttggg tcatttggta   1140
```

```
aaggaaaagt atgatacaga tttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatcccaa acgactcact    1500
cct                                                                  1503

<210> SEQ ID NO 97
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 97
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta    240 cgtcagcagc agtttaatgt ccaggctctt gtggcggtgg agaccatgc aagcaagcag    300 atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
gacaacagag tcattgatct taggacatca actagtcagg cagtcttccg tctccagtct    600
ggcatcgccc atctcttccg agaaacttta attaacaaag ttttgtgga aatccaaact    660 cctaaaatta tttcagctgc cagtgaagga ggagccaatg tttttactgt gtcatatttt    720
aaaaataatg catacctggc tcagtcccca cagctatata agcaaatgtg catttgtgct    780
gattttgaga aggttttctc tattggacca gtattcagag cggaagactc taatacccat    840
agacatctaa ctgagtttgt tggtttggac attgaaatgg cttttaatta ccattaccac    900
gaagttatgg aagaaattgc tgacaccatg gtacaaatat tcaaaggact tcaagaaagg    960
tttcagactg aaattcaaac agtgaataaa cagttcccat ctgagccatt caaattttg    1020 gagccaactc taagactaga atattctgaa gcattggcta tgcttaggga agctggagtc    1080
gaaatgggag atgaagacga tctgagcaca ccaaatgaaa agctgttggg tcatttggta    1140
aaggaaaagt atgatacaga tttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatcccaa acgactcact    1500
cct                                                                  1503

<210> SEQ ID NO 98
```

<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 98

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg agaccatgc aagcaagcag      300
atggttaaat ttgctgccaa catcaacaaa gagagcattg tggatgtaga aggtgttgtg     360
agaaaagtga atcagaaaat ggaagctgt acacagcaag acgttgagtt acatgttcag      420
aagatttatg tgatcagttt ggctgaaccc cgtctgcccc tgcagctgga tgatgctgtt     480
cggcctgagg cagaaggaga agaggaagga agagctactg ttaaccagga tacaagatta     540
gacaacagag tcattgatct taggacatca actagtcagg cagtcttccg tctccagtct     600
ggcatcgtcc atctcttccg agaaacttta attaacaaag ttttgtgga atccaaact      660
cctaaaatta tttcagctgc cagtgaagga ggagccaatg ttttactgt gtcatatttt      720
aaaaataatg catacctggc tcagtcccca agctatata agcaaatgtg catttgtgct      780
gattttgaga aggttttctc tattggacca gtattcagag cggaagactc taatacccat     840
agacatctaa ctgagtttgt tggtttggac attgaaatgg cttttaatta ccattaccac     900
gaagttatgg aagaaattgc tgacaccatg gtacaaatat caaaggact tcaagaaagg      960
tttcagactg aaattcaaac agtgaataaa cagttcccat ctgagccatt caaattttg     1020
gagccaactc taagactaga atattctgaa gcattggcta tgcttaggga agctggagtc    1080
gaaatgggag atgaagacga tctgagcaca ccaaatgaaa agctgttggg tcatttggta    1140
aggaaaagt atgatacaga ttttatatt cttgataaat atccattggc tgtaagacct     1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt    1440
ctgggattgc ataatgttcg tcagacctcc atgttccctc gtgatcccaa acgactcact    1500
cct                                                                  1503
```

<210> SEQ ID NO 99
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 99

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
```

```
cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
gacaacagag tcattgatct taggacatca actagtcagg cagtcttccg tctccagtct    600
ggcatcgccc atctcttccg agaaacttta attaacaaag ttttgtggaa atccaaact    660 cctaaaatta tttcagctgc cagtgaagga ggagccaatg tttttactgt gtcatatttt    720
aaaaataatg catacctggc tcagtcccca cagctatata gcaaatgtg cattgcggct    780 gattttgaga aggttttctc tattggacca gtattcagag cggaagactc taatacccat    840
agacatctaa ctgagtttgt tggtttggac attgaaatgg cttttaatta ccattaccac    900
gaagttatgg aagaaattgc tgacaccatg gtacaaatat tcaaaggact tcaagaaagg    960
tttcagactg aaattcaaac agtgaataaa cagttcccat ctgagccatt caaatttttg   1020
gagccaactc taagactaga atattctgaa gcattggcta tgcttaggga agctggagtc   1080
gaaatgggag atgaagacga tctgagcaca ccaaatgaaa agctgttggg tcatttggta   1140
aaggaaaagt atgatacaga ttttatatt cttgataaat atccattggc tgtaagacct   1200
ttctatacca tgcctgaccc aagaaatccc aaacagtcca actcttacga tatgttcatg   1260
agaggagaag aaatattgtc aggagctcaa agaatacatg atcctcaact gctaacagag   1320
agagctttac atcatggaat tgatttggag aaaattaagg cttacattga ttccttccgc   1380
tttggagccc ctcctcatgc tggtggaggc attggattgg aacgagttac tatgctgttt   1440
ctgggattgc ataatgttcg tcagacctcc atgttccctc gtgatcccaa acgactcact   1500
cct                                                                 1503
```

<210> SEQ ID NO 100
<211> LENGTH: 1503
<212> TYPE: DNA
<213> ORGANISM: Artificial Sequence
<220> FEATURE:
<223> OTHER INFORMATION: DRS polynucleotide encoding polypetide variant
      with reduced cysteine content

<400> SEQUENCE: 100

```
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgcttc ttagtccta     240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
gacaacagag tcattgatct taggacatca actagtcagg cagtcttccg tctccagtct    600
ggcatcgtcc atctcttccg agaaacttta attaacaaag ttttgtggaa atccaaact    660 cctaaaatta tttcagctgc cagtgaagga ggagccaatg tttttactgt gtcatatttt    720
```

```
aaaaataatg catacctggc tcagtcccca cagctatata agcaaatgtg cattgcggct    780
gattttgaga aggttttctc tattggacca gtattcagag cggaagactc taatacccat    840
agacatctaa ctgagtttgt tggtttggac attgaaatgg cttttaatta ccattaccac    900
gaagttatgg aagaaattgc tgacaccatg gtacaaatat caaaggact tcaagaaagg    960 tttcagactg aaattcaaac agtgaataaa cagttcccat ctgagccatt caaattttg    1020 gagccaactc taagactaga atattctgaa gcattggcta tgcttaggga agctggagtc   1080
gaaatgggag atgaagacga tctgagcaca ccaaatgaaa agctgttggg tcatttggta   1140
aaggaaaagt atgatacaga ttttatatt cttgataaat atccattggc tgtaagacct    1200
ttctatacca tgcctgaccc aagaaatccc aaacagtcca actcttacga tatgttcatg    1260
agaggagaag aaatattgtc aggagctcaa agaatacatg atcctcaact gctaacagag    1320
agagctttac atcatggaat tgatttggag aaaattaagg cttacattga ttccttccgc    1380
tttggagccc ctcctcatgc tggtggaggc attggattgg aacgagttac tatgctgttt   1440
ctgggattgc ataatgttcg tcagacctcc atgttccctc gtgatcccaa acgactcact   1500
cct                                                                 1503

<210> SEQ ID NO 101
<211> LENGTH: 546
<212> TYPE: DNA
<213> ORGANISM: Homo sapiens

<400> SEQUENCE: 101
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta    240 cgtcagcagc agtttaatgt ccaggctctt gtggcggtgg agaccatgc aagcaagcag    300 atggttaaat ttgctgccaa catcaacaaa gagagcattg tggatgtaga aggtgttgtg   360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga tacaagatta    540
gacaac                                                              546

<210> SEQ ID NO 102
<211> LENGTH: 540
<212> TYPE: DNA
<213> ORGANISM: Homo sapiens

<400> SEQUENCE: 102
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta    240 cgtcagcagc agtttaatgt ccaggctctt gtggcggtgg agaccatgc aagcaagcag    300 atggttaaat ttgctgccaa catcaacaaa gagagcattg tggatgtaga aggtgttgtg   360
agaaaagtga atcagaaaat tggaagctgt acacagcaag acgttgagtt acatgttcag    420
```
aagatttatg tgatcagttt ggctgaaccc cgtctgcccc tgcagctgga tgatgctgtt    480
cggcctgagg cagaaggaga agaggaagga agagctactg ttaaccagga tacaagatta    540

<210> SEQ ID NO 103
<211> LENGTH: 534
<212> TYPE: DNA
<213> ORGANISM: Homo sapiens

<400> SEQUENCE: 103
atgcccagcg ccagcgccag ccgcaagagt caggagaagc cgcgggagat catggacgcg    60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta    240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccagga taca    534

<210> SEQ ID NO 104
<211> LENGTH: 528
<212> TYPE: DNA
<213> ORGANISM: Homo sapiens

<400> SEQUENCE: 104
atgcccagcg ccagcgccag ccgcaagagt caggagaagc cgcgggagat catggacgcg    60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta    240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaaggaga agaggaagga agagctactg ttaaccag    528

<210> SEQ ID NO 105
<211> LENGTH: 522
<212> TYPE: DNA
<213> ORGANISM: Homo sapiens

<400> SEQUENCE: 105
atgcccagcg ccagcgccag ccgcaagagt caggagaagc cgcgggagat catggacgcg    60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgctt cttagtccta    240 cgtcagcagc agtttaatgt ccaggctctt gtggcggtgg gagaccatgc aagcaagcag    300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480

-continued

| cggcctgagg cagaaggaga agaggaagga agagctactg tt | 522 |

<210> SEQ ID NO 106
<211> LENGTH: 516
<212> TYPE: DNA
<213> ORGANISM: Homo sapiens

<400> SEQUENCE: 106

| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggga acagtgctt cttagtccta | 240 |
| cgtcagcagc agtttaatgt ccaggctctt gtggcggtgg gagaccatgc aagcaagcag | 300 |
| atggttaaat tgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctgcccc tgcagctgga tgatgctgtt | 480 |
| cggcctgagg cagaaggaga agaggaagga agagct | 516 |

<210> SEQ ID NO 107
<211> LENGTH: 510
<212> TYPE: DNA
<213> ORGANISM: Homo sapiens

<400> SEQUENCE: 107

| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggga acagtgctt cttagtccta | 240 |
| cgtcagcagc agtttaatgt ccaggctctt gtggcggtgg gagaccatgc aagcaagcag | 300 |
| atggttaaat tgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctgcccc tgcagctgga tgatgctgtt | 480 |
| cggcctgagg cagaaggaga agaggaagga | 510 |

<210> SEQ ID NO 108
<211> LENGTH: 504
<212> TYPE: DNA
<213> ORGANISM: Homo sapiens

<400> SEQUENCE: 108

| atgcccagcg ccagcgccag ccgcaagagt caggagaagc cgcgggagat catggacgcg | 60 |
| gcggaagatt atgctaaaga gagatatgga atatcttcaa tgatacaatc acaagaaaaa | 120 |
| ccagatcgag ttttggttcg ggttagagac ttgacaatac aaaaagctga tgaagttgtt | 180 |
| tgggtacgtg caagagttca tacaagcaga gctaaaggga acagtgctt cttagtccta | 240 |
| cgtcagcagc agtttaatgt ccaggctctt gtggcggtgg gagaccatgc aagcaagcag | 300 |
| atggttaaat tgctgccaa catcaacaaa gagagcattg tggatgtaga aggtgttgtg | 360 |
| agaaaagtga atcagaaaat tggaagctgt acacagcaag acgttgagtt acatgttcag | 420 |
| aagatttatg tgatcagttt ggctgaaccc cgtctgcccc tgcagctgga tgatgctgtt | 480 | cggcctgagg cagaaggaga agag     504

<210> SEQ ID NO 109
<211> LENGTH: 498
<212> TYPE: DNA
<213> ORGANISM: Homo sapiens

<400> SEQUENCE: 109
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgcttc ttagtccta    240
cgtcagcagc agtttaatgt ccaggctctt gtggcggtgg agaccatgc aagcaagcag     300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg cagaagga    498

<210> SEQ ID NO 110
<211> LENGTH: 492
<212> TYPE: DNA
<213> ORGANISM: Homo sapiens

<400> SEQUENCE: 110
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgcttc ttagtccta    240
cgtcagcagc agtttaatgt ccaggctctt gtggcggtgg agaccatgc aagcaagcag     300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcctgagg ca    492

<210> SEQ ID NO 111
<211> LENGTH: 486
<212> TYPE: DNA
<213> ORGANISM: Homo sapiens

<400> SEQUENCE: 111
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga acagtgcttc ttagtccta    240
cgtcagcagc agtttaatgt ccaggctctt gtggcggtgg agaccatgc aagcaagcag     300
atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggctgaaccc cgtctgcccc tgcagctgga tgatgctgtt    480
cggcct    486

<210> SEQ ID NO 112
<211> LENGTH: 480
<212> TYPE: DNA
<213> ORGANISM: Homo sapiens

<400> SEQUENCE: 112

```
atgcccagcg ccagcgccag ccgcaagagt caggagaagc cgcgggagat catggacgcg    60
gcggaagatt atgctaaaga gagatatgga atatcttcaa tgatacaatc acaagaaaaa   120
ccagatcgag ttttggttcg ggttagagac ttgacaatac aaaaagctga tgaagttgtt   180
tgggtacgtg caagagttca tacaagcaga gctaaaggga acagtgctt cttagtccta   240
cgtcagcagc agtttaatgt ccaggctctt gtggcggtgg agaccatgc aagcaagcag    300
atggttaaat tgctgccaa catcaacaaa gagagcattg tggatgtaga aggtgttgtg   360
agaaaagtga atcagaaaat tggaagctgt acacagcaag acgttgagtt acatgttcag   420
aagatttatg tgatcagttt ggctgaaccc cgtctgcccc tgcagctgga tgatgctgtt   480
```

<210> SEQ ID NO 113
<211> LENGTH: 474
<212> TYPE: DNA
<213> ORGANISM: Homo sapiens

<400> SEQUENCE: 113

```
atgcccagcg ccagcgccag ccgcaagagt caggagaagc cgcgggagat catggacgcg    60
gcggaagatt atgctaaaga gagatatgga atatcttcaa tgatacaatc acaagaaaaa   120
ccagatcgag ttttggttcg ggttagagac ttgacaatac aaaaagctga tgaagttgtt   180
tgggtacgtg caagagttca tacaagcaga gctaaaggga acagtgctt cttagtccta   240
cgtcagcagc agtttaatgt ccaggctctt gtggcggtgg agaccatgc aagcaagcag    300
atggttaaat tgctgccaa catcaacaaa gagagcattg tggatgtaga aggtgttgtg   360
agaaaagtga atcagaaaat tggaagctgt acacagcaag acgttgagtt acatgttcag   420
aagatttatg tgatcagttt ggctgaaccc cgtctgcccc tgcagctgga tgat         474
```

<210> SEQ ID NO 114
<211> LENGTH: 468
<212> TYPE: DNA
<213> ORGANISM: Homo sapiens

<400> SEQUENCE: 114

```
atgcccagcg ccagcgccag ccgcaagagt caggagaagc cgcgggagat catggacgcg    60
gcggaagatt atgctaaaga gagatatgga atatcttcaa tgatacaatc acaagaaaaa   120
ccagatcgag ttttggttcg ggttagagac ttgacaatac aaaaagctga tgaagttgtt   180
tgggtacgtg caagagttca tacaagcaga gctaaaggga acagtgctt cttagtccta   240
cgtcagcagc agtttaatgt ccaggctctt gtggcggtgg agaccatgc aagcaagcag    300
atggttaaat tgctgccaa catcaacaaa gagagcattg tggatgtaga aggtgttgtg   360
agaaaagtga atcagaaaat tggaagctgt acacagcaag acgttgagtt acatgttcag   420
aagatttatg tgatcagttt ggctgaaccc cgtctgcccc tgcagctg                468
```

<210> SEQ ID NO 115
<211> LENGTH: 462
<212> TYPE: DNA
<213> ORGANISM: Homo sapiens

<400> SEQUENCE: 115

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg gagaccatgc aagcaagcag     300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctgcccc tg                        462
```

<210> SEQ ID NO 116
<211> LENGTH: 456
<212> TYPE: DNA
<213> ORGANISM: Homo sapiens

<400> SEQUENCE: 116

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg gagaccatgc aagcaagcag     300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc cgtctg                                456
```

<210> SEQ ID NO 117
<211> LENGTH: 450
<212> TYPE: DNA
<213> ORGANISM: Homo sapiens

<400> SEQUENCE: 117

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
tgggtacgtg caagagttca tacaagcaga gctaaaggga acagtgctt cttagtccta      240
cgtcagcagc agtttaatgt ccaggctctt gtggcggtgg gagaccatgc aagcaagcag     300
atggttaaat ttgctgccaa catcaacaaa gagagcattg tggatgtaga aggtgttgtg     360
agaaaagtga atcagaaaat tggaagctgt acacagcaag acgttgagtt acatgttcag     420
aagatttatg tgatcagttt ggctgaaccc                                       450
```

<210> SEQ ID NO 118
<211> LENGTH: 444
<212> TYPE: DNA
<213> ORGANISM: Homo sapiens

<400> SEQUENCE: 118

```
atgcccagcg ccagcgccag ccgcaagagt caggagaagc cgcgggagat catggacgcg      60
gcggaagatt atgctaaaga gagatatgga atatcttcaa tgatacaatc acaagaaaaa     120
ccagatcgag ttttggttcg ggttagagac ttgacaatac aaaaagctga tgaagttgtt     180
```

```
tgggtacgtg caagagttca tacaagcaga gctaaaggga aacagtgctt cttagtccta    240
cgtcagcagc agtttaatgt ccaggctctt gtggcggtgg agaccatgc aagcaagcag     300 atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagttt ggct                                           444

<210> SEQ ID NO 119
<211> LENGTH: 438
<212> TYPE: DNA
<213> ORGANISM: Homo sapiens

<400> SEQUENCE: 119
atgcccagcg ccagcgccag ccgcaagagt caggagaagc cgcgggagat catggacgcg     60
gcggaagatt atgctaaaga gagatatgga atatcttcaa tgatacaatc acaagaaaaa    120
ccagatcgag ttttggttcg ggttagagac ttgacaatac aaaaagctga tgaagttgtt    180
tgggtacgtg caagagttca tacaagcaga gctaaaggga aacagtgctt cttagtccta    240
cgtcagcagc agtttaatgt ccaggctctt gtggcggtgg agaccatgc aagcaagcag     300 atggttaaat ttgctgccaa catcaacaaa gagagcattg tggatgtaga aggtgttgtg    360
agaaaagtga atcagaaaat tggaagctgt acacagcaag acgttgagtt acatgttcag    420
aagatttatg tgatcagt                                                  438

<210> SEQ ID NO 120
<211> LENGTH: 453
<212> TYPE: DNA
<213> ORGANISM: Homo sapiens

<400> SEQUENCE: 120
gccagcgcca gccgcaagag tcaggagaag ccgcgggaga tcatggacgc ggcggaagat     60
tatgctaaag agagatatgg aatatcttca atgatacaat cacaagaaaa accagatcga    120
gttttggttc gggttagaga cttgacaata caaaaagctg atgaagttgt ttgggtacgt    180
gcaagagttc atacaagcag agctaaaggg aaacagtgct tcttagtcct acgtcagcag    240
cagtttaatg tccaggctct gtggcggtg ggagaccatg caagcaagca gatggttaaa    300
tttgctgcca acatcaacaa agagagcatt gtggatgtag aaggtgttgt gagaaaagtg    360
aatcagaaaa ttggaagctg tacacagcaa gacgttgagt tacatgttca agagatttat    420
gtgatcagtt tggctgaacc ccgtctgccc ctg                                 453

<210> SEQ ID NO 121
<211> LENGTH: 447
<212> TYPE: DNA
<213> ORGANISM: Homo sapiens

<400> SEQUENCE: 121
gccagccgca agagtcagga gaagccgcgg gagatcatgg acgcggcgga agattatgct     60
aaagagagat atggaatatc ttcaatgata caatcacaag aaaaaccaga tcgagttttg    120
gttcgggtta gagacttgac aatacaaaaa gctgatgaag ttgtttgggt acgtgcaaga    180
gttcatacaa gcagagctaa agggaaacag tgcttcttag tcctacgtca gcagcagttt    240
aatgtccagg ctcttgtggc ggtgggagac catgcaagca agcagatggt taaatttgct    300
gccaacatca acaaagagag cattgtggat gtagaaggtg ttgtgagaaa agtgaatcag    360
```

```
aaaattggaa gctgtacaca gcaagacgtt gagttacatg ttcagaagat ttatgtgatc    420
agtttggctg aacccegtct gcccctg                                        447

<210> SEQ ID NO 122
<211> LENGTH: 441
<212> TYPE: DNA
<213> ORGANISM: Homo sapiens

<400> SEQUENCE: 122
cgcaagagtc aggagaagcc gcgggagatc atggacgcgg cggaagatta tgctaaagag     60
agatatggaa tatcttcaat gatacaatca caagaaaaac cagatcgagt tttggttcgg    120
gttagagact tgacaataca aaaagctgat gaagttgttt gggtacgtgc aagagttcat    180
acaagcagag ctaaagggaa acagtgcttc ttagtcctac gtcagcagca gtttaatgtc    240
caggctcttg tggcggtggg agaccatgca agcaagcaga tggttaaatt tgctgccaac    300
atcaacaaag agagcattgt ggatgtagaa ggtgttgtga gaaaagtgaa tcagaaaatt    360
ggaagctgta cacagcaaga cgttgagtta catgttcaga gatttatgt gatcagtttg    420 gctgaacccc gtctgcccct g                                              441

<210> SEQ ID NO 123
<211> LENGTH: 435
<212> TYPE: DNA
<213> ORGANISM: Homo sapiens

<400> SEQUENCE: 123
agtcaggaga agccgcggga gatcatggac gcggcggaag attatgctaa agagagatat     60
ggaatatctt caatgataca atcacaagaa aaaccagatc gagttttggt tcgggttaga    120
gacttgacaa tacaaaaagc tgatgaagtt gtttgggtac gtgcaagagt tcatacaagc    180
agagctaaag ggaaacagtg cttcttagtc ctacgtcagc agcagtttaa tgtccaggct    240
cttgtggcgg tgggagacca tgcaagcaag cagatggtta aatttgctgc caacatcaac    300
aaagagagca ttgtggatgt agaaggtgtt gtgagaaaag tgaatcagaa aattggaagc    360
tgtacacagc aagacgttga gttacatgtt cagaagattt atgtgatcag tttggctgaa    420
ccccgtctgc ccctg                                                     435

<210> SEQ ID NO 124
<211> LENGTH: 429
<212> TYPE: DNA
<213> ORGANISM: Homo sapiens

<400> SEQUENCE: 124
gagaagccgc gggagatcat ggacgcggcg gaagattatg ctaaagagag atatggaata     60
tcttcaatga tacaatcaca agaaaaacca gatcgagttt tggttcgggt tagagacttg    120
acaatacaaa aagctgatga agttgtttgg gtacgtgcaa gagttcatac aagcagagct    180
aaagggaaac agtgcttctt agtcctacgt cagcagcagt ttaatgtcca ggctcttgtg    240
gcggtgggag accatgcaag caagcagatg gttaaatttg ctgccaacat caacaaagag    300
agcattgtgg atgtagaagg tgttgtgaga aaagtgaatc agaaaattgg aagctgtaca    360
cagcaagacg ttgagttaca tgttcagaag atttatgtga tcagtttggc tgaaccccgt    420
ctgcccctg                                                            429

<210> SEQ ID NO 125
<211> LENGTH: 423
```

```
<212> TYPE: DNA
<213> ORGANISM: Homo sapiens

<400> SEQUENCE: 125
ccgcgggaga tcatggacgc ggcggaagat tatgctaaag agagatatgg aatatcttca      60
atgatacaat cacaagaaaa accagatcga gttttggttc gggttagaga cttgacaata     120
caaaaagctg atgaagttgt ttgggtacgt gcaagagttc atacaagcag agctaaaggg     180
aaacagtgct tcttagtcct acgtcagcag cagtttaatg tccaggctct tgtggcggtg     240
ggagaccatg caagcaagca gatggttaaa tttgctgcca acatcaacaa agagagcatt     300
gtggatgtag aaggtgttgt gagaaaagtg aatcagaaaa ttggaagctg tacacagcaa     360
gacgttgagt tacatgttca agagatttat gtgatcagtt tggctgaacc ccgtctgccc     420
ctg                                                                    423

<210> SEQ ID NO 126
<211> LENGTH: 417
<212> TYPE: DNA
<213> ORGANISM: Homo sapiens

<400> SEQUENCE: 126
gagatcatgg acgcggcgga agattatgct aaagagagat atggaatatc ttcaatgata      60
caatcacaag aaaaaccaga tcgagttttg gttcgggtta gagacttgac aatcaaaaa     120 gctgatgaag ttgtttgggt acgtgcaaga gttcatacaa gcagagctaa agggaaacag     180
tgcttcttag tcctacgtca gcagcagttt aatgtccagg ctcttgtggc ggtgggagac     240
catgcaagca agcagatggt taaatttgct gccaacatca caaagagag cattgtggat      300 gtagaaggtg ttgtgagaaa agtgaatcag aaaattggaa gctgtacaca gcaagacgtt     360
gagttacatg ttcagaagat ttatgtgatc agtttggctg aaccccgtct gcccctg        417

<210> SEQ ID NO 127
<211> LENGTH: 411
<212> TYPE: DNA
<213> ORGANISM: Homo sapiens

<400> SEQUENCE: 127
atggacgcgg cggaagatta tgctaaagag agatatggaa tatcttcaat gatacaatca      60
caagaaaaac cagatcgagt tttggttcgg gttagagact tgacaataca aaaagctgat     120
gaagttgttt gggtacgtgc aagagttcat acaagcagag ctaaagggaa acagtgcttc     180
ttagtcctac gtcagcagca gtttaatgtc caggctcttg tggcggtggg agaccatgca     240
agcaagcaga tggttaaatt tgctgccaac atcaacaaag agagcattgt ggatgtagaa     300
ggtgttgtga gaaagtgaa tcagaaaatt ggaagctgta cacagcaaga cgttgagtta      360
catgttcaga gatttatgt gatcagtttg gctgaacccc gtctgcccct g                411

<210> SEQ ID NO 128
<211> LENGTH: 405
<212> TYPE: DNA
<213> ORGANISM: Homo sapiens

<400> SEQUENCE: 128
gcggcggaag attatgctaa agagagatat ggaatatctt caatgataca atcacaagaa      60
aaaccagatc gagttttggt tcgggttaga gacttgacaa tacaaaaagc tgatgaagtt     120
gtttgggtac gtgcaagagt tcatacaagc agagctaaag ggaaacagtg cttcttagtc     180
```

```
ctacgtcagc agcagtttaa tgtccaggct cttgtggcgg tgggagacca tgcaagcaag    240
cagatggtta aatttgctgc caacatcaac aaagagagca ttgtggatgt agaaggtgtt    300
gtgagaaaag tgaatcagaa aattggaagc tgtacacagc aagacgttga gttacatgtt    360
cagaagattt atgtgatcag tttggctgaa ccccgtctgc ccctg                    405

<210> SEQ ID NO 129
<211> LENGTH: 399
<212> TYPE: DNA
<213> ORGANISM: Homo sapiens

<400> SEQUENCE: 129
gcggcggaag attatgctaa agagagatat ggaatatctt caatgataca atcacaagaa     60
aaaccagatc gagttttggt tcgggttaga gacttgacaa tacaaaaagc tgatgaagtt    120
gtttgggtac gtgcaagagt tcatacaagc agagctaaag ggaaacagtg cttcttagtc    180
ctacgtcagc agcagtttaa tgtccaggct cttgtggcgg tgggagacca tgcaagcaag    240
cagatggtta aatttgctgc caacatcaac aaagagagca ttgtggatgt agaaggtgtt    300
gtgagaaaag tgaatcagaa aattggaagc tgtacacagc aagacgttga gttacatgtt    360
cagaagattt atgtgatcag tttggctgaa ccccgtctg                           399

<210> SEQ ID NO 130
<211> LENGTH: 393
<212> TYPE: DNA
<213> ORGANISM: Homo sapiens

<400> SEQUENCE: 130
gcggcggaag attatgctaa agagagatat ggaatatctt caatgataca atcacaagaa     60
aaaccagatc gagttttggt tcgggttaga gacttgacaa tacaaaaagc tgatgaagtt    120
gtttgggtac gtgcaagagt tcatacaagc agagctaaag ggaaacagtg cttcttagtc    180
ctacgtcagc agcagtttaa tgtccaggct cttgtggcgg tgggagacca tgcaagcaag    240
cagatggtta aatttgctgc caacatcaac aaagagagca ttgtggatgt agaaggtgtt    300
gtgagaaaag tgaatcagaa aattggaagc tgtacacagc aagacgttga gttacatgtt    360
cagaagattt atgtgatcag tttggctgaa ccc                                 393

<210> SEQ ID NO 131
<211> LENGTH: 411
<212> TYPE: DNA
<213> ORGANISM: Homo sapiens

<400> SEQUENCE: 131
atgcaggaga agccgcggga gatcatggac gcggcggaag attatgctaa agagagatat     60
ggaatatctt caatgataca atcacaagaa aaaccagatc gagttttggt tcgggttaga    120
gacttgacaa tacaaaaagc tgatgaagtt gtttgggtac gtgcaagagt tcatacaagc    180
agagctaaag ggaaacagtg cttcttagtc ctacgtcagc agcagtttaa tgtccaggct    240
cttgtggcgg tgggagacca tgcaagcaag cagatggtta aatttgcttg caacatcaac    300
aaagagagca ttgtggatgt agaaggtgtt gtgagaaaag tgaatcagaa aattggaagc    360
tgtacacagc aagacgttga gttacatgtt cagaagattt atgtgatcag t             411

<210> SEQ ID NO 132
<211> LENGTH: 405
<212> TYPE: DNA
<213> ORGANISM: Homo sapiens
```

<400> SEQUENCE: 132

```
atgaagccgc gggagatcat ggacgcggcg aagattatg ctaaagagag atatggaata      60
tcttcaatga tacaatcaca agaaaaacca gatcgagttt tggttcgggt tagagacttg    120
acaatacaaa aagctgatga agttgtttgg gtacgtgcaa gagttcatac aagcagagct    180
aaagggaaac agtgcttctt agtcctacgt cagcagcagt ttaatgtcca ggctcttgtg    240
gcggtgggag accatgcaag caagcagatg gttaaatttg cttgcaacat caacaaagag    300
agcattgtgg atgtagaagg tgttgtgaga aaagtgaatc agaaaattgg aagctgtaca    360
cagcaagacg ttgagttaca tgttcagaag atttatgtga tcagt                    405
```

<210> SEQ ID NO 133
<211> LENGTH: 405
<212> TYPE: DNA
<213> ORGANISM: Homo sapiens

<400> SEQUENCE: 133

```
atgaagccgc gggagatcat ggacgcggcg aagattatg ctaaagagag atatggaata      60
tcttcaatga tacaatcaca agaaaaacca gatcgagttt tggttcgggt tagagacttg    120
acaatacaaa aagctgatga agttgtttgg gtacgtgcaa gagttcatac aagcagagct    180
aaagggaaac agtgcttctt agtcctacgt cagcagcagt ttaatgtcca ggctcttgtg    240
gcggtgggag accatgcaag caagcagatg gttaaatttg cttgcaacat caacaaagag    300
agcattgtgg atgtagaagg tgttgtgaga aaagtgaatc agaaaattgg aagctgtaca    360
cagcaagacg ttgagttaca tgttcagaag atttatgtga tcagt                    405
```

<210> SEQ ID NO 134
<211> LENGTH: 393
<212> TYPE: DNA
<213> ORGANISM: Homo sapiens

<400> SEQUENCE: 134

```
atgatcatgg acgcggcgga agattatgct aaagagagat atggaatatc ttcaatgata     60
caatcacaag aaaaaccaga tcgagttttg gttcgggtta gagacttgac aatacaaaaa   120
gctgatgaag ttgtttgggt acgtgcaaga gttcatacaa gcagagctaa agggaaacag   180
tgcttcttag tcctacgtca gcagcagttt aatgtccagg ctcttgtggc ggtgggagac   240
catgcaagca agcagatggt taaatttgct tgcaacatca acaaagagag cattgtggat   300
gtagaaggtg ttgtgagaaa agtgaatcag aaaattggaa gctgtacaca gcaagacgtt   360
gagttacatg ttcagaagat ttatgtgatc agt                                393
```

<210> SEQ ID NO 135
<211> LENGTH: 381
<212> TYPE: DNA
<213> ORGANISM: Homo sapiens

<400> SEQUENCE: 135

```
atggcggaag attatgctaa agagagatat ggaatatctt caatgataca atcacaagaa     60
aaaccagatc gagttttggt tcgggttaga gacttgacaa tacaaaaagc tgatgaagtt   120
gtttgggtac gtgcaagagt tcatacaagc agagctaaag ggaaacagtg cttcttagtc   180
ctacgtcagc agcagtttaa tgtccaggct cttgtggcgg tgggagacca tgcaagcaag   240
cagatggtta aatttgcttg caacatcaac aaagagagca ttgtggatgt agaaggtgtt   300
```

```
gtgagaaaag tgaatcagaa aattggaagc tgtacacagc aagacgttga gttacatgtt      360
cagaagattt atgtgatcag t                                                381
```

<210> SEQ ID NO 136
<211> LENGTH: 21
<212> TYPE: DNA
<213> ORGANISM: Artificial Sequence
<220> FEATURE:
<223> OTHER INFORMATION: Primer

<400> SEQUENCE: 136

```
cagttcccat ctgagccatt c                                                21
```

<210> SEQ ID NO 137
<211> LENGTH: 25
<212> TYPE: DNA
<213> ORGANISM: Artificial Sequence
<220> FEATURE:
<223> OTHER INFORMATION: primer

<400> SEQUENCE: 137

```
gactagaata ttctgaagca ttggc                                            25
```

<210> SEQ ID NO 138
<211> LENGTH: 26
<212> TYPE: DNA
<213> ORGANISM: Artificial Sequence
<220> FEATURE:
<223> OTHER INFORMATION: Primer

<400> SEQUENCE: 138

```
ccagtctggc atcgcccatc tcttcc                                           26
```

<210> SEQ ID NO 139
<211> LENGTH: 26
<212> TYPE: DNA
<213> ORGANISM: Artificial Sequence
<220> FEATURE:
<223> OTHER INFORMATION: Primer

<400> SEQUENCE: 139

```
ccagtctggc atcgtccatc tcttcc                                           26
```

<210> SEQ ID NO 140
<211> LENGTH: 21
<212> TYPE: DNA
<213> ORGANISM: Artificial Sequence
<220> FEATURE:
<223> OTHER INFORMATION: Primer

<400> SEQUENCE: 140

```
cagttcccat ctgagccatt c                                                21
```

<210> SEQ ID NO 141
<211> LENGTH: 42
<212> TYPE: DNA
<213> ORGANISM: Artificial Sequence
<220> FEATURE:
<223> OTHER INFORMATION: Primer

<400> SEQUENCE: 141

```
gggttaggga taggcttacc agccaaactg atcacataaa tc                         42
```

<210> SEQ ID NO 142
<211> LENGTH: 41

<212> TYPE: DNA
<213> ORGANISM: Artificial Sequence
<220> FEATURE:
<223> OTHER INFORMATION: Primer

<400> SEQUENCE: 142
gggttaggga taggcttacc gggttcagcc aaactgatca c                41

<210> SEQ ID NO 143
<211> LENGTH: 40
<212> TYPE: DNA
<213> ORGANISM: Artificial Sequence
<220> FEATURE:
<223> OTHER INFORMATION: Primer

<400> SEQUENCE: 143
gggttaggga taggcttacc cagacggggt tcagccaaac                 40

<210> SEQ ID NO 144
<211> LENGTH: 41
<212> TYPE: DNA
<213> ORGANISM: Artificial Sequence
<220> FEATURE:
<223> OTHER INFORMATION: Primer

<400> SEQUENCE: 144
gggttaggga taggcttacc cagctgcagg ggcagacggg g               41

<210> SEQ ID NO 145
<211> LENGTH: 41
<212> TYPE: DNA
<213> ORGANISM: Artificial Sequence
<220> FEATURE:
<223> OTHER INFORMATION: Primer

<400> SEQUENCE: 145
gggttaggga taggcttacc atcatccagc tgcagggca g                41

<210> SEQ ID NO 146
<211> LENGTH: 42
<212> TYPE: DNA
<213> ORGANISM: Artificial Sequence
<220> FEATURE:
<223> OTHER INFORMATION: Primer

<400> SEQUENCE: 146
gggttaggga taggcttacc aacagcatca tccagctgca gg              42

<210> SEQ ID NO 147
<211> LENGTH: 41
<212> TYPE: DNA
<213> ORGANISM: Artificial Sequence
<220> FEATURE:
<223> OTHER INFORMATION: Primer

<400> SEQUENCE: 147
gggttaggga taggcttacc aggccgaaca gcatcatcca g               41

<210> SEQ ID NO 148
<211> LENGTH: 41
<212> TYPE: DNA
<213> ORGANISM: Artificial Sequence
<220> FEATURE:
<223> OTHER INFORMATION: Primer

<400> SEQUENCE: 148
gggttaggga taggcttacc tgcctcaggc cgaacagcat c                41

<210> SEQ ID NO 149
<211> LENGTH: 41
<212> TYPE: DNA
<213> ORGANISM: Artificial Sequence
<220> FEATURE:
<223> OTHER INFORMATION: Primer

<400> SEQUENCE: 149
gggttaggga taggcttacc tccttctgcc tcaggccgaa c                41

<210> SEQ ID NO 150
<211> LENGTH: 41
<212> TYPE: DNA
<213> ORGANISM: Artificial Sequence
<220> FEATURE:
<223> OTHER INFORMATION: Primer

<400> SEQUENCE: 150
gggttaggga taggcttacc ctcttctcct tctgcctcag g                41

<210> SEQ ID NO 151
<211> LENGTH: 41
<212> TYPE: DNA
<213> ORGANISM: Artificial Sequence
<220> FEATURE:
<223> OTHER INFORMATION: Primer

<400> SEQUENCE: 151
gggttaggga taggcttacc tccttcctct tctccttctg c                41

<210> SEQ ID NO 152
<211> LENGTH: 41
<212> TYPE: DNA
<213> ORGANISM: Artificial Sequence
<220> FEATURE:
<223> OTHER INFORMATION: Primer

<400> SEQUENCE: 152
gggttaggga taggcttacc agctcttcct tcctcttctc c                41

<210> SEQ ID NO 153
<211> LENGTH: 41
<212> TYPE: DNA
<213> ORGANISM: Artificial Sequence
<220> FEATURE:
<223> OTHER INFORMATION: Primer

<400> SEQUENCE: 153
gggttaggga taggcttacc ctggttaaca gtagctcttc c                41

<210> SEQ ID NO 154
<211> LENGTH: 41
<212> TYPE: DNA
<213> ORGANISM: Artificial Sequence
<220> FEATURE:
<223> OTHER INFORMATION: Primer

<400> SEQUENCE: 154
gggttaggga taggcttacc tgtatcctgg ttaacagtag c                41

<210> SEQ ID NO 155
<211> LENGTH: 41
<212> TYPE: DNA
<213> ORGANISM: Artificial Sequence

```
<220> FEATURE:
<223> OTHER INFORMATION: Primer

<400> SEQUENCE: 155
gggttaggga taggcttacc taatcttgta tcctggttaa c                           41

<210> SEQ ID NO 156
<211> LENGTH: 42
<212> TYPE: DNA
<213> ORGANISM: Artificial Sequence
<220> FEATURE:
<223> OTHER INFORMATION: Primer

<400> SEQUENCE: 156
gggttaggga taggcttacc gttgtctaat cttgtatcct gg                          42

<210> SEQ ID NO 157
<211> LENGTH: 34
<212> TYPE: DNA
<213> ORGANISM: Artificial Sequence
<220> FEATURE:
<223> OTHER INFORMATION: Primer

<400> SEQUENCE: 157
gaaggagata taccatgagc gccagcgcca gccg                                   34

<210> SEQ ID NO 158
<211> LENGTH: 34
<212> TYPE: DNA
<213> ORGANISM: Artificial Sequence
<220> FEATURE:
<223> OTHER INFORMATION: Primer

<400> SEQUENCE: 158
gaaggagata taccatgagc gccagccgca agag                                   34

<210> SEQ ID NO 159
<211> LENGTH: 35
<212> TYPE: DNA
<213> ORGANISM: Artificial Sequence
<220> FEATURE:
<223> OTHER INFORMATION: Primer

<400> SEQUENCE: 159
gaaggagata taccatgagc cgcaagagtc aggag                                  35

<210> SEQ ID NO 160
<211> LENGTH: 34
<212> TYPE: DNA
<213> ORGANISM: Artificial Sequence
<220> FEATURE:
<223> OTHER INFORMATION: Primer

<400> SEQUENCE: 160
gaaggagata taccatgaag agtcaggaga agcc                                   34

<210> SEQ ID NO 161
<211> LENGTH: 35
<212> TYPE: DNA
<213> ORGANISM: Artificial Sequence
<220> FEATURE:
<223> OTHER INFORMATION: Primer

<400> SEQUENCE: 161
gaaggagata tcatatgcag gagaagccgc gggag                                  35
```

<210> SEQ ID NO 162
<211> LENGTH: 35
<212> TYPE: DNA
<213> ORGANISM: Artificial Sequence
<220> FEATURE:
<223> OTHER INFORMATION: Primer

<400> SEQUENCE: 162
gaaggagata tcatatgaag ccgcgggaga tcatg                       35

<210> SEQ ID NO 163
<211> LENGTH: 36
<212> TYPE: DNA
<213> ORGANISM: Artificial Sequence
<220> FEATURE:
<223> OTHER INFORMATION: Primer

<400> SEQUENCE: 163
gaaggagata tcatatgcgg gagatcatgg acgcgg                      36

<210> SEQ ID NO 164
<211> LENGTH: 33
<212> TYPE: DNA
<213> ORGANISM: Artificial Sequence
<220> FEATURE:
<223> OTHER INFORMATION: Primer

<400> SEQUENCE: 164
gaaggagata tcatatgatc atggacgcgg cgg                         33

<210> SEQ ID NO 165
<211> LENGTH: 36
<212> TYPE: DNA
<213> ORGANISM: Artificial Sequence
<220> FEATURE:
<223> OTHER INFORMATION: Primer

<400> SEQUENCE: 165
gaaggagata tcatatggcg gaagattatg ctaaag                      36

<210> SEQ ID NO 166
<211> LENGTH: 30
<212> TYPE: DNA
<213> ORGANISM: Artificial Sequence
<220> FEATURE:
<223> OTHER INFORMATION: Primer

<400> SEQUENCE: 166
gaaggagata tcatatggat tatgctaaag                             30

<210> SEQ ID NO 167
<211> LENGTH: 40
<212> TYPE: DNA
<213> ORGANISM: Artificial Sequence
<220> FEATURE:
<223> OTHER INFORMATION: Primer

<400> SEQUENCE: 167
accgatcaca tatgcaggag aagccgcggg agatcatgga                  40

<210> SEQ ID NO 168
<211> LENGTH: 39
<212> TYPE: DNA
<213> ORGANISM: Artificial Sequence
<220> FEATURE:
<223> OTHER INFORMATION: Primer -continued

```
<400> SEQUENCE: 168
aagcttacgc atatgaagcc gcgggagatc atggacgcg                              39

<210> SEQ ID NO 169
<211> LENGTH: 40
<212> TYPE: DNA
<213> ORGANISM: Artificial Sequence
<220> FEATURE:
<223> OTHER INFORMATION: Primer

<400> SEQUENCE: 169
aactgttacc atatgatcat ggacgcggcg gaagattatg                             40

<210> SEQ ID NO 170
<211> LENGTH: 42
<212> TYPE: DNA
<213> ORGANISM: Artificial Sequence
<220> FEATURE:
<223> OTHER INFORMATION: Primer

<400> SEQUENCE: 170
aactgtcatc atatggcgga agattatgct aaagagagat at                         42

<210> SEQ ID NO 171
<211> LENGTH: 33
<212> TYPE: DNA
<213> ORGANISM: Artificial Sequence
<220> FEATURE:
<223> OTHER INFORMATION: Primer

<400> SEQUENCE: 171
tgacggctcg agactgatca cataaatctt ctg                                    33

<210> SEQ ID NO 172
<211> LENGTH: 47
<212> TYPE: DNA
<213> ORGANISM: Artificial Sequence
<220> FEATURE:
<223> OTHER INFORMATION: Primer

<400> SEQUENCE: 172
gcagatggtt aaatttgctt gcaacatcaa caaagagagc attgtgg                    47
```